(12) United States Patent
Ang et al.

(10) Patent No.: US 10,400,223 B2
(45) Date of Patent: *Sep. 3, 2019

(54) BIOCATALYSTS AND METHODS FOR THE SYNTHESIS OF ARMODAFINIL

(71) Applicant: CODEXIS, INC., Redwood City, CA (US)

(72) Inventors: Ee Lui Ang, Singapore (SG); Oscar Alvizo, Fremont, CA (US); Behnaz Behrouzian, Sunnyvale, CA (US); Michael D. Clay, Menlo Park, CA (US); Steven J. Collier, Concord, MA (US); Ellen D. Eberhard, Fallbrook, CA (US); Fu Fan, Singapore (SG); Shiwei Song, Singapore (SG); Derek J. Smith, Singapore (SG); Magnus Widegren, Craigavon (GB); Robert Wilson, San Francisco, CA (US); Junye Xu, Singapore (SG); Jun Zhu, Chandler, AZ (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,684

(22) Filed: Aug. 27, 2018

(65) Prior Publication Data

US 2018/0371431 A1    Dec. 27, 2018

Related U.S. Application Data

(60) Continuation of application No. 15/903,264, filed on Feb. 23, 2018, now Pat. No. 10,087,426, which is a continuation of application No. 15/698,319, filed on Sep. 7, 2017, now Pat. No. 9,938,509, which is a continuation of application No. 15/352,970, filed on Nov. 16, 2016, now Pat. No. 9,765,306, which is a continuation of application No. 15/159,578, filed on May 19, 2016, now Pat. No. 9,528,095, which is a continuation of application No. 14/997,277, filed on Jan. 15, 2016, now Pat. No. 9,365,835, which is a division of application No. 13/992,138, filed as application No. PCT/US2011/063809 on Dec. 7, 2011, now Pat. No. 9,267,159.

(60) Provisional application No. 61/421,123, filed on Dec. 8, 2010.

(51) Int. Cl.
| | |
|---|---|
| *C12N 9/02* | (2006.01) |
| *C12P 11/00* | (2006.01) |
| *C12P 13/02* | (2006.01) |
| *C12P 41/00* | (2006.01) |

(52) U.S. Cl.
CPC ............ *C12N 9/0073* (2013.01); *C12P 11/00* (2013.01); *C12P 13/02* (2013.01); *C12P 41/002* (2013.01); *C12Y 114/13022* (2013.01); *Y02P 20/52* (2015.11)

(58) Field of Classification Search
CPC ........ C12N 9/0073; C12P 13/02; C12P 11/00; C12P 41/002; C12Y 114/13022; Y02P 20/52
See application file for complete search history.

(56) References Cited

U.S. PATENT DOCUMENTS

| | | |
|---|---|---|
| 4,927,885 A | 5/1990 | Lafon |
| 5,840,552 A | 11/1998 | Holt et al. |
| 6,117,679 A | 9/2000 | Stemmer et al. |
| 6,162,816 A | 12/2000 | Bohlin et al. |
| 6,369,085 B1 | 4/2002 | Cotton et al. |
| 6,376,246 B1 | 4/2002 | Crameri et al. |
| 6,537,746 B2 | 5/2003 | Arnold et al. |
| 6,586,182 B1 | 7/2003 | Patten et al. |
| 7,105,296 B2 | 9/2006 | Brammucci et al. |
| 7,132,570 B2 | 11/2006 | Neckebrock et al. |
| 7,214,520 B2 | 5/2007 | Iwaki et al. |
| 7,297,346 B2 | 11/2007 | Corvari et al. |
| 7,316,918 B2 | 1/2008 | Riva et al. |
| 7,541,168 B2 | 6/2009 | Iwaki et al. |
| 7,553,646 B2 | 6/2009 | Olivo et al. |
| 9,267,159 B2 | 2/2016 | Ang et al. |
| 9,365,835 B2 | 6/2016 | Ang et al. |
| 9,765,306 B2 | 9/2017 | Ang et al. |
| 9,938,509 B2 | 4/2018 | Ang et al. |
| 2003/0087403 A1 | 5/2003 | Cheng et al. |
| 2008/0004447 A1 | 1/2008 | Gustavsson |
| 2008/0220990 A1 | 9/2008 | Fox |
| 2009/0312196 A1 | 12/2009 | Colbeck et al. |

FOREIGN PATENT DOCUMENTS

| | | |
|---|---|---|
| EP | 795024 B1 | 2/2003 |
| WO | 2007027328 A2 | 3/2007 |
| WO | 2011/071982 A2 | 6/2011 |

OTHER PUBLICATIONS

Cotton, et al., "Asymmetric Synthesis of Esomeprazole," Tetrahedon Asymetry vol. 11-18:3819, 2000.

(Continued)

*Primary Examiner* — Delia M Ramirez
(74) *Attorney, Agent, or Firm* — Codexis, Inc.

(57) ABSTRACT

The present invention relates to non-naturally occurring polypeptides useful for preparing armodafinil, polynucleotides encoding the polypeptides, and methods of using the polypeptides. The non-naturally occurring polypeptides of the present invention are effective in carrying out biocatalytic conversion of the (i) 2-(benzhydrylsulfinyl)acetamide to (−)-2-[(R)-(diphenylmethyl)sulfinyl]acetamide (armodafinil), or (ii) benzhydryl-thioacetic acid to (R)-2-(benzhydrylsulfinyl)acetic acid, which is a pivotal intermediate in the synthesis of armodafinil, in enantiomeric excess.

15 Claims, No Drawings

Specification includes a Sequence Listing.

(56) References Cited

OTHER PUBLICATIONS

Sheng et al., "Mechanistic Studies of Cyclohexanone Monooxygenase: Chemical Properties of Intermediates Involved in Catalysis" Biochemistry 40 37:11156-67, 2001.

Malito et al, "Revealing the Moonlighting Role of NADP in the Structure of a Flavin-Containing Monooxygenase" Pro. Natl. Acad. Sci. 101(36):13157-13162, 2004.

Light et al, "Studies on the Chirality of Sulfoxidation Catalyzed by Bacterial Flavoenzyme Cyclohexanone Monooxygenase and Hog Liver Flavin Adenine Dinucleotide Containing Monooxygenase" Biochemistry, 21 (10):2490-8, 1982.

Reetz et al., "Directed Evolution of Cyclohexanone Monooxygenases: Enantioselective Biocatalysts for the Oxidation of Prochiral Thioethers," Angew Chem Int. Ed, 43:4078-4081, 2004.

Pasta et al., "Synthesis of Chiral Benzyl Alkyl Sulfoxides by Cyclohexanone Monooxygenase from Acinetobacter NCIB 9871" Tetrahedron: Asymmetry 6(4) 933-936, 1995.

Yeung et al., "Prochiral Sulfoxidation as a probe for Flavin-Containing Monooxygenases, In Methods in Molecular Biology: Cytochrome P450 Protocols," Meth. Mol. Biol. 320:163-172, 2005.

Alphand et al., "Towards Large-Scale Synthetic Applications of Baeyer-Villiger Monooxygenases," Trends Biotechnology 21(7):318-323, 2003.

Chen et al., "Acinetobacter Cyclohexanone Monooxygenase: Gene Cloning and Sequence Determination," J. Bacteriol. 170 (2), 781-789, 1988.

Genbank No. Q9F7E4 dated Oct. 31, 2006.
Genbank No. AAG10021 dated Sep. 3, 2000.
Genbank No. AAA21892 dated Apr. 24, 1993.
Genbank No. BAA86293 dated Nov. 20, 2008.
Genbank No. P12015 dated Nov. 4, 2008.

Secundo, et al., "Asymetric Oxidation of Sulfides by Cyclohexanone Monooxygenase," Tetrahedron: Asymmetry, 4(9) 1981-1982, 1993.

International Search Report and Written Opinion to PCT/US2010/059398 dated Oct. 25, 2011.

Secundo, et al, "Cheminform Abstract: Asymmetric Oxidation of Sulfides by Cyclohexanone Monooxygenase," Cheminform, 25, 1994.

Chen, et al., "Asymmetric oxidations at sulfur catalyzed by engineered strains that overexpress cyclohexanone monooxygenase," New J Chem, 23, 827, 1999.

Bocola, et al., "Converting Phenylacetone Monooxygenase into Phenylcyclohexanone Monooxygenase by Rational Design: Towards Practical Baeyer-Villiger Monooxygenases," Adv. Synth. Catal. 347, 979.

Hollman, et al., "A Light-Driven Stereoselective Biocatalytic Oxidation," Angew Chemie, 119, 2961, 2007.

Mihovilovic, et al., "Asymmetric Baeyer-Villiger Oxidations of 4-Mono- and 4,4-Disubstituted Cyclohexanones by Whole Cells of Engineered *Escherichia Coli*," J. Org. Chem. 66:733-738, 2001.

Mihovilovic, et a., Microbial Baeyer-Villiger Oxidation: Stereopreference and Substrate Acceptance of Cyclohexanone Monooxygenase Mutants Prepared by Directed Evolution, Org. Ltrs., vol. 8, No. 6, 1221, 2006.

Mirza, et al., "Crystal Structures of Cyclohexanone Monooxygenase Reveal Complex Domain Movements and a Sliding Cofactor," J. Am. Chem. Soc. vol. 131, No. 25, 8850, 2009.

Reetz, et al., "Directed Evolution as a Method to Create Enantioselective Cyclohexanone Monooxygenases for Catalysis in Baeyer-Villiger Reactions," Angew Chem Int. Ed, 43:4075-4078, 2004.

Schulz, et al., "Towards Practical Biocatalytic Baeyer-Villiger Reactions: applying a thermostable enzyme in the gram-scale synthesis of optically-active lactones in a two-liquid-phase system," Beilstein J. Org. Chem., vol. 1:30, 2005.

Cheesman, et al., "Critical role of Histidine Residues in Cyclohexanone Monooxygenase Expression, Cofactor Binding and Catalysis," ChemicoBiol Interact. vol. 146, 157-164, 2003.

Clouthier, C.M., et al., "Designing new Baeyer-Villiger monooxygenases using restricted CASTing," J. Org. Chem., 71(22):8431-7 [2006].

Garnock-Jones, K.P., et al., "Armodafinil," CNS Drugs, 23(9): 793-803 [2009].

Kayser, M.M., "'Designer reagents' recombinant microorganisms: new and powerful tools for organic synthesis," Tetrahedron, 65:947-974 [2009].

Mihovilovic, M.D., et al., "Biooxidations in Chiral Synthesis," in Asymmetric Organic Synthesis with Enzymes, Wiley-VCH Verlag GmbH & Co KGaA, Chapter 9, pp. 229-274, [2008].

Olivo, H.F., et al., "Microbial oxidation/amidation of benzhydrylsulfanyl acetic acid. Synthesis of (+)-modafinil," Tetrahedron: Asymmetry, 16:3507-3511 [2005].

Schulz, F., "Monooxygenases. Experiments to turn a class of enzymes into a toolbox for biocatalysis," Dissertation, pp. 1-233 [2007].

UniProt Accession No. Q9R2F5_9GAMM, retrieved Mar. 24, 2012 from www.uniprot.org/uniprot.

International Search Report from International Application No. PCT/US2011/063809.

Kayser et al., "New Bioorganic Reagents: Evolved Cyclohexanone Monooxygenase—Why Is It More Selective?," J. Org. Chem., 71:8424-8430 [2006].

Shainsky et al., "Rapid Methods for High-Throughput Detection of Sulfoxides," Applied and Environ. Microbiol. 75 (14): 4711-19 [Jul. 2009].

Sun et al., "Synthesis of Optically Active 2,5-Dialkylcyclohexane-1,4-diols and Their Application in the Asymmetric Oxidation of Sulfides," Synthesis 16: 2513-18 [2008].

Branden, C., et al., "Introduction to Protein Structure," Garland Publishing Inc., New York, p. 247 [1991].

Witowski, A., et al., "Conversion of a beta-ketoacyl synthase to a malonyl decarboxylase by replacement of the active-site cysteine with glutamine," Biochemistry, 38:11643-11650 [1999].

Seffernick, J.L., et al., "Melamine Deaminase and Atrazine Chlorohydrolase: 98 Percent Identical but Functionally Different," J Bacteriology, 183(8):2405-2410 [2001].

Chen et al., GenBank Accession No. BAA86293, Nov. 1999.
Chen et al., GenBank Accession No. AB006902, Jul. 2003.

SEQUENCE LISTING

<160> NUMBER OF SEQ ID NOS: 146

<210> SEQ ID NO 1
<211> LENGTH: 1629
<212> TYPE: DNA
<213> ORGANISM: Artificial Sequence
<220> FEATURE:
<223> OTHER INFORMATION: Codon optimized CHMO from Acinetobacter sp
      NCIMB9871

<400> SEQUENCE: 1

| | | | | | |
|---|---|---|---|---|---|
| atgtctcaga | agatggattt | cgatgccatc | gtgatcggtg | ggggctttgg | cggtctgtat | 60 |
| gccgttaaaa | aactgcgcga | tgaactggag | ctgaaagttc | aagccttcga | caaggcaact | 120 |
| gacgtagcgg | gtacatggta | ctggaaccgc | tacccgggtg | cactgaccga | taccgaaacc | 180 |
| catttgtatt | gttattcctg | ggacaaggaa | ctgttgcaga | gtttggaaat | caaaagaaa | 240 |
| tacgtgcaag | gtccagacgt | gcgcaaatat | ctgcagcagg | ttgccgaaaa | acacgactta | 300 |
| aaaaaagct | accagttcaa | caccgcagtc | caatctgccc | actacaacga | agcggacgct | 360 |
| ctgtgggaag | taactacgga | atacggggat | aagtacaccg | cacgtttcct | gattactgcc | 420 |
| ttaggtttgc | tgtctgcacc | taacctgcca | aatatcaagg | gcatcaatca | gtttaaaggc | 480 |
| gaactgcacc | atacttcccg | ctggccggat | gacgtgagtt | cgaaggcaa | acgtgtgggt | 540 |
| gtgatcggca | caggctctac | cggcgtgcaa | gttatcacgg | cagtggcgcc | actggccaag | 600 |
| cacctgacgg | tgtttcagcg | tagtgcccag | tactcggtcc | cgatcggtaa | cgatccactg | 660 |
| agcgaagaag | acgtcaagaa | gatcaaagat | aactatgata | aaatctggga | tggtgtttgg | 720 |
| aacagtgcgc | tggccttcgg | cctgaatgaa | tctactgtgc | cggccatgtc | cgtaagtgcg | 780 |
| gaagagcgta | agcggttttt | tgagaaggcg | tggcaaaccg | gcggtggttt | tcgtttttatg | 840 |
| ttcgaaacct | tggtgatat | tgccacgaac | atggaagcta | acattgaggc | acaaaattt | 900 |
| attaaaggta | aaatcgcgga | gatcgtcaaa | gatccggcga | tcgcccaaaa | actgatgccg | 960 |
| caggatctgt | acgcaaaacg | ccctctgtgt | gactccgggt | actataatac | gttcaatcgc | 1020 |
| gacaacgtac | gtctggagga | tgtcaaagca | aatccgatcg | tcgagatcac | cgaaaacggc | 1080 |
| gtgaaactgg | aaaacggcga | tttcgtggag | ctggacatgc | tgatctgcgc | gacgggtttt | 1140 |
| gatgcggtag | acggcaacta | tgttcgcatg | gatatccaag | ggaaaaacgg | tctggccatg | 1200 |
| aaggattact | ggaaagaggg | cccgtctagc | tacatgggcg | taaccgtgaa | taattaccca | 1260 |
| aacatgttta | tggttctggg | tccaaacggt | ccattcacca | acctgccgcc | tagcattgaa | 1320 |
| agtcaagttg | aatggattag | cgatactatc | cagtataccg | tcgaaaataa | cgtggaatct | 1380 |
| attgaagcca | cgaaggaagc | ggaggaacag | tggacccaaa | cctgcgccaa | tattgcggag | 1440 |
| atgaccctgt | ttccaaaagc | ccagagctgg | attttggg | cgaacattcc | aggcaagaag | 1500 |
| aacaccgtgt | actttatttt | gggtgggctg | aaagagtacc | gctcagcttt | ggcgaattgt | 1560 |
| aaaaatcatg | cgtatgaagg | ctttgatatt | cagctgcaac | gttctgacat | caaacaacca | 1620 |
| gcgaatgcg | | | | | | 1629 |

<210> SEQ ID NO 2
<211> LENGTH: 543
<212> TYPE: PRT
<213> ORGANISM: Acinetobacter sp NCIMB9871

<400> SEQUENCE: 2

```
Met Ser Gln Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Asp Lys Ala Thr Asp Val Ala Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Leu Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Leu Leu
    130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Phe Arg Phe Met Phe Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Tyr Ala Lys Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
                405                 410                 415
```

```
Asn Asn Tyr Pro Asn Met Phe Met Val Leu Gly Pro Asn Gly Pro Phe
            420                 425                 430
Thr Asn Leu Pro Pro Ser Ile Glu Ser Gln Val Glu Trp Ile Ser Asp
            435                 440                 445
Thr Ile Gln Tyr Thr Val Glu Asn Asn Val Glu Ser Ile Glu Ala Thr
    450                 455                 460
Lys Glu Ala Glu Glu Gln Trp Thr Gln Thr Cys Ala Asn Ile Ala Glu
465                 470                 475                 480
Met Thr Leu Phe Pro Lys Ala Gln Ser Trp Ile Phe Gly Ala Asn Ile
                485                 490                 495
Pro Gly Lys Lys Asn Thr Val Tyr Phe Tyr Leu Gly Gly Leu Lys Glu
                500                 505                 510
Tyr Arg Ser Ala Leu Ala Asn Cys Lys Asn His Ala Tyr Glu Gly Phe
            515                 520                 525
Asp Ile Gln Leu Gln Arg Ser Asp Ile Lys Gln Pro Ala Asn Ala
            530                 535                 540

<210> SEQ ID NO 3
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 3
atgtctcaga agatggattt cgatgccatc gtgatcggtg ggggctttgg cggtctgtat      60
gccgttaaaa aactgcgcga tgaactggag ctgaaagttc aagccttcga aaggcaact     120 gacgtagcgg gtacatggta ctggaaccgc taccgggtg cactgaccga taccgaaacc      180
catttgtatt gttattcctg gacaaggaa ctgttgcaga gtttggaaat caaaagaaa      240 tacgtgcaag gtccagacgt gcgcaaatat ctgcagcagg ttgccgaaaa acacgactta      300
aaaaaaagct accagttcaa caccgcagtc caatctgccc actacaacga agcggacgct      360
ctgtgggaag taactacgga atacggggat aagtacaccg cacgtttcct gattactgcc      420
ttaggtctgc tgtctgcacc taacctgcca aatatcaagg gcatcaatca gtttaaaggc      480
gaactgcacc atacttcccg ctggccggat gacgtgagtt cgaaggcaa acgtgtgggt      540 gtgatcggca caggctctac cggcgtgcaa gttatcacgg cagtggcgcc actggccaag      600
cacctgacgg tgtttcagcg tagtgcccag tactcggtcc cgatcggtaa cgatccactg      660
agcgaagaag acgtcaagaa gatcaaagat aactatgata aaatctggga tggtgtttgg      720
aacagtgcgc tggccttcgg cctgaatgaa tctactgtgc cggccatgtc cgtaagtgcg      780
gaagagcgta agcggttttt tgagaaggcg tggcaaaccg gcggtggtat cggttttacg      840
atcgaaacct ttggtgatat tgccacgaac atggaagcta acattgaggc acaaaatttt      900
atcaaaggta aatcgcggga gatcgtcaaa gatccggcga tcgcccaaaa actgatgccg      960
caggatctgt acgcacgtcg ccctctgtgt gactccgggt actataatac gttcaatcgc     1020
gacaacgtac gtctggagga tgtcaaagca aatccgatcg tcgagatcac cgaaaacggc     1080
gtgaaactgg aaaacggcga tttcgtggag ctggacatgc tgatctgcgc gacgggtttt     1140
gatgcggtag acggcaacta tgttcgcatg gatatccaag ggaaaaacgg tctggccatg     1200
aaggattact ggaagagggg cccgtctagc tacatgggcg taaccgtgaa taattaccca     1260
aacatgttta tggttctggg tccaaacggt ccatcaggta acgcaccgcc tagcattgaa     1320
```

-continued

```
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg attttggggg cgaacattcc aggcaagaag    1500
aacaccgtgt actttattt gggtgggctg aaagagtacc gctcagcttt ggcgaattgt     1560
aaaaatcatg cgtatgaagg ctttgatatt cagctgcaac gttctgacat caaacaacca    1620
gcgaatgcg                                                            1629
```

<210> SEQ ID NO 4
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 4

```
Met Ser Gln Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Ala Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Leu Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Leu Leu
    130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Thr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300
```

| | | | | | | | | | | | |
|---|---|---|---|---|---|---|---|---|---|---|---|
|Ile|Ala|Glu|Ile|Val|Lys|Asp|Pro|Ala|Ile|Ala|Gln|Lys|Leu|Met|Pro|
|305| | | |310| | | |315| | | |320| | | |

Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Glu Asn Gly Asp Phe
            355                 360                 365

Val Glu Leu Asp Met Leu Ile Cys Ala Thr Gly Phe Asp Ala Val Asp
        370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
                405                 410                 415

Asn Asn Tyr Pro Asn Met Phe Met Val Leu Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Phe Gly Ala Asn Ile
                485                 490                 495

Pro Gly Lys Lys Asn Thr Val Tyr Phe Tyr Leu Gly Leu Lys Glu
            500                 505                 510

Tyr Arg Ser Ala Leu Ala Asn Cys Lys Asn His Ala Tyr Glu Gly Phe
        515                 520                 525

Asp Ile Gln Leu Gln Arg Ser Asp Ile Lys Gln Pro Ala Asn Ala
    530                 535                 540

<210> SEQ ID NO 5
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 5

```
atgtctcaga gatggatttt cgatgccatc gtgatcggtg ggggctttgg cggtctgtat      60
gccgttaaaa aactgcgcga tgaactggag ctgaaagttc aagccttcga aaggcaact     120
gacgtagcgg gtacatggta ctggaaccgc tacccgggtg tgctgaccga taccgaaacc    180
catttgtatt gttattcctg ggacaaggaa ctgttgcaga gtttggaaat caaaagaaa     240
tacgtgcaag gtccagacgt gcgcaaatat ctgcagcagg ttgccgaaaa acacgactta    300
aaaaaaagct accagttcaa caccgcagtc aatctgcccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gaactgcacc atacttcccg ctggccggat gacatgagtt cgaaggcaa acgtgtgggt    540
gtgatcggca caggctctac cggcgtgcaa gttatcacgg cagtggcgcc actggccaag    600
cacctgacgg tgtttcagcg tagtgccag tactcggtcc cgatcggtaa cgatccactg    660
agcgaagaag acgtcaagaa gatcaaagat aactatgata aaatctggga tggtgtttgg    720
```

```
aacagtgcgc tggccttcgg cctgaatgaa tctactgtgc cggccatgtc cgtaagtgcg      780
gaagagcgta aagcggtttt tgagaaggcg tggcaaaccg gcggtggtat cggttttttac     840 atcgaaacct ttggtgatat tgccacgaac atggaagcta acattgaggc acaaaatttt      900
atcaaaggta aaatcgcgga gatcgtcaaa gatccggcga tcgcccaaaa actgatgccg      960
caggatctgt acgcacgtcg ccctctgtgt gactccgggt actataatac gttcaatcgc     1020
gacaacgtac gtctggagga tgtcaaagca aatccgatcg tcgagatcac cgaaaacggc     1080
gtgaaactgg aaaacggcga tttcgtggag ctggacatgc tgatctgcgc gacgggtttt     1140
gatgcggtag acggcaacta tgttcgcatg gatatccaag ggaaaaacgg tctggccatg     1200
aaggattact ggaaagaggg cccgtctagc tacatgggcg taaccgtgaa taattaccca     1260
aacatgttta tggttctggg tccaaacggt ccatctggta acgctccgcc tagcattgaa     1320
agtcaagttg aatggattag cgatactatc cagtataccg tcgaaaataa cgtggaatct     1380
attgaagcca cgaaggaagc ggaggaacag tggacccaaa cctgcgccaa tattgcggag     1440
atgaccctgt ttccaaaagc ccagagcctg attttggggg cgaacattcc aggcaagaag     1500
aacaccgtgt acttttattt gggtgggctg aaagagtacc gctcagcttt ggcgaattgt     1560
aaaaatcatg cgtatgaagg ctttgatatt cagccgcaac gttctgacat caaacaacca     1620
gcgaatgcg                                                              1629
```

<210> SEQ ID NO 6
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 6

```
Met Ser Gln Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Ala Gly Thr Trp Tyr Trp
        35                  40                  45

Asn Arg Tyr Pro Gly Val Leu Thr Asp Thr Glu Thr His Leu Tyr Cys
    50                  55                  60

Tyr Ser Trp Asp Lys Glu Leu Leu Gln Ser Leu Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Asp Met Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
```

```
            195                 200                 205
Ala Gln Tyr Ser Val Pro Ile Gly Asn Asp Pro Leu Ser Glu Glu Asp
        210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
                405                 410                 415

Asn Asn Tyr Pro Asn Met Phe Met Val Leu Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Phe Gly Ala Asn Ile
                485                 490                 495

Pro Gly Lys Lys Asn Thr Val Tyr Phe Tyr Leu Gly Gly Leu Lys Glu
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 7
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 7
atgtctacca agatggattt cgatgccatc gtgatcggtg ggggctttgg cggtctgtat      60
gccgttaaaa aactgcgcga tgaactggag ctgaaagttc aagccttcga gaaggcaact     120
```

```
gacgtagcgg gtacatggta ctggaaccgc tacccgggtg tgctgaccga taccgaaacc    180
catttgtatt gttattcctg ggacaaggaa ctgttgcaga gtttggaaat caaaagaaa     240
tacgtgcaag gtccagacgt gcgcaaatat ctgcagcagg ttgccgaaaa acacgactta    300
aaaaaaagct accagttcaa caccgcagtc aatctgccc actacaacga agcggacgct     360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gaactgcacc atacttcccg ctggccggat gacatgagtt tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaaaccg gcggtggtat cggttttttac   840
atcgaaacct ttggtgatat tgccacgaac atggaagcta acattgaggc acaaaatttt    900
atcaaaggta aaatcgcgga gatcgtcaaa gatccggcga tcgcccaaaa actgatgccg    960
caggatctgt acgcacgtcg ccctctgtgt gactccgggt actataatac gttcaatcgc   1020
gacaacgtac gtctggagga tgtcaaagca atccgatcg tcgagatcac cgaaaacggc    1080
gtgaaactgg aaaacggcga tttcgtggag ctggacatgc tgatctgcgc gacgggtttt   1140
gatgcggtag acggcaacta tgttcgcatg gatatccaag ggaaaaacgg tctggccatg   1200
aaggattact ggaagagggg cccgtctagc tacatgggcg taaccgtgaa taattaccca   1260
aacatgttta tggttctggg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg attttggggg cgaacattcc aggcaagaag   1500
aacaccgtgt acttttattt gggtgggctg aaagagtacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 8
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 8

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Ala Gly Thr Trp Tyr Trp
        35                  40                  45

Asn Arg Tyr Pro Gly Val Leu Thr Asp Thr Glu Thr His Leu Tyr Cys
    50                  55                  60

Tyr Ser Trp Asp Lys Glu Leu Leu Gln Ser Leu Glu Ile Lys Lys Lys
65                  70                  75                  80

Tyr Val Gln Gly Pro Asp Val Arg Lys Tyr Leu Gln Gln Val Ala Glu
                85                  90                  95
```

```
Lys His Asp Leu Lys Lys Ser Tyr Gln Phe Asn Thr Ala Val Gln Ser
                100                 105                 110

Ala His Tyr Asn Glu Ala Asp Ala Leu Trp Glu Val Thr Thr Glu Tyr
                115                 120                 125

Gly Asp Lys Tyr Thr Ala Arg Phe Leu Ile Thr Ala Leu Gly Gly Leu
            130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Asp Met Ser Phe Glu Gly
                165                 170                 175

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Ser
            195                 200                 205

Ala Gln Tyr Ser Val Pro Ile Gly Asn Asp Pro Leu Ser Glu Glu Asp
            210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
            275                 280                 285

Thr Asn Met Glu Ala Asn Ile Glu Ala Gln Asn Phe Ile Lys Gly Lys
            290                 295                 300

Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
            355                 360                 365

Val Glu Leu Asp Met Leu Ile Cys Ala Thr Gly Phe Asp Ala Val Asp
            370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
                405                 410                 415

Asn Asn Tyr Pro Asn Met Phe Met Val Leu Gly Pro Asn Gly Pro Ser
            420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
        450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Phe Gly Ala Asn Ile
                485                 490                 495

Pro Gly Lys Lys Asn Thr Val Tyr Phe Tyr Leu Gly Gly Leu Lys Glu
            500                 505                 510
```

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
    530                 535                 540

<210> SEQ ID NO 9
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 9

```
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtagcgg gtacatggta ctggaaccgc tacccgggtg tgctgaccga taccgaaacc     180
catttgtatt gttattcctg gacaaggaa ctgttgcaga gtatggaaat caaaaagaaa     240
tacgtgcaag gtccagacgt gcgcaaatat ctgcagcagg ttgccgaaaa acacgactta     300
aaaaaaagct accagttcaa caccgcagtc aatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gaactgcacc atacttcccg ctggccggat gacatgagtt cgaaggcaa cgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagaa gatcaaagat aactatgata aatctggga tggtgtttgg     720
aacagtgcgc tggccttcgg cctgaatgaa tctactgtgc cggccatgtc cgtaagtgcg     780
gaagagcgta agcggttttt tgagaaggcg tggcaaaccg gcggtggtat cggtttttac     840
atcgaaacct ttggtgatat tgccacgaac atggaagcta acattgaggc acaaaattt     900
atcaaaggta aaatcgcgga tcgtcaaa gatccggcga tcgcccaaaa actgatgccg     960
caggatctgt acgcacgtcg ccctctgtgt gactccgggt actataatac gttcaatcgc    1020
gacaacgtac gtctggagga tgtcaaagca aatccgatcg tcgagatcac cgaaacggc    1080
gtgaaactgg aaaacggcga tttcgtggag ctggacatgc tgatctgcgc gacgggtttt    1140
gatgcggtag acggcaacta tgttcgcatg gatatccaag ggaaaaacgg tctggccatg    1200
aaggattact ggaaagaggg cccgtctagc tacatgggcg taaccgtgaa taattaccca    1260
aacatgttta tggttctggg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg attttgggg cgaacattcc aggcaagaag    1500
aacaccgtgt actttattt gggtgggctg aaagagtacc gctcagcttt ggcgaattgt    1560
aaaaatcatg cgtatgaagg ctttgatatt cagccgcaac gttctgacat caaacaacca    1620
gcgaatgcg                                                           1629
```

<210> SEQ ID NO 10
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 10

```
Met Ser Thr Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Ala Gly Thr Trp Tyr Trp
                35                  40                  45

Asn Arg Tyr Pro Gly Val Leu Thr Asp Thr Glu Thr His Leu Tyr Cys
50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Met Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
290                 295                 300

Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
```

```
            405                 410                 415
Asn Asn Tyr Pro Asn Met Phe Met Val Leu Gly Pro Asn Gly Pro Ser
            420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Phe Gly Ala Asn Ile
                485                 490                 495

Pro Gly Lys Lys Asn Thr Val Tyr Phe Tyr Leu Gly Gly Leu Lys Glu
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
        530                 535                 540
```

<210> SEQ ID NO 11
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 11

```
atgtctacca agatggattt cgatgccatc gtgatcggtg ggggcttttgg cggtctgtat     60
gccgttaaaa aactgcgcga tgaactggag ctgaaagttc aagccttcga gaaggcaact    120
gacgtagcgg gtacatggta ctggaaccgc tacccgggtg ccctgaccga taccgaaacc    180
catttgtatt gttattcctg ggacaaggaa ctgttgcaga gtatggaaat caaaagaaa     240
tacgtgcaag gtccagacgt gcgcaaatat ctgcagcagg ttgccgaaaa acacgactta    300
aaaaaaagct accagttcaa caccgcagtc caatctgccc actacaacga gcggacgct     360
ctgtgggaag taactacgga atacggggat aagtacaccg cacgtttcct gattactgcc    420
ttaggtgggc tgtctgcacc taacctgcca atatcaagg gcatcaatca gtttaaaggc     480
gaactgcacc atacttcccg ctggccggat gacgttagtt tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta agcggttttt tgagaaggcg tggcaaaccg gcggtggtat cggtttttac    840
atcgaaacct ttggtgatat tgccacgaac atggaagcta acattgaggc acaaaatttt    900
atcaaaggta aatcgcgga tcgtcaaa gatccggcga tcgcccaaaa actgatgccg     960
caggatctgt acgcacgtcg ccctctgtgt gactccgggt actataatac gttcaatcgc   1020
gacaacgtac gtctggagga tgtcaaagca aatccgatcg tcgagatcac cgaaaacggc   1080
gtgaaactgg aaaacggcga tttcgtggag ctggacatgc tgatctgcgc gacgggtttt   1140
gatgcggtag acggcaacta tgttcgcatg gatatccaag ggaaaaacgg tctggccatg   1200
aaggattact ggaagagggg cccgtctagc tacatgggcg taaccgtgaa taattaccca   1260
aacatgttta tggttagcgg tccaaacggt ccatctggta acgctccgcc tagcattgaa   1320
```

-continued

```
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg attttggggg cgaacattcc aggcaagaag    1500
aacaccgcgt attttatttt gggtgggctg aaagagtacc gctcagcttt ggcgaattgt    1560
aaaaatcatg cgtatgaagg ctttgatatt cagccgcaac gttctgacat caaacaacca    1620
gcgaatgcg                                                             1629
```

<210> SEQ ID NO 12
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 12

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Ala Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300
```

```
Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
            325                 330                 335

Thr Phe Asn Arg Asp Asn Val Arg Leu Glu Asp Val Lys Ala Asn Pro
        340                 345                 350

Ile Val Glu Ile Thr Glu Asn Gly Val Lys Leu Glu Asn Gly Asp Phe
    355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
            405                 410                 415

Asn Asn Tyr Pro Asn Met Phe Met Val Ser Gly Pro Asn Gly Pro Ser
        420                 425                 430

Gly Asn Ala Pro Pro Ser Ile Glu Ser Gln Val Glu Trp Ile Ser Asp
    435                 440                 445

Thr Ile Gln Tyr Thr Val Glu Asn Asn Val Glu Ser Ile Glu Ala Thr
450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Phe Gly Ala Asn Ile
            485                 490                 495

Pro Gly Lys Lys Asn Thr Ala Tyr Phe Tyr Leu Gly Gly Leu Lys Glu
        500                 505                 510

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
530                 535                 540

<210> SEQ ID NO 13
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 13
atgtctacca agatggattt cgatgccatc gtgatcggtg ggggctttgg cggtctgtat      60
gccgttaaaa aactgcgcga tgaactggag ctgaaagttc aagccttcga aaggcaact     120 gacgtagcgg gtacatggta ctggaaccgc tacccgggtg ccctgaccga taccgaaacc    180
catttgtatt gttattcctg ggacaaggaa ctgttgcaga gtatggaaat caaaaagaaa    240
tacgtgcaag gtccagacgt gcgcaaatat ctgcagcagg ttgccgaaaa acacgactta    300
aaaaaaagct accagttcaa caccgcagtc aatctgccc actacaacga gcggacgct     360 ctgtgggaag taactacgga atacggggat aagtacaccg cacgtttcct gattactgcc    420
ttaggtctgc tgtctgcacc taacctgcca aatatcaagg gcatcaatca gtttaaaggc    480
gaactgcacc atacttcccg ctggccggat gacgttagtt tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
```

```
aacagtgcgc tggccttcgg cctgaatgaa tctactgtgc cggccatgtc cgtaagtgcg      780
gaagagcgta aagcggtttt tgagaaggcg tggcaaaccg gcggtggtat cggttttttac    840 atcgaaacct ttggtgatat tgccacgaac atggaagcta acattgaggc acaaaatttt     900
atcaaaggta aatcgcgga gatcgtcaaa gatccggcga tcgcccaaaa actgatgccg      960
caggatctgt acgcacgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag ggaaaaacgg tctggccatg    1200
aaggattact ggaaagaggg cccgtctagc tacatgggcg taaccgtgaa taattaccca    1260
aacatgttta tggttctggg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg attttggggg cgaacattcc aggcaagaag    1500
aacaccgtgt acttttattt gggtgggctg aaagagtacc gctcagcttt ggcgaattgt    1560
aaaaatcatg cgtatgaagg ctttgatatt cagctgcaac gttctgacat caaacaacca    1620
gcgaatgcg                                                            1629
```

<210> SEQ ID NO 14
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 14

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Ala Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Leu Leu
    130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190
```

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
                405                 410                 415

Asn Asn Tyr Pro Asn Met Phe Met Val Leu Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Phe Gly Ala Asn Ile
                485                 490                 495

Pro Gly Lys Lys Asn Thr Val Tyr Phe Tyr Leu Gly Gly Leu Lys Glu
            500                 505                 510

Tyr Arg Ser Ala Leu Ala Asn Cys Lys Asn His Ala Tyr Glu Gly Phe
        515                 520                 525

Asp Ile Gln Leu Gln Arg Ser Asp Ile Lys Gln Pro Ala Asn Ala
    530                 535                 540

<210> SEQ ID NO 15
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 15
atgtctacca agatggattt cgatgccatc gtgatcggtg ggggctttgg cggtctgtat     60
gccgttaaaa aactgcgcga tgaactggag ctgaaagttc aagccttcga gaaggcaact    120

```
gacgtaggcg gtacatggta ctggaaccgc tacccgggtg ccctgaccga taccgaaacc      180
catttgtatt gttattcctg ggacaaggaa ctgttgcaga gtatggaaat caaaagaaa       240 tacgtgcaag gtccagacgt gcgcaaatat ctgcagcagg ttgccgaaaa acacgactta      300
aaaaaaagct accagttcaa caccgcagtc caatctgccc actacaacga agcggacgct      360
ctgtgggaag taactacgga atacgggat aagtacaccg cacgtttcct gattactgcc       420
ttaggtgggc tgtctgcacc taacctgcca aatatcaagg gcatcaatca gtttaaaggc      480
gaactgcacc atactggccg ctggccggat gacgttagtt tcgaaggcaa acgtgtgggt      540
gtgatcggca caggctctac cggcgtgcaa gttatcacgg cagtggcgcc actggccaag      600
cacctgacgg tgtttcagcg tagtgcccag tactcggtcc cgatcggtaa cgatccactg      660
agcgaagaag acgtcaagaa gatcaaagat aactatgata aaatctggga tggtgtttgg      720
aacagtgcgc tggccttcgg cctgaatgaa tctactgtgc cggccatgtc cgtaagtgcg      780
gaagagcgta aagcggtttt tgagaaggcg tggcaaaccg gcggtggtat cggttttac       840 atcgaaaccct ttggtgatat tgccacgaac atggaagcta acattgaggc acaaaatttt    900
atcaaaggta aaatcgcgga gatcgtcaaa gatccggcga tcgcccaaaa actgatgccg      960
caggatctgt acgcacgtcg ccctctgtgt gactccgggt actataatac gttcaatcgc      1020
gacaacgtac gtctggagga tgtcaaagca aatccgatcg tcgagatcac cgaaaacggc      1080
gtgaaactgg aaaacggcga tttcgtggag ctggacatgc tgatctgcgc gacgggtttt      1140
gatgcggtag acggcaacta tgttcgcatg gatatccaag ggaaaaacgg tctggccatg      1200
aaggattact ggaaagaggg cccgtctagc tacatgggcg taaccgtgaa taattaccca      1260
aacatgttta tggttagcgg tccaaacggt ccatctggta acgctccgcc tagcattgaa      1320
agtcaagttg aatggattag cgatactatc cagtataccg tcgaaaataa cgtggaatct      1380
attgaagcca cgaaggaagc ggaggaacag tggacccaaa cctgcgccaa tattgcggag      1440
atgaccctgt ttccaaaagc ccagagcctg atttttgggg cgaacattcc aggcaagaag      1500
aacaccgcgt attttatttt gggtgggctg aaaaactacc gctcagcttt ggcgaattgt      1560
aaaaatcatg cgtatgaagg ctttgatatt cagccgcaac gttctgacat caaacaacca      1620
gcgaatgcg                                                              1629
```

<210> SEQ ID NO 16
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 16

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
                20                  25                  30

Val Gln Ala Phe Glu Lys Ala Thr Asp Val Gly Gly Thr Trp Tyr Trp
            35                  40                  45

Asn Arg Tyr Pro Gly Ala Leu Thr Asp Thr Glu Thr His Leu Tyr Cys
        50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu

-continued

```
                  85                  90                  95
Lys His Asp Leu Lys Lys Ser Tyr Gln Phe Asn Thr Ala Val Gln Ser
            100                 105                 110
Ala His Tyr Asn Glu Ala Asp Ala Leu Trp Glu Val Thr Thr Glu Tyr
            115                 120                 125
Gly Asp Lys Tyr Thr Ala Arg Phe Leu Ile Thr Ala Leu Gly Gly Leu
            130                 135                 140
Ser Ala Pro Asn Leu Pro Asn Ile Lys Gly Ile Asn Gln Phe Lys Gly
145                 150                 155                 160
Glu Leu His His Thr Gly Arg Trp Pro Asp Asp Val Ser Phe Glu Gly
            165                 170                 175
Lys Arg Val Gly Val Ile Gly Thr Gly Ser Thr Gly Val Gln Val Ile
            180                 185                 190
Thr Ala Val Ala Pro Leu Ala Lys His Leu Thr Val Phe Gln Arg Ser
            195                 200                 205
Ala Gln Tyr Ser Val Pro Ile Gly Asn Asp Pro Leu Ser Glu Glu Asp
            210                 215                 220
Val Lys Lys Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
            245                 250                 255
Ser Val Ser Ala Glu Glu Arg Lys Ala Val Phe Glu Lys Ala Trp Gln
            260                 265                 270
Thr Gly Gly Gly Ile Gly Phe Tyr Ile Glu Thr Phe Gly Asp Ile Ala
            275                 280                 285
Thr Asn Met Glu Ala Asn Ile Glu Ala Gln Asn Phe Ile Lys Gly Lys
            290                 295                 300
Ile Ala Glu Ile Val Lys Asp Pro Ala Ile Ala Gln Lys Leu Met Pro
305                 310                 315                 320
Gln Asp Leu Tyr Ala Arg Arg Pro Leu Cys Asp Ser Gly Tyr Tyr Asn
            325                 330                 335
Thr Phe Asn Arg Asp Asn Val Arg Leu Glu Asp Val Lys Ala Asn Pro
            340                 345                 350
Ile Val Glu Ile Thr Glu Asn Gly Val Lys Leu Glu Asn Gly Asp Phe
            355                 360                 365
Val Glu Leu Asp Met Leu Ile Cys Ala Thr Gly Phe Asp Ala Val Asp
            370                 375                 380
Gly Asn Tyr Val Arg Met Asp Ile Gln Gly Lys Asn Gly Leu Ala Met
385                 390                 395                 400
Lys Asp Tyr Trp Lys Glu Gly Pro Ser Ser Tyr Met Gly Val Thr Val
            405                 410                 415
Asn Asn Tyr Pro Asn Met Phe Met Val Ser Gly Pro Asn Gly Pro Ser
            420                 425                 430
Gly Asn Ala Pro Pro Ser Ile Glu Ser Gln Val Glu Trp Ile Ser Asp
            435                 440                 445
Thr Ile Gln Tyr Thr Val Glu Asn Val Glu Ser Ile Glu Ala Thr
            450                 455                 460
Lys Glu Ala Glu Glu Gln Trp Thr Gln Thr Cys Ala Asn Ile Ala Glu
465                 470                 475                 480
Met Thr Leu Phe Pro Lys Ala Gln Ser Leu Ile Phe Gly Ala Asn Ile
            485                 490                 495
Pro Gly Lys Lys Asn Thr Ala Tyr Phe Tyr Leu Gly Gly Leu Lys Asn
            500                 505                 510
```

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 17
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 17

| | | | | | |
|---|---|---|---|---|---|
| atgtctacca | agatggattt | cgatgccatc | gtgatcggtg | ggggctttgg | cggtctgtat | 60 |
| gccgttaaaa | aactgcgcga | tgaactggag | ctgaaagttc | aagccttcga | gaaggcaact | 120 |
| gacgtaggcg | gtacatggta | ctggaaccgc | tacccgggtg | ccctgaccga | taccgaaacc | 180 |
| catttgtatt | gttattcctg | ggacaaggaa | ctgttgcaga | gtatggaaat | caaaaagaaa | 240 |
| tacgtgcaag | gtccagacgt | gcgcaaatat | ctgcagcagg | ttgccgaaaa | acacgactta | 300 |
| aaaaaaagct | accagttcaa | caccgcagtc | caatctgccc | actacaacga | agcggacgct | 360 |
| ctgtgggaag | taactacgga | atacggggat | aagtacaccg | cacgtttcct | gattactgcc | 420 |
| ttaggtgggc | tgtctgcacc | taacctgcca | aatatcaagg | gcatcaatca | gtttaaggc | 480 |
| gaactgcacc | atactggccg | ctggccggat | gacgttagtt | tcgaaggcaa | acgtgtgggt | 540 |
| gtgatcggca | caggctctac | cggcgtgcaa | gttatcacgg | cagtggcgcc | actggccaag | 600 |
| cacctgacgg | tgtttcagcg | tagtgcccag | tactcggtcc | cgatcggtaa | cgatccactg | 660 |
| agcgaagaag | acgtcaagaa | gatcaaagat | aactatgata | aaatctggga | tggtgtttgg | 720 |
| aacagtgcgc | tggccttcgg | cctgaatgaa | tctactgtgc | cggccatgtc | cgtaagtgcg | 780 |
| gaagagcgta | aagcggtttt | tgagaaggcg | tggcaaaccg | cgggtggtat | cggttttac | 840 |
| atcgaaacct | ttggtgatat | tgccacgaac | atggaagcta | acattgaggc | acaaaatttt | 900 |
| atcaaaggta | aaatcgcgga | gatcgtcaaa | gatccggaaa | tcgcccaaaa | actgatgccg | 960 |
| caggatctgt | acgcacgtcg | ccctctgtgt | gactccgggt | actataatac | gttcaatcgc | 1020 |
| gacaacgtac | gtctggagga | tgtcaaagca | aatccgatcg | tcgagatcac | cgaaaacggc | 1080 |
| gtgaaactgg | aaaacggcga | tttcgtggag | ctggacatgc | tgatctgcgc | gacgggtttt | 1140 |
| gatgcggtag | acggcaacta | tgttcgcatg | gatatccaag | ggaaaaacgg | tctggccatg | 1200 |
| aaggattact | ggaaagaggg | cccgtctagc | tacatgggcg | taaccgtgaa | taattaccca | 1260 |
| aacatgttta | tggttagcgg | tccaaacggt | ccatctggta | acgctccgcc | tagcattgaa | 1320 |
| agtcaagttg | aatggattag | cgatactatc | cagtataccg | tcgaaaataa | cgtggaatct | 1380 |
| attgaagcca | cgaaggaagc | ggaggaacag | tggacccaaa | cctgcgccaa | tattgcggag | 1440 |
| atgaccctgt | ttccaaaagc | ccagagcctg | attttttgggg | cgaacattcc | aggcaagaag | 1500 |
| aacaccgcgt | atttttattt | gggtgggctg | aaagagtacc | gctcagcttt | ggcgaattgt | 1560 |
| aaaaatcatg | cgtatgaagg | ctttgatatt | cagccgcaac | gttctgacat | caaacaacca | 1620 |
| gcgaatgcg | | | | | | 1629 |

<210> SEQ ID NO 18
<211> LENGTH: 543
<212> TYPE: PRT
<213> ORGANISM: Artificial Sequence
<220> FEATURE:

<223> OTHER INFORMATION: Variant of CHMO from Acinetobacter sp NCIMB9871

<400> SEQUENCE: 18

```
Met Ser Thr Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Gly Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Glu Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Lys Asn Gly Leu Ala Met
385                 390                 395                 400
```

```
Lys Asp Tyr Trp Lys Glu Gly Pro Ser Ser Tyr Met Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Phe Gly Ala Asn Ile
                485                 490                 495

Pro Gly Lys Lys Asn Thr Ala Tyr Phe Tyr Leu Gly Gly Leu Lys Glu
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540
```

<210> SEQ ID NO 19
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 19

| | | |
|---|---|---|
| atgtctacca agatggattt cgatgccatc gtgatcggtg ggggctttgg cggtctgtat | 60 |
| gccgttaaaa aactgcgcga tgaactggag ctgaaagttc aagccttcga agaggcaact | 120 |
| gacgtaggcg gtacatggta ctggaaccgc tacccgggtg ccctgaccga taccgaaacc | 180 |
| catttgtatt gttattcctg ggacaaggaa ctgttgcaga gtatggaaat caaaagaaa | 240 |
| tacgtgcaag gtccagacgt gcgcaaatat ctgcagcagg ttgccgaaaa acacgactta | 300 |
| aaaaaaagct accagttcaa caccgcagtc aatctgccc actacaacga agcggacgct | 360 |
| ctgtgggaag taactacgga atacgggat aagtacaccg cacgtttcct gattactgcc | 420 |
| ttaggtgggc tgtctgcacc taacctgcca aatatcaagg gcatcaatca gtttaaaggc | 480 |
| gaactgcacc atactggccg ctggccggat gacgttagtt tcgaaggcaa acgtgtgggt | 540 |
| gtgatcggca caggctctac cggcgtgcaa gttatcacgg cagtggcgcc actggccaag | 600 |
| cacctgacgg tgtttcagcg tagtgcccag tactcggtcc cgatcggtaa cgatccactg | 660 |
| agcgaagaag acgtcaagaa gatcaaagat aactatgata aaatctggga tggtgtttgg | 720 |
| aacagtgcgc tggccttcgg cctgaatgaa tctactgtgc cggccatgtc cgtaagtgcg | 780 |
| gaagagcgta agcggtttt tgagaaggcg tggcaaaccg gcggtggtat cggtttttac | 840 |
| atcgaaacct tggtgatat tgccacgaac atggaagcta acattgaggc acaaaatttt | 900 |
| atcaaaggta aaatcgcgga gatcgtcaaa gatccggcga tcgcccaaaa actgatgccg | 960 |
| caggatctgt acgcacgtcg ccctctgtgt gactccgggt actataatac gttcaatcgc | 1020 |
| gacaacgtac gtctggagga tgtcaaagca aatccgatcg tcgagatcac cgaaaacggc | 1080 |
| gtgaaactgg aaaacggcga tttcgtggag ctggacatgc tgatctgcgc gacgggtttt | 1140 |
| gatgcggtag acgcaactca tgttcgcatg gatatccaag ggaaaaacgg tctggccatg | 1200 |
| aaggattact ggaagagggg cccgtctagc tacctgggcg taaccgtgaa taattaccca | 1260 |

-continued

```
aacatgttta tggttaacgg tccaaacggt ccatttggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagggtctg attttggggg cgacattcc aggcaagaag     1500 aacaccgcgt attttattt gggtgggctg aaaaactacc gctcagcttt ggcgaattgt     1560
aaaaatcatg cgtatgaagg ctttgatatt cagccgcaac gttctgacat caaacaacca    1620
gcgaatgcg                                                            1629
```

<210> SEQ ID NO 20
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 20

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Gly Arg Trp Pro Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
```

```
                290                 295                 300
Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Glu Asn Gly Asp Phe
                355                 360                 365

Val Glu Leu Asp Met Leu Ile Cys Ala Thr Gly Phe Asp Ala Val Asp
                370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Asn Gly Pro Asn Gly Pro Phe
                420                 425                 430

Gly Asn Ala Pro Pro Ser Ile Glu Ser Gln Val Glu Trp Ile Ser Asp
                435                 440                 445

Thr Ile Gln Tyr Thr Val Glu Asn Asn Val Glu Ser Ile Glu Ala Thr
                450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Gly Leu Ile Phe Gly Ala Asn Ile
                485                 490                 495

Pro Gly Lys Lys Asn Thr Ala Tyr Phe Tyr Leu Gly Gly Leu Lys Asn
                500                 505                 510

Tyr Arg Ser Ala Leu Ala Asn Cys Lys Asn His Ala Tyr Glu Gly Phe
                515                 520                 525

Asp Ile Gln Pro Gln Arg Ser Asp Ile Lys Gln Pro Ala Asn Ala
                530                 535                 540

<210> SEQ ID NO 21
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 21
atgtctacca agatggattt cgatgccatc gtgatcggtg ggggctttgg cggtctgtat      60
gccgttaaaa aactgcgcga tgaactggag ctgaaagttc aagccttcga agggcaact       120 gacatcggcg gtacatggta ctggaaccgc tacccgggtg ccctgaccga taccgaaacc     180
catttgtatt gttattcctg gacaaggaa ctgttgcaga gtatggaaat caaaagaaa       240 tacgtgcaag gtccagacgt gcgcaaatat ctgcagcagg ttgccgaaaa acacgactta     300
aaaaaaagct accagttcaa caccgcagtc aatctgccc actacaacga agcggacgct      360
ctgtgggaag taactacgga atacggggat aagtacaccg cacgtttcct gattactgcc    420
ttaggtgggc tgtctgcacc taacctgcca aatatcaagg gcatcaatca gtttaaaggc     480
gaactgcacc atactggccg ctggccggat gacgttagtt tcgaaggcaa acgtgtgggt    540
gtgatcggca aggctctac cggcgtgcaa gttatcacgg cagtggcgcc actggccaag     600
cacctgacgg tgtttcagcg tagtgcccag tactcggtcc cgatcggtaa cgatccactg     660
```

```
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaaaccg gcggtggtat cggttttttac   840 atcgaaacct ttggtgatat tgccacgaac atggaagcta acattgaggc acaaaatttt    900
atcaaaggta aaatcgcgga gatcgtcaaa gatccggcga tcgcccaaaa actgatgccg    960
cagggtctgt acgcacgtcg ccctctgtgt gactccgggt actataatac gttcaatcgc   1020
gacaacgtac gtctggagga tgtcaaagca aatccgatcg tcgagatcac cgaaaacggc   1080
gtgaaactgg aaaacggcga tttcgtggag ctggacatgc tgatctgcgc gacgggtttt   1140
gatgcggtag acggcaacta tgttcgcatg gatatccaag ggaaaaacgg tctggccatg   1200
aaggattact ggaaagaggg cccgtctagc tacatgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg atttcagggg cgaacattcc aggcaagaag   1500
aacaccgcgt atttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                            1629

<210> SEQ ID NO 22
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 22

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Ile Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Gly Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190
```

```
Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Gly Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Ile Ser Gly Ala Asn Ile
                485                 490                 495

Pro Gly Lys Lys Asn Thr Ala Tyr Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540
```

<210> SEQ ID NO 23
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 23
atgtctacca agatggattt cgatgccatc gtgatcggtg ggggctttgg cggtctgtat    60

```
gccgttaaaa aactgcgcga tgaactggag ctgaaagttc aagccttcga gaaggcaact    120
gacatcggcg gtacatggta ctggaaccgc tacccgggtg ccctgaccga taccgaaacc    180
catttgtatt gttattcctg ggacaaggaa ctgttgcaga gtatggaaat caaaaagaaa    240
tacgtgcaag gtccagacgt gcgcaaatat ctgcagcagg ttgccgaaaa acacgactta    300
aaaaaaagct accagttcaa caccgcagtc aatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gaactgcacc atactggccg ctggccggat gacgttagtt cgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aatctggga tggtgtttgg    720
aacagtgcgc tggccttcgg cctgaatgaa tctactgtgc cggccatgtc cgtaagtgcg    780
gaagagcgta agcggttttt tgagaaggcg tggcaaaccg gcggtggtat cggtttttac    840
atcgaaaccct ttggtgatat tgccacgaac atggaagcta acattgaggc acaaaatttt    900
atcaaaggta aatcgcgga gatcgtcaaa gatccggcga tcgcccaaaa actgatgccg    960
cagggtctgt acgcacgtcg ccctctgtgt gactccgggt actataatac gttcaatcgc   1020
gacaacgtac gtctggagga tgtcaaagca atccgatcg tcgagatcac cgaaaacggc   1080
gtgaaactgg aaaacggcga tttcgtggag ctggacatgc tgatctgcgc gacgggtttt   1140
gatgcggtag acggcaacta tgttcgcatg gatatccaag ggaaaaacgg tctggccatg   1200
aaggattact ggaaagaggg cccgtctagc tacatgggcg taaccgtgaa taattaccca   1260
aacatgtttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccga tattgcggag   1440
atgacccctgt ttccaaaagc ccagagcctg atttcagggg cgaacattcc aggcaagaag   1500
aacaccgcgt attttttattt gggtgggctg aaaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 24
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 24

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Ile Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80
```

-continued

```
Tyr Val Gln Gly Pro Asp Val Arg Lys Tyr Leu Gln Gln Val Ala Glu
                 85                  90                  95
Lys His Asp Leu Lys Lys Ser Tyr Gln Phe Asn Thr Ala Val Gln Ser
            100                 105                 110
Ala His Tyr Asn Glu Ala Asp Ala Leu Trp Glu Val Thr Thr Glu Tyr
            115                 120                 125
Gly Asp Lys Tyr Thr Ala Arg Phe Leu Ile Thr Ala Leu Gly Gly Leu
            130                 135                 140
Ser Ala Pro Asn Leu Pro Asn Ile Lys Gly Ile Asn Gln Phe Lys Gly
145                 150                 155                 160
Glu Leu His His Thr Gly Arg Trp Pro Asp Asp Val Ser Phe Glu Gly
                165                 170                 175
Lys Arg Val Gly Val Ile Gly Thr Gly Ser Thr Gly Val Gln Val Ile
            180                 185                 190
Thr Ala Val Ala Pro Leu Ala Lys His Leu Thr Val Phe Gln Arg Ser
            195                 200                 205
Ala Gln Tyr Ser Val Pro Ile Gly Asn Asp Pro Leu Ser Glu Glu Asp
            210                 215                 220
Val Lys Lys Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
                245                 250                 255
Ser Val Ser Ala Glu Glu Arg Lys Ala Val Phe Glu Lys Ala Trp Gln
            260                 265                 270
Thr Gly Gly Gly Ile Gly Phe Tyr Ile Glu Thr Phe Gly Asp Ile Ala
            275                 280                 285
Thr Asn Met Glu Ala Asn Ile Glu Ala Gln Asn Phe Ile Lys Gly Lys
            290                 295                 300
Ile Ala Glu Ile Val Lys Asp Pro Ala Ile Ala Gln Lys Leu Met Pro
305                 310                 315                 320
Gln Gly Leu Tyr Ala Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
            340                 345                 350
Ile Val Glu Ile Thr Glu Asn Gly Val Lys Leu Glu Asn Gly Asp Phe
            355                 360                 365
Val Glu Leu Asp Met Leu Ile Cys Ala Thr Gly Phe Asp Ala Val Asp
            370                 375                 380
Gly Asn Tyr Val Arg Met Asp Ile Gln Gly Lys Asn Gly Leu Ala Met
385                 390                 395                 400
Lys Asp Tyr Trp Lys Glu Gly Pro Ser Ser Tyr Met Gly Val Thr Val
                405                 410                 415
Asn Asn Tyr Pro Asn Met Phe Met Val Ser Gly Pro Asn Gly Pro Ser
            420                 425                 430
Gly Asn Ala Pro Pro Ser Ile Glu Ser Gln Val Glu Trp Ile Ser Asp
            435                 440                 445
Thr Ile Gln Tyr Thr Val Glu Asn Asn Val Glu Ser Ile Glu Ala Thr
            450                 455                 460
Lys Glu Ala Glu Glu Gln Trp Thr Gln Thr Cys Ala Asp Ile Ala Glu
465                 470                 475                 480
Met Thr Leu Phe Pro Lys Ala Gln Ser Leu Ile Ser Gly Ala Asn Ile
                485                 490                 495
Pro Gly Lys Lys Asn Thr Ala Tyr Phe Tyr Leu Gly Gly Leu Lys Asn
```

```
                500             505                 510
Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
            530                 535             540

<210> SEQ ID NO 25
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 25
atgtctacca agatggattt cgatgccatc gtgatcggtg ggggctttgg cggtctgtat      60
gccgttaaaa aactgcgcga tgaactggag ctgaaagttc aagccttcga agaggcaact    120
gacgtaggcg gtacatggta ctggaaccgc tacccgggtg ccctgaccga taccgaaacc    180
catttgtatt gttattcctg gacaaggaa ctgttgcaga gtatggaaat caaaaagaaa     240
tacgtgcaag gtccagacgt gcgcaaatat ctgcagcagg ttgccgaaaa acacgactta    300
aaaaaaagct accagttcaa caccgcagtc caatctgccc actacaacga gcggacgct     360 ctgtgggaag taactacgga atacgggat aagtacaccg cacgtttcct gattactgcc     420
ttaggtgggc tgtctgcacc taacctgcca aatatcaagg gcatcaatca gtttaaaggc    480
gaactgcacc atactggccg ctggccggat gacgttagtt cgaaggcaa acgtgtgggt     540 gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaaaccg cggtggtat cggttttac      840 atcgaaacct ttggtgatat tgtgacgaac atggaagcta acattgaggc acaaaatttt    900
atcaaaggta aatcgcgga atcgtcaaa gatccggcga tcgcccaaaa actgatgccg      960
caggatctgt acgcacgtcg ccctctgtgt gactccgggt actataatac gttcaatcgc   1020
gacaacgtac gtctggagga tgtcaaagca atccgatcg tcgagatcac cgaaaacggc    1080
gtgaaactgg aaaacggcga tttcgtggag ctggacatgc tgatctgcgc gacgggtttt   1140
gatgcggtag acggcaacta tgttcgcatg gatatccaag ggaaaaacgg tctggccatg   1200
aaggattact ggaaagaggg cccgtctagc tacatgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttttgggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629

<210> SEQ ID NO 26
<211> LENGTH: 543
<212> TYPE: PRT
<213> ORGANISM: Artificial Sequence
```

<220> FEATURE:
<223> OTHER INFORMATION: Variant of CHMO from Acinetobacter sp NCIMB9871

<400> SEQUENCE: 26

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Gly Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Lys Asn Gly Leu Ala Met
385                 390                 395                 400
```

Lys Asp Tyr Trp Lys Glu Gly Pro Ser Ser Tyr Met Gly Val Thr Val
            405                 410                 415

Asn Asn Tyr Pro Asn Met Phe Met Val Ser Gly Pro Asn Gly Pro Ser
        420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
        450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
            485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
        530                 535                 540

<210> SEQ ID NO 27
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 27

```
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaagaaa      240
tacgtgcaag gtccagacgt gcgcaaatat ctgcagcagg ttgccgaaaa acacgactta     300
aaaaaaagct accagttcaa caccgcagtc aatctgcccc actacaacga agcggacgct     360
ctgtgggaag taactacgga atacggggat aagtacaccg cacgtttcct gattactgcc     420
ttaggtgggt tgtctgcacc taacctgcca aatatcaagg gcatcaatca gtttaaaggc     480
gaactgctgc atactggccg ctggccggat gacgttagtt tcgaaggcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaaaccg gcggtggtat cggtttttac     840
atcgaaacct ttggtgatat tgtgacgaac atggaagcta acattgaggc acaaaatttt     900
atcaaaggta aaatcgcgga atcgtcaaa gatccggcga tcgcccaaaa actgatgccg     960
cagggcctgt acgcacgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatcgcgtag acggcaacta tgttcgcatg gatatccaag ggaaaacgg tctggccatg    1200
aaggattact ggaaagaggg cccgtctagc tacatgggcg taaccgtgaa taattaccca    1260
```

```
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccga tattgcggag   1440
atgaccctgt ttccaaaagc ccagagcctg gttttgggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 28
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 28

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu Leu His Thr Gly Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Val
        275                 280                 285
```

```
Thr Asn Met Glu Ala Asn Ile Glu Ala Gln Asn Phe Ile Lys Gly Lys
    290                 295                 300
Ile Ala Glu Ile Val Lys Asp Pro Ala Ile Ala Gln Lys Leu Met Pro
305                 310                 315                 320
Gln Gly Leu Tyr Ala Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
            340                 345                 350
Ile Val Glu Ile Thr Glu Asn Gly Val Lys Leu Glu Asn Gly Asp Phe
        355                 360                 365
Val Glu Leu Asp Met Leu Ile Cys Ala Thr Gly Phe Asp Arg Val Asp
370                 375                 380
Gly Asn Tyr Val Arg Met Asp Ile Gln Gly Lys Asn Gly Leu Ala Met
385                 390                 395                 400
Lys Asp Tyr Trp Lys Glu Gly Pro Ser Ser Tyr Met Gly Val Thr Val
                405                 410                 415
Asn Asn Tyr Pro Asn Met Phe Met Val Ser Gly Pro Asn Gly Pro Ser
            420                 425                 430
Gly Asn Ala Pro Pro Ser Ile Glu Ser Gln Val Glu Trp Ile Ser Asp
        435                 440                 445
Thr Ile Gln Tyr Thr Val Glu Asn Asn Val Glu Ser Ile Glu Ala Thr
450                 455                 460
Lys Glu Ala Glu Glu Gln Trp Thr Gln Thr Cys Ala Asp Ile Ala Glu
465                 470                 475                 480
Met Thr Leu Phe Pro Lys Ala Gln Ser Leu Val Phe Gly Ala Asn Ile
                485                 490                 495
Pro Gly Lys Lys Asn Thr Ala Ile Phe Tyr Leu Gly Gly Leu Lys Asn
            500                 505                 510
Tyr Arg Ser Ala Leu Ala Asn Cys Lys Asn His Ala Tyr Glu Gly Phe
        515                 520                 525
Asp Ile Gln Pro Gln Arg Ser Asp Ile Lys Gln Pro Ala Asn Ala
530                 535                 540

<210> SEQ ID NO 29
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 29
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaagaaa      240 tacgtgcaag gtccagacgt gcgcaaatat ctgcagcagg ttgccgaaaa acacgactta     300
aaaaaaagct accagttcaa caccgcagtc aatctgccc actacaacga gcggacgct      360 ctgtgggaag taactacgga atacggggat aagtacaccg cacgtttcct gattactgcc     420
ttaggtgggc tgtctgcacc taacctgcca aatatcaagg gcatcaatca gtttaaaggc     480
gaactgcacc atactggccg ctggccggat gacgttagtt tcgaaggcaa acgtgtgggt     540
gtgatcggca caggctctac cggcgtgcaa gttatcacgg cagtggcgcc actggccaag     600
caccctgacg gtgtttcagcg tagtgcccag tactcggtcc cgatcggtaa cgatccactg     660
```

-continued

```
agcgaagaag acgtcaagaa gatcaaagat aactatgata aaatctggga tggtgtttgg      720
aacagtgcgc tggccttcgg cctgaatgaa tctactgtgc cggccatgtc cgtaagtgcg      780
gaagagcgta aagcggtttt tgagaaggcg tggcaaaccg gcggtggtat cggttttac       840 atcgaaacct ttggtgatat tgtgacgaac atggaagcta acattgaggc acaaaatttt      900
atcaaaggta aaatcgcgga gatcgtcaaa gatccggcga tcgcccaaaa actgatgccg      960
cagggcctgt acgcacgtcg ccctctgtgt gactccgggt actataatac gttcaatcgc     1020
gacaacgtac gtctggagga tgccaaagca aatccgatcg tcgagatcac cgaaaacggc     1080
gtgaaactgg aaaacggcga tttcgtggag ctggacatgc tgatctgcgc gacgggtttt     1140
gatgcggtag acggcaacta tgttcgcatg gatatccaag ggaaaaacgg tctggccatg     1200
aaggattact ggaagagggg cccgtctagc tacatgggcg taaccgtgaa taattaccca     1260
aacatgttta tggttagcgg tccaaacggt ccatctggta acgctccgcc tagcattgaa     1320
agtcaagttg aatggattag cgatactatc cagtataccg tcgaaaataa cgtggaatct     1380
attgaagcca cgaaggaagc ggaggaacag tggacccaaa cctgcgccga tattgcggag     1440 atgacctgt ttccaaaagc ccagggtctg gtctttgggg cgaacattcc aggcaagaag      1500
aacaccgcga tcttttattt gggtgggctg aaaaactacc gctcagcttt ggcgaattgt     1560
aaaaatcatg cgtatgaagg ctttgatatt cagccgcaac gttctgacat cgaacaacca     1620
gcgaatgcg                                                             1629
```

<210> SEQ ID NO 30
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 30

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Gly Arg Trp Pro Asp Asp Val Ser Phe Glu Gly
                165                 170                 175

Lys Arg Val Gly Val Ile Gly Thr Gly Ser Thr Gly Val Gln Val Ile
```

```
              180                 185                 190
Thr Ala Val Ala Pro Leu Ala Lys His Leu Thr Val Phe Gln Arg Ser
            195                 200                 205
Ala Gln Tyr Ser Val Pro Ile Gly Asn Asp Pro Leu Ser Glu Glu Asp
            210                 215                 220
Val Lys Lys Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
                245                 250                 255
Ser Val Ser Ala Glu Glu Arg Lys Ala Val Phe Glu Lys Ala Trp Gln
            260                 265                 270
Thr Gly Gly Gly Ile Gly Phe Tyr Ile Glu Thr Phe Gly Asp Ile Val
            275                 280                 285
Thr Asn Met Glu Ala Asn Ile Glu Ala Gln Asn Phe Ile Lys Gly Lys
            290                 295                 300
Ile Ala Glu Ile Val Lys Asp Pro Ala Ile Ala Gln Lys Leu Met Pro
305                 310                 315                 320
Gln Gly Leu Tyr Ala Arg Arg Pro Leu Cys Asp Ser Gly Tyr Tyr Asn
                325                 330                 335
Thr Phe Asn Arg Asp Asn Val Arg Leu Glu Asp Ala Lys Ala Asn Pro
            340                 345                 350
Ile Val Glu Ile Thr Glu Asn Gly Val Lys Leu Glu Asn Gly Asp Phe
            355                 360                 365
Val Glu Leu Asp Met Leu Ile Cys Ala Thr Gly Phe Asp Ala Val Asp
            370                 375                 380
Gly Asn Tyr Val Arg Met Asp Ile Gln Gly Lys Asn Gly Leu Ala Met
385                 390                 395                 400
Lys Asp Tyr Trp Lys Glu Gly Pro Ser Ser Tyr Met Gly Val Thr Val
                405                 410                 415
Asn Asn Tyr Pro Asn Met Phe Met Val Ser Gly Pro Asn Gly Pro Ser
            420                 425                 430
Gly Asn Ala Pro Pro Ser Ile Glu Ser Gln Val Glu Trp Ile Ser Asp
            435                 440                 445
Thr Ile Gln Tyr Thr Val Glu Asn Asn Val Glu Ser Ile Glu Ala Thr
            450                 455                 460
Lys Glu Ala Glu Glu Gln Trp Thr Gln Thr Cys Ala Asp Ile Ala Glu
465                 470                 475                 480
Met Thr Leu Phe Pro Lys Ala Gln Gly Leu Val Phe Gly Ala Asn Ile
                485                 490                 495
Pro Gly Lys Lys Asn Thr Ala Ile Phe Tyr Leu Gly Gly Leu Lys Asn
            500                 505                 510
Tyr Arg Ser Ala Leu Ala Asn Cys Lys Asn His Ala Tyr Glu Gly Phe
            515                 520                 525
Asp Ile Gln Pro Gln Arg Ser Asp Ile Glu Gln Pro Ala Asn Ala
            530                 535                 540

<210> SEQ ID NO 31
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 31
atgtctacca agatggattt cgatgccatc gtgatcggtg ggggctttgg cggtctgtat        60
```

```
gccgttaaaa aactgcgcga tgaactggag ctgaaagttc aagccttcga gaaggcaact    120
gacattggcg gtacatggta ctggaaccgc tacccgggtg ccctgaccga taccgaaacc    180
catttgtatt gttattcctg ggacaaggaa ctgttgcaga gtatggaaat caaaaagaaa    240
tacgtgcaag gtccagacgt gcgcaaatat ctgcagcagg ttgccgaaaa acacgactta    300
aaaaaaagct accagttcaa caccgcagtc caatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gaactgcacc atactggccg ctggccggat gacgttagtt cgaaggcaa acgtgtgggt     540 gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aatctggga tggtgtttgg     720 aacagtgcgc tggccttcgg cctgaatgaa tctactgtgc cggccatgtc cgtaagtgcg    780
gaagagcgta aagcggtttt tgagaaggcg tggcaaaccg gcggtggtat cggtttttac    840
atcgaaacct ttggtgatat tgtgacgaac atggaagcta acattgaggc acaaaatttt    900
atcaaaggta aaatcgcgga gatcgtcaaa gatccggcga tcgcccaaaa actgatgccg    960
caggatctgt acgcacgtcg ccctctgtgt gactccgggt actataatac gttcaatcgc   1020
gacaacgtac gtctggagga tgtcaaagca aatccgatcg tcgagatcac cgaaaacggc   1080
gtgaaactgg aaaacggcga tttcgtggag ctggacatgc tgatctgcgc gacgggtttt   1140
gatgcggtag acggcaacta tgttcgcatg gatatccaag ggaaaaacgg tctggccatg   1200
aaggattact ggaagagggg cccgtctagc tacatgggcg taaccgtgaa taattaccca   1260 aacatgtttta tggttagcgg tccaaacggt ccatctggta acgctccgcc tagcattgaa    1320
agtcaagttg aatggattag cgatactatc cagtataccg tcgaaaataa cgtggaatct   1380
attgaagcca cgaaggaagc ggaggaacag tggacccaaa cctgcgccga tattgcggag   1440 atgacccctgt ttccaaaagc ccagagcctg gtctttgggg cgaacattcc aggcaagaag   1500
aacaccgcga tctttattt gggtgggctg aaaaactacc gctcagcttt ggcgaattgt    1560
aaaaatcatg cgtatgaagg cttttgatatt cagccgcaac gttctgacat caaacaacca   1620
gcgaatgcg                                                           1629
```

<210> SEQ ID NO 32
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 32

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Ile Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80
```

```
Tyr Val Gln Gly Pro Asp Val Arg Lys Tyr Leu Gln Gln Val Ala Glu
                85                  90                  95
Lys His Asp Leu Lys Lys Ser Tyr Gln Phe Asn Thr Ala Val Gln Ser
                100                 105                 110
Ala His Tyr Asn Glu Ala Asp Ala Leu Trp Glu Val Thr Thr Glu Tyr
                115                 120                 125
Gly Asp Lys Tyr Thr Ala Arg Phe Leu Ile Thr Ala Leu Gly Gly Leu
        130                 135                 140
Ser Ala Pro Asn Leu Pro Asn Ile Lys Gly Ile Asn Gln Phe Lys Gly
145                 150                 155                 160
Glu Leu His His Thr Gly Arg Trp Pro Asp Val Ser Phe Glu Gly
                165                 170                 175
Lys Arg Val Gly Val Ile Gly Thr Gly Ser Thr Gly Val Gln Val Ile
                180                 185                 190
Thr Ala Val Ala Pro Leu Ala Lys His Leu Thr Val Phe Gln Arg Ser
                195                 200                 205
Ala Gln Tyr Ser Val Pro Ile Gly Asn Asp Pro Leu Ser Glu Glu Asp
        210                 215                 220
Val Lys Lys Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
                245                 250                 255
Ser Val Ser Ala Glu Glu Arg Lys Ala Val Phe Glu Lys Ala Trp Gln
                260                 265                 270
Thr Gly Gly Gly Ile Gly Phe Tyr Ile Glu Thr Phe Gly Asp Ile Val
        275                 280                 285
Thr Asn Met Glu Ala Asn Ile Glu Ala Gln Asn Phe Ile Lys Gly Lys
        290                 295                 300
Ile Ala Glu Ile Val Lys Asp Pro Ala Ile Ala Gln Lys Leu Met Pro
305                 310                 315                 320
Gln Asp Leu Tyr Ala Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
                340                 345                 350
Ile Val Glu Ile Thr Glu Asn Gly Val Lys Leu Glu Asn Gly Asp Phe
        355                 360                 365
Val Glu Leu Asp Met Leu Ile Cys Ala Thr Gly Phe Asp Ala Val Asp
        370                 375                 380
Gly Asn Tyr Val Arg Met Asp Ile Gln Gly Lys Asn Gly Leu Ala Met
385                 390                 395                 400
Lys Asp Tyr Trp Lys Glu Gly Pro Ser Ser Tyr Met Gly Val Thr Val
                405                 410                 415
Asn Asn Tyr Pro Asn Met Phe Met Val Ser Gly Pro Asn Gly Pro Ser
                420                 425                 430
Gly Asn Ala Pro Pro Ser Ile Glu Ser Gln Val Glu Trp Ile Ser Asp
        435                 440                 445
Thr Ile Gln Tyr Thr Val Glu Asn Asn Val Glu Ser Ile Glu Ala Thr
        450                 455                 460
Lys Glu Ala Glu Glu Gln Trp Thr Gln Thr Cys Ala Asp Ile Ala Glu
465                 470                 475                 480
Met Thr Leu Phe Pro Lys Ala Gln Ser Leu Val Phe Gly Ala Asn Ile
                485                 490                 495
```

| Pro | Gly | Lys | Lys | Asn | Thr | Ala | Ile | Phe | Tyr | Leu | Gly | Gly | Leu | Lys | Asn |
|---|---|---|---|---|---|---|---|---|---|---|---|---|---|---|---|
| | | | 500 | | | | 505 | | | | 510 | | | | |

| Tyr | Arg | Ser | Ala | Leu | Ala | Asn | Cys | Lys | Asn | His | Ala | Tyr | Glu | Gly | Phe |
|---|---|---|---|---|---|---|---|---|---|---|---|---|---|---|---|
| | 515 | | | | 520 | | | | 525 | | | | | | |

| Asp | Ile | Gln | Pro | Gln | Arg | Ser | Asp | Ile | Lys | Gln | Pro | Ala | Asn | Ala |
|---|---|---|---|---|---|---|---|---|---|---|---|---|---|---|
| 530 | | | | 535 | | | | 540 | | | | | | |

<210> SEQ ID NO 33
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 33

| | |
|---|---|
| atgtctacca agatggattt cgatgccatc gtgatcggtg ggggctttgg cggtctgtat | 60 |
| gccgttaaaa aactgcgcga tgaactggag ctgaaagttc aagccttcga gaaggcaact | 120 |
| gacattggcg gtacatggta ctggaaccgc tacccgggtg ccctgaccga taccgaaacc | 180 |
| catttgtatt gttattcctg gacaaggaa ctgttgcaga gtatggaaat caaaagaaa | 240 |
| tacgtgcaag gtccagacgt gcgcaaatat ctgcagcagg ttgccgaaaa acacgactta | 300 |
| aaaaaagct accagttcaa caccgcagtc caatctgccc actacaacga agcggacgct | 360 |
| ctgtgggaag taactacgga atacggggat aagtacaccg cacgtttcct gattactgcc | 420 |
| ttaggtgggc tgtctgcacc taacctgcca aatatcaagg gcatcaatca gtttaaaggc | 480 |
| gaactgctgc atactggccg ctggccggat gacgttagtt cgaaagcaa acgtgtgggt | 540 |
| gtgatcggca caggctctac cggcgtgcaa gttatcacgg cagtggcgcc actggccaag | 600 |
| cacctgacgg tgtttcagcg tagtgcccag tactcggtcc cgatcggtaa cgatccactg | 660 |
| agcgaagaag acgtcaagaa gatcaaagat aactatgata aatctggga tggtgtttgg | 720 |
| aacagtgcgc tggccttcgg cctgaatgaa tctactgtgc cggccatgtc cgtaagtgcg | 780 |
| gaagagcgta agcggttttt tgagaaggcg tggcaaaccg gcggtggtat cggtttttac | 840 |
| atcgaaacct tggtgatat tgtgacgaac atggaagcta acattgaggc acaaaatttt | 900 |
| atcaaaggta aaatcgcgga gatcgtcaaa gatccggcga tcgcccaaaa actgatgccg | 960 |
| cagggcctgt acgcacgtcg ccctctgtgt gactccgggt actataatac gttcaatcgc | 1020 |
| gacaacgtac gtctggagga tgtcaaagca aatccgatcg tcgagatcac cgaaaacggc | 1080 |
| gtgaaactgg aaaacggcga tttcgtggag ctggacatgc tgatctgcgc gacgggtttt | 1140 |
| gatcgcgtag acggcaacta tgttcgcatg gatatccaag ggaaaaacgg tctggccatg | 1200 |
| aaggattact ggaaagaggg cccgtctagc tacatgggcg taaccgtgaa taattaccca | 1260 |
| aacatgttta tggttagcgg tccaaacggt ccatctggta acgctccgcc tagcattgaa | 1320 |
| agtcaagttg aatggattag cgatactatc cagtataccg tcgaaaataa cgtggaatct | 1380 |
| attgaagcca cgaaggaagc ggaggaacag tggacccaaa cctgcgccga tattgcggag | 1440 |
| atgaccctgt ttccaaaagc ccagggcctg gtctttgggg cgaacattcc aggcaagaag | 1500 |
| aacaccgcga tcttttattt gggtgggctg aaaaactacc gctcagcttt ggcgaattgt | 1560 |
| aaaaatcatg cgtatgaagg ctttgatatt cagccgcaac gttctgacat caaacaacca | 1620 |
| gcgaatgcg | 1629 |

<210> SEQ ID NO 34
<211> LENGTH: 543
<212> TYPE: PRT

<213> ORGANISM: Artificial Sequence
<220> FEATURE:
<223> OTHER INFORMATION: Variant of CHMO from Acinetobacter sp NCIMB9871

<400> SEQUENCE: 34

| | | | | | | | | | | | | | | |
|---|---|---|---|---|---|---|---|---|---|---|---|---|---|---|
| Met | Ser | Thr | Lys | Met | Asp | Phe | Asp | Ala | Ile | Val | Ile | Gly | Gly | Phe |
| 1 | | | | 5 | | | | | 10 | | | | | 15 |
| Gly | Gly | Leu | Tyr | Ala | Val | Lys | Lys | Leu | Arg | Asp | Glu | Leu | Glu | Leu | Lys |
| | | | 20 | | | | | 25 | | | | | 30 | | |
| Val | Gln | Ala | Phe | Glu | Lys | Ala | Thr | Asp | Ile | Gly | Gly | Thr | Trp | Tyr | Trp |
| | | 35 | | | | | 40 | | | | | 45 | | | |
| Asn | Arg | Tyr | Pro | Gly | Ala | Leu | Thr | Asp | Thr | Glu | Thr | His | Leu | Tyr | Cys |
| 50 | | | | | 55 | | | | | 60 | | | | | |
| Tyr | Ser | Trp | Asp | Lys | Glu | Leu | Leu | Gln | Ser | Met | Glu | Ile | Lys | Lys | Lys |
| 65 | | | | | 70 | | | | | 75 | | | | | 80 |
| Tyr | Val | Gln | Gly | Pro | Asp | Val | Arg | Lys | Tyr | Leu | Gln | Val | Ala | Glu |
| | | | | 85 | | | | | 90 | | | | | 95 |
| Lys | His | Asp | Leu | Lys | Lys | Ser | Tyr | Gln | Phe | Asn | Thr | Ala | Val | Gln | Ser |
| | | | 100 | | | | | 105 | | | | | 110 | | |
| Ala | His | Tyr | Asn | Glu | Ala | Asp | Ala | Leu | Trp | Glu | Val | Thr | Thr | Glu | Tyr |
| | | 115 | | | | | 120 | | | | | 125 | | | |
| Gly | Asp | Lys | Tyr | Thr | Ala | Arg | Phe | Leu | Ile | Thr | Ala | Leu | Gly | Gly | Leu |
| 130 | | | | | 135 | | | | | 140 | | | | | |
| Ser | Ala | Pro | Asn | Leu | Pro | Asn | Ile | Lys | Gly | Ile | Asn | Gln | Phe | Lys | Gly |
| 145 | | | | | 150 | | | | | 155 | | | | | 160 |
| Glu | Leu | Leu | His | Thr | Gly | Arg | Trp | Pro | Asp | Asp | Val | Ser | Phe | Glu | Ser |
| | | | | 165 | | | | | 170 | | | | | 175 | |
| Lys | Arg | Val | Gly | Val | Ile | Gly | Thr | Gly | Ser | Thr | Gly | Val | Gln | Val | Ile |
| | | | 180 | | | | | 185 | | | | | 190 | | |
| Thr | Ala | Val | Ala | Pro | Leu | Ala | Lys | His | Leu | Thr | Val | Phe | Gln | Arg | Ser |
| | | 195 | | | | | 200 | | | | | 205 | | | |
| Ala | Gln | Tyr | Ser | Val | Pro | Ile | Gly | Asn | Asp | Pro | Leu | Ser | Glu | Glu | Asp |
| 210 | | | | | 215 | | | | | 220 | | | | | |
| Val | Lys | Lys | Ile | Lys | Asp | Asn | Tyr | Asp | Lys | Ile | Trp | Asp | Gly | Val | Trp |
| 225 | | | | | 230 | | | | | 235 | | | | | 240 |
| Asn | Ser | Ala | Leu | Ala | Phe | Gly | Leu | Asn | Glu | Ser | Thr | Val | Pro | Ala | Met |
| | | | | 245 | | | | | 250 | | | | | 255 | |
| Ser | Val | Ser | Ala | Glu | Glu | Arg | Lys | Ala | Val | Phe | Glu | Lys | Ala | Trp | Gln |
| | | | 260 | | | | | 265 | | | | | 270 | | |
| Thr | Gly | Gly | Gly | Ile | Gly | Phe | Tyr | Ile | Glu | Thr | Phe | Gly | Asp | Ile | Val |
| | | 275 | | | | | 280 | | | | | 285 | | | |
| Thr | Asn | Met | Glu | Ala | Asn | Ile | Glu | Ala | Gln | Asn | Phe | Ile | Lys | Gly | Lys |
| | 290 | | | | | 295 | | | | | 300 | | | | |
| Ile | Ala | Glu | Ile | Val | Lys | Asp | Pro | Ala | Ile | Ala | Gln | Lys | Leu | Met | Pro |
| 305 | | | | | 310 | | | | | 315 | | | | | 320 |
| Gln | Gly | Leu | Tyr | Ala | Arg | Arg | Pro | Leu | Cys | Asp | Ser | Gly | Tyr | Tyr | Asn |
| | | | | 325 | | | | | 330 | | | | | 335 | |
| Thr | Phe | Asn | Arg | Asp | Asn | Val | Arg | Leu | Glu | Asp | Val | Lys | Ala | Asn | Pro |
| | | | 340 | | | | | 345 | | | | | 350 | | |
| Ile | Val | Glu | Ile | Thr | Glu | Asn | Gly | Val | Lys | Leu | Glu | Asn | Gly | Asp | Phe |
| | | | | 355 | | | | | 360 | | | | | 365 | |
| Val | Glu | Leu | Asp | Met | Leu | Ile | Cys | Ala | Thr | Gly | Phe | Asp | Arg | Val | Asp |
| | 370 | | | | | 375 | | | | | 380 | | | | |
| Gly | Asn | Tyr | Val | Arg | Met | Asp | Ile | Gln | Gly | Lys | Asn | Gly | Leu | Ala | Met |

```
                385                 390                 395                 400
Lys Asp Tyr Trp Lys Glu Gly Pro Ser Ser Tyr Met Gly Val Thr Val
                            405                 410                 415

Asn Asn Tyr Pro Asn Met Phe Met Val Ser Gly Pro Asn Gly Pro Ser
                    420                 425                 430

Gly Asn Ala Pro Pro Ser Ile Glu Ser Gln Val Glu Trp Ile Ser Asp
                435                 440                 445

Thr Ile Gln Tyr Thr Val Glu Asn Asn Val Glu Ser Ile Glu Ala Thr
            450                 455                 460

Lys Glu Ala Glu Glu Gln Trp Thr Gln Thr Cys Ala Asp Ile Ala Glu
465                 470                 475                 480

Met Thr Leu Phe Pro Lys Ala Gln Gly Leu Val Phe Gly Ala Asn Ile
                485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
        530                 535                 540

<210> SEQ ID NO 35
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 35
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaagaaa     240
tacgtgcaag gtccagacgt gcgcaaatat ctgcagcagg ttgccgaaaa acacgactta     300
aaaaaaagct accagttcaa caccgcagtc caatctgccc actacaacga gcggacgct      360 ctgtgggaag taactacgga atacggggat aagtacaccg cacgtttcct gattactgcc     420
ttaggtgggc tgtctgcacc taacctgcca aatatcaagg gcatcaatca gtttaaaggc     480
gaactgctgc atactggccg ctggccggat gacgttagtt tcgaaagcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaaaccg cgcggtggtat cggttttac      840 atcgaaacct ttggtgatat tgtgacgaac atggaagcta acattgaggc acaaaatttt     900
atcaaaggta aaatcgcgga gatcgtcaaa gatccggcga tcgcccaaaa actgatgccg     960
cagggcctgt acgcacgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag ggaaaaacgg tctggccatg    1200
```

-continued

```
aaggattact ggaaagaggg cccgtctagc tacatgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccga tattgcggag    1440
atgaccctgt ttccaaaagc ccagagcctg gttttgggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                             1629
```

<210> SEQ ID NO 36
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 36

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu Leu His Thr Gly Arg Trp Pro Asp Asp Val Ser Phe Glu Ser
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Val
        275                 280                 285
```

```
Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Gly Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Lys Asn Gly Leu Ala Met
385                 390                 395                 400

Lys Asp Tyr Trp Lys Glu Gly Pro Ser Tyr Met Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Ser Ile Glu Ser Gln Val Glu Trp Ile Ser Asp
                435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asp Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
                515                 520                 525

Asp Ile Gln Pro Gln Arg Ser Asp Ile Lys Gln Pro Ala Asn Ala
    530                 535                 540

<210> SEQ ID NO 37
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 37
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaagcaa      240 tacgtgcaag gtccagacgt gcgcaaatat ctgcagcagg ttgccgaaaa acacgactta     300
aaaaaaagct accagttcaa caccgcagtc caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gaactgcacc atactgcccg ctggccggat gacgttagtt tcgaaggcaa acgtgtgggt     540
gtgatcggca caggctctac cggcgtgcaa gttatcacgg cagtggcgcc actggccaag     600
```

-continued

```
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaaaccg gcggtggtat cggttttttac   840 atcgaaacct ttggtgatat tgtgacgaac atggaagcta acattgaggc acaaaatttt    900
atcaaaggta aaatcgcgga gatcgtcaaa gatccggcga tcgcccaaaa actgatgccg    960
caggatctgt acgcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttttttgggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 38
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 38

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Ala Arg Trp Pro Asp Asp Val Ser Phe Glu Gly
                165                 170                 175
```

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Ser
            195                 200                 205

Ala Gln Tyr Ser Val Pro Ile Gly Asn Asp Pro Leu Ser Glu Glu Asp
        210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
290                 295                 300

Ile Ala Glu Ile Val Lys Asp Pro Ala Ile Ala Gln Lys Leu Met Pro
305                 310                 315                 320

Gln Asp Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
530                 535                 540

<210> SEQ ID NO 39
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 39

```
atgtctacca agatggattt cgatgccatc gtgatcggtg ggggctttgg cggtctgtat      60
gccgttaaaa aactgcgcga tgaactggag ctgaaagttc aagccttcga aaggcaact      120
gacgtaggcg gtacatggta ctggaaccgc tacccgggtg ccctgaccga taccgaaacc     180
catttgtatt gttattcctg ggacaaggaa ctgttgcaga gtatggaaat caaaaagaaa     240
tacgtgcaag gtccagacgt gcgcaaatat ctgcagcagg ttgccgaaaa acacgactta     300
aaaaaaagct accagttcaa caccgcagtc aatctgcccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gaactgcacc atactgcccg ctggccggat gacgttagtt tcgaaggcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta aagcggtttt tgagaaggcg tggcaaaccg gcggtggtat cggttttttac    840
atcgaaacct ttggtgatat tgtgacgaac atggaagcta acattgaggc acaaaatttt    900
atcaaaggta aaatcgcgga gatcgtcaaa gatccggcga tcgcccaaaa actgatgccg     960
caggatctgt acgcacgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag ggcgtaacgg tctggccatg    1200
aaggattact ggaaagaggg cccgtctagc tacatgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtgaatct    1380
attgaagcca cgaaggaagc ggaggaacag tggacccaaa cctgcgccaa tattgcggag    1440
atgacccctgt ttccaaaagc ccagagcctg gtttttgggg cgaacattcc aggcaagaag    1500
aacaccgcga tctttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                           1629
```

<210> SEQ ID NO 40
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 40

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys

-continued

```
                65                  70                  75                  80

Tyr Val Gln Gly Pro Asp Val Arg Lys Tyr Leu Gln Val Ala Glu
                             85                  90                  95

Lys His Asp Leu Lys Lys Ser Tyr Gln Phe Asn Thr Ala Val Gln Ser
                            100                 105                 110

Ala His Tyr Asn Glu Ala Asp Ala Leu Trp Glu Val Thr Glu Tyr
                            115                 120                 125

Gly Asp Lys Tyr Thr Ala Arg Phe Leu Ile Thr Ala Leu Gly Gly Leu
        130                 135                 140

Ser Ala Pro Asn Leu Pro Asn Ile Lys Gly Ile Asn Gln Phe Lys Gly
        145                 150                 155                 160

Glu Leu His His Thr Ala Arg Trp Pro Asp Val Ser Phe Glu Gly
                            165                 170                 175

Lys Arg Val Gly Val Ile Gly Thr Gly Ser Thr Gly Val Gln Val Ile
                            180                 185                 190

Thr Ala Val Ala Pro Leu Ala Lys His Leu Thr Val Phe Gln Arg Ser
                            195                 200                 205

Ala Gln Tyr Ser Val Pro Ile Gly Asn Asp Pro Leu Ser Glu Glu Asp
                            210                 215                 220

Val Lys Lys Ile Lys Asp Asn Tyr Asp Lys Ile Trp Asp Gly Val Trp
        225                 230                 235                 240

Asn Ser Ala Leu Ala Phe Gly Leu Asn Glu Ser Thr Val Pro Ala Met
                            245                 250                 255

Ser Val Ser Ala Glu Glu Arg Lys Ala Val Phe Glu Lys Ala Trp Gln
                            260                 265                 270

Thr Gly Gly Gly Ile Gly Phe Tyr Ile Glu Thr Phe Gly Asp Ile Val
                            275                 280                 285

Thr Asn Met Glu Ala Asn Ile Glu Ala Gln Asn Phe Ile Lys Gly Lys
                            290                 295                 300

Ile Ala Glu Ile Val Lys Asp Pro Ala Ile Ala Gln Lys Leu Met Pro
        305                 310                 315                 320

Gln Asp Leu Tyr Ala Arg Arg Pro Leu Cys Asp Ser Gly Tyr Tyr Asn
                            325                 330                 335

Thr Phe Asn Arg Asp Asn Val Arg Leu Glu Asp Val Lys Ala Asn Pro
                            340                 345                 350

Ile Val Glu Ile Thr Glu Asn Gly Val Lys Leu Glu Asn Gly Asp Phe
                            355                 360                 365

Val Glu Leu Asp Met Leu Ile Cys Ala Thr Gly Phe Asp Ala Val Asp
                            370                 375                 380

Gly Asn Tyr Val Arg Met Asp Ile Gln Gly Arg Asn Gly Leu Ala Met
        385                 390                 395                 400

Lys Asp Tyr Trp Lys Glu Gly Pro Ser Ser Tyr Met Gly Val Thr Val
                            405                 410                 415

Asn Asn Tyr Pro Asn Met Phe Met Val Ser Gly Pro Asn Gly Pro Ser
                            420                 425                 430

Gly Asn Ala Pro Pro Ser Ile Glu Ser Gln Val Glu Trp Ile Ser Asp
                            435                 440                 445

Thr Ile Gln Tyr Thr Val Glu Asn Asn Val Glu Ser Ile Glu Ala Thr
                            450                 455                 460

Lys Glu Ala Glu Glu Gln Trp Thr Gln Thr Cys Ala Asn Ile Ala Glu
        465                 470                 475                 480

Met Thr Leu Phe Pro Lys Ala Gln Ser Leu Val Phe Gly Ala Asn Ile
                            485                 490                 495
```

```
Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 41
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 41
atgtctacca agatggattt cgatgccatc gtgatcggtg ggggctttgg cggtctgtat      60
gccgttaaaa aactgcgcga tgaactggag ctgaaagttc aagccttcga agggcaact      120 gacgtaggcg gtacatggta ctggaaccgc tacccgggtg ccctgaccga taccgaaacc     180
catttgtatt gttattcctg ggacaaggaa ctgttgcaga gtatggaaat caaaagaaa     240 tacgtgcaag gtccagacgt gcgcaaatat ctgcagcagg ttgccgaaaa acacgtatta     300
aaaaaaagct accagttcaa caccgcagtc aatctgccc actacaacga gcggacgct      360 ctgtgggaag taactacgga atacggggat aagtacaccg cacgtttcct gattactgcc     420
ttaggtgggc tgtctgcacc taacctgcca aatatcaagg catcaatca gtttaaaggc     480 gacctgcacc atactcccg ctggccggat gacgttagta tcgaaggcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaagccg gcggtggtat cggttttttac     840 atcgaaacct tggtgatat tgtgacgaac atggaagcta acattgaggc acaaaatttt     900 atcaaggta aatcgcgga atcgtcaaa gatccggcga tcgcccaaaa actgatgccg       960
cagatgctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaacggcga tttcgtggag ctggacatgc tgatctgcgc gacgggtttt    1140
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg gttttggggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629

<210> SEQ ID NO 42
<211> LENGTH: 543
```

```
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 42
```

| | | | | | | | | | | | | | | |
|---|---|---|---|---|---|---|---|---|---|---|---|---|---|---|
| Met | Ser | Thr | Lys | Met | Asp | Phe | Asp | Ala | Ile | Val | Ile | Gly | Gly | Phe |
| 1 | | | | 5 | | | | | 10 | | | | | 15 |

| | | | | | | | | | | | | | | |
|---|---|---|---|---|---|---|---|---|---|---|---|---|---|---|
| Gly | Gly | Leu | Tyr | Ala | Val | Lys | Lys | Leu | Arg | Asp | Glu | Leu | Glu | Leu | Lys |
| | | | 20 | | | | 25 | | | | 30 | | | |

| | | | | | | | | | | | | |
|---|---|---|---|---|---|---|---|---|---|---|---|---|
| Val | Gln | Ala | Phe | Glu | Lys | Ala | Thr | Asp | Val | Gly | Gly | Thr | Trp | Tyr | Trp |
| | | 35 | | | | 40 | | | | 45 | | | |

| Asn | Arg | Tyr | Pro | Gly | Ala | Leu | Thr | Asp | Thr | Glu | Thr | His | Leu | Tyr | Cys |
| 50 | | | | | 55 | | | | | 60 | | | | |

| Tyr | Ser | Trp | Asp | Lys | Glu | Leu | Leu | Gln | Ser | Met | Glu | Ile | Lys | Lys | Lys |
| 65 | | | | 70 | | | | | 75 | | | | | 80 |

| Tyr | Val | Gln | Gly | Pro | Asp | Val | Arg | Lys | Tyr | Leu | Gln | Gln | Val | Ala | Glu |
| | | | 85 | | | | 90 | | | | 95 | | | |

| Lys | His | Val | Leu | Lys | Lys | Ser | Tyr | Gln | Phe | Asn | Thr | Ala | Val | Gln | Ser |
| | | | 100 | | | | 105 | | | | 110 | | | |

| Ala | His | Tyr | Asn | Glu | Ala | Asp | Ala | Leu | Trp | Glu | Val | Thr | Thr | Glu | Tyr |
| | | | 115 | | | | 120 | | | | 125 | | | |

| Gly | Asp | Lys | Tyr | Thr | Ala | Arg | Phe | Leu | Ile | Thr | Ala | Leu | Gly | Gly | Leu |
| | 130 | | | | | 135 | | | | | 140 | | | |

| Ser | Ala | Pro | Asn | Leu | Pro | Asn | Ile | Lys | Gly | Ile | Asn | Gln | Phe | Lys | Gly |
| 145 | | | | | 150 | | | | | 155 | | | | | 160 |

| Asp | Leu | His | His | Thr | Ala | Arg | Trp | Pro | Asp | Asp | Val | Ser | Ile | Glu | Gly |
| | | | | 165 | | | | | 170 | | | | | 175 |

| Lys | Arg | Val | Gly | Val | Ile | Gly | Thr | Gly | Ser | Thr | Gly | Val | Gln | Val | Ile |
| | | | 180 | | | | | 185 | | | | | 190 | | |

| Thr | Ala | Val | Ala | Pro | Leu | Ala | Lys | His | Leu | Thr | Val | Phe | Gln | Arg | Ser |
| | | 195 | | | | | 200 | | | | | 205 | | | |

| Ala | Gln | Tyr | Ser | Val | Pro | Ile | Gly | Asn | Asp | Pro | Leu | Ser | Glu | Glu | Asp |
| | 210 | | | | | 215 | | | | | 220 | | | | |

| Val | Lys | Lys | Ile | Lys | Asp | Asn | Tyr | Asp | Lys | Ile | Trp | Asp | Gly | Val | Trp |
| 225 | | | | | 230 | | | | | 235 | | | | | 240 |

| Asn | Ser | Ala | Leu | Ala | Phe | Gly | Leu | Asn | Glu | Ser | Thr | Val | Pro | Ala | Met |
| | | | | 245 | | | | | 250 | | | | | 255 |

| Ser | Val | Ser | Ala | Glu | Glu | Arg | Lys | Ala | Val | Phe | Glu | Lys | Ala | Trp | Gln |
| | | | 260 | | | | | 265 | | | | | 270 | | |

| Ala | Gly | Gly | Gly | Ile | Gly | Phe | Tyr | Ile | Glu | Thr | Phe | Gly | Asp | Ile | Val |
| | | 275 | | | | | 280 | | | | | 285 | | | |

| Thr | Asn | Met | Glu | Ala | Asn | Ile | Glu | Ala | Gln | Asn | Phe | Ile | Lys | Gly | Lys |
| | 290 | | | | | 295 | | | | | 300 | | | | |

| Ile | Ala | Glu | Ile | Val | Lys | Asp | Pro | Ala | Ile | Ala | Gln | Lys | Leu | Met | Pro |
| 305 | | | | | 310 | | | | | 315 | | | | | 320 |

| Gln | Met | Leu | Lys | Ala | Arg | Arg | Pro | Leu | Cys | Asp | Ser | Gly | Tyr | Tyr | Asn |
| | | | | 325 | | | | | 330 | | | | | 335 |

| Thr | Phe | Asn | Arg | Asp | Asn | Val | Arg | Leu | Glu | Asp | Val | Lys | Ala | Asn | Pro |
| | | | 340 | | | | | 345 | | | | | 350 | | |

| Ile | Val | Glu | Ile | Thr | Glu | Asn | Gly | Val | Lys | Leu | Lys | Asn | Gly | Asp | Phe |
| | | 355 | | | | | 360 | | | | | 365 | | | |

| Val | Glu | Leu | Asp | Met | Leu | Ile | Cys | Ala | Thr | Gly | Phe | Asp | Ala | Val | Asp |
| | 370 | | | | | 375 | | | | | 380 | | | | |

```
Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
    530                 535                 540
```

<210> SEQ ID NO 43
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 43

```
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc taccgggtg ccctgaccga taccgaaacc     180
catttgtatt gttattcctg ggacaaggaa ctgttgcaga gtatggaaat caaaagaaa     240 tacgtgcaag gtccagacgt gcgcaaatat ctgcagcagg ttgccgaaaa acacgtatta     300 aaaaaagct accagttcaa caccgcagtc aatctgccc actacaacga gcggacgct      360 ctgtgggaag taactacgga atacggggat aagtacaccg cacgtttcct gattactgcc     420
ttaggtgggc tgtctgcacc taacctgcca aatatcaagg gcatcaatca gtttaaggc      480 gaactgcacc atactgcccg ctggccggat gacgttagta tcgaaggcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaatccg cggtgggtat cggttttttac     840 atcgaaaccct ttggtgatat tgtgacgaac atggaagcta acattgaggc acaaaatttt     900
atcaaaggta aatcgcgga gatcgtcaaa gatccggcga tcgcccaaaa actgatgccg     960
cagatgctgt acgcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaaacggcga tttcgtggag ctggacatgc tgatctgcgc gacgggtttt    1140
gatgcggtag acggcaacta tgttcgcatg gatatccaag ggcgtaacgg tctggccatg    1200
```

-continued

```
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg gttttggggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 44
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 44

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
```

```
                275                 280                 285
Thr Asn Met Glu Ala Asn Ile Glu Ala Gln Asn Phe Ile Lys Gly Lys
    290                 295                 300
Ile Ala Glu Ile Val Lys Asp Pro Ala Ile Ala Gln Lys Leu Met Pro
305                 310                 315                 320
Gln Met Leu Tyr Ala Arg Arg Pro Leu Cys Asp Ser Gly Tyr Tyr Asn
            325                 330                 335
Thr Phe Asn Arg Asp Asn Val Arg Leu Glu Asp Val Lys Ala Asn Pro
        340                 345                 350
Ile Val Glu Ile Thr Glu Asn Gly Val Lys Leu Lys Asn Gly Asp Phe
    355                 360                 365
Val Glu Leu Asp Met Leu Ile Cys Ala Thr Gly Phe Asp Ala Val Asp
370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
            405                 410                 415
Asn Asn Tyr Pro Asn Met Phe Met Val Ser Gly Pro Asn Gly Pro Ser
        420                 425                 430
Gly Asn Ala Pro Pro Ser Ile Glu Ser Gln Val Glu Trp Ile Ser Asp
    435                 440                 445
Thr Ile Gln Tyr Thr Val Glu Asn Asn Val Glu Ser Ile Glu Ala Thr
    450                 455                 460
Lys Glu Ala Glu Glu Gln Trp Thr Gln Thr Cys Ala Asn Ile Ala Glu
465                 470                 475                 480
Met Thr Leu Phe Pro Lys Ala Gln Ser Leu Val Phe Gly Ala Asn Ile
            485                 490                 495
Pro Gly Lys Lys Asn Thr Ala Ile Phe Tyr Leu Gly Gly Leu Lys Asn
        500                 505                 510
Tyr Arg Ser Ala Leu Ala Asn Cys Lys Asn His Ala Tyr Glu Gly Phe
    515                 520                 525
Asp Ile Gln Pro Gln Arg Ser Asp Ile Lys Gln Pro Ala Asn Ala
    530                 535                 540

<210> SEQ ID NO 45
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 45
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaagaaa      240 tacgtgcaag gtccagacgt gcgcaaatat ctgcagcagg ttgccgaaaa acacgactta     300
aaaaaaagct accagttcaa caccgcagtc aatctgccc actacaacga agcgacgct      360 ctgtgggccg taactacgga atacggggat aagtacaccg cacgtttcct gattactgcc     420
ttaggtgggc tgtctgcacc taacctgcca aatatcaagg gcatcaatca gtttaaaggc     480
gaactgcacc atactgcccg ctggccggat gacgttagta tcgaaggcaa acgtgtgggt     540
gtgatcggca caggctctac cggcgtgcaa gttatcacgg cagtggcgcc actggccaag     600
```

```
cacctgacgg tgtttcagcg tagtgcccag tactcggtcc cgatcggtaa cgatccactg    660
agcgaagaag acgtcaagaa gatcaaagat aactatgata aatctggga tggtgtttgg     720 aacagtgcgc tggccttcgg cctgaatgaa tctactgtgc cggccatgtc cgtaagtgcg    780
gaagagcgta aagcggtttt tgagaaggcg tggcaatccg gcggtggtat cggttttac     840 atcgaaacct ttggtgatat tgtgacgaac atggaagcta acattgaggc acaaaatttt    900
atcaaaggta aatcgcgga gatcgtcaaa gatccggcga tcgcccaaaa actgatgccg     960
cagatgctgt acgcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaacggcga tttcgtggag ctggacatgc tgatctgcgc gacgggtttt   1140
gatgcggtag acggcaacta tgttcgcatg gatatccaag gcgtaacgg tctggccatg    1200 aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttttggggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 46
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 46

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
                20                  25                  30

Val Gln Ala Phe Glu Lys Ala Thr Asp Val Gly Gly Thr Trp Tyr Trp
            35                  40                  45

Asn Arg Tyr Pro Gly Ala Leu Thr Asp Thr Glu Thr His Leu Tyr Cys
        50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Ala Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Glu Leu His His Thr Ala Arg Trp Pro Asp Asp Val Ser Ile Glu Gly
                165                 170                 175
```

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
290                 295                 300

Ile Ala Glu Ile Val Lys Asp Pro Ala Ile Ala Gln Lys Leu Met Pro
305                 310                 315                 320

Gln Met Leu Tyr Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
530                 535                 540

<210> SEQ ID NO 47
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 47

```
atgtctacca agatggattt cgatgccatc gtgatcggtg ggggctttgg cggtctgtat      60
gccgttaaaa aactgcgcga tgaactggag ctgaaagttc aagccttcga aaggcaact      120
gacgtaggcg gtacatggta ctggaaccgc tacccgggtg ccctgaccga taccgaaacc    180
catttgtatt gttattcctg gacaaggaa ctgttgcaga gtatggaaat caaaaagaaa     240
tacgtgcaag gtccagacgt gcgcaaatat ctgcagcagg ttgccgaaaa acacgtatta    300
aaaaaaagtt accagttcaa caccgcagtc caatctgccc actacaacga agcggacgct    360
ctgtgggaag taactacgga atacgggat aagtacaccg cacgtttcct gattactgcc     420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt   540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg   720
aacagtgcgc tggccttcgg cctgaatgaa tctactgtgc cggccatgtc cgtaagtgcg    780
gaagagcgta agcggttttt tgagaaggcg tggcaatccg gcggtggtat cggtttttac    840
atcgaaacct ttggtgatat tgtgacgaac atggaagcta acattgaggc acaaaatttt   900
atcaaaggta aatcgcgga gatcgtcaaa gatccggcga tcgcccaaaa actgatgccg   960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag gcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg gttttgggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 48
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 48

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60
```

-continued

```
Tyr Ser Trp Asp Lys Glu Leu Leu Gln Ser Met Glu Ile Lys Lys Lys
 65                  70                  75                  80

Tyr Val Gln Gly Pro Asp Val Arg Lys Tyr Leu Gln Gln Val Ala Glu
                 85                  90                  95

Lys His Val Leu Lys Lys Ser Tyr Gln Phe Asn Thr Ala Val Gln Ser
                100                 105                 110

Ala His Tyr Asn Glu Ala Asp Ala Leu Trp Glu Val Thr Thr Glu Tyr
                115                 120                 125

Gly Asp Lys Tyr Thr Ala Arg Phe Leu Ile Thr Ala Leu Gly Gly Leu
            130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
                165                 170                 175

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Ser
            195                 200                 205

Ala Gln Tyr Ser Val Pro Ile Gly Asn Asp Pro Leu Ser Glu Glu Asp
        210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
                260                 265                 270

Ser Gly Gly Gly Ile Gly Phe Tyr Ile Glu Thr Phe Gly Asp Ile Val
            275                 280                 285

Thr Asn Met Glu Ala Asn Ile Glu Ala Gln Asn Phe Ile Lys Gly Lys
        290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Lys Asn Gly Asp Phe
            355                 360                 365

Val Glu Leu Asp Met Leu Ile Cys Ala Thr Gly Phe Asp Ala Val Asp
        370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
        450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
```

```
                485                 490                 495
Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
            530                 535                 540

<210> SEQ ID NO 49
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 49
atgtctacca agatggattt cgatgccatc gtgatcggtg ggggctttgg cggtctgtat       60
gccgttaaaa aactgcgcga tgaactggag ctgaaggttc aagccttcga gaaggcaact      120
gacgtaggcg gtacatggta ctggaaccgc tacccgggtg ccctgaccga taccgaaacc      180
catttgtatt gttattcctg gacaaggaa ctgttgcaga gtatggaaat caaaagaaa       240 tacgtgcaag gtccagacgt gcgcaaatat ctgcagcagg ttgccgaaaa acacgtatta      300
aaaaaaagtt accagttcaa caccgcagtc aatctgcccc actacaacga agcggacgct      360
ctgtgggaag taactacgga atacggggat aagtacaccg cacgtttcct gattactgcc      420
ttaggtgggc tgtctgcacc taacctgcca aatatcaagg gcatcaatca gtttaaaggc      480
gacctgcacc atactggccg ctggccggat gacgttagta tcgaaggcaa acgtgtgggt      540
gtgatcggca caggctctac cggcgtgcaa gttatcacgg cagtggcgcc actggccaag      600
cacctgacgg tgtttcagcg tagtgcccag tactcggtcc cgatcggtaa cgatccactg      660
agcgaagaag acgtcaagaa gatcaaagat aactatgata aaatctggga tggtgtttgg      720
aacagtgcgc tggccttcgg cctgaatgaa tctactgtgc cggccatgtc cgtaagtgcg      780
gaagagcgta agcggttttt tgagaaggcg tggcaatccg gcggtggtat cggtttttac      840
atcgaaacct ttggtgatat tgtgacgaac atggaagcta acattgaggc acaaaatttt      900
atcaaaggta aaatcgcgga gatcgtcaaa gatccggcga tcgcccaaaa actgatgccg      960
caggacctga aggcacgtcg ccctctgtgt gactccgggt actataatac gttcaatcgc     1020
gacaacgtac gtctggagga tgtcaaagca aatccgatcg tcgagatcac cgaaaacggc     1080
gtgaaactga aaacggcga tttcgtggag ctggacatgc tgatctgcgc gacgggtttt     1140
gatgcggtag acggcaacta tgttcgcatg gatatccaag gcgtaacgg tctggccatg     1200 aaggattact ggaagagggg cccgtctagc tacctgggcg taaccgtgaa taattaccca     1260
aacatgttta tggttagcgg tccaaacggt ccatctggta acgctccgcc tagcattgaa     1320
agtcaagttg aatggattag cgatactatc cagtataccg tcgaaaataa cgtggaatct     1380
attgaagcca cgaaggaagc ggaggaacag tggacccaaa cctgcgccaa tattgcggag     1440
atgaccctgt tccagaagc ccagagcctg gttttggggg cgaacattcc aggcaagaag     1500
aacaccgcga tctttattt gggtgggctg aaaaactacc gctcagcttt ggcgaattgt     1560
aaaaatcatg cgtatgaagg ctttgatatt cagccgcaac gttctgacat caaacaacca     1620
gcgaatgcg                                                             1629

<210> SEQ ID NO 50
```

```
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 50
```

Met Ser Thr Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Gly Arg Trp Pro Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
    370                 375                 380

```
Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
            405                 410                 415

Asn Asn Tyr Pro Asn Met Phe Met Val Ser Gly Pro Asn Gly Pro Ser
        420                 425                 430

Gly Asn Ala Pro Pro Ser Ile Glu Ser Gln Val Glu Trp Ile Ser Asp
    435                 440                 445

Thr Ile Gln Tyr Thr Val Glu Asn Asn Val Glu Ser Ile Glu Ala Thr
450                 455                 460

Lys Glu Ala Glu Glu Gln Trp Thr Gln Thr Cys Ala Asn Ile Ala Glu
465                 470                 475                 480

Met Thr Leu Phe Pro Glu Ala Gln Ser Leu Val Phe Gly Ala Asn Ile
            485                 490                 495

Pro Gly Lys Lys Asn Thr Ala Ile Phe Tyr Leu Gly Gly Leu Lys Asn
        500                 505                 510

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
    530                 535                 540
```

<210> SEQ ID NO 51
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 51

```
atgtctacca agatggattt cgatgccatc gtgatcggtg ggggctttgg cggtctgtat      60
gccgttaaaa aactgcgcga tgaactggag ctgaaagttc aagccttcga agaggcaact     120
gacgtaggcg gtacatggta ctggaaccgc tacccgggtg ccctgaccga taccgaaacc     180
catttgtatt gttattcctg gacaaggaa ctgttgcaga gtatggaaat caaaaagaaa      240
tacgtgcaag gtccagacgt gcgcaaatat ctgcagcagg ttgccgaaaa acacgtatta     300 aaaaaagtt accagttcaa caccgcagtc caatctgccc actacaacga agcggacgct      360
ctgtgggaag taactacgga atacggggat aagtacaccg cacgtttcct gattactgcc     420
ttaggtgggc tgtccgcacc taacctgcca aatatcaagg catcaatca gtttaaaggc      480 gacctgcacc atactgcccg ctggccggat gacgttagta tcgaaggcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagga gatcaaagat aactatgata aaatctggga tggtgtttgg     720
aacagtgcgc tggccttcgg cctgaatgaa tctactgtgc cggccatgtc cgtaagtgcg     780
gaagagcgta aagcggtttt tgagaaggcg tggcaatccg gcggtggtat cggtttttac     840
atcgaaacct tggtgatat gtgacgaac atggaagcta acattgaggc acaaaattt       900 atcaaaggta aatcgcgga atcgtcaaa gatccggcga tcgcccaaaa actgatgccg       960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaacggcga tttcgtggag ctggacatgc tgatctgcgc gacgggtttt    1140
```

```
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttttgggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 52
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 52

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Glu Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270
```

Ser Gly Gly Gly Ile Gly Phe Tyr Ile Glu Thr Phe Gly Asp Ile Val
            275                 280                 285

Thr Asn Met Glu Ala Asn Ile Glu Ala Gln Asn Phe Ile Lys Gly Lys
        290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 53
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 53
atgtctacca agatggattt cgatgccatc gtgatcggtg ggggctttgg cggtctgtat     60
gccgttaaaa aactgcgcga tgaactggag ctgaaagttc aagccttcga agaggcaact    120
gacgtaggcg gtacatggta ctggaaccgc taccccgggtg ccctgaccga taccgaaacc    180
catttgtatt gttattcctg ggacaaggaa ctgttgcaga gtatggaaat caaaaagaaa    240
tacgcgcaag gtccagacgt gcgcaaatat ctgcagcagg ttgccgaaaa acacgtatta    300
aaaaaaagtt accagttcaa caccgcaatg caatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540

-continued

```
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aatctggga tggtgtttgg     720 aacagtgcgc tggccttcgg cctgaatgaa tctactgtgc cggccatgtc cgtaagtgcg    780
gaagagcgta aagcggtttt tgagaaggcg tggcaatccg gcggtggtat cggttttttac   840 atcgaaacct ttggtgatat tgtgacgaac atggaagcta acattgaggc acaaaatttt    900
atcaaaggta aaatcgcgga gatcgtcaaa gatccggcga tcgcccaaaa actgatgccg    960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaacggcga tttcgtggag ctggacatgc tgatctgcgc gacgggtttt     1140
gatgcggtag acggcaacta tgttcgcatg gatatccaag gcgtaacgg tctggccatg     1200 aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg gttttggggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 54
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 54

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
50                  55                  60

Tyr Ser Trp Asp Lys Glu Leu Leu Gln Ser Met Glu Ile Lys Lys Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
```

```
                165                 170                 175
Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Ser
            195                 200                 205

Ala Gln Tyr Ser Val Pro Ile Gly Asn Asp Pro Leu Ser Glu Glu Asp
        210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 55
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871
```

<400> SEQUENCE: 55

```
atgtctacca agatggattt cgatgccatc gtgatcggtg ggggctttgg cggtctgtat      60
gccgttaaaa aactgcgcga tgaactggag ctgaaagttc aagccttcga aaggcaact     120
gacgtaggcg gtacatggta ctggaaccgc tacccgggtg ccctgaccga taccgaaacc    180
catttgtatt gttattcctg ggacaaggaa ctgttgcaga gtatggaaat caaaaagaaa    240
tacgtgcaag gtccagacgt gcgcaaatat ctgcagcagg ttgccgaaaa acacgtatta    300
aaaaaagtt accgttcaa caccgcagtc caatctgccc actacaacga agcggacgct      360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tagtgccag tactcggtcc cgatcggtaa cgatccactg     660
agcgaagaag acgtcaagaa gatcaaagat aactatgata aatctgggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggtttttac    840
atcgaaacct ttggtgatat tgtgacgaac atggaagcta acattgaggc acaaaatttt    900
atcaaaggta aaatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag gcgtaacgg tctggccatg    1200
aaggattact ggaaagaggg cccgtctagc tacctgggcg taaccgtgaa taattaccca   1260
aacatgttta tggttagcgg tccaaaccgt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gtttttgggg cgaacattcc aggcaagaag   1500
aacaccgcga tcttttattt gggtgggctg aaaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 56
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 56

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60
```

```
Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
            115                 120                 125

Gly Asp Lys Tyr Thr Ala Arg Phe Leu Ile Thr Ala Leu Gly Gly Leu
            130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
            165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
            195                 200                 205

Ala Gln Tyr Ser Val Pro Ile Gly Asn Asp Pro Leu Ser Glu Glu Asp
210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
            245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
            275                 280                 285

Thr Asn Met Glu Ala Asn Ile Glu Ala Gln Asn Phe Ile Lys Gly Lys
            290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
            325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
            355                 360                 365

Val Glu Leu Asp Met Leu Ile Cys Ala Thr Gly Phe Asp Ala Val Asp
            370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
            405                 410                 415

Asn Asn Tyr Pro Asn Met Phe Met Val Ser Gly Pro Asn Arg Pro Ser
            420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
            450                 455                 460

Lys Glu Ala Glu Glu Gln Trp Thr Gln Thr Cys Ala Asn Ile Ala Glu
465                 470                 475                 480
```

```
Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
        530                 535                 540

<210> SEQ ID NO 57
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 57
```

| | | | | |
|---|---|---|---|---|
| atgtctacca | agatggattt | cgatgccatc | gtgatcggtg | ggggctttgg cggtctgtat | 60 |
| gccgttaaaa | aactgcgcga | tgaactggag | ctgaaagttc | aagccttcga gaaggcaact | 120 |
| gacgtaggcg | gtacatggta | ctggaaccgc | tacccgggtg | ccctgaccga taccgaaacc | 180 |
| catttgtatt | gttattcctg | ggacaaggaa | ctgttgcaga | gtatggaaat caaaaagaaa | 240 |
| tacgcgcaag | gtccagacgt | gcgcaaatat | ctgcagcagg | ttgccgaaaa acacgtatta | 300 |
| aaaaaaagtt | accagttcaa | caccgcagtc | caatctgccc | actacaacga agcggacgct | 360 |
| ctgtgggaag | taactacgga | atacggggat | aagtacaccg | cacgtttcct gattactgcc | 420 |
| ttaggtgggc | tgtctgcacc | taacctgcca | aatatcaagg | gcatcaatca gtttaaaggc | 480 |
| gacctgcacc | atactgcccg | ctggccggat | gacgttagta | tcgaaggcaa acgtgtgggt | 540 |
| gtgatcggca | aggctctaca | cggcgtgcaa | gttatcacgg | cagtggcgcc actggccaag | 600 |
| cacctgacgg | tgtttcagcg | tagtgcccag | tactcggtcc | cgatcggtaa cgatccactg | 660 |
| agcgaagaag | acgtcaagaa | gatcaaagat | aactatgata | aaatctggga tggtgtttgg | 720 |
| aacagtgcgc | tggccttcgg | cctgaatgaa | tctactgtgc | cggccatgtc cgtaagtgcg | 780 |
| gaagagcgta | agcggttttt | tgagaaggcg | tggcaatccg | gcggtggtat cggtttttac | 840 |
| atcgaaacct | ttggtgatat | tgtgacgaac | atggaagcta | acattgaggc acaaaatttt | 900 |
| atcaaaggta | aaatcgcgga | gatcgtcaaa | gatccggcga | tcgcccaaaa actgatgccg | 960 |
| caggacctga | aggcacgtcg | ccctctgtgt | gactccgggt | actataatac gttcaatcgc | 1020 |
| gacaacgtac | gtctggagga | tgtcaaagca | aatccgatcg | tcgagatcac cgaaaacggc | 1080 |
| gtgaaactga | aaacggcga | tttcgtggag | ctggacatgc | tgatctgcgc gacgggtttt | 1140 |
| gatgcggtag | acggcaacta | tgttcgcatg | gatatccaag | gcgtaacgg tctggccatg | 1200 |
| aaggattact | ggaagagggg | cccgtctagc | tacctgggcg | taaccgtgaa taattaccca | 1260 |
| aacatgttta | tggttagcgg | tccaaacggt | ccatctggta | acgctccgcc tagcattgaa | 1320 |
| agtcaagttg | aatggattag | cgatactatc | cagtataccg | tcgaaaataa cgtggaatct | 1380 |
| attgaagcca | cgaaggaagc | ggaggaacag | tggacccaaa | cctgcgccaa tattgcggag | 1440 |
| atgacccctgt | ttccaaaagc | ccagagcctg | gttttggggg | cgaacattcc aggcaagaag | 1500 |
| aacaccgcga | tctttttattt | gggtgggctg | aaaaactacc | gctcagcttt ggcgaattgt | 1560 |
| aaaaatcatg | cgtatgaagg | ctttgatatt | cagccgcaac | gttctgacat caaacaacca | 1620 |
| gcgaatgcg  |            |            |            |                      | 1629 |

-continued

```
<210> SEQ ID NO 58
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 58
```

| | | | | | | | | | | | | | | |
|---|---|---|---|---|---|---|---|---|---|---|---|---|---|---|
| Met | Ser | Thr | Lys | Met | Asp | Phe | Asp | Ala | Ile | Val | Ile | Gly | Gly | Phe |
| 1 | | | | 5 | | | | | 10 | | | | | 15 |

| Gly | Gly | Leu | Tyr | Ala | Val | Lys | Lys | Leu | Arg | Asp | Glu | Leu | Glu | Leu | Lys |
|---|---|---|---|---|---|---|---|---|---|---|---|---|---|---|---|
| | | | 20 | | | | 25 | | | | | 30 | | | |

| Val | Gln | Ala | Phe | Glu | Lys | Ala | Thr | Asp | Val | Gly | Gly | Thr | Trp | Tyr | Trp |
|---|---|---|---|---|---|---|---|---|---|---|---|---|---|---|---|
| | | 35 | | | | | 40 | | | | | 45 | | | |

| Asn | Arg | Tyr | Pro | Gly | Ala | Leu | Thr | Asp | Thr | Glu | Thr | His | Leu | Tyr | Cys |
|---|---|---|---|---|---|---|---|---|---|---|---|---|---|---|---|
| | 50 | | | | | 55 | | | | | 60 | | | | |

| Tyr | Ser | Trp | Asp | Lys | Glu | Leu | Leu | Gln | Ser | Met | Glu | Ile | Lys | Lys | Lys |
|---|---|---|---|---|---|---|---|---|---|---|---|---|---|---|---|
| 65 | | | | | 70 | | | | | 75 | | | | | 80 |

| Tyr | Ala | Gln | Gly | Pro | Asp | Val | Arg | Lys | Tyr | Leu | Gln | Gln | Val | Ala | Glu |
|---|---|---|---|---|---|---|---|---|---|---|---|---|---|---|---|
| | | | | 85 | | | | | 90 | | | | | 95 | |

| Lys | His | Val | Leu | Lys | Lys | Ser | Tyr | Gln | Phe | Asn | Thr | Ala | Val | Gln | Ser |
|---|---|---|---|---|---|---|---|---|---|---|---|---|---|---|---|
| | | | 100 | | | | | 105 | | | | | 110 | | |

| Ala | His | Tyr | Asn | Glu | Ala | Asp | Ala | Leu | Trp | Glu | Val | Thr | Thr | Glu | Tyr |
|---|---|---|---|---|---|---|---|---|---|---|---|---|---|---|---|
| | | 115 | | | | | 120 | | | | | 125 | | | |

| Gly | Asp | Lys | Tyr | Thr | Ala | Arg | Phe | Leu | Ile | Thr | Ala | Leu | Gly | Gly | Leu |
|---|---|---|---|---|---|---|---|---|---|---|---|---|---|---|---|
| | 130 | | | | | 135 | | | | | 140 | | | | |

| Ser | Ala | Pro | Asn | Leu | Pro | Asn | Ile | Lys | Gly | Ile | Asn | Gln | Phe | Lys | Gly |
|---|---|---|---|---|---|---|---|---|---|---|---|---|---|---|---|
| 145 | | | | | 150 | | | | | 155 | | | | | 160 |

| Asp | Leu | His | His | Thr | Ala | Arg | Trp | Pro | Asp | Asp | Val | Ser | Ile | Glu | Gly |
|---|---|---|---|---|---|---|---|---|---|---|---|---|---|---|---|
| | | | | 165 | | | | | 170 | | | | | 175 | |

| Lys | Arg | Val | Gly | Val | Ile | Gly | Thr | Gly | Ser | Thr | Gly | Val | Gln | Val | Ile |
|---|---|---|---|---|---|---|---|---|---|---|---|---|---|---|---|
| | | | 180 | | | | | 185 | | | | | 190 | | |

| Thr | Ala | Val | Ala | Pro | Leu | Ala | Lys | His | Leu | Thr | Val | Phe | Gln | Arg | Ser |
|---|---|---|---|---|---|---|---|---|---|---|---|---|---|---|---|
| | | 195 | | | | | 200 | | | | | 205 | | | |

| Ala | Gln | Tyr | Ser | Val | Pro | Ile | Gly | Asn | Asp | Pro | Leu | Ser | Glu | Glu | Asp |
|---|---|---|---|---|---|---|---|---|---|---|---|---|---|---|---|
| | 210 | | | | | 215 | | | | | 220 | | | | |

| Val | Lys | Lys | Ile | Lys | Asp | Asn | Tyr | Asp | Lys | Ile | Trp | Asp | Gly | Val | Trp |
|---|---|---|---|---|---|---|---|---|---|---|---|---|---|---|---|
| 225 | | | | | 230 | | | | | 235 | | | | | 240 |

| Asn | Ser | Ala | Leu | Ala | Phe | Gly | Leu | Asn | Glu | Ser | Thr | Val | Pro | Ala | Met |
|---|---|---|---|---|---|---|---|---|---|---|---|---|---|---|---|
| | | | | 245 | | | | | 250 | | | | | 255 | |

| Ser | Val | Ser | Ala | Glu | Glu | Arg | Lys | Ala | Val | Phe | Glu | Lys | Ala | Trp | Gln |
|---|---|---|---|---|---|---|---|---|---|---|---|---|---|---|---|
| | | | 260 | | | | | 265 | | | | | 270 | | |

| Ser | Gly | Gly | Gly | Ile | Gly | Phe | Tyr | Ile | Glu | Thr | Phe | Gly | Asp | Ile | Val |
|---|---|---|---|---|---|---|---|---|---|---|---|---|---|---|---|
| | | 275 | | | | | 280 | | | | | 285 | | | |

| Thr | Asn | Met | Glu | Ala | Asn | Ile | Glu | Ala | Gln | Asn | Phe | Ile | Lys | Gly | Lys |
|---|---|---|---|---|---|---|---|---|---|---|---|---|---|---|---|
| | 290 | | | | | 295 | | | | | 300 | | | | |

| Ile | Ala | Glu | Ile | Val | Lys | Asp | Pro | Ala | Ile | Ala | Gln | Lys | Leu | Met | Pro |
|---|---|---|---|---|---|---|---|---|---|---|---|---|---|---|---|
| 305 | | | | | 310 | | | | | 315 | | | | | 320 |

| Gln | Asp | Leu | Lys | Ala | Arg | Arg | Pro | Leu | Cys | Asp | Ser | Gly | Tyr | Tyr | Asn |
|---|---|---|---|---|---|---|---|---|---|---|---|---|---|---|---|
| | | | | 325 | | | | | 330 | | | | | 335 | |

| Thr | Phe | Asn | Arg | Asp | Asn | Val | Arg | Leu | Glu | Asp | Val | Lys | Ala | Asn | Pro |
|---|---|---|---|---|---|---|---|---|---|---|---|---|---|---|---|
| | | | 340 | | | | | 345 | | | | | 350 | | |

| Ile | Val | Glu | Ile | Thr | Glu | Asn | Gly | Val | Lys | Leu | Lys | Asn | Gly | Asp | Phe |
|---|---|---|---|---|---|---|---|---|---|---|---|---|---|---|---|
| | | 355 | | | | | 360 | | | | | 365 | | | |

| Val | Glu | Leu | Asp | Met | Leu | Ile | Cys | Ala | Thr | Gly | Phe | Asp | Ala | Val | Asp |

```
Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
            405                 410                 415

Asn Asn Tyr Pro Asn Met Phe Met Val Ser Gly Pro Asn Gly Pro Ser
                420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
            530                 535                 540
```

<210> SEQ ID NO 59
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 59

```
atgtctacca agatggattt cgatgccatc gtgatcggtg ggggctttgg cggtctgtat    60
gccgttaaaa aactgcgcga tgaactggag ctgaaagttc aagccttcga aggcaact     120 gacgtaggcg gtacatggta ctggaaccgc tacccgggtg ccctgaccga taccgaaacc   180
catttgtatt gttattcctg ggacaaggaa ctgttgcaga gtatggaaat caaaaccaaa   240
tacgcgcaag gtccagacgt gcgcaaatat ctgcagcagg ttgccgaaaa acacgtatta   300 aaaaaagtt accagttcaa caccgcagtc caatctgccc actacaacga agcggacgct    360
ctgtgggaag taactacgga atacggggat aagtacaccg cacgtttcct gattactgcc   420
ttaggtgggc tgtctgcacc taacctgcca aatatcaagg gcatcaatca gtttaaaggc   480
gacctgcacc atactgcccg ctggccggat gacgttagta tcgaaggcaa acgtgtgggt   540
gtgatcggca caggctctac cggcgtgcaa gttatcacgg cagtggcgcc actggccaag   600
cacctgacgg tgtttcagcg tagtgcccag tactcggtcc cgatcggtaa cgatccactg   660
agcgaagaag acgtcaagaa gatcaaagat aactatgata aaatctggga tggtgtttgg   720
aacagtgcgc tggccttcgg cctgaatgaa tctactgtgc cggccatgtc cgtaagtgcg   780
gaagagcgta agcggttttt tgagaaggcg tggcaatccg gcggtggtat cggttttttac   840 atcgaaacct tggtgatat tgtgacgaac atggaagcta acattgaggc acaaatttt    900 atcaaaggta aaatcgcgga atcgtcaaa gatccggcga tcgcccaaaa actgatgccg    960
caggacctga aggcacgtcg ccctctgtgt gactccgggt actataatac gttcaatcgc    1020
gacaacgtac gtctgaagga tgtcaaagca aatccgatcg tcgagatcac cgaaaacggc    1080
gtgaaactga aaacggcga tttcgtggag ctggacatgc tgatctgcgc gacgggtttt    1140
```

```
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg gttttggggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 60
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 60

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270
```

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 61
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 61
atgtctacca agatggattt cgatgccatc gtgatcggtg ggggctttgg cggtctgtat     60
gccgttaaaa aactgcgcga tgaactggag ctgaaagttc aagccttcga aggcaact     120 gacgtaggcg gtacatggta ctggaaccgc tacccgggtg ccctgaccga taccgaaacc     180
catttgtatt gttattcctg ggacaaggaa ctgttgcaga gtatggaaat caaaacgaaa     240
tacgtccaag gtccagacgt gcgcaaatat ctgcagcagg ttgccgaaaa acacgtatta     300 aaaaaagtt accagttcaa caccgcagtc caatctgccc actacaacga agcggacgct     360
ctgtgggaag taactacgga atacggggat aagtacaccg caaagttcct gattactgcc     420
ttaggtgggc tgtctgcgcc taacctgcca aatatcaagg gcatcaatca gtttaaaggc     480
gacctgcacc atactgcccg ctggccggat ggcgttagta tcgaaggcaa acgtgtgggt     540

-continued

```
gtggtcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggttttttac   840 atcgaaacct ttggtgatat tgtgacgaac atggaagcta acattgaggc acaaaatttt    900
atcaaaggta aaatcgcgga tcgtcaaa gatccggcga ccgcccaaaa actgatgccg    960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaaacggcga tttcgtggag ctggacgtac tgatctgcgc gacgggtttt    1140
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg gtttttgggg cgaacattcc aggcaagaag    1500
aacaccgcga tcttttatt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 62
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 62

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Val Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Lys Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160
```

```
Asp Leu His His Thr Ala Arg Trp Pro Asp Gly Val Ser Ile Glu Gly
                165                 170                 175
Lys Arg Val Gly Val Gly Thr Gly Ser Thr Gly Val Gln Val Ile
            180                 185                 190
Thr Ala Val Ala Pro Leu Ala Lys His Leu Thr Val Phe Gln Arg Ser
            195                 200                 205
Ala Gln Tyr Ser Val Pro Ile Gly Asn Asp Pro Leu Ser Glu Glu Asp
            210                 215                 220
Val Lys Lys Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
                245                 250                 255
Ser Val Ser Ala Glu Glu Arg Lys Ala Val Phe Glu Lys Ala Trp Gln
                260                 265                 270
Ser Gly Gly Gly Ile Gly Phe Tyr Ile Glu Thr Phe Gly Asp Ile Val
            275                 280                 285
Thr Asn Met Glu Ala Asn Ile Glu Ala Gln Asn Phe Ile Lys Gly Lys
            290                 295                 300
Ile Ala Glu Ile Val Lys Asp Pro Ala Thr Ala Gln Lys Leu Met Pro
305                 310                 315                 320
Gln Asp Leu Lys Ala Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
                340                 345                 350
Ile Val Glu Ile Thr Glu Asn Gly Val Lys Leu Lys Asn Gly Asp Phe
            355                 360                 365
Val Glu Leu Asp Val Leu Ile Cys Ala Thr Gly Phe Asp Ala Val Asp
            370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
                420                 425                 430
Gly Asn Ala Pro Pro Ser Ile Glu Ser Gln Val Glu Trp Ile Ser Asp
            435                 440                 445
Thr Ile Gln Tyr Thr Val Glu Asn Asn Val Glu Ser Ile Glu Ala Thr
            450                 455                 460
Lys Glu Ala Glu Glu Gln Trp Thr Gln Thr Cys Ala Asn Ile Ala Glu
465                 470                 475                 480
Met Thr Leu Phe Pro Lys Ala Gln Ser Leu Val Phe Gly Ala Asn Ile
                485                 490                 495
Pro Gly Lys Lys Asn Thr Ala Ile Phe Tyr Leu Gly Gly Leu Lys Asn
            500                 505                 510
Tyr Arg Ser Ala Leu Ala Asn Cys Lys Asn His Ala Tyr Glu Gly Phe
            515                 520                 525
Asp Ile Gln Pro Gln Arg Ser Asp Ile Lys Gln Pro Ala Asn Ala
            530                 535                 540

<210> SEQ ID NO 63
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871
```

<400> SEQUENCE: 63

```
atgtctacca agatggattt cgatgccatc gtgatcggtg ggggctttgg cggtctgtat          60
gccgttaaaa aactgcgcga tgaactggag ctgaaagttc aagccttcga␣aaggcaact          120
gacgtaggcg gtacatggta ctggaaccgc tacccgggtg ccctgaccga taccgaaacc         180
catttgtatt gttattcctg ggacaaggaa ctgttgcaga gtatggaaat caaaagaaa          240
tacgtgcaag gtccagacgt gcgcaaatat ctgcagcagg ttgccgaaaa acacgtatta         300
aaaaaaagtt accagttcaa caccgcagtc caatctgccc actacaacga agcggacgct         360
ctgtgggaag taactacgga atacgggat aagtacaccg cacgtttcct gattactgcc          420
ttaggtgggc tgtctgcacc taacctgcca aatatcaagg gcatcaatca gtttaaaggc         480
gacctgcacc atactgcccg ctggccggat gacgttagta tcgaaggcaa acgtgtgggt         540
gtgatcggca caggctctac cggcgtgcaa gttatcacgg cagtggcgcc actggccaag         600
cacctgacgg tgtttcagcg tagtgcccag tactcggtcc cgatcggtaa cgatccactg         660
agcgaagaag acgtcaagaa gatcaaagat aactatgata aatctggga tggtgtttgg          720
aacagtgcgc tggccttcgg cctgaatgaa tctactgtgc cggccatgtc cgtaagtgcg         780
gaagagcgta agcggttttt tgagaaggcg tggcaatccg gcggtggtat cggttttac           840
atcgaaacct ttggtgatat tgtgacgaac atggaagcta acattgaggc acaaaatttt         900
atcaaaggta aaatcgcgga gatcgtcaaa gatccggcga tcgcccaaaa actgatgccg         960
caggacctga aggcacgtcg ccctctgtgt gactccgggt actataatac gttcaatcgc        1020
gacaacgtac gtctggagga tgtcaaagca aatccgatcg tcgagatcac cgaaaacggc        1080
gtgaaactga aaacggcga tttcgtggag ctggacatgc tgatctgcgc gacgggtttt         1140
gatgcggtag acggcaacta tgttcgcatg gatatccaag ggcgtaacgg tctggccatg         1200
aaggattact ggaaagaggg cccgtctagc tacctgggcg taaccgtgaa taattaccca         1260
aacatgttta tggttagcgg tccaaaccgc ccatctggta acgctccgcc tagcattgaa         1320
agtcaagttg aatggattag cgatactatc cagtataccg tcgaaaataa cgtggaatct         1380
attgaagcca cgaaggaagc ggaggaacag tggatccaaa cctgcgccaa tctggcggag         1440
atgaccctgt ttccaaaagc ccagagcctg gttttggggg cgaacattcc aggcaagaag        1500
aacaccgcga tcttttattt gggtgggctg aaaaactacc gctcagcttt ggcgaattgt        1560
aaaaatcatg cgtatgaagg ctttgatatt cagccgcaac gttctgacat caaacaacca        1620
gcgaatgcg                                                                1629
```

<210> SEQ ID NO 64
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 64

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
```

```
            50                  55                  60
Tyr Ser Trp Asp Lys Glu Leu Leu Gln Ser Met Glu Ile Lys Lys
 65                  70                  75                  80

Tyr Val Gln Gly Pro Asp Val Arg Lys Tyr Leu Gln Gln Val Ala Glu
                 85                  90                  95

Lys His Val Leu Lys Lys Ser Tyr Gln Phe Asn Thr Ala Val Gln Ser
                100                 105                 110

Ala His Tyr Asn Glu Ala Asp Ala Leu Trp Glu Val Thr Thr Glu Tyr
                115                 120                 125

Gly Asp Lys Tyr Thr Ala Arg Phe Leu Ile Thr Ala Leu Gly Gly Leu
130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
                165                 170                 175

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Ser
                195                 200                 205

Ala Gln Tyr Ser Val Pro Ile Gly Asn Asp Pro Leu Ser Glu Glu Asp
210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
                260                 265                 270

Ser Gly Gly Gly Ile Gly Phe Tyr Ile Glu Thr Phe Gly Asp Ile Val
                275                 280                 285

Thr Asn Met Glu Ala Asn Ile Glu Ala Gln Asn Phe Ile Lys Gly Lys
                290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Lys Asn Gly Asp Phe
                355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Arg Pro Ser
                420                 425                 430

Gly Asn Ala Pro Pro Ser Ile Glu Ser Gln Val Glu Trp Ile Ser Asp
                435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Leu Ala Glu
465                 470                 475                 480
```

```
Met Thr Leu Phe Pro Lys Ala Gln Ser Leu Val Phe Gly Ala Asn Ile
            485                 490                 495
Pro Gly Lys Lys Asn Thr Ala Ile Phe Tyr Leu Gly Gly Leu Lys Asn
            500                 505                 510
Tyr Arg Ser Ala Leu Ala Asn Cys Lys Asn His Ala Tyr Glu Gly Phe
            515                 520                 525
Asp Ile Gln Pro Gln Arg Ser Asp Ile Lys Gln Pro Ala Asn Ala
            530                 535                 540

<210> SEQ ID NO 65
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 65
```

| | | | | | |
|---|---|---|---|---|---|
| atgtctacca | agatggattt | cgatgccatc | gtgatcggtg | ggggctttgg | cggtctgtat | 60 |
| gccgttaaaa | aactgcgcga | tgaactggag | ctgaaagttc | aagccttcga | gaaggcaact | 120 |
| gacgtaggcg | gtacatggta | ctggaaccgc | tacccgggtg | ccctgaccga | taccgaaacc | 180 |
| catttgtatt | gttattcctg | ggacaaggaa | ctgttgcaga | gtatggaaat | caaaacgaaa | 240 |
| tacatccaag | gtccagacgt | gcgcaaatat | ctgcagcagg | ttgccgaaaa | acacgtatta | 300 |
| aaaaaaagtt | accagttcaa | caccgcagtc | caatctgccc | actacaacga | agcggacgct | 360 |
| ctgtgggaag | taactacgga | atacggggat | aagtacaccg | cacgtttcct | gattactgcc | 420 |
| ttaggtgggc | tgtctgcacc | taacctgcca | aatatcaagg | gcatcaatca | gtttaaaggc | 480 |
| gacctgtacc | atactgcccg | ctggccggat | gacgttagta | tcgaaggcaa | acgtgtgggt | 540 |
| gtgatcggca | caggctctac | cggcgtgcaa | gttatcacgg | cagtggcgcc | actggccaag | 600 |
| cacctgacgg | tgtttcagcg | tagtgcccag | tactcggtcc | cgatcggtaa | cgatccactg | 660 |
| agcgaagaag | acgtcaagaa | gatcaaagat | aactatgata | aaatctggga | tggtgtttgg | 720 |
| aacagtgcgc | tggccttcgg | cctgaatgaa | tctactgtgc | cggccatgtc | cgtaagtgcg | 780 |
| gaagagcgta | aagcggtttt | tgagaaggcg | tggcaatccg | cgcgtggtat | cggttttttac | 840 |
| atcgaaacct | tggtgatat | tgtgacggac | atggaagcta | acattgaggc | acaaaatttt | 900 |
| atcaaaggta | aaatcgcgga | gatcgtcaaa | gatccggcga | tcgcccaaaa | actgacgccg | 960 |
| caggacctga | aggcacgtcg | ccctctgtgt | gactccgggt | actataatac | gttcaatcgc | 1020 |
| gacaacgtac | gtctggagga | tgtcaaagca | aatccgatcg | tcgagatcac | cgaaaacggc | 1080 |
| gtgaaactga | aaaacggcga | tttcgtggag | ctggacatgc | tgatctgcgc | gacgggtttt | 1140 |
| gatgcggtag | acggcaacta | tgttcgcatg | gatatccaag | gcgtaacgg | tctggccatg | 1200 |
| aaggattact | ggaaagaggg | cccgtctagc | tacctgggcg | taaccgtgaa | taattaccca | 1260 |
| aacatgttta | tggttagcgg | tccaaaccgc | ccatctggta | acgctccgcc | tagcattgaa | 1320 |
| agtcaagttg | aatggattag | cgatactatc | cagtataccg | tcgaaaataa | cgtggaatct | 1380 |
| attgaagcca | cgaaggaagc | ggaggaacag | tggacccaaa | cctgcgccaa | tattgcggag | 1440 |
| atgaccctgt | ttccaaaagc | ccagagcctg | gttttggg | cgaacattcc | aggcaagaag | 1500 |
| aacaccgcga | tcttttattt | gggtgggctg | aaaaactacc | gctcagcttt | ggcgaattgt | 1560 |
| aaaaatcatg | cgtatgaagg | ctttgatatt | cagccgcaac | gttctgacat | caaacaacca | 1620 |
| gcgaatgcg | | | | | | 1629 |

<210> SEQ ID NO 66
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 66

```
Met Ser Thr Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
                20                  25                  30

Val Gln Ala Phe Glu Lys Ala Thr Asp Val Gly Gly Thr Trp Tyr Trp
            35                  40                  45

Asn Arg Tyr Pro Gly Ala Leu Thr Asp Thr Glu Thr His Leu Tyr Cys
50                  55                  60

Tyr Ser Trp Asp Lys Glu Leu Leu Gln Ser Met Glu Ile Lys Thr Lys
65                  70                  75                  80

Tyr Ile Gln Gly Pro Asp Val Arg Lys Tyr Leu Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
130                 135                 140

Ser Ala Pro Asn Leu Pro Asn Ile Lys Gly Ile Asn Gln Phe Lys Gly
145                 150                 155                 160

Asp Leu Tyr His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asp Met Glu Ala Asn Ile Glu Ala Gln Asn Phe Ile Lys Gly Lys
290                 295                 300

Ile Ala Glu Ile Val Lys Asp Pro Ala Ile Ala Gln Lys Leu Thr Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365
```

| | | | | | | | | | | | | |
|---|---|---|---|---|---|---|---|---|---|---|---|---|
|Val|Glu|Leu|Asp|Met|Leu|Ile|Cys|Ala|Thr|Gly|Phe|Asp|Ala|Val|Asp|
| |370| | | |375| | | | |380| | | | | |

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Arg Pro Ser
                420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
530                 535                 540

<210> SEQ ID NO 67
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 67

```
atgtctacca agatggattt cgatgccatc gtgatcggtg ggggctttgg cggtctgtat      60
gccgttaaaa aactgcgcga tgaactggag ctgaaagttc aagccttcga aaggcaact     120
gacgtaggcg gtacatggta ctggaaccgc tacccgggtg ccctgaccga taccgaaacc    180
catttgtatt gttattcctg ggacaaggaa ctgttgcaga gtatggaaat caaaacgaaa    240
tacgcacaag gtccagacgt gcgcaaatat ctgcagcagg ttgccgaaaa acacgtatta    300
aaaaaagtt accagttcaa caccgcagtc aatctgccc actacaacga agcggacgct      360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgtacc atactgcccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggttttac     840
atcgaaacct ttggtgatat tgtgacgaac atggaagcta acattgaggc acaaaatttt    900
atcaaggta aaatcgcgga atcgtcaaa gatccggcga tcgcccaaaa actgatgccg      960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
```

-continued

```
gtgaaactga aaaacggcga tttcgtggag ctggacatgc tgatctgcgc gacgggtttt    1140
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggatccaaa cctgcgccaa tattgcggag    1440
atgaccctgt ttccaaaagc ccagagcctg gtttttgggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 68
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 68

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
                20                  25                  30

Val Gln Ala Phe Glu Lys Ala Thr Asp Val Gly Gly Thr Trp Tyr Trp
            35                  40                  45

Asn Arg Tyr Pro Gly Ala Leu Thr Asp Thr Glu Thr His Leu Tyr Cys
        50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu Tyr His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
```

```
            260                 265                 270
Ser Gly Gly Gly Ile Gly Phe Tyr Ile Glu Thr Phe Gly Asp Ile Val
            275                 280                 285

Thr Asn Met Glu Ala Asn Ile Glu Ala Gln Asn Phe Ile Lys Gly Lys
            290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Lys Asn Gly Asp Phe
                355                 360                 365

Val Glu Leu Asp Met Leu Ile Cys Ala Thr Gly Phe Asp Ala Val Asp
            370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
            450                 455                 460

Lys Glu Ala Glu Glu Gln Trp Ile Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
            530                 535                 540

<210> SEQ ID NO 69
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 69
atgtctacca agatggattt cgatgccatc gtgatcggtg ggggctttgg cggtctgtat      60
gccgttaaaa aactgcgcga tgaactggag ctgaaagttc aagccttcga aaggcaact     120 gacgtaggcg gtacatggta ctggaaccgc tacccgggtg ccctgaccga taccgaaacc    180
catttgtatt gttattcctg ggacaaggaa ctgttgcaga gtatggaaat caaaacgaaa    240
tacgtacaag gtccagacgt gcgcaaatat ctgcagcagg ttgccgaaaa acacgtatta    300
aaaaaaagtt accagttcaa caccgcagtc caatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
```

-continued

```
gacctgcacc atactgcccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggttttttac   840 atcgaaacct ttggtgatat tgtgacgaac atggaagcta acattgaggc acaaaatttt    900
atcaaaggta aaatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaagagggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggatccaaa cctgcgccaa tattgcggag   1440
atgaccctgt ttccaaaagc ccagagcctg gttttggggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                            1629
```

<210> SEQ ID NO 70
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 70

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Val Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160
```

Asp Leu His His Thr Ala Arg Trp Pro Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Gln Thr Cys Ala Asn Ile Ala Glu
465                 470                 475                 480

Met Thr Leu Phe Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 71
<211> LENGTH: 1629
<212> TYPE: DNA
<213> ORGANISM: Artificial Sequence
<220> FEATURE:

<223> OTHER INFORMATION: Variant of CHMO from Acinetobacter sp NCIMB9871

<400> SEQUENCE: 71

```
atgtctacca agatggattt cgatgccatc gtgatcggtg ggggctttgg cggtctgtat      60
gccgttaaaa aactgcgcga tgaactggag ctgaaagttc aagccttcga aaggcaact     120
gacgtaggcg gtacatggta ctggaaccgc tacccgggtg ccctgaccga taccgaaacc    180
catttgtatt gttattcctg ggacaaggaa ctgttgcaga gtatggaaat caaaaagaaa    240
tacgtgcaag gtccagacgt gcgcaaatat ctgcagcagg ttgccgaaaa acacgtatta    300
aaaaaaagtt accagttcaa caccgcagtc aatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg cggtggtat cggttttttac    840
atcgaaacct ttggtgatat tgcgacgaac atggaagcta acattgaggc acaaaatttt    900
atcaaaggta aaatcgcgga atcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactgg agaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgacccctgt ttccaaaagc ccagagcctg gtttttgggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 72
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 72

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45
```

-continued

```
Asn Arg Tyr Pro Gly Ala Leu Thr Asp Thr Glu Thr His Leu Tyr Cys
 50                  55                  60
Tyr Ser Trp Asp Lys Glu Leu Leu Gln Ser Met Glu Ile Lys Lys
 65                  70                  75                  80
Tyr Val Gln Gly Pro Asp Val Arg Lys Tyr Leu Gln Gln Val Ala Glu
                 85                  90                  95
Lys His Val Leu Lys Lys Ser Tyr Gln Phe Asn Thr Ala Val Gln Ser
                100                 105                 110
Ala His Tyr Asn Glu Ala Asp Ala Leu Trp Glu Val Thr Thr Glu Tyr
                115                 120                 125
Gly Asp Lys Tyr Thr Ala Arg Phe Leu Ile Thr Ala Leu Gly Gly Leu
130                 135                 140
Ser Ala Pro Asn Leu Pro Asn Ile Lys Gly Ile Asn Gln Phe Lys Gly
145                 150                 155                 160
Asp Leu His His Thr Ala Arg Trp Pro Asp Asp Val Ser Ile Glu Gly
                165                 170                 175
Lys Arg Val Gly Val Ile Gly Thr Gly Ser Thr Gly Val Gln Val Ile
                180                 185                 190
Thr Ala Val Ala Pro Leu Ala Lys His Leu Thr Val Phe Gln Arg Ser
                195                 200                 205
Ala Gln Tyr Ser Val Pro Ile Gly Asn Asp Pro Leu Ser Glu Glu Asp
                210                 215                 220
Val Lys Lys Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
                245                 250                 255
Ser Val Ser Ala Glu Glu Arg Lys Ala Val Phe Glu Lys Ala Trp Gln
                260                 265                 270
Ser Gly Gly Gly Ile Gly Phe Tyr Ile Glu Thr Phe Gly Asp Ile Ala
                275                 280                 285
Thr Asn Met Glu Ala Asn Ile Glu Ala Gln Asn Phe Ile Lys Gly Lys
                290                 295                 300
Ile Ala Glu Ile Val Lys Asp Pro Ala Ile Ala Gln Lys Leu Met Pro
305                 310                 315                 320
Gln Asp Leu Lys Ala Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
                340                 345                 350
Ile Val Glu Ile Thr Glu Asn Gly Val Lys Leu Glu Asn Gly Asp Phe
                355                 360                 365
Val Glu Leu Asp Met Leu Ile Cys Ala Thr Gly Phe Asp Ala Val Asp
370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
                420                 425                 430
Gly Asn Ala Pro Pro Ser Ile Glu Ser Gln Val Glu Trp Ile Ser Asp
                435                 440                 445
Thr Ile Gln Tyr Thr Val Glu Asn Asn Val Glu Ser Ile Glu Ala Thr
450                 455                 460
Lys Glu Ala Glu Glu Gln Trp Thr Gln Thr Cys Ala Asn Ile Ala Glu
```

```
                465                 470                 475                 480
Met Thr Leu Phe Pro Lys Ala Gln Ser Leu Val Phe Gly Ala Asn Ile
                        485                 490                 495

Pro Gly Lys Lys Asn Thr Ala Ile Phe Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Pro Ala Asn Ala
        530                 535                 540

<210> SEQ ID NO 73
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 73
atgtctacca agatggattt cgatgccatc gtgatcggtg ggggctttgg cggtctgtat      60
gccgttaaaa aactgcgcga tgaactggag ctgaaagttc aagccttcga agaggcaact    120
gacgtaggcg gtacatggta ctggaaccgc tacccgggtg ccctgaccga taccgaaacc    180
catttgtatt gttattcctg ggacaaggaa ctgttgcaga gtatggaaat caaaagaaa     240 tacgtgcaag gtccagacgt gcgcaaatat ctgcagcagg ttgccgaaaa acacgtatta    300
aaaaaaagtt accagttcaa caccgcagtc caatctgccc actacaacga gcggacgct     360 ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactggccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcggtaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta agcggttttt tgagaaggcg tggcaatccg gcggtggtat cggttttttac    840 atcgaaacct tggtgatat tgtgacgaac atggaagcta acattgaggc acaaaatttt    900 atcaaggta aaatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactgg agaacggcga tttcgtggag ctggacatgc tgatctgcgc gacgggtttt   1140
gatgcggtag acggcaacta tgttcgcatg gatatccaag gcgtaacgg tctggccatg   1200 aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttttgggg cgaacattcc aggcaagaag   1500
aacaccgcga tcttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 74
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 74

```
Met Ser Thr Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Gly Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365
```

```
Val Glu Leu Asp Met Leu Ile Cys Ala Thr Gly Phe Asp Ala Val Asp
    370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
                420                 425                 430
Gly Asn Ala Pro Pro Ser Ile Glu Ser Gln Val Glu Trp Ile Ser Asp
            435                 440                 445
Thr Ile Gln Tyr Thr Val Glu Asn Asn Val Glu Ser Ile Glu Ala Thr
    450                 455                 460
Lys Glu Ala Glu Glu Gln Trp Thr Gln Thr Cys Ala Asn Ile Ala Glu
465                 470                 475                 480
Met Thr Leu Phe Pro Lys Ala Gln Ser Leu Val Phe Gly Ala Asn Ile
                485                 490                 495
Pro Gly Lys Lys Asn Thr Ala Ile Phe Tyr Leu Gly Gly Leu Lys Asn
                500                 505                 510
Tyr Arg Ser Ala Leu Ala Asn Cys Lys Asn His Ala Tyr Glu Gly Phe
            515                 520                 525
Asp Ile Gln Pro Gln Arg Ser Asp Ile Lys Gln Pro Ala Asn Ala
    530                 535                 540

<210> SEQ ID NO 75
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 75
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc taccgggtg ccctgaccga taccgaaacc      180
catttgtatt gttattcctg ggacaaggaa ctgttgcaga gtatggaaat caaaaagaaa     240
tacgtgcaag gtccagacgt gcgcaaatat ctgcagcagg ttgccgaaaa acacgtatta     300 aaaaaagtt accagttcaa caccgcagtc aatctgccc actacaacga agcggacgct       360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcggtaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt gagaaggcg tggcaatccg gcggtggtat cggttttttac     840 atcgaaacct ttggtgatat cgtgacgaac atggaagcta acattgaggc acaaaatttt     900
atcaaaggta aaatcgcgga gatcgtcaaa gatccggcga tcgcccaaaa actgatgccg     960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
```

-continued

```
gtgaaactga aaaacggcga tttcgtggag ctggacatgc tgatctgcgc gacgggtttt    1140
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440 atgacccctgt gtccaaaagc ccagagcctg ttttttgggg cgaacattcc aggcaagaag    1500
aacaccgcga tcttttattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                             1629
```

<210> SEQ ID NO 76
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 76

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Val Gln Gly Pro Asp Val Arg Lys Tyr Leu Gln Val Ala Glu
                85                  90                  95

Lys His Val Leu Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255
```

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Gly Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Cys Pro Lys Ala Gln Ser Leu Val Phe Gly Ala Asn Ile
                485                 490                 495

Pro Gly Lys Lys Asn Thr Ala Ile Phe Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 77
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 77
atgtctacca agatggattt cgatgccatc gtgatcggtg ggggctttgg cggtctgtat      60
gccgttaaaa aactcgcgga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480

```
gacctgcacc atactgcccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgata aatctgggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggttttac     840 atcgaaacct ttggtgatat tttaacgaac atggaagcta acattgaggc acaaaatttt    900
atcaaaggta aatcgcgga  gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaacggcga  tttcgtggag ctggacatgc tgatctgcgc gacgggtttt   1140
gatgcggtag acggcaacta tgttcgcatg gatatccaag gcgtaacgg  tctggccatg   1200 aaggattact ggaaagaggg cccgtctagc tacctgggcg taaccgtgaa taattaccca   1260
aacatgttta tggttagcgg tccaaaccgt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttaaagggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 78
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 78

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
```

```
            145                 150                 155                 160
        Asp Leu His His Thr Ala Arg Trp Pro Asp Val Ser Ile Glu Gly
                        165                 170                 175

Lys Arg Val Gly Val Ile Gly Thr Gly Ser Thr Gly Val Gln Val Ile
                        180                 185                 190

Thr Ala Val Ala Pro Leu Ala Lys His Leu Thr Val Phe Gln Arg Thr
                        195                 200                 205

Ala Gln Tyr Ser Val Pro Ile Ser Asn Asp Pro Leu Ser Glu Glu Asp
                210                 215                 220

Val Lys Lys Ile Lys Asp Asn Tyr Asp Lys Ile Trp Asp Gly Val Trp
        225                 230                 235                 240

Asn Ser Ala Leu Ala Phe Gly Leu Asn Glu Ser Thr Val Pro Ala Met
                        245                 250                 255

Ser Val Ser Ala Glu Glu Arg Lys Ala Val Phe Glu Lys Ala Trp Gln
                        260                 265                 270

Ser Gly Gly Gly Ile Gly Phe Tyr Ile Glu Thr Phe Gly Asp Ile Leu
                        275                 280                 285

Thr Asn Met Glu Ala Asn Ile Glu Ala Gln Asn Phe Ile Lys Gly Lys
                290                 295                 300

Ile Ala Glu Ile Val Lys Asp Pro Ala Ile Ala Gln Lys Leu Met Pro
        305                 310                 315                 320

Gln Asp Leu Lys Ala Arg Arg Pro Leu Cys Asp Ser Gly Tyr Tyr Asn
                        325                 330                 335

Thr Phe Asn Arg Asp Asn Val Arg Leu Glu Asp Val Lys Ala Asn Pro
                        340                 345                 350

Ile Val Glu Ile Thr Glu Asn Gly Val Lys Leu Lys Asn Gly Asp Phe
                        355                 360                 365

Val Glu Leu Asp Met Leu Ile Cys Ala Thr Gly Phe Asp Ala Val Asp
                370                 375                 380

Gly Asn Tyr Val Arg Met Asp Ile Gln Gly Arg Asn Gly Leu Ala Met
        385                 390                 395                 400

Lys Asp Tyr Trp Lys Glu Gly Pro Ser Tyr Leu Gly Val Thr Val
                        405                 410                 415

Asn Asn Tyr Pro Asn Met Phe Met Val Ser Gly Pro Asn Arg Pro Ser
                        420                 425                 430

Gly Asn Ala Pro Pro Ser Ile Glu Ser Gln Val Glu Trp Ile Ser Asp
                        435                 440                 445

Thr Ile Gln Tyr Thr Val Glu Asn Asn Val Glu Ser Ile Glu Ala Thr
                450                 455                 460

Lys Glu Ala Glu Glu Gln Trp Thr Gln Thr Cys Ala Asn Ile Ala Glu
        465                 470                 475                 480

Met Thr Leu Phe Pro Lys Ala Gln Ser Leu Val Lys Gly Ala Asn Ile
                        485                 490                 495

Pro Gly Lys Lys Asn Thr Ala Ile Lys Tyr Leu Gly Gly Leu Lys Asn
                        500                 505                 510

Tyr Arg Ser Ala Leu Ala Asn Cys Lys Asn His Ala Tyr Glu Gly Phe
                        515                 520                 525

Asp Ile Gln Pro Gln Arg Ser Asp Ile Lys Gln Pro Ala Asn Ala
                        530                 535                 540

<210> SEQ ID NO 79
<211> LENGTH: 1629
<212> TYPE: DNA
<213> ORGANISM: Artificial Sequence
```

<220> FEATURE:
<223> OTHER INFORMATION: Variant of CHMO from Acinetobacter sp NCIMB9871

<400> SEQUENCE: 79

```
atgtctacca agatggattt cgatgccatc gtgatcggtg ggggctttgg cggtctgtat      60
gccgttaaaa aactgcgcga tgaactggag ctgaaagttc aagccttcga aaggcaact      120
gacgtaggcg gtacatggta ctggaaccgc tacccgggtg ccctgaccga taccgaaacc    180
catttgtatt gttattcctg ggacaaggaa ctgttgcaga gtatggaaat caaaaccaaa    240
tacgtgcaag gtccagacgt gcgcaaatat ctgcagcagg ttgccgaaaa acacgtatta    300
aaaaaaagtt accagttcaa caccgcagtc caatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tagtgcccag tactcggtcc cgatcagcaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggttttttac    840
atcgaaacct ttggtgatat tgtgacgaac atggaagcta acattgaggc acaaaatttt    900
atcaaaggta aaatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag gcgtaacgg tctggccatg   1200
aaggattact ggaagagggg cccgtctagc tacctgggcg taaccgtgaa taattaccca   1260
aacatgtta tggttagcgg tccaaacggt ccatctggta acgctccgcc tcgcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttaaagggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 80
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 80

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45
```

```
Asn Arg Tyr Pro Gly Ala Leu Thr Asp Thr Glu Thr His Leu Tyr Cys
 50                  55                  60

Tyr Ser Trp Asp Lys Glu Leu Leu Gln Ser Met Glu Ile Lys Thr Lys
 65                  70                  75                  80

Tyr Val Gln Gly Pro Asp Val Arg Lys Tyr Leu Gln Gln Val Ala Glu
                 85                  90                  95

Lys His Val Leu Lys Lys Ser Tyr Gln Phe Asn Thr Ala Val Gln Ser
                100                 105                 110

Ala His Tyr Asn Glu Ala Asp Ala Leu Trp Glu Val Thr Thr Glu Tyr
            115                 120                 125

Gly Asp Lys Tyr Thr Ala Arg Phe Leu Ile Thr Ala Leu Gly Gly Leu
        130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
                165                 170                 175

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Ser
            195                 200                 205

Ala Gln Tyr Ser Val Pro Ile Ser Asn Asp Pro Leu Ser Glu Glu Asp
        210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
            385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Arg Ile Glu Ser Gln Val Glu Trp Ile Ser Asp
            435                 440                 445

Thr Ile Gln Tyr Thr Val Glu Asn Asn Val Glu Ser Ile Glu Ala Thr
        450                 455                 460
```

```
Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Lys Gly Ala Asn Ile
            485                 490                 495

Pro Gly Lys Lys Asn Thr Ala Ile Lys Tyr Leu Gly Gly Leu Lys Asn
        500                 505                 510

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
    530                 535                 540

<210> SEQ ID NO 81
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 81
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttgtcacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaatccg gcggtggtat cggttttttac     840 atcgaaacct ttggtgatat tgtgacgaac atggaagcta acattgaggc acaaaatttt     900
atcaaaggta aaatcgcgga gatcgtcaaa gatccggcga tcgcccaaaa actgatgccg     960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaaacggcga tttcgtggag ctggacatgc tgatctgcgc gacgggtttt    1140
gatgcggtag acggcaacta tgttcgcatg gatatccaag gcgtaacgg tctggccatg    1200 aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggacccaaa cctgcgccaa tattgcggag    1440
atgaccctgt ttccaaaagc ccagagcctg gttaaggggc gaacattcc aggcaagaag    1500 aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
``` gcgaatgcg                                                             1629

<210> SEQ ID NO 82
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 82

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Val
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Val
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe

```
        355                 360                 365
Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Ser Ile Glu Ser Gln Val Glu Trp Ile Ser Asp
                435                 440                 445

Thr Ile Gln Tyr Thr Val Glu Asn Asn Val Glu Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Lys Gly Ala Asn Ile
                485                 490                 495

Pro Gly Lys Lys Asn Thr Ala Ile Lys Tyr Leu Gly Gly Leu Lys Asn
                500                 505                 510

Tyr Arg Ser Ala Leu Ala Asn Cys Lys Asn His Ala Tyr Glu Gly Phe
                515                 520                 525

Asp Ile Gln Pro Gln Arg Ser Asp Ile Lys Gln Pro Ala Asn Ala
    530                 535                 540

<210> SEQ ID NO 83
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 83
atgtctacca agatggattt cgatgccatc gtgatcggtg ggggctttgg cggtctgtat      60
gccgttaaaa aactgcgcga tgaactggag ctgaaagttc aagccttcga agaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaagaaa      240 tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttatcacgg cagtggcgcc actggccaag     600
cacctgacgg tgtttcagcg tagtgcccag tactcggtcc cgatcagcaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggtttt tgagaaggcg tggcaatccg cgcgtggtat cggttttac      840 atcgaaacct ttggtgatat tgtgacgaac atggaagcta acattgaggc acaaaatttt     900
atcaaaggta aaatcgcgga gatcgtcaaa gatccggcga tcgcccaaaa actgatgccg     960
caggacctga aggcacgtcg ccctctgtgt gactccgggt actataatac gttcaatcgc    1020
```

-continued

```
gacaacgtac gtctggagga tgtcaaagca aatccgatcg tcgagatcac cgaaaacggc   1080
gtgaaactga aaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440 atgacccctgt ttccaaaagc ccagagcctg gtttttgggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 84
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 84

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Lys Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255
```

-continued

```
Ser Val Ser Ala Glu Glu Arg Lys Ala Val Phe Glu Lys Ala Trp Gln
            260                 265                 270
Ser Gly Gly Gly Ile Gly Phe Tyr Ile Glu Thr Phe Gly Asp Ile Val
        275                 280                 285
Thr Asn Met Glu Ala Asn Ile Glu Ala Gln Asn Phe Ile Lys Gly Lys
    290                 295                 300
Ile Ala Glu Ile Val Lys Asp Pro Ala Ile Ala Gln Lys Leu Met Pro
305                 310                 315                 320
Gln Asp Leu Lys Ala Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
            340                 345                 350
Ile Val Glu Ile Thr Glu Asn Gly Val Lys Leu Lys Asn Gly Asp Phe
        355                 360                 365
Val Glu Leu Asp Met Leu Ile Cys Ala Thr Gly Phe Asp Ala Val Asp
    370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
            420                 425                 430
Gly Asn Ala Pro Pro Ser Ile Glu Ser Gln Val Glu Trp Ile Ser Asp
        435                 440                 445
Thr Ile Gln Tyr Thr Val Glu Asn Asn Val Glu Ser Ile Glu Ala Thr
    450                 455                 460
Lys Glu Ala Glu Glu Gln Trp Thr Gln Thr Cys Ala Asn Ile Ala Glu
465                 470                 475                 480
Met Thr Leu Phe Pro Lys Ala Gln Ser Leu Val Phe Gly Ala Asn Ile
                485                 490                 495
Pro Gly Lys Lys Asn Thr Ala Ile Lys Tyr Leu Gly Gly Leu Lys Asn
            500                 505                 510
Tyr Arg Ser Ala Leu Ala Asn Cys Lys Asn His Ala Tyr Glu Gly Phe
        515                 520                 525
Asp Ile Gln Pro Gln Arg Ser Asp Ile Lys Gln Pro Ala Asn Ala
    530                 535                 540
```

<210> SEQ ID NO 85
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 85

```
atgtctacca agatggattt cgatgccatc gtgatcggtg ggggctttgg cggtctgtat    60
gccgttaaaa aactgcgcga tgaactggag ctgaaagttc aagccttcga agggcaact    120
gacgtaggcg gtacatggta ctggaaccgc taccccgggtg ccctgaccga taccgaaacc   180
catttgtatt gttattcctg ggacaaggaa ctgttgcaga gtatggaaat caaaaccaaa   240
tacgcgcaag gtccagacgt gcgcaaatat ctgcagcagg ttgccgaaaa acacgtatta   300
aaaaaaagtt accagttcaa caccgcagtc caatctgccc actacaacga agcggacgct   360
ctgtgggaag taactacgga atacgggat aagtacaccg cacgtttcct gattactgcc    420
```

```
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttatcacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgata aatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggttttttac   840
atcgaaacct ttggtgatat tgtgacgaac atggaagcta acattgaggc acaaaatttt    900
atcaaaggta aaatcgcgga atcgtcaaa gatccggcga tcgcccaaaa actgatgccg     960
caggacctga aggcacgtcg ccctctgtgt gactccgggt actataatac gttcaatcgc   1020
gacaacgtac gtctggagga tgtcaaagca atccgatcg tcgagatcac cgaaaacggc    1080
gtgaaactga aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaaccgt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggacccaaa cctgcgccaa tattgcggag   1440
atgaccctgt ttccaaaagc ccagagcctg gttttgggg cgaacattcc aggcaagaag   1500
aacaccgcga tctttttattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 86
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 86

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
            165                 170                 175

Lys Arg Val Gly Val Ile Gly Thr Gly Ser Thr Gly Val Gln Val Ile
        180                 185                 190

Thr Ala Val Ala Pro Leu Ala Lys His Leu Thr Val Phe Gln Arg Thr
    195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
            245                 250                 255

Ser Val Ser Ala Glu Glu Arg Lys Ala Val Phe Glu Lys Ala Trp Gln
        260                 265                 270

Ser Gly Gly Gly Ile Gly Phe Tyr Ile Glu Thr Phe Gly Asp Ile Val
    275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
            325                 330                 335

Thr Phe Asn Arg Asp Asn Val Arg Leu Glu Asp Val Lys Ala Asn Pro
        340                 345                 350

Ile Val Glu Ile Thr Glu Asn Gly Val Lys Leu Lys Asn Gly Asp Phe
    355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
            405                 410                 415

Asn Asn Tyr Pro Asn Met Phe Met Val Ser Gly Pro Asn Arg Pro Ser
        420                 425                 430

Gly Asn Ala Pro Pro Ser Ile Glu Ser Gln Val Glu Trp Ile Ser Asp
    435                 440                 445

Thr Ile Gln Tyr Thr Val Glu Asn Asn Val Ser Ile Glu Ala Thr
    450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Leu Val Phe Gly Ala Asn Ile
            485                 490                 495

Pro Gly Lys Lys Asn Thr Ala Ile Phe Tyr Leu Gly Gly Leu Lys Asn
        500                 505                 510

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
    530                 535                 540

<210> SEQ ID NO 87
<211> LENGTH: 1629
<212> TYPE: DNA

<213> ORGANISM: Artificial Sequence
<220> FEATURE:
<223> OTHER INFORMATION: Variant of CHMO from Acinetobacter sp NCIMB9871

<400> SEQUENCE: 87

```
atgtctacca agatggattt cgatgccatc gtgatcggtg ggggcttttgg cggtctgtat      60
gccgttaaaa aactgcgcga tgaactggag ctgaaagttc aagccttcga␣gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag␣gtccagacgt␣gcgcaaatat ctgcagcagg␣ttgccgaaaa acacgtatta     300
aaaaaagtt accagttcaa caccgcaatg caatctgccc actacaacga agcggacgct     360
ctgtgggaag taactacgga atacggggat aagtacaccg cacgttttcct gattactgcc     420
ttaggtgggc tgtctgcacc taacctgcca aatatcaagg␣gcatcaatca gtttaaaggc     480
gacctgcacc␣atactggtcg␣ctggccggat␣gacgttagta␣tcgaaggcaa␣acgtgtgggt     540
gtgatcggca caggctctac cggcgtgcaa gttattacgg␣cagtggcgcc actggccaag     600
cacctgacgg tgtttcagcg tacggcccag tactcggtcc cgatcagcaa cgatccactg     660
agcgaagaag␣acgtcaagga aatcaaagat␣aactatgata aaatctggga tggtgtttgg     720
aacagtgcgc tggccttcgg cctgaatgaa tctactgtgc cggccatgtc cgtaagtgcg     780
gaagagcgta aagcggtttt␣tgagaaggcg␣tggcaatgcg␣gcggtggtat␣cggttttttac     840
atcgaaacct␣ttggtgatat␣tctgacgaac atggaagcta acattgaggc acaaaattt␣t     900
atcaaaggta aaatcgcgga gatcgtcaaa gatccggcga␣tcgcccaaaa␣actgatgccg     960
caggacctga aggcacgtcg␣ccctctgtgt␣gactccgggt actatagcac␣gttcaatcgc    1020
gacaacgtac gtctggagga tgtcaaagca aatccgatcg tcgagatcac cgaaaacggc    1080
gtgaaactgg aaaacggcga tttcgtggag␣ctggacatgc tgatctgcgc gacgggttt␣t    1140
gatgcggtag␣acggcaacta tgttcgcatg gatatccaag␣gcgtaacgg␣tctggccatg    1200
aaggattact␣ggaaagaggg cccgtctagc tacctgggcg␣taaccgtgaa taattaccca    1260
aacatgtttta tggttagcgg tccaaacggt ccatctggta acgctccgcc tagcattgaa    1320
agtcaagttg aatggattag␣cgatactatc cagtataccg tcgaaaataa cgtggaatct    1380
attgaagcca cgaaggaagc ggaggaacag tggattcaaa cctgcgccaa tattgcggag    1440
atgaccctgt gtccagaggc ccagagcctg gttaaagggg cgaacattcc aggcaagaag    1500
aacaccgcga tcaaatattt␣gggtgggctg aaaaactacc␣gctcagcttt␣t ggcgaattgt    1560
aaaaatcatg cgtatgaagg␣ctttgatatt cagccgcaac␣gttctgacat caaacaacca    1620
gcgaatgcg                                                             1629
```

<210> SEQ ID NO 88
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 88

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp

```
                35                  40                  45
Asn Arg Tyr Pro Gly Ala Leu Thr Asp Thr Glu Thr His Leu Tyr Cys
 50                  55                  60
Tyr Ser Trp Asp Lys Glu Leu Leu Gln Ser Met Glu Ile Lys Thr Lys
 65                  70                  75                  80
Tyr Ala Gln Gly Pro Asp Val Arg Lys Tyr Leu Gln Gln Val Ala Glu
                 85                  90                  95
Lys His Val Leu Lys Lys Ser Tyr Gln Phe Asn Thr Ala Met Gln Ser
                100                 105                 110
Ala His Tyr Asn Glu Ala Asp Ala Leu Trp Glu Val Thr Thr Glu Tyr
                115                 120                 125
Gly Asp Lys Tyr Thr Ala Arg Phe Leu Ile Thr Ala Leu Gly Gly Leu
130                 135                 140
Ser Ala Pro Asn Leu Pro Asn Ile Lys Gly Ile Asn Gln Phe Lys Gly
145                 150                 155                 160
Asp Leu His His Thr Gly Arg Trp Pro Asp Asp Val Ser Ile Glu Gly
                165                 170                 175
Lys Arg Val Gly Val Ile Gly Thr Gly Ser Thr Gly Val Gln Val Ile
                180                 185                 190
Thr Ala Val Ala Pro Leu Ala Lys His Leu Thr Val Phe Gln Arg Thr
            195                 200                 205
Ala Gln Tyr Ser Val Pro Ile Ser Asn Asp Pro Leu Ser Glu Glu Asp
            210                 215                 220
Val Lys Glu Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
                245                 250                 255
Ser Val Ser Ala Glu Glu Arg Lys Ala Val Phe Glu Lys Ala Trp Gln
                260                 265                 270
Cys Gly Gly Gly Ile Gly Phe Tyr Ile Glu Thr Phe Gly Asp Ile Leu
                275                 280                 285
Thr Asn Met Glu Ala Asn Ile Glu Ala Gln Asn Phe Ile Lys Gly Lys
            290                 295                 300
Ile Ala Glu Ile Val Lys Asp Pro Ala Ile Ala Gln Lys Leu Met Pro
305                 310                 315                 320
Gln Asp Leu Lys Ala Arg Arg Pro Leu Cys Asp Ser Gly Tyr Tyr Ser
                325                 330                 335
Thr Phe Asn Arg Asp Asn Val Arg Leu Glu Asp Val Lys Ala Asn Pro
                340                 345                 350
Ile Val Glu Ile Thr Glu Asn Gly Val Lys Leu Glu Asn Gly Asp Phe
                355                 360                 365
Val Glu Leu Asp Met Leu Ile Cys Ala Thr Gly Phe Asp Ala Val Asp
            370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
                420                 425                 430
Gly Asn Ala Pro Pro Ser Ile Glu Ser Gln Val Glu Trp Ile Ser Asp
                435                 440                 445
Thr Ile Gln Tyr Thr Val Glu Asn Asn Val Glu Ser Ile Glu Ala Thr
            450                 455                 460
```

| Lys | Glu | Ala | Glu | Glu | Gln | Trp | Ile | Gln | Thr | Cys | Ala | Asn | Ile | Ala | Glu |
|---|---|---|---|---|---|---|---|---|---|---|---|---|---|---|---|
| 465 | | | | 470 | | | | 475 | | | | 480 | | | |

| Met | Thr | Leu | Cys | Pro | Glu | Ala | Gln | Ser | Leu | Val | Lys | Gly | Ala | Asn | Ile |
|---|---|---|---|---|---|---|---|---|---|---|---|---|---|---|---|
| | | | | 485 | | | | 490 | | | | 495 | | | |

| Pro | Gly | Lys | Lys | Asn | Thr | Ala | Ile | Lys | Tyr | Leu | Gly | Gly | Leu | Lys | Asn |
|---|---|---|---|---|---|---|---|---|---|---|---|---|---|---|---|
| | 500 | | | | | 505 | | | | 510 | | | | | |

| Tyr | Arg | Ser | Ala | Leu | Ala | Asn | Cys | Lys | Asn | His | Ala | Tyr | Glu | Gly | Phe |
|---|---|---|---|---|---|---|---|---|---|---|---|---|---|---|---|
| | 515 | | | | 520 | | | | 525 | | | | | | |

| Asp | Ile | Gln | Pro | Gln | Arg | Ser | Asp | Ile | Lys | Gln | Pro | Ala | Asn | Ala | |
|---|---|---|---|---|---|---|---|---|---|---|---|---|---|---|---|
| 530 | | | | 535 | | | | 540 | | | | | | | |

<210> SEQ ID NO 89
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 89

```
atgtctacca agatggattt cgatgccatc gtgatcggtg ggggctttgg cggtctgtat      60
gccgttaaaa aactgcgcga tgaactggag ctgaaagttc aagccttcga aaggcaact     120
gacgtaggcg gtacatggta ctggaaccgc tacccgggtg ccctgaccga taccgaaacc     180
catttgtatt gttattcctg gacaaggaa ctgttgcaga gtatgaaat caaaaccaaa      240
tacgcgcaag gtccagacgt gcgcaaatat ctgcagcagg ttgccgaaaa acacgtatta     300
aaaaaaagtt accagttcaa caccgcaatg caatctgccc actacaacga gcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca aggctctac cggcgtgcaa gttattacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaatgcg cgcggtggtat cggttttttac     840
atcgaaaccct ttggtgatat tgcgacgaac atggaagcta acattgaggc acaaaatttt     900
atcaaaggta aaatcgcgga gatcgtcaaa gatccggcga tcgcccaaaa actgatgccg     960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaaacggcga tttcgtggag ctggacatgc tgatctgcgc gacgggtttt    1140
gatgcggtag acggcaacta tgttcgcatg gatatccaag gcgtaacgg tctggccatg    1200
aaggattact ggaagagggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc agtataccg tcgaaaataa cgtggaatct    1380
attgaagcca cgaaggaagc ggaggaacag tggattcaaa cctgcgccaa tattgcggag    1440
atgaccctgt ttccagaggc ccagagcctg gttaaagggg cgaacattcc aggcaagaag    1500
aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
```

<210> SEQ ID NO 90
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 90

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Cys Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350
```

```
Ile Val Glu Ile Thr Glu Asn Gly Val Lys Leu Lys Asn Gly Asp Phe
            355                 360                 365

Val Glu Leu Asp Met Leu Ile Cys Ala Thr Gly Phe Asp Ala Val Asp
        370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
            405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Leu Val Lys Gly Ala Asn Ile
            485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
            530                 535                 540
```

<210> SEQ ID NO 91
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 91

```
atgtctacca agatggattt cgatgccatc gtgatcggtg ggggctttgg cggtctgtat     60
gccgttaaaa aactgcgcga tgaactggag ctgaaagttc aagccttcga aaggcaact    120
gacgtaggcg gtacatggta ctggaaccgc tacccgggtg ccctgaccga taccgaaacc    180
catttgtatt gttattcctg ggacaaggaa ctgttgcaga gtatggaaat caaaaccaaa    240
tacgcgcaag gtccagacgt gcgcaaatat ctgcagcagg ttgccgaaaa acacgtatta    300
aaaaaagttt accagttcaa caccgcaatg caatctgccc actacaacga gcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta agcggtttt tgagaaggcg tggcaatgcg gcggtggtat cggttttttac    840
atcgaaacct ttggtgatat tctgacgaac atggaagcta acattgaggc acaaattttt    900
atcaaaggta aatcgcgga gatcgtcaaa gatccggcga tcgcccaaaa actgatgccg    960
caggacctga aggcacgtcg ccctctgtgt gactccgggt actataatac gttcaatcgc   1020
```

-continued

```
gacaacgtac gtctggagga tgtcaaagca atccgatcg tcgagatcac cgaaaacggc      1080
gtgaaactga aaacggcga tttcgtggag ctggacatgc tgatctgcgc gacgggtttt      1140
gatgcggtag acggcaacta tgttcgcatg gatatccaag ggcgtaacgg tctggccatg     1200
aaggattact ggaaagaggg cccgtctagc tacctgggcg taaccgtgaa taattaccca     1260
aacatgttta tggttagcgg tccaaacggt ccatctggta acgctccgcc tagcattgaa     1320
agtcaagttg aatggattag cgatactatc cagtataccg tcgaaaataa cgtggaatct     1380
attgaagcca cgaaggaagc ggaggaacag tggattcaaa cctgcgccaa tattgcggag     1440
atgaccctgt ttccagaggc ccagagcctg gttaaagggg cgaacattcc aggcaagaag     1500
aacaccgcga tcaaatattt gggtgggctg aaaaactacc gctcagcttt ggcgaattgt     1560
aaaaatcatg cgtatgaagg ctttgatatt cagccgcaac gttctgacat caaagaacca     1620
gcgaatgcg                                                              1629
```

<210> SEQ ID NO 92
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 92

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
```

|  | | 245 | | | | 250 | | | | 255 | |
|---|---|---|---|---|---|---|---|---|---|---|---|

Ser Val Ser Ala Glu Glu Arg Lys Ala Val Phe Glu Lys Ala Trp Gln
    260                 265                 270

Cys Gly Gly Gly Ile Gly Phe Tyr Ile Glu Thr Phe Gly Asp Ile Leu
            275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Leu Val Lys Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Glu Pro Ala Asn Ala
    530                 535                 540

<210> SEQ ID NO 93
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 93

```
atgtctacca agatggattt cgatgccatc gtgatcggtg ggggctttgg cggtctgtat      60
gccgttaaaa aactgcgcga tgaactggag ctgaaagttc aagccttcga agaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caagaaaaaa     240
tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360
ctgtgggaag taactacgga atacggggat aagtacaccg cacgtttcct gattactgcc     420
```

```
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttgtcacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgata aatctggga tggtgtttgg    720 aacagtgcgc tggccttcgg cctgaatgaa tctactgtgc cggccatgtc cgtaagtgcg    780
gaagagcgta aagcggtttt tgagaaggcg tggcaatgcg gcggtggtat cggttttac     840 atcgaaacct ttggtgatat tctgacgaac atggaagcta acattgaggc acaaaatttt    900
atcaaaggta aaatcgcgga gatcgtcaaa gatccggcga tcgcccaaaa actgatgccg    960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggattcaaa cctgcgccaa tattgcggag    1440
atgaccctgt gtccagaggc tcagagcctg gttaaagggg cgaacattcc aggcaagaag    1500
aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 94
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 94

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Glu Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
            165                 170                 175

Lys Arg Val Gly Val Ile Gly Thr Gly Ser Thr Gly Val Gln Val Val
            180                 185                 190

Thr Ala Val Ala Pro Leu Ala Lys His Leu Thr Val Phe Gln Arg Thr
            195                 200                 205

Ala Gln Tyr Ser Val Pro Ile Ser Asn Asp Pro Leu Ser Glu Glu Asp
210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
            245                 250                 255

Ser Val Ser Ala Glu Glu Arg Lys Ala Val Phe Glu Lys Ala Trp Gln
            260                 265                 270

Cys Gly Gly Gly Ile Gly Phe Tyr Ile Glu Thr Phe Gly Asp Ile Leu
            275                 280                 285

Thr Asn Met Glu Ala Asn Ile Glu Ala Gln Asn Phe Ile Lys Gly Lys
            290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
            325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
            355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
            405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
            435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Ile Ala Glu
465                 470                 475                 480

Met Thr Leu Cys Pro Glu Ala Gln Ser Leu Val Lys Gly Ala Asn Ile
            485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
            530                 535                 540

<210> SEQ ID NO 95
<211> LENGTH: 1629

<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 95

```
atgtctacca agatggattt cgatgccatc gtgatcggtg ggggctttgg cggtctgtat        60
gccgttaaaa aactgcgcga tgaactggag ctgaaagttc aagccttcga aaggcaact        120
gacgtaggcg gtacatggta ctggaaccgc tacccgggtg ccctgaccga taccgaaacc      180
catttgtatt gttattcctg ggacaaggaa ctgttgcaga gtatggaaat caaaaccaaa       240
tacgcgcaag gtccagacgt gcgcaaatat ctgcagcagg ttgccgaaaa acacgtatta      300
aaaaaagtt accagttcaa caccgcaatg caatctgccc actacaacga agcggacgct        360
ctgtgggaag taactacgga atacggggat aagtacaccg cacgtttcct gattactgcc      420
ttaggtgggc tgtctgcacc taacctgcca aatatcaagg gcatcaatca gtttaaaggc      480
gacctgcacc atactgcccg ctggccggat gacgttagta tcgaaggcaa acgtgtgggt      540
gtgatcggca caggctctac cggcgtgcaa gttattacgg cagtggcgcc actggccaag      600
cacctgacgg tgtttcagcg tacggcccag tactcggtcc cgatcagcaa cgatccactg      660
agcgaagaag acgtcaagaa gatcaaagat aactatgata aaatctggga tggtgtttgg      720
aacagtgcgc tggccttcgg cctgaatgaa tctactgtgc cggccatgtc cgtaagtgcg      780
gaagagcgta aagcggtttt tgagaaggcg tggcaatccg gcggtggtat cggtttttac      840
atcgaaacct ttggtgatat tctgacgaac atggaagcta acattgaggc acaaaatttt       900
atcaaaggta aatcgcgga atcgtcaaa gatccggcgc tgcccaaaa actgatgccg        960
caggacctga aggcacgtcg cccctctgtgt gactccgggt actataatac gttcaatcgc      1020
gacaacgtac gtctggagga tgtcaaagca aatccgatcg tcgagatcac cgaaaacggc      1080
gtgaaactgg aaaacggcga tttcgtggag ctggacatgc tgatctgcgc gacgggtttt      1140
gatgcggtag acggcaacta tgttcgcatg gatatccaag gcgtaacgg tctggccatg        1200
aaggattact ggaaagaggg cccgtctagc tacctgggcg taaccgtgaa taattaccca      1260
aacatgttta tggttagcgg tccaaacggt ccatctggta acgctccgcc tagcattgaa      1320
agtcaagttg aatggattag cgatactatc cagtataccg tcgaaaataa cgtggaatct      1380
attgaagcca cgaaggaagc ggaggaacag tggattcaaa cctgcgccaa tattgcggag      1440
atgaccctgt gtccagaggc ccagagcctg gttaaagggg cgaacattcc aggcaagaag      1500
aacaccgcga tcaaatattt gggtgggctg aaaaactacc gctcagcttt ggcgaattgt      1560
aaaaatcatg cgtatgaagg ctttgatatt cagccgcaac gttctgacat caaacaacca      1620
gcgaatgcg                                                               1629
```

<210> SEQ ID NO 96
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 96

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30
```

```
Val Gln Ala Phe Glu Lys Ala Thr Asp Val Gly Gly Thr Trp Tyr Trp
         35                  40                  45

Asn Arg Tyr Pro Gly Ala Leu Thr Asp Thr Glu Thr His Leu Tyr Cys
 50                  55                  60

Tyr Ser Trp Asp Lys Glu Leu Leu Gln Ser Met Glu Ile Lys Thr Lys
 65                  70                  75                  80

Tyr Ala Gln Gly Pro Asp Val Arg Lys Tyr Leu Gln Gln Val Ala Glu
                 85                  90                  95

Lys His Val Leu Lys Lys Ser Tyr Gln Phe Asn Thr Ala Met Gln Ser
             100                 105                 110

Ala His Tyr Asn Glu Ala Asp Ala Leu Trp Glu Val Thr Thr Glu Tyr
             115                 120                 125

Gly Asp Lys Tyr Thr Ala Arg Phe Leu Ile Thr Ala Leu Gly Gly Leu
         130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                 165                 170                 175

Lys Arg Val Gly Val Ile Gly Thr Gly Ser Thr Gly Val Gln Val Ile
             180                 185                 190

Thr Ala Val Ala Pro Leu Ala Lys His Leu Thr Val Phe Gln Arg Thr
         195                 200                 205

Ala Gln Tyr Ser Val Pro Ile Ser Asn Asp Pro Leu Ser Glu Glu Asp
         210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                 245                 250                 255

Ser Val Ser Ala Glu Glu Arg Lys Ala Val Phe Glu Lys Ala Trp Gln
                 260                 265                 270

Ser Gly Gly Gly Ile Gly Phe Tyr Ile Glu Thr Phe Gly Asp Ile Leu
         275                 280                 285

Thr Asn Met Glu Ala Asn Ile Glu Ala Gln Asn Phe Ile Lys Gly Lys
         290                 295                 300

Ile Ala Glu Ile Val Lys Asp Pro Ala Leu Ala Gln Lys Leu Met Pro
305                 310                 315                 320

Gln Asp Leu Lys Ala Arg Arg Pro Leu Cys Asp Ser Gly Tyr Tyr Asn
                 325                 330                 335

Thr Phe Asn Arg Asp Asn Val Arg Leu Glu Asp Val Lys Ala Asn Pro
                 340                 345                 350

Ile Val Glu Ile Thr Glu Asn Gly Val Lys Leu Glu Asn Gly Asp Phe
             355                 360                 365

Val Glu Leu Asp Met Leu Ile Cys Ala Thr Gly Phe Asp Ala Val Asp
         370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                 405                 410                 415

Asn Asn Tyr Pro Asn Met Phe Met Val Ser Gly Pro Asn Gly Pro Ser
                 420                 425                 430

Gly Asn Ala Pro Pro Ser Ile Glu Ser Gln Val Glu Trp Ile Ser Asp
             435                 440                 445

Thr Ile Gln Tyr Thr Val Glu Asn Asn Val Glu Ser Ile Glu Ala Thr
```

```
                    450              455              460
Lys Glu Ala Glu Glu Gln Trp Ile Gln Thr Cys Ala Asn Ile Ala Glu
465                 470              475                  480

Met Thr Leu Cys Pro Glu Ala Gln Ser Leu Val Lys Gly Ala Asn Ile
                485              490                  495

Pro Gly Lys Lys Asn Thr Ala Ile Lys Tyr Leu Gly Gly Leu Lys Asn
            500              505              510

Tyr Arg Ser Ala Leu Ala Asn Cys Lys Asn His Ala Tyr Glu Gly Phe
        515              520              525

Asp Ile Gln Pro Gln Arg Ser Asp Ile Lys Gln Pro Ala Asn Ala
        530              535              540

<210> SEQ ID NO 97
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 97
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg gacaaggaa ctgttgcaga gtatggaaat caaaaccaaa      240
tacgcgcaag gtccagacgt gcgcaaatat ctgcagcagg ttgccgaaaa acacgtatta     300 aaaaaagtt accagttcaa caccgcaatg caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaggc     480 gacctgcacc atactgcccg ctggccggat gacgttagta tcgaaggcaa acgtgtgggt     540
gtgatcggca caggctctac cggcgtgcaa gttgtcacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgata aatctgggga tggtgttttgg    720 aacagtgcgc tggccttcgg cctgaatgaa tctactgtgc cggccatgtc cgtaagtgcg     780
gaagagcgta agcggttttt tgagaaggcg tggcaatccg cggtggtat cggtttttac      840 atcgaaacct ttggtgatat tgcgacgaac atggaagcta acattgaggc acaaaatttt     900
atcaaaggta aaatcgcgga tcgtcaaa gatccggcga tcgcccaaaa actgatgccg       960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag gcgtaacgg tctggccatg    1200 aaggattact ggaaagaggg cccgtctagc tacctgggcg taaccgtgaa taattaccca    1260
aacatgttta tggttagcgg tccaaacggt ccatctggta acgctccgcc tagcattgaa    1320
agtcaagttg aatggattag cgatactatc cagtataccg tcgaaaataa cgtggaatct    1380
attgaagcca cgaaggaagc ggaggaacag tggattcaaa cctgcgccaa tattgcggag    1440
atgaccctgt ttccagaggc ccagagcctg gttaaagggg cgaacattcc aggcaagaag    1500
aacaccgcga tcaaatattt gggtgggctg aaaaactacc gctcagcttt ggcgaattgt    1560
```

```
aaaaatcatg cgtatgaagg ctttgatatt cagccgcaac gttctgacat caaacaacca      1620
gcgaatgcg                                                              1629
```

<210> SEQ ID NO 98
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 98

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Val
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350
```

```
Ile Val Glu Ile Thr Glu Asn Gly Val Lys Leu Glu Asn Gly Asp Phe
            355                 360                 365
Val Glu Leu Asp Met Leu Ile Cys Ala Thr Gly Phe Asp Ala Val Asp
    370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
            405                 410                 415
Asn Asn Tyr Pro Asn Met Phe Met Val Ser Gly Pro Asn Gly Pro Ser
            420                 425                 430
Gly Asn Ala Pro Pro Ser Ile Glu Ser Gln Val Glu Trp Ile Ser Asp
            435                 440                 445
Thr Ile Gln Tyr Thr Val Glu Asn Asn Val Glu Ser Ile Glu Ala Thr
    450                 455                 460
Lys Glu Ala Glu Glu Gln Trp Ile Gln Thr Cys Ala Asn Ile Ala Glu
465                 470                 475                 480
Met Thr Leu Phe Pro Glu Ala Gln Ser Leu Val Lys Gly Ala Asn Ile
            485                 490                 495
Pro Gly Lys Lys Asn Thr Ala Ile Lys Tyr Leu Gly Leu Lys Asn
            500                 505                 510
Tyr Arg Ser Ala Leu Ala Asn Cys Lys Asn His Ala Tyr Glu Gly Phe
            515                 520                 525
Asp Ile Gln Pro Gln Arg Ser Asp Ile Lys Gln Pro Ala Asn Ala
            530                 535                 540

<210> SEQ ID NO 99
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 99
atgtctacca agatggattt cgatgccatc gtgatcggtg ggggctttgg cggtctgtat        60
gccgttaaaa aactgcgcga tgaactggag ctgaaagttc aagccttcga aggcaact         120 gacgtaggcg gtacatggta ctggaaccgc tacccgggtg ccctgaccga taccgaaacc       180
catttgtatt gttattcctg ggacaaggaa ctgttgcaga gtatggaaat caagaaaaaa       240
tacgcgcaag gtccagacgt gcgcaaatat ctgcagcagg ttgccgaaaa acacgtatta       300
aaaaaaagtt accagttcaa caccgcaatg caatctgccc actacaacga agcggacgct       360
ctgtgggaag taactacgga atacggggat aagtacaccg cacgtttcct gattactgcc       420
ttaggtgggc tgtctgcacc taacctgcca aatatcaagg gcatcaatca gtttaaaggc       480
gacctgcacc atactggtcg ctggccggat gacgttagta tcgaaggcaa acgtgtgggt       540
gtgatcggca caggctctac cggcgtgcaa gttattacgg cagtggcgcc actggccaag       600
cacctgacgg tgtttcagcg tacggcccag tactcggtcc cgatcagcaa cgatccactg       660
agcgaagaag acgtcaagaa gatcaaagat aactatgata aaatctggga tggtgtttgg       720
aacagtgcgc tggccttcgg cctgaatgaa tctactgtgc cggccatgtc cgtaagtgcg       780
gaagagcgta agcggtttt tgagaaggcg tggcaatgcg gcggtggtat cggttttac        840 atcgaaacct ttggtgatat tctgacgaac atggaagcta acattgaggc acaaatttt       900 atcaaaggta aatcgcgga gatcgtcaaa gatccggcgc tggcccaaaa actgatgccg       960
```

```
caggacctga aggcacgtcg ccctctgtgt gactccgggt actataatac gttcaatcgc   1020
gacaacgtac gtctggagga tgtcaaagca atccgatcg tcgagatcac cgaaaacggc    1080
gtgaaactgg aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt gtccagaggc ccagagcctg gttaaagggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 100
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 100

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Glu Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Gly Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240
```

```
Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
        260                 265                 270

Cys Gly Gly Gly Ile Gly Phe Tyr Ile Glu Thr Phe Gly Asp Ile Leu
            275                 280                 285

Thr Asn Met Glu Ala Asn Ile Glu Ala Gln Asn Phe Ile Lys Gly Lys
        290                 295                 300

Ile Ala Glu Ile Val Lys Asp Pro Ala Leu Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Ser Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Gln Thr Cys Ala Asn Ile Ala Glu
465                 470                 475                 480

Met Thr Leu Cys Pro Glu Ala Gln Ser Leu Val Lys Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 101
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 101
atgtctacca agatggattt cgatgccatc gtgatcggtg ggggctttgg cggtctgtat      60
gccgttaaaa aactgcgcga tgaactggag ctgaaagttc aagccttcga agaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300 aaaaaagtt accagttcaa caccgcaatg caatctgccc actacaacga agcggacgct     360
```

```
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatccg gcggtggtat cggttttttac   840 atcgaaacct ttggtgatat tgtgacgaac atggaagcta acattgaggc acaaaatttt    900
atcaaaggta aatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactgg aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tagcattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt gtccagaggc ccagagcctg gttaaagggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629

<210> SEQ ID NO 102
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 102

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
```

```
                130                 135                 140
Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
                165                 170                 175

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Thr
                195                 200                 205

Ala Gln Tyr Ser Val Pro Ile Ser Asn Asp Pro Leu Ser Glu Glu Asp
                210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
                260                 265                 270

Ser Gly Gly Gly Ile Gly Phe Tyr Ile Glu Thr Phe Gly Asp Ile Val
                275                 280                 285

Thr Asn Met Glu Ala Asn Ile Glu Ala Gln Asn Phe Ile Lys Gly Lys
                290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Glu Asn Gly Asp Phe
                355                 360                 365

Val Glu Leu Asp Met Leu Ile Cys Ala Thr Gly Phe Asp Ala Val Asp
                370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Ser Ile Glu Ser Gln Val Glu Trp Ile Ser Asp
                435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Ile Ala Glu
465                 470                 475                 480

Met Thr Leu Cys Pro Glu Ala Gln Ser Leu Val Lys Gly Ala Asn Ile
                485                 490                 495

Pro Gly Lys Lys Asn Thr Ala Ile Lys Tyr Leu Gly Gly Leu Lys Asn
                500                 505                 510

Tyr Arg Ser Ala Leu Ala Asn Cys Lys Asn His Ala Tyr Glu Gly Phe
                515                 520                 525

Asp Ile Gln Pro Gln Arg Ser Asp Ile Lys Gln Pro Ala Asn Ala
                530                 535                 540

<210> SEQ ID NO 103
```

<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 103

```
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360
ctgtgggaag taactacgga atacgggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttgtcacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgata aaatctggga tggtgttttgg     720
aacagtgcgc tggccttcgg cctgaatgaa tctactgtgc cggccatgtc cgtaagtgcg     780
gaagagcgta agcggttttt tgagaaggcg tggcaatccg gcggtggtat cggttttttac     840
atcgaaacct ttggtgatat tgtgacgaac atggaagcta acattgaggc acaaaattt     900
atcaaaggta aaatcgcgga gatcgtcaaa gatccggcga tcgcccaaaa actgatgccg     960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag gcgtaacgg tctggccatg    1200
aaggattact ggaaagaggg cccgtctagc tacctgggcg taaccgtgaa taattaccca    1260
aacatgtttta tggttagcgg tccaaacggt ccatctggta acgctccgcc tagcattgaa    1320
agtcaagttg aatggattag cgatactatc cagtataccg tcgaaaataa cgtgaatct    1380
attgaagcca cgaaggaagc ggaggaacag tggattcaaa cctgcgccaa tattgcggag    1440
atgaccctgt ttccagaggc ccaaagcctg gttaaagggg cgaacattcc aggcaagaag    1500
aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 104
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 104

```
Met Ser Thr Lys Met Asp Phe Asp Ala Ile Val Ile Gly Gly Gly Phe
1               5                   10                  15
Gly Gly Leu Tyr Ala Val Lys Lys Leu Arg Asp Glu Leu Glu Leu Lys
            20                  25                  30
```

```
Val Gln Ala Phe Glu Lys Ala Thr Asp Val Gly Gly Thr Trp Tyr Trp
         35                  40                  45

Asn Arg Tyr Pro Gly Ala Leu Thr Asp Thr Glu Thr His Leu Tyr Cys
         50                  55                  60

Tyr Ser Trp Asp Lys Glu Leu Leu Gln Ser Met Glu Ile Lys Thr Lys
 65                  70                  75                  80

Tyr Ala Gln Gly Pro Asp Val Arg Lys Tyr Leu Gln Gln Val Ala Glu
                 85                  90                  95

Lys His Val Leu Lys Lys Ser Tyr Gln Phe Asn Thr Ala Met Gln Ser
                100                 105                 110

Ala His Tyr Asn Glu Ala Asp Ala Leu Trp Glu Val Thr Thr Glu Tyr
                115                 120                 125

Gly Asp Lys Tyr Thr Ala Arg Phe Leu Ile Thr Ala Leu Gly Gly Leu
                130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
                165                 170                 175

Lys Arg Val Gly Val Ile Gly Thr Gly Ser Thr Gly Val Gln Val Val
                180                 185                 190

Thr Ala Val Ala Pro Leu Ala Lys His Leu Thr Val Phe Gln Arg Thr
                195                 200                 205

Ala Gln Tyr Ser Val Pro Ile Ser Asn Asp Pro Leu Ser Glu Glu Asp
                210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
                260                 265                 270

Ser Gly Gly Gly Ile Gly Phe Tyr Ile Glu Thr Phe Gly Asp Ile Val
                275                 280                 285

Thr Asn Met Glu Ala Asn Ile Glu Ala Gln Asn Phe Ile Lys Gly Lys
                290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Glu Asn Gly Asp Phe
                355                 360                 365

Val Glu Leu Asp Met Leu Ile Cys Ala Thr Gly Phe Asp Ala Val Asp
                370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Ser Ile Glu Ser Gln Val Glu Trp Ile Ser Asp
                435                 440                 445
```

| Thr | Ile | Gln | Tyr | Thr | Val | Glu | Asn | Asn | Val | Glu | Ser | Ile | Glu | Ala | Thr |
|---|---|---|---|---|---|---|---|---|---|---|---|---|---|---|---|
|  | 450 |  |  |  | 455 |  |  |  | 460 |  |  |  |  |  |  |

| Lys | Glu | Ala | Glu | Glu | Gln | Trp | Ile | Gln | Thr | Cys | Ala | Asn | Ile | Ala | Glu |
|---|---|---|---|---|---|---|---|---|---|---|---|---|---|---|---|
| 465 |  |  |  |  | 470 |  |  |  |  | 475 |  |  |  |  | 480 |

| Met | Thr | Leu | Phe | Pro | Glu | Ala | Gln | Ser | Leu | Val | Lys | Gly | Ala | Asn | Ile |
|---|---|---|---|---|---|---|---|---|---|---|---|---|---|---|---|
|  |  |  |  | 485 |  |  |  |  | 490 |  |  |  |  | 495 |  |

| Pro | Gly | Lys | Lys | Asn | Thr | Ala | Ile | Lys | Tyr | Leu | Gly | Gly | Leu | Lys | Asn |
|---|---|---|---|---|---|---|---|---|---|---|---|---|---|---|---|
|  |  |  | 500 |  |  |  |  | 505 |  |  |  |  | 510 |  |  |

| Tyr | Arg | Ser | Ala | Leu | Ala | Asn | Cys | Lys | Asn | His | Ala | Tyr | Glu | Gly | Phe |
|---|---|---|---|---|---|---|---|---|---|---|---|---|---|---|---|
|  |  | 515 |  |  |  |  | 520 |  |  |  |  | 525 |  |  |  |

| Asp | Ile | Gln | Pro | Gln | Arg | Ser | Asp | Ile | Lys | Gln | Pro | Ala | Asn | Ala |
|---|---|---|---|---|---|---|---|---|---|---|---|---|---|---|
| 530 |  |  |  |  | 535 |  |  |  |  | 540 |  |  |  |  |

<210> SEQ ID NO 105
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 105

| atgtctacca | agatggattt | cgatgccatc | gtgatcggtg | ggggctttgg | cggtctgtat | 60 |
|---|---|---|---|---|---|---|
| gccgttaaaa | aactgcgcga | tgaactggag | ctgaaagttc | aagccttcga | agaggcaact | 120 |
| gacgtaggcg | gtacatggta | ctggaaccgc | tacccgggtg | ccctgaccga | taccgaaacc | 180 |
| catttgtatt | gttattcctg | ggacaaggaa | ctgttgcaga | gtatggaaat | caaaaccaaa | 240 |
| tacgcgcaag | gtccagacgt | gcgcaaatat | ctgcagcagg | ttgccgaaaa | acacgtatta | 300 |
| aaaaaaagtt | accagttcaa | caccgcaatg | caatctgccc | actacaacga | agcggacgct | 360 |
| ctgtgggaag | taactacgga | atacggggat | aagtacaccg | cacgtttcct | gattactgcc | 420 |
| ttaggtgggc | tgtctgcacc | taacctgcca | aatatcaagg | gcatcaatca | gtttaaaggc | 480 |
| gacctgcacc | atactgcccg | ctggccggat | gacgttagta | tcgaaggcaa | acgtgtgggt | 540 |
| gtgatcggca | caggctctac | cggcgtgcaa | gttattacgg | cagtggcgcc | actggccaag | 600 |
| cacctgacgg | tgtttcagcg | tacggcccag | tactcggtcc | cgatcagcaa | cgatccactg | 660 |
| agcgaagaag | acgtcaagaa | gatcaaagat | aactatgata | aaatctggga | tggtgtttgg | 720 |
| aacagtgcgc | tggccttcgg | cctgaatgaa | tctactgtgc | cggccatgtc | cgtaagtgcg | 780 |
| gaagagcgta | agcggttttt | tgagaaggcg | tggcaatgcg | gcggtggtat | cgcttttttac | 840 |
| atcgaaacct | ttggtgatat | tgcgacgaac | atggaagcta | acattgaggc | acaaaatttt | 900 |
| atcaaaggta | aaatcgcgga | gatcgtcaaa | gatccggcga | tcgcccaaaa | actgatgccg | 960 |
| caggacctga | aggcacgtcg | ccctctgtgt | gactccgggt | actataatac | gttcaatcgc | 1020 |
| gacaacgtac | gtctggagga | tgtcaaagca | aatccgatcg | tcgagatcac | cgaaaacggc | 1080 |
| gtgaaactga | aaaacggcga | tttcgtggag | ctggacatgc | tgatctgcgc | gacgggtttt | 1140 |
| gatgcggtag | acggcaacta | tgttcgcatg | gatatccaag | ggcgtaacgg | tctggccatg | 1200 |
| aaggattact | ggaagagggg | cccgtctagc | tacctgggcg | taaccgtgaa | taattaccca | 1260 |
| aacatgttta | tggttagcgg | tccaaacggt | ccatctggta | acgctccgcc | tagcattgaa | 1320 |
| agtcaagttg | aatggattag | cgatactatc | cagtataccg | tcgaaaataa | cgtggaatct | 1380 |
| attgaagcca | cgaaggaagc | ggaggaacag | tggattcaaa | cctgcgccaa | tattgcggag | 1440 |
| atgaccctgt | ttccagaggc | ccagagcctg | gttaaagggg | cgaacattcc | aggcaagaag | 1500 |
| aacaccgcga | tcaaatattt | gggtgggctg | aaaaactacc | gctcagcttt | ggcgaattgt | 1560 |

```
aaaaatcatg cgtatgaagg ctttgatatt cagccgcaac gttctgacat caaacaacca   1620
gcgaatgcg                                                            1629
```

<210> SEQ ID NO 106  
<211> LENGTH: 543  
<212> TYPE: PRT  
<213> ORGANISM: Artificial Sequence  
<220> FEATURE:  
<223> OTHER INFORMATION: Variant of CHMO from Acinetobacter sp NCIMB9871

<400> SEQUENCE: 106

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Cys Gly Gly Gly Ile Ala Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
```

```
              340               345               350
Ile Val Glu Ile Thr Glu Asn Gly Val Lys Leu Lys Asn Gly Asp Phe
                355               360               365
Val Glu Leu Asp Met Leu Ile Cys Ala Thr Gly Phe Asp Ala Val Asp
            370               375               380
Gly Asn Tyr Val Arg Met Asp Ile Gln Gly Arg Asn Gly Leu Ala Met
385               390               395               400
Lys Asp Tyr Trp Lys Glu Gly Pro Ser Ser Tyr Leu Gly Val Thr Val
                405               410               415
Asn Asn Tyr Pro Asn Met Phe Met Val Ser Gly Pro Asn Gly Pro Ser
                420               425               430
Gly Asn Ala Pro Pro Ser Ile Glu Ser Gln Val Glu Trp Ile Ser Asp
                435               440               445
Thr Ile Gln Tyr Thr Val Glu Asn Asn Val Glu Ser Ile Glu Ala Thr
            450               455               460
Lys Glu Ala Glu Glu Gln Trp Ile Gln Thr Cys Ala Asn Ile Ala Glu
465               470               475               480
Met Thr Leu Phe Pro Glu Ala Gln Ser Leu Val Lys Gly Ala Asn Ile
                485               490               495
Pro Gly Lys Lys Asn Thr Ala Ile Lys Tyr Leu Gly Gly Leu Lys Asn
                500               505               510
Tyr Arg Ser Ala Leu Ala Asn Cys Lys Asn His Ala Tyr Glu Gly Phe
            515               520               525
Asp Ile Gln Pro Gln Arg Ser Asp Ile Lys Gln Pro Ala Asn Ala
        530               535               540

<210> SEQ ID NO 107
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 107
atgtctacca agatggattt cgatgccatc gtgatcggtg ggggctttgg cggtctgtat      60
gccgttaaaa aactgcgcga tgaactggag ctgaaagttc aagccttcga agggcaact      120 gacgtaggcg gtacatggta ctggaaccgc taccccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgatg acatctggga tggtgtttgg     720
aacagtgcgc tggccttcgg cctgaatgaa tctactgtgc cggccatgtc cgtaagtgcg     780
gaagagcgta agcggttttt gagaaggcg tggcaatgcg gcggtggtat cggttttta c    840 atcgaaacct tggtgatat tgcgacgaac atggaagcta acattgaggc acaaattttt     900
atcaaaggta aaatcgcgga gatcgtcaaa gatccggcga tcgcccaaaa actgatgccg     960
```

```
caggacctga aggcacgtcg ccctctgtgt gactccgggt actataatac gttcaatcgc    1020
gacaacgtac gtctggagga tgtcaaagca atccgatcg tcgagatcac cgaaaacggc    1080
gtgaaactga aaacggcga tttcgtggag ctggacatgc tgatctgcgc gacgggtttt    1140
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tatgattgaa    1320
agtcaagttg aatggattag cgatactatc cagtataccg tcgaaaataa cgtggaatct    1380
attgaagcca cgaaggaagc ggaggaacag tggattcaaa cctgcgccaa tattgcggag    1440
atgaccctgt ttccagaggc ccagagccag ttttttgggg cgaacattcc aggcaagaag    1500
aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                             1629
```

<210> SEQ ID NO 108
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 108

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Ile Trp Asp Gly Val Trp
225                 230                 235                 240
```

Asn Ser Ala Leu Ala Phe Gly Leu Asn Glu Ser Thr Val Pro Ala Met
            245                 250                 255

Ser Val Ser Ala Glu Glu Arg Lys Ala Val Phe Glu Lys Ala Trp Gln
        260                 265                 270

Cys Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Met Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Gln Val Phe Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 109
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 109
atgtctacca agatggattt cgatgccatc gtgatcggtg ggggctttgg cggtctgtat      60
gccgttaaaa aactgcgcga tgaactggag ctgaaagttc aagccttcga agaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360

-continued

```
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcagcaa cgatccactg    660
agcgaagaag acgtcaagga aatcaaagat aactatgata aaatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatgcg cgtggtggtat cggttttttac   840 atcgaaacct ttggtgatat tgcgacgaac atggaagcta acattgaggc acaaaatttt    900
atcaaaggta aatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt gcccagaggc ccagagccag gtttttgggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                            1629
```

<210> SEQ ID NO 110
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 110

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125
```

-continued

```
Gly Asp Lys Tyr Thr Ala Arg Phe Leu Ile Thr Ala Leu Gly Gly Leu
130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
            165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
            195                 200                 205

Ala Gln Tyr Ser Val Pro Ile Ser Asn Asp Pro Leu Ser Glu Glu Asp
210                 215                 220

Val Lys Glu Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
                260                 265                 270

Cys Gly Gly Gly Ile Gly Phe Tyr Ile Glu Thr Phe Gly Asp Ile Ala
            275                 280                 285

Thr Asn Met Glu Ala Asn Ile Glu Ala Gln Asn Phe Ile Lys Gly Lys
        290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Met Ile Glu Ser Gln Val Glu Trp Ile Ser Asp
        435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Ile Ala Glu
465                 470                 475                 480

Met Thr Leu Cys Pro Glu Ala Gln Ser Gln Val Phe Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
530                 535                 540
```

<210> SEQ ID NO 111
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 111

```
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg gacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga gcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaatgcg gcggtggtat cggttttttac     840
atcgaaacct ttggtgatat tgcgacgaac atggaagcta acattgaggc acaaaatttt     900
atcaaaggta aatcgcggga gatcgtcgaa gatccggcga tcgcccaaaa actgatgccg     960
caggacctga aggcacgtcg ccctctgtgt gactccgggt actataatac gttcaatcgc    1020
gacaacgtac gtctggagga tgtcaaagca aatccgatcg tcgagatcac cgaaaacggc    1080
gtgaaactga aaacggcga tttcgtggag ctggacatgc tgatctgcgc gacgggtttt    1140
gatgcggtag acggcaacta tgttcgcatg gatatccaag gcgtaacgg tctggccatg    1200
aaggattact ggaagagggg cccgtctagc tacctgggcg taaccgtgaa taattaccca    1260
aacatgttta tggttagcgg tccaaacggt ccatctggta acgctccgcc tatgattgaa    1320
agtcaagttg aatggattag cgatactatc cagtataccg tcgaaaataa cgtggaatct    1380
attgaagcca cgaaggaagc ggaggaacag tggattcaaa cctgcgccaa tattgcggag    1440
atgaccctgt ttccagaggc ccagagccag gttaaagggg cgaacattcc aggcaagaag    1500
aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                          1629
```

<210> SEQ ID NO 112
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 112

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
```

-continued

```
               20                  25                  30
Val Gln Ala Phe Glu Lys Ala Thr Asp Val Gly Gly Thr Trp Tyr Trp
            35                  40                  45
Asn Arg Tyr Pro Gly Ala Leu Thr Asp Thr Glu Thr His Leu Tyr Cys
        50                  55                  60
Tyr Ser Trp Asp Lys Glu Leu Leu Gln Ser Met Glu Ile Lys Thr Lys
65                  70                  75                  80
Tyr Ala Gln Gly Pro Asp Val Arg Lys Tyr Leu Gln Gln Val Ala Glu
                85                  90                  95
Lys His Val Leu Lys Lys Ser Tyr Gln Phe Asn Thr Ala Met Gln Ser
            100                 105                 110
Ala His Tyr Asn Glu Ala Asp Ala Leu Trp Glu Val Thr Thr Glu Tyr
        115                 120                 125
Gly Asp Lys Tyr Thr Ala Arg Phe Leu Ile Thr Ala Leu Gly Gly Leu
    130                 135                 140
Ser Ala Pro Asn Leu Pro Asn Ile Lys Gly Ile Asn Gln Phe Lys Gly
145                 150                 155                 160
Asp Leu His His Thr Ala Arg Trp Pro Asp Val Ser Ile Glu Gly
                165                 170                 175
Lys Arg Val Gly Val Ile Gly Thr Gly Ser Thr Gly Val Gln Val Ile
            180                 185                 190
Thr Ala Val Ala Pro Leu Ala Lys His Leu Thr Val Phe Gln Arg Thr
        195                 200                 205
Ala Gln Tyr Ser Val Pro Ile Ser Asn Asp Pro Leu Ser Glu Glu Asp
    210                 215                 220
Val Lys Lys Ile Lys Asp Asn Tyr Asp Lys Ile Trp Asp Gly Val Trp
225                 230                 235                 240
Asn Ser Ala Leu Ala Phe Gly Leu Asn Glu Ser Thr Val Pro Ala Met
                245                 250                 255
Ser Val Ser Ala Glu Glu Arg Lys Ala Val Phe Glu Lys Ala Trp Gln
            260                 265                 270
Cys Gly Gly Gly Ile Gly Phe Tyr Ile Glu Thr Phe Gly Asp Ile Ala
        275                 280                 285
Thr Asn Met Glu Ala Asn Ile Glu Ala Gln Asn Phe Ile Lys Gly Lys
    290                 295                 300
Ile Ala Glu Ile Val Glu Asp Pro Ala Ile Ala Gln Lys Leu Met Pro
305                 310                 315                 320
Gln Asp Leu Lys Ala Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
            340                 345                 350
Ile Val Glu Ile Thr Glu Asn Gly Val Lys Leu Lys Asn Gly Asp Phe
        355                 360                 365
Val Glu Leu Asp Met Leu Ile Cys Ala Thr Gly Phe Asp Ala Val Asp
    370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
            420                 425                 430
Gly Asn Ala Pro Pro Met Ile Glu Ser Gln Val Glu Trp Ile Ser Asp
        435                 440                 445
```

```
Thr Ile Gln Tyr Thr Val Glu Asn Asn Val Glu Ser Ile Glu Ala Thr
    450                 455                 460
Lys Glu Ala Glu Glu Gln Trp Ile Gln Thr Cys Ala Asn Ile Ala Glu
465                 470                 475                 480
Met Thr Leu Phe Pro Glu Ala Gln Ser Gln Val Lys Gly Ala Asn Ile
                485                 490                 495
Pro Gly Lys Lys Asn Thr Ala Ile Lys Tyr Leu Gly Gly Leu Lys Asn
            500                 505                 510
Tyr Arg Ser Ala Leu Ala Asn Cys Lys Asn His Ala Tyr Glu Gly Phe
        515                 520                 525
Asp Ile Gln Pro Gln Arg Ser Asp Ile Lys Gln Pro Ala Asn Ala
    530                 535                 540

<210> SEQ ID NO 113
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 113
atgtctacca agatggattt cgatgccatc gtgatcggtg ggggctttgg cggtctgtat      60
gccgttaaaa aactgcgcga tgaactggag ctgaaagttc aagccttcga agaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300 aaaaaagtt accagttcaa caccgcaatg caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcagcaa cgatccactg     660
agcgaagaag acgtcaagga catcaaagat aactatgata aaatctggga tggtgtttgg     720
aacagtgcgc tggccttcgg cctgaatgaa tctactgtgc cggccatgtc cgtaagtgcg     780
gaagagcgta agcggttttt tgagaaggcg tggcaatgcg gcggtggtat cggttttac     840 atcgaaacct ttggtgatat tgcgacgaac atggaagcta acattgaggc acaaaatttt     900
atcaaaggta aaatcgcgga tcgtcgaa gatccggcga tcgcccaaaa actgatgccg     960
caggacctga aggcacgtcg ccctctgtgt gactccgggt actataatac gttcaatcgc    1020
gacaacgtac gtctggagga tgtcaaagca atccgatcg tcgagatcac cgaaaacggc    1080
gtgaaactga aaaacggcga tttcgtggag ctggacatgc tgatctgcgc gacgggtttt    1140
gatgcggtag acggcaacta tgttcgcatg gatatccaag gcgtaacgg tctggccatg    1200 aaggattact ggaaagaggg cccgtctagc tacctgggcg taaccgtgaa taattaccca    1260
aacatgttta tggttagcgg tccaaacggt ccatctggta acgctccgcc tatgattgaa    1320
agtcaagttg aatggattag cgatactatc cagtataccg tcgaaaataa cgtggaatct    1380
attgaagcca cgaaggaagc ggaggaacag tggattcaaa cctgcgccaa tattgcggag    1440
atgaccctgt ttccagaggc ccagagcctg gttaaggggg cgaacattcc aggcaagaag    1500
```

```
aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                              1629
```

<210> SEQ ID NO 114
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 114

```
Met Ser Thr Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Asp Ile Lys Asp Asn Tyr Asp Lys Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Cys Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Glu Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335
```

```
Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Met Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Leu Val Lys Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 115
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 115
atgtctacca agatggattt cgatgccatc gtgatcggtg ggggctttgg cggtctgtat      60
gccgttaaaa aactgcgcga tgaactggag ctgaaagttc aagccttcga agaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga agcggacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgttagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgatg acatctggga tggtgtttgg     720
aacagtgcgc tggccttcgg cctgaatgaa tctactgtgc cggccatgtc cgtaagtgcg     780
gaagagcgta agcggttttt tgagaaggcg tggcaatctg gcggtggtat cggtttttac     840
atcgaaacct ttggtgatat tgcgacgaac atggaagcta acattgaggc acaaaatttt     900
```

```
atcaaaggta aaatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt gtccagaggc ccagagccag gtttttgggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 116
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 116

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Asp Ile Trp Asp Gly Val Trp
```

```
                    225                 230                 235                 240
        Asn Ser Ala Leu Ala Phe Gly Leu Asn Glu Ser Thr Val Pro Ala Met
                        245                 250                 255

Ser Val Ser Ala Glu Glu Arg Lys Ala Val Phe Glu Lys Ala Trp Gln
                        260                 265                 270

Ser Gly Gly Gly Ile Gly Phe Tyr Ile Glu Thr Phe Gly Asp Ile Ala
                        275                 280                 285

Thr Asn Met Glu Ala Asn Ile Glu Ala Gln Asn Phe Ile Lys Gly Lys
                        290                 295                 300

Ile Ala Glu Ile Val Lys Asp Pro Ala Ile Ala Gln Lys Leu Met Pro
        305                 310                 315                 320

Gln Asp Leu Lys Ala Arg Arg Pro Leu Cys Asp Ser Gly Tyr Tyr Asn
                        325                 330                 335

Thr Phe Asn Arg Asp Asn Val Arg Leu Glu Asp Val Lys Ala Asn Pro
                        340                 345                 350

Ile Val Glu Ile Thr Glu Asn Gly Val Lys Leu Lys Asn Gly Asp Phe
                        355                 360                 365

Val Glu Leu Asp Met Leu Ile Cys Ala Thr Gly Phe Asp Ala Val Asp
                        370                 375                 380

Gly Asn Tyr Val Arg Met Asp Ile Gln Gly Arg Asn Gly Leu Ala Met
        385                 390                 395                 400

Lys Asp Tyr Trp Lys Glu Gly Pro Ser Ser Tyr Leu Gly Val Thr Val
                        405                 410                 415

Asn Asn Tyr Pro Asn Met Phe Met Val Ser Gly Pro Asn Gly Pro Ser
                        420                 425                 430

Gly Asn Ala Pro Pro Met Ile Glu Ser Gln Val Glu Trp Ile Ser Asp
                        435                 440                 445

Thr Ile Gln Tyr Thr Val Glu Asn Asn Val Glu Ser Ile Glu Ala Thr
                        450                 455                 460

Lys Glu Ala Glu Glu Gln Trp Ile Gln Thr Cys Ala Asn Ile Ala Glu
        465                 470                 475                 480

Met Thr Leu Cys Pro Glu Ala Gln Ser Gln Val Phe Gly Ala Asn Ile
                        485                 490                 495

Pro Gly Lys Lys Asn Thr Ala Ile Lys Tyr Leu Gly Gly Leu Lys Asn
                        500                 505                 510

Tyr Arg Ser Ala Leu Ala Asn Cys Lys Asn His Ala Tyr Glu Gly Phe
                        515                 520                 525

Asp Ile Gln Pro Gln Arg Ser Asp Ile Lys Gln Pro Ala Asn Ala
                        530                 535                 540

<210> SEQ ID NO 117
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 117
atgtctacca agatggattt cgatgccatc gtgatcggtg ggggctttgg cggtctgtat      60
gccgttaaaa aactgcgcga tgaactggag ctgaaagttc aagccttcga aaggcaact      120 gacgtaggcg gtacatggta ctggaaccgc tacccgggtg ccctgaccga taccgaaacc     180
catttgtatt gttattcctg gacaaggaa ctgttgcaga gtatggaaat caaaaccaaa       240
tacgcgcaag gtccagacgt gcgcaaatat ctgcagcagg ttgccgaaaa acacgtatta     300
```

```
aaaaaaagtt accagttcaa caccgcaatg caatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgatg acatctggga tggtgtttgg    720
aacagtgcgc tggccttcgg cctgaatgaa tctactgtgc cggccatgtc cgtaagtgcg    780
gaagagcgta aagcggtttt tgagaaggcg tggcaatgcg gcggtggtat cggttttttac    840 atcgaaacct ttggtgatat tgcgacgaac atggaagcta acattgaggc acaaaatttt    900
atcaaaggta aaatcgcgga gatcgtcaaa gatccggcga tcgcccaaaa actgatgccg    960
caggacctga aggcacgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag gcgtaacggg tctggccatg   1200
aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440 atgacccttgt ttccagaggc ccagagccag gttaaggggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 118
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 118

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125
```

Gly Asp Lys Tyr Thr Ala Arg Phe Leu Ile Thr Ala Leu Gly Gly Leu
130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
        165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Asp Ile Trp Asp Gly Val Trp
225                 230                 235                 240

Asn Ser Ala Leu Ala Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Cys Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
        340                 345                 350

Ile Val Glu Ile Thr Glu Asn Gly Val Lys Leu Lys Asn Gly Asp Phe
            355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
        420                 425                 430

Gly Asn Ala Pro Pro Met Ile Glu Ser Gln Val Glu Trp Ile Ser Asp
            435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Gln Val Lys Gly Ala Asn Ile
                485                 490                 495

Pro Gly Lys Lys Asn Thr Ala Ile Lys Tyr Leu Gly Gly Leu Lys Asn
        500                 505                 510

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
530                 535                 540

<210> SEQ ID NO 119
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 119

```
atgtctacca agatggattt cgatgccatc gtgatcggtg ggggctttgg cggtctgtat      60
gccgttaaaa aactgcgcga tgaactggag ctgaaagttc aagccttcga aaggcaact     120
gacgtaggcg gtacatggta ctggaaccgc tacccgggtg ccctgaccga taccgaaacc    180
catttgtatt gttattcctg gacaaggaa ctgttgcaga gtatggaaat caaaaccaaa    240
tacgcgcaag gtccagacgt gcgcaaatat ctgcagcagg ttgccgaaaa acacgtatta    300
aaaaaaagtt accagttcaa caccgcaatg caatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgccagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgatg acatctggga tggtgtttgg    720
aacagtaaac tggggttcgg cctgaatgaa tctactgtgc cggccatgtc cgtaagtgcg    780
gaagagcgta aagcggtttt tgagaaggcg tggcaatctg gcggtggtat cggttttac    840
atcgaaacct ttggtgatat tgcgacgaac atggaagcta acattgaggc acaaaatttt    900
atcaaagta aaatcgcgga gatcgtcaaa gatccggcga tcgcccaaaa actgactccg    960
caggacctga agtaccgtcg ccctctgtgt gactccgggt actataatac gttcaatcgc   1020
gacaacgtac gtctggagga tgtcaaagca aatccgatcg tcgagatcac cgaaaacggc   1080
gtgaaactgg aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt ttccagaggc ccagagccag gttaaagggg cgaacattcc aggcaagaag   1500
gataccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 120
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 120

```
Met Ser Thr Lys Met Asp Phe Asp Ala Ile Val Ile Gly Gly Gly Phe
1               5                   10                  15
```

```
Gly Gly Leu Tyr Ala Val Lys Lys Leu Arg Asp Glu Leu Glu Leu Lys
                20                  25                  30

Val Gln Ala Phe Glu Lys Ala Thr Asp Val Gly Gly Thr Trp Tyr Trp
         35                  40                  45

Asn Arg Tyr Pro Gly Ala Leu Thr Asp Thr Glu Thr His Leu Tyr Cys
 50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                 85                  90                  95

Lys His Val Leu Lys Lys Ser Tyr Gln Phe Asn Thr Ala Met Gln Ser
             100                 105                 110

Ala His Tyr Asn Glu Ala Asp Ala Leu Trp Glu Val Thr Thr Glu Tyr
         115                 120                 125

Gly Asp Lys Tyr Thr Ala Arg Phe Leu Ile Thr Ala Leu Gly Gly Leu
     130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Thr Pro
305                 310                 315                 320

Gln Asp Leu Lys Tyr Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Val Ser Gly Pro Asn Gly Pro Ser
            420                 425                 430

Gly Asn Ala Pro Pro Met Ile Glu Ser Gln Val Glu Trp Ile Ser Asp
```

435                 440                 445
Thr Ile Gln Tyr Thr Val Glu Asn Asn Val Glu Ser Ile Glu Ala Thr
              450                 455                 460
Lys Glu Ala Glu Glu Gln Trp Ile Gln Thr Cys Ala Asn Ile Ala Glu
465                 470                 475                 480
Met Thr Leu Phe Pro Glu Ala Gln Ser Gln Val Lys Gly Ala Asn Ile
                          485                 490                 495
Pro Gly Lys Lys Asp Thr Ala Ile Lys Tyr Leu Gly Gly Leu Lys Asn
                    500                 505                 510
Tyr Arg Ser Ala Leu Ala Asn Cys Lys Asn His Ala Tyr Glu Gly Phe
              515                 520                 525
Asp Ile Gln Pro Gln Arg Ser Asp Ile Lys Gln Pro Ala Asn Ala
        530                 535                 540

<210> SEQ ID NO 121
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 121

| | |
|---|---:|
| atgtctacca agatggattt cgatgccatc gtgatcggtg ggggctttgg cggtctgtat | 60 |
| gccgttaaaa aactgcgcga tgaactggag ctgaaagttc aagccttcga agggcaact | 120 |
| gacgtaggcg gtacatggta ctggaaccgc tacccgggtg ccctgaccga taccgaaacc | 180 |
| catttgtatt gttattcctg ggacaaggaa ctgttgcaga gtatggaaat caaaaccaaa | 240 |
| tacgcgcaag gtccagacgt gcgcaaatat ctgcagcagg ttgccgaaaa acacgtatta | 300 |
| aaaaaaagtt accagttcaa caccgcaatg caatctgccc actacaacga gcggacgct | 360 |
| ctgtgggaag taactacgga atacggggat aagtacaccg cacgtttcct gattactgcc | 420 |
| ttaggtgggc tgtctgcacc taacctgcca aatatcaagg gcatcaatca gtttaaaggc | 480 |
| gacctgcacc atactgcccg ctggccggat gacgccagta tcgaaggcaa acgtgtgggt | 540 |
| gtgatcggca caggctctac cggcgtgcaa gttattacgg cagtggcgcc actggccaag | 600 |
| cacctgacgg tgtttcagcg tacggcccag tactcggtcc cgatcagcaa cgatccactg | 660 |
| agcgaagaag acgtcaagaa gatcaaagat aactatgatg acatctggga tggtgtttgg | 720 |
| aacagtaaac tggggttcgg cctgaatgaa tctactgtgc cggccatgtc cgtaagtgcg | 780 |
| gaagagcgta agcggttttt tgagaaggcg tggcaatctg cggtggtat cggttttac | 840 |
| atcgaaacct ttggtgatat tgcgacgaac atggaagcta acattgaggc acaaaatttt | 900 |
| atcaaaggta aaatcgcgga gatcgtcaaa gatccggcga tcgcccaaaa actgactccg | 960 |
| caggacctga aggcacgtcg ccctctgtgt gactccgggt actataatac gttcaatcgc | 1020 |
| gacaacgtac gtctggagga tgtcaaagca aatccgatcg tcgagatcac cgaaaacggc | 1080 |
| gtgaaactgg aaaacggcga tttcgtggag ctggacatgc tgatctgcgc gacgggtttt | 1140 |
| gatgcggtag acggcaacta tgttcgcatg gatatccaag gcgtaacgg tctggccatg | 1200 |
| aaggattact ggaaagaggg cccgtctagc tacctgggcg taaccgtgaa taattaccca | 1260 |
| aacatgttta tggttagcgg tccaaacggt ccatctggta acgctccgcc tatgattgaa | 1320 |
| agtcaagttg aatggattag cgatactatc cagtataccg tcgaaaataa cgtggaatct | 1380 |
| attgaagcca cgaaggaagc ggaggaacag tggattcaaa cctgcgccaa tattgcggag | 1440 |
| atgaccctgt ttccagaggc ccagagccag gttaaggggg cgaacattcc aggcaagaag | 1500 |

```
aacaccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 122
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 122

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Gly Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Thr Pro
305                 310                 315                 320

Gln Asp Leu Lys Ala Arg Arg Pro Leu Cys Asp Ser Gly Tyr Tyr Asn
                325                 330                 335
```

```
Thr Phe Asn Arg Asp Asn Val Arg Leu Glu Asp Val Lys Ala Asn Pro
                340                 345                 350

Ile Val Glu Ile Thr Glu Asn Gly Val Lys Leu Glu Asn Gly Asp Phe
            355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Met Ile Glu Ser Gln Val Glu Trp Ile Ser Asp
    435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Gln Val Lys Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
    530                 535                 540

<210> SEQ ID NO 123
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 123
atgtctacca agatggattt cgatgccatc gtgatcggtg ggggctttgg cggtctgtat      60
gccgttaaaa aactgcgcga tgaactggag ctgaaagttc aagccttcga aggcaact       120 gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt gcgcaaatat ctgcagcagg ttgccgaaaa acacgtatta     300
aaaaaaagtt accagttcaa caccgcaatg caatctgccc actacaacga gcggacgct      360 ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgccagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcagcaa cgatccactg     660
agcgaagaag acgtcaagaa gatcaaagat aactatgatg acatctggga tggtgtttgg     720
aacagtaaac tggggttcgg cctgaatgaa tctactgtgc cggccatgtc cgtaagtgcg     780
gaagagcgta aagcggtttt tgagaaggcg tggcaatctg gcggtggtat cggttttac      840 atcgaaacct tggtgatat tgcgacgaac atggaagcta acattgaggc acaaaatttt     900
```

```
atcaaaggta aaatcgcgga gatcgtcaaa gatccggcga tcgcccaaaa actgctgccg    960
caggacctga agtaccgtcg ccctctgtgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaagagggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt ttccagaggc ccagagccag gttttttgggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 124
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 124

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
    210                 215                 220
```

```
Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
            245                 250                 255

Ser Val Ser Ala Glu Glu Arg Lys Ala Val Phe Glu Lys Ala Trp Gln
        260                 265                 270

Ser Gly Gly Gly Ile Gly Phe Tyr Ile Glu Thr Phe Gly Asp Ile Ala
    275                 280                 285

Thr Asn Met Glu Ala Asn Ile Glu Ala Gln Asn Phe Ile Lys Gly Lys
290                 295                 300

Ile Ala Glu Ile Val Lys Asp Pro Ala Ile Ala Gln Lys Leu Leu Pro
305                 310                 315                 320

Gln Asp Leu Lys Tyr Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Met Ile Glu Ser Gln Val Glu Trp Ile Ser Asp
        435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Gln Val Phe Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
530                 535                 540
```

<210> SEQ ID NO 125
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 125
atgtctacca agatggattt cgatgccatc gtgatcggtg ggggctttgg cggtctgtat     60
gccgttaaaa aactgcgcga tgaactggag ctgaaagttc aagccttcga gaaggcaact    120
gacgtaggcg gtacatggta ctggaaccgc tacccgggtg ccctgaccga taccgaaacc    180
catgtttatt gttattcctg ggacaaggaa ctgttgcaga gtatggaaat caaaaccaaa    240
tacgcgcaag gtccagacgt gcgcaaatat ctgcagcagg ttgccgaaaa acacgtatta    300

```
aaaaaaagtt accagttcaa caccgcaatg caatctgccc actacaacga agcggacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgttagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgatg acatctggga tggtgtttgg    720
aacagtaaac tggggttcgg cctgaatgaa tctactgtgc cggccatgtc cgtaagtgcg    780
gaagagcgta aagcggtttt tgagaaggcg tggcaatctg gctcaggtat cggttttac     840 atcgaaacct ttggtgatat tgcgacgaac atggaagcta acattgaggc acaaaatttt    900
atcaaaggta aaatcgcgga atcgtcaaa gatccggcga tcgcccaaaa actgatgccg    960
caggacctga aggcacgtcg ccctgtttgt gactccgggt actataatac gttcaatcgc   1020
gacaacgtac gtctggagga tgtcaaagca aatccgatcg tcgagatcac cgaaaacggc   1080
gtgaaactga aaaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt gtccagaggc ccagagccag gttttgggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                           1629
```

<210> SEQ ID NO 126
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 126

```
Met Ser Thr Lys Met Asp Phe Asp Ala Ile Val Ile Gly Gly Phe
1               5                  10                 15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Val Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
```

```
            115                 120                 125
Gly Asp Lys Tyr Thr Ala Arg Phe Leu Ile Thr Ala Leu Gly Gly Leu
130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Val Ser Ile Glu Gly
                    165                 170                 175

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Thr
                195                 200                 205

Ala Gln Tyr Ser Val Pro Ile Ser Asn Asp Pro Leu Ser Glu Glu Asp
210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Ser Gly Ile Gly Phe Tyr Ile Glu Thr Phe Gly Asp Ile Ala
            275                 280                 285

Thr Asn Met Glu Ala Asn Ile Glu Ala Gln Asn Phe Ile Lys Gly Lys
        290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Val Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Lys Leu Lys Asn Gly Asp Phe
                355                 360                 365

Val Glu Leu Asp Met Leu Ile Cys Ala Thr Gly Phe Asp Ala Val Asp
        370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430

Gly Asn Ala Pro Pro Met Ile Glu Ser Gln Val Glu Trp Ile Ser Asp
            435                 440                 445

Thr Ile Gln Tyr Thr Val Glu Asn Asn Val Glu Ser Ile Glu Ala Thr
        450                 455                 460

Lys Glu Ala Glu Glu Gln Trp Ile Gln Thr Cys Ala Asn Ile Ala Glu
465                 470                 475                 480

Met Thr Leu Cys Pro Glu Ala Gln Ser Gln Val Phe Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
        530                 535                 540
```

<210> SEQ ID NO 127
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 127

```
atgtctacca agatggattt cgatgccatc gtgatcggtg ggggctttgg cggtctgtat      60
gccgttaaaa aactgcgcga tgaactggag ctgaaagttc aagccttcga agggcaact     120
gacgtaggcg gtacatggta ctggaaccgc tacccgggtg ccctgaccga taccgaaacc    180
catgtttatt gttattcctg ggacaaggaa ctgttgcaga gtatggaaat caaaaccaaa    240
tacgcgcaag gtccagacgt gcgcaaatat ctgcagcagg ttgccgaaaa acacgtatta    300
aaaaaagtt accagttcaa caccgcaatg caatctgccc actacaacga gcggacgct    360
ctgtgggaag taactacgga atacgggat aagtacaccg cacgtttcct gattactgcc    420
ttaggtgggc tgtctgcacc taacctgcca aatatcaagg gcatcaatca gtttaaggc    480
gacctgcacc atactgcccg ctggccggat gacgttagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcagcaa cgatccactg    660
agcgaagaag acgtcaagaa gatcaaagat aactatgatg acatctggga tggtgtttgg    720
aacagtaaac tggggttcgg cctgaatgaa tctactgtgc cggccatgtc cgtaagtgcg    780
gaagagcgta agcggtttt tgagaaggcg tggcaatctg caacggtat cggttttttac    840
atcgaaacct ttggtgatat tgcgacgaac atggaagcta acattgaggc acaaaatttt    900
atcaaaggta aatcgcgga tcgtcaaaa gatccggcga tcgcccaaaa actgatgccg    960
caggacctga aggcacgtcg ccctgtttgt gactccgggt actataatac gttcaatcgc   1020
gacaacgtac gtctggagga tgtcaaagca aatccgatcg tcgagatcac cgaaaacggc   1080
gtgaaactga aaacggcga tttcgtggag ctggacatgc tgatctgcgc gacgggtttt   1140
gatgcggtag acggcaacta tgttcgcatg gatatccaag ggcgtaacgg tctggccatg   1200
aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattcaaa cctgcgccaa tattgcggag   1440
atgaccctgt gtccagaggc ccagagccag gttttggg cgaacattcc aggcaagaag   1500
aacaccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                            1629
```

<210> SEQ ID NO 128
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 128

```
Met Ser Thr Lys Met Asp Phe Asp Ala Ile Val Ile Gly Gly Gly Phe
1               5                   10                  15
```

```
Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Val Tyr Cys
 50                  55                  60

Tyr Ser Trp Asp Lys Glu Leu Leu Gln Ser Met Glu Ile Lys Thr Lys
 65                  70                  75                  80

Tyr Ala Gln Gly Pro Asp Val Arg Lys Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Val Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ser Asn Asp Pro Leu Ser Glu Glu Asp
 210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Ser Gly Asn Gly Ile Gly Phe Tyr Ile Glu Thr Phe Gly Asp Ile Ala
        275                 280                 285

Thr Asn Met Glu Ala Asn Ile Glu Ala Gln Asn Phe Ile Lys Gly Lys
 290                 295                 300

Ile Ala Glu Ile Val Lys Asp Pro Ala Ile Ala Gln Lys Leu Met Pro
305                 310                 315                 320

Gln Asp Leu Lys Ala Arg Arg Pro Val Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Lys Asn Gly Asp Phe
        355                 360                 365

Val Glu Leu Asp Met Leu Ile Cys Ala Thr Gly Phe Asp Ala Val Asp
 370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430
```

Gly Asn Ala Pro Pro Met Ile Glu Ser Gln Val Glu Trp Ile Ser Asp
            435                 440                 445

Thr Ile Gln Tyr Thr Val Glu Asn Asn Val Glu Ser Ile Glu Ala Thr
        450                 455                 460

Lys Glu Ala Glu Glu Gln Trp Ile Gln Thr Cys Ala Asn Ile Ala Glu
465                 470                 475                 480

Met Thr Leu Cys Pro Glu Ala Gln Ser Gln Val Phe Gly Ala Asn Ile
                485                 490                 495

Pro Gly Lys Lys Asn Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
            530                 535                 540

<210> SEQ ID NO 129
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 129

```
atgtctacca agatggattt cgatgccatc gtgatcggtg ggggctttgg cggtctgtat      60
gccgttaaaa aactgcgcga tgaactggag ctgaaagttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
tacgcgcaag gtccagacgt cgcatgtat ctgcagcagg ttgccgaaaa acacgtatta     300
aaaaaaagtt accagttcaa caccgcaatg caatctgccc actacaacga agtcgacgct     360
ctgtgggaag taactacgga atacggggat aagtacaccg cacgtttcct gattactgcc     420
ttaggtgggc tgtctgcacc taacctgcca aatatcaagg gcatcaatca gtttaaaggc     480
gacctgcacc atactgcccg ctggccggat gacgccagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcatcaa cgatccactg     660
agcgaagaag acgtcaagaa gatcaaagat aactatgatg acatctggga tggtgtttgg     720
aacagtaaac tggggttcgg cctgaatgaa tctactgtgc cggccatgtc cgtaagtgcg     780
gaagagcgtt acgcggtttt tgagaaggcg tggcaatctg cggtggtat cggtttttac     840 atcgaaacct tggtgatat tgcgacgaac cgtgaagcta acattgaggc acaaaatttt     900
atcaaaggta aatcgcgga gatcgtccat gatccggcga tcgcccaaaa actgactccg     960
caggacctga gtaccgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag gcgtaacgg tctggccatg    1200 aaggattact ggaaagaggg cccgtctagc tacctgggcg taaccgtgaa taattaccca    1260
aacatgttta tggttagcgg tccaaacggt ccatctggta acgctccgcc tatgattgaa    1320
agtcaagttg aatggattag cgatactatc cagtataccg tcgaaaataa cgtggaatct    1380
attgaagcca cgaaggaagc ggaggaacag tggattcaaa cctgcgccaa tattgcggag    1440
```

```
atgaccctgt tccagaggc ccagagccag gttaaagggg cgaacattcc aggcaagaag    1500
gataccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629

<210> SEQ ID NO 130
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 130
```

Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Met Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Val Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ile Asn Asp Pro Leu Ser Glu Glu Asp
    210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Tyr Ala Val Phe Glu Lys Ala Trp Gln
            260                 265                 270

Ser Gly Gly Gly Ile Gly Phe Tyr Ile Glu Thr Phe Gly Asp Ile Ala
        275                 280                 285

Thr Asn Arg Glu Ala Asn Ile Glu Ala Gln Asn Phe Ile Lys Gly Lys
    290                 295                 300

Ile Ala Glu Ile Val His Asp Pro Ala Ile Ala Gln Lys Leu Thr Pro
305                 310                 315                 320

Gln Asp Leu Lys Tyr Arg Arg Pro Leu Cys Asp Ser Gly Tyr Tyr Asn

```
                325                 330                 335
Thr Phe Asn Arg Asp Asn Val Arg Leu Glu Asp Val Lys Ala Asn Pro
            340                 345                 350
Ile Val Glu Ile Thr Glu Asn Gly Val Lys Leu Glu Asn Gly Asp Phe
        355                 360                 365
Val Glu Leu Asp Met Leu Ile Cys Ala Thr Gly Phe Asp Ala Val Asp
    370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
            420                 425                 430
Gly Asn Ala Pro Pro Met Ile Glu Ser Gln Val Glu Trp Ile Ser Asp
        435                 440                 445
Thr Ile Gln Tyr Thr Val Glu Asn Asn Val Glu Ser Ile Glu Ala Thr
    450                 455                 460
Lys Glu Ala Glu Glu Gln Trp Ile Gln Thr Cys Ala Asn Ile Ala Glu
465                 470                 475                 480
Met Thr Leu Phe Pro Glu Ala Gln Ser Gln Val Lys Gly Ala Asn Ile
                485                 490                 495
Pro Gly Lys Lys Asp Thr Ala Ile Lys Tyr Leu Gly Gly Leu Lys Asn
            500                 505                 510
Tyr Arg Ser Ala Leu Ala Asn Cys Lys Asn His Ala Tyr Glu Gly Phe
        515                 520                 525
Asp Ile Gln Pro Gln Arg Ser Asp Ile Lys Gln Pro Ala Asn Ala
    530                 535                 540

<210> SEQ ID NO 131
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 131
atgtctacca agatggattt cgatgccatc gtgatcggtg ggggctttgg cggtctgtat      60
gccgttaaaa aactgcgcga tgaactggag ctgaaagttc aagccttcga aaggcaggc     120
gacgtaggcg gtacatggta ctggaaccgc tacccgggtg ccctgaccga taccgaaacc    180
catttgtatt gttattcctg ggacaaggaa ctgttgcagg agatggaaat caaaaccaaa    240
tacgcgcaag gtccagacgt gcgcatgtat ctgcagcagg ttgccgaaaa acacgtatta    300
aaaaaagtt accagttcaa caccgcaatg caatctgccc actacaacga agtcgacgct    360
ctgtgggaag taactacgga atacggggat aagtacaccg cacgtttcct gattactgcc    420
ttaggtgggc tgtctgcacc taacctgcca aatatcaagg gcatcaatca gtttaaaggc    480
gacctgcacc atactgcccg ctggccggat gacgccagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcatcaa cgatccactg    660
agcgaagaag acgtcaagaa gatcaaagat aactatgatg acatctggga tggtgtttgg    720
aacagtaaac tggggttcgg cctgaatgaa tctactgtgc cggccatgtc cgtaagtgcg    780
gaagagcgtt acgcggtttt tgagaaggcg tggcaatctg gcggtggtat cggttttttac    840
```

```
atcgaaacct tggtgatat tgcgacgaac cgtgaagcta acattgaggc acaaaatttt    900
atcaaaggta aaatcgcgga gatcgtcaaa gatccggcga tcgcccaaaa actgactccg    960
caggacctga agtttcgtcg ccctctgtgt gactccgggt actataatac gttcaatcgc    1020
gacaacgtac gtctggagga tgtcaaagca aatccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag gcgtaacgg tctggccatg    1200 aaggattact ggaaagaggg cccgtctagc tacctgggcg taaccgtgaa taattaccca    1260
aacatgttta tggttagcgg tccaaacggt ccatctggta acgctccgcc tatgattgaa    1320
agtcaagttg aatggattag cgatactatc cagtataccg tcgaaaataa cgtggaatct    1380
attgaagcca cgaaggaagc ggaggaacag tggattcaaa cctgcgccaa tattgcggag    1440
atgaccctgt ttccagaggc ccagagccag gttaaagggg cgaacattcc aaataagaag    1500
gataccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                             1629
```

<210> SEQ ID NO 132
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 132

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Gly Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Glu Met Glu Ile Lys Thr Lys
65                  70                  75                  80

Tyr Ala Gln Gly Pro Asp Val Arg Met Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Val Asp Ala Leu Trp Glu Val Thr Thr Glu Tyr
        115                 120                 125

Gly Asp Lys Tyr Thr Ala Arg Phe Leu Ile Thr Ala Leu Gly Gly Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ile Asn Asp Pro Leu Ser Glu Glu Asp
    210                 215                 220
```

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
            245                 250                 255

Ser Val Ser Ala Glu Glu Arg Tyr Ala Val Phe Glu Lys Ala Trp Gln
        260                 265                 270

Ser Gly Gly Gly Ile Gly Phe Tyr Ile Glu Thr Phe Gly Asp Ile Ala
            275                 280                 285

Thr Asn Arg Glu Ala Asn Ile Glu Ala Gln Asn Phe Ile Lys Gly Lys
        290                 295                 300

Ile Ala Glu Ile Val Lys Asp Pro Ala Ile Ala Gln Lys Leu Thr Pro
305                 310                 315                 320

Gln Asp Leu Lys Phe Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
        370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Met Ile Glu Ser Gln Val Glu Trp Ile Ser Asp
        435                 440                 445

Thr Ile Gln Tyr Thr Val Glu Asn Asn Val Glu Ser Ile Glu Ala Thr
450                 455                 460

Lys Glu Ala Glu Glu Gln Trp Ile Gln Thr Cys Ala Asn Ile Ala Glu
465                 470                 475                 480

Met Thr Leu Phe Pro Glu Ala Gln Ser Gln Val Lys Gly Ala Asn Ile
                485                 490                 495

Pro Asn Lys Lys Asp Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525

Asp Ile Gln Pro Gln Arg Ser Asp Ile Lys Gln Pro Ala Asn Ala
    530                 535                 540

<210> SEQ ID NO 133
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 133
atgtctacca agatggattt cgatgccatc gtgatcggtg ggggctttgg cggtctgtat      60
gccgttaaaa aactgcgcga tgaactggag ctggaggttc aagccttcga gaaggcaact     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240

```
tacgcgcaag gtccagacgt gcgcaactat ctgcagcagg ttgccgaaaa acacgtatta      300
aaaaaaagtt accagttcaa caccgcaatg caatctgccc actacaacga agtcgacgct      360
ctgtgggaag taactacgga atacggggat aagtacaccg cacgtttcct gattactgcc      420
ttaggttctc tgtctgcacc taacctgcca aatatcaagg gcatcaatca gtttaaaggc      480
gacctgcacc atactgcccg ctggccggat gacgccagta tcgaaggcaa acgtgtgggt      540
gtgatcggca caggctctac cggcgtgcaa gttattacgg cagtggcgcc actggccaag      600
cacctgacgg tgtttcagcg tacggcccag tactcggtcc cgatcatcaa cgatgtactg      660
agcgaagaag acgtcaagaa gatcaaagat aactatgatg acatctggga tggtgtttgg      720
aacagtaaac tggggttcgg cctgaatgaa tctactgtgc cggccatgtc cgtaagtgcg      780
gaagagcgtt acgcggtttt tgagaaggcg tggcaatctg cgcgggtat cggttttac       840 atcgaaacct ttggtgatat tgcgacgaac cgtgaagcta acattgaggc acaaaatttt      900
atcaaaggta aaatcgcgga gatcgtccat gatccggcga tcgcccaaaa actgactccg      960
caggacctga agtaccgtcg ccctctgtgt gactccgggt actataatac gttcaatcgc     1020
gacaacgtac gtctggagga tgtcaaagca aatccgatcg tcgagatcac cgaaaacggc     1080
gtgagtctga aaacggcga tttcgtggag ctggacatgc tgatctgcgc gacgggtttt     1140
gatgcggtag acggcaacta tgttcgcatg gatatccaag gcgtaacgg tctggccatg      1200 aaggattact ggaaagaggg cccgtctagc tacctgggcg taaccgtgaa taattaccca     1260
aacatgttta tggttagcgg tccaaacggt ccatctggta acgctccgcc tatgattgaa     1320
agtcaagttg aatggattag cgatactatc cagtataccg tcgaaaataa cgtggaatct     1380
attgaagcca cgaaggaagc ggaggaacag tggattcaaa cctgcgccga tattgcggag     1440 atgacctgt ttccagaggc ccagagccag gttaaagggg cgaacattcc aggcaagaag      1500
gataccgcga tcaaatattt gggtgggctg aaaaactacc gctcagcttt ggcgaattgt     1560
aaaaatcatg cgtatgaagg ctttgatatt cagccgcaac gttctgacat caaacaacca     1620
gcgaatgcg                                                             1629
```

<210> SEQ ID NO 134
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 134

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Glu
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Asn Tyr Leu Gln Gln Val Ala Glu
                85                  90                  95

Lys His Val Leu Lys Lys Ser Tyr Gln Phe Asn Thr Ala Met Gln Ser
            100                 105                 110
```

-continued

```
Ala His Tyr Asn Glu Val Asp Ala Leu Trp Glu Val Thr Glu Tyr
        115                 120                 125
Gly Asp Lys Tyr Thr Ala Arg Phe Leu Ile Thr Ala Leu Gly Ser Leu
130                 135                 140
Ser Ala Pro Asn Leu Pro Asn Ile Lys Gly Ile Asn Gln Phe Lys Gly
145                 150                 155                 160
Asp Leu His His Thr Ala Arg Trp Pro Asp Asp Ala Ser Ile Glu Gly
                165                 170                 175
Lys Arg Val Gly Val Ile Gly Thr Gly Ser Thr Gly Val Gln Val Ile
                180                 185                 190
Thr Ala Val Ala Pro Leu Ala Lys His Leu Thr Val Phe Gln Arg Thr
            195                 200                 205
Ala Gln Tyr Ser Val Pro Ile Ile Asn Asp Val Leu Ser Glu Glu Asp
        210                 215                 220
Val Lys Lys Ile Lys Asp Asn Tyr Asp Asp Ile Trp Asp Gly Val Trp
225                 230                 235                 240
Asn Ser Lys Leu Gly Phe Gly Leu Asn Glu Ser Thr Val Pro Ala Met
                245                 250                 255
Ser Val Ser Ala Glu Glu Arg Tyr Ala Val Phe Glu Lys Ala Trp Gln
                260                 265                 270
Ser Gly Ala Gly Ile Gly Phe Tyr Ile Glu Thr Phe Gly Asp Ile Ala
            275                 280                 285
Thr Asn Arg Glu Ala Asn Ile Glu Ala Gln Asn Phe Ile Lys Gly Lys
        290                 295                 300
Ile Ala Glu Ile Val His Asp Pro Ala Ile Ala Gln Lys Leu Thr Pro
305                 310                 315                 320
Gln Asp Leu Lys Tyr Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
                340                 345                 350
Ile Val Glu Ile Thr Glu Asn Gly Val Ser Leu Glu Asn Gly Asp Phe
            355                 360                 365
Val Glu Leu Asp Met Leu Ile Cys Ala Thr Gly Phe Asp Ala Val Asp
        370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
                420                 425                 430
Gly Asn Ala Pro Pro Met Ile Glu Ser Gln Val Glu Trp Ile Ser Asp
            435                 440                 445
Thr Ile Gln Tyr Thr Val Glu Asn Asn Val Glu Ser Ile Glu Ala Thr
        450                 455                 460
Lys Glu Ala Glu Glu Gln Trp Ile Gln Thr Cys Ala Asp Ile Ala Glu
465                 470                 475                 480
Met Thr Leu Phe Pro Glu Ala Gln Ser Gln Val Lys Gly Ala Asn Ile
                485                 490                 495
Pro Gly Lys Lys Asp Thr Ala Ile Lys Tyr Leu Gly Gly Leu Lys Asn
                500                 505                 510
Tyr Arg Ser Ala Leu Ala Asn Cys Lys Asn His Ala Tyr Glu Gly Phe
            515                 520                 525
Asp Ile Gln Pro Gln Arg Ser Asp Ile Lys Gln Pro Ala Asn Ala
```

<210> SEQ ID NO 135
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 135

```
atgtctacca agatggattt cgatgccatc gtgatcggtg ggggctttgg cggtctgtat      60
gccgttaaaa aactgcgcga tgaactggag ctgaaggttc aagccttcga aaggcaact     120
gacgtaggcg gtacatggta ctggaaccgc tacccgggtg ccctgaccga taccgaaacc     180
catttgtatt gttattcctg gacaaggaa ctgttgcaga gtatggaaat caaaaccaaa     240
tacgcgcaac atccagacgt gcgcaactat ctgcagcagg ttgccgaaaa acacgtatta     300
aaaaaagtt accagttcaa caccgcaatg caatctgccc actacaacga agtcgacgct     360
ctgtgggaag taactacgga atacgggat aagtacaccg cacgtttcct gattactgcc     420
ttaggttctc tgtctgcacc taacctgcca aatatcaagg gcatcaatca gtttaaaggc     480
gacctgcacc atactgcccg ctggccggat gacgccagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcatcaa cgatgtactg     660
agcgaagaag acgtcaagaa gatcaaagat aactatgatg acatctggga tggtgtttgg     720
aacagtaaac tggggttcgg cctgaatgaa tctactgtgc cggccatgtc cgtaagtgcg     780
gaagagcgtt acgcggtttt tgagaaggcg tggcaatctg gcgcgggtat cgcgttttac     840
atcgaaaacct ttggtgatat tgcgacgaac cgtgaagcta acattgaggc acaaaattt     900
atcaaaggta aaatcgcgga atcgtccat gatccggcga tcgcccaaaa actgactccg     960
caggacctga gtaccgtcg ccctctgtgt gactccgggt actataatac gttcaatcgc    1020
gacaacgtac gtctggagga tgtcaaagca aatccgatcg tcgagatcac cgaaaacggc    1080
gtgagtctgg aaaacggcga tttcgtggag ctggacatgc tgatctgcgc gacgggtttt    1140
gatgcggtag acggcaacta tgttcgcatg gatatccaag ggcgtaacgg tctggccatg    1200
aaggattact ggaaagaggg cccgtctagc tacctgggcg taaccgtgaa taattaccca    1260
aacatgttta tggttagcgg tccaaacggt ccatctggta acgctccgcc tatgattgaa    1320
agtcaagttg aatggattag cgatactatc cagtataccg tcgaaaataa cgtggaatct    1380
attgaagcca cgaaggaagc ggaggaacag tggattgaca cctgcgccga tattgcggag    1440
atgacccttg tgccagaggc ccagagccag gttaaagggg cgaacattcc aaataagaag    1500
gataccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 136
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 136

Met Ser Thr Lys Met Asp Phe Asp Ala Ile Val Ile Gly Gly Gly Phe

-continued

```
1               5                   10                  15
Gly Gly Leu Tyr Ala Val Lys Lys Leu Arg Asp Glu Leu Glu Leu Lys
                20                  25                  30

Val Gln Ala Phe Glu Lys Ala Thr Asp Val Gly Gly Thr Trp Tyr Trp
                35                  40                  45

Asn Arg Tyr Pro Gly Ala Leu Thr Asp Thr Glu Thr His Leu Tyr Cys
 50                  55                  60

Tyr Ser Trp Asp Lys Glu Leu Leu Gln Ser Met Glu Ile Lys Thr Lys
 65                  70                  75                  80

Tyr Ala Gln His Pro Asp Val Arg Asn Tyr Leu Gln Gln Val Ala Glu
                85                  90                  95

Lys His Val Leu Lys Lys Ser Tyr Gln Phe Asn Thr Ala Met Gln Ser
                100                 105                 110

Ala His Tyr Asn Glu Val Asp Ala Leu Trp Glu Val Thr Thr Glu Tyr
                115                 120                 125

Gly Asp Lys Tyr Thr Ala Arg Phe Leu Ile Thr Ala Leu Gly Ser Leu
                130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Ala Ser Ile Glu Gly
                165                 170                 175

Lys Arg Val Gly Val Ile Gly Thr Gly Ser Thr Gly Val Gln Val Ile
                180                 185                 190

Thr Ala Val Ala Pro Leu Ala Lys His Leu Thr Val Phe Gln Arg Thr
                195                 200                 205

Ala Gln Tyr Ser Val Pro Ile Ile Asn Asp Val Leu Ser Glu Glu Asp
                210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Tyr Ala Val Phe Glu Lys Ala Trp Gln
                260                 265                 270

Ser Gly Ala Gly Ile Ala Phe Tyr Ile Glu Thr Phe Gly Asp Ile Ala
                275                 280                 285

Thr Asn Arg Glu Ala Asn Ile Glu Ala Gln Asn Phe Ile Lys Gly Lys
                290                 295                 300

Ile Ala Glu Ile Val His Asp Pro Ala Ile Ala Gln Lys Leu Thr Pro
305                 310                 315                 320

Gln Asp Leu Lys Tyr Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
                340                 345                 350

Ile Val Glu Ile Thr Glu Asn Gly Val Ser Leu Glu Asn Gly Asp Phe
                355                 360                 365

Val Glu Leu Asp Met Leu Ile Cys Ala Thr Gly Phe Asp Ala Val Asp
                370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
                420                 425                 430
```

```
Gly Asn Ala Pro Pro Met Ile Glu Ser Gln Val Glu Trp Ile Ser Asp
                435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Asp Thr Cys Ala Asp Ile Ala Glu
465                 470                 475                 480

Met Thr Leu Leu Pro Glu Ala Gln Ser Gln Val Lys Gly Ala Asn Ile
                485                 490                 495

Pro Asn Lys Lys Asp Thr Ala Ile Lys Tyr Leu Gly Gly Leu Lys Asn
                500                 505                 510

Tyr Arg Ser Ala Leu Ala Asn Cys Lys Asn His Ala Tyr Glu Gly Phe
            515                 520                 525

Asp Ile Gln Pro Gln Arg Ser Asp Ile Lys Gln Pro Ala Asn Ala
            530                 535                 540

<210> SEQ ID NO 137
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 137
atgtctacca agatggattt cgatgccatc gtgatcggtg ggggctttgg cggtctgtat      60
gccgttaaaa aactgcgcga tgaactggag ctgaaggttc aagccttcga agaggcaact     120
gacgtaggcg gtacatggta ctggaaccgc tacccgggtg ccctgaccga taccgaaacc     180
catttgtatt gttattcctg gacaaggaa ctgttgcaga gtatggaaat caaaaccaaa     240
tacgcgcaac atccagacgt gcgcaactat ctgcagcagg ttgccgaaaa acacgtatta     300
aaaaaaagtt accagttcaa caccgcaatg caatctgccc actacaacga agtcgacgct     360
ctgtgggaag taactacgga atacggggat aagtacaccg cacgtttcct gattactgcc     420
ttaggttctc tgtctgcacc taacctgcca aatatcaagg gcatcaatca gtttaaaggc     480
gacctgcacc atactgcccg ctggccggat gacgccagta tcgaaggcaa acgtgtgggt     540
gtgatcggca caggctctac cggcgtgcaa gttattacgg cagtggcgcc actggccaag     600
cacctgacgg tgtttcagcg tacggcccag tactcggtcc cgatcatcaa cgatgtactg     660
agcgaagaag acgtcaagaa gatcaaagat aactatgatg acatctggga tggtgtttgg     720
aacagtaaac tggggttcgg cctgaatgaa tctactgtgc cggccatgtc cgtaagtgcg     780
gaagagcgtt acgcggtttt tgagaaggcg tggcaatctg gcgcgggtat cgcgttttac     840
atcgaaacct ttggtgatat tgcgacgaac cgtgaagcta acattgaggc acaaaatttt     900
atcaaaggta aaatcgcgga gatcgtccat gatccggcga tcgcccaaaa actgactccg     960
caggacctga gtaccgtcg ccctctgtgt gactccgggt actataatac gttcaatcgc    1020
gacaacgtac gtctggagga tgtcaaagca atccgatcg tcgagatcac cgaaaacggc    1080
gtgaaactgg aaaacggcga tttcgtggag ctggacatgc tgatctgcgc gacgggtttt    1140
gatgcggtag acggcaacta tgttcgcatg gatatccaag gcgtaacgg tctggccatg    1200 aaggattact ggaagagggg cccgtctagc tacctgggcg taaccgtgaa taattaccca    1260 aacatgtta tggttagcgg tccaaacggt ccatctggta acgctccgcc tatgattgaa    1320
agtcaagttg aatggattag cgatactatc cagtataccg tcgaaaataa cgtggaatct    1380
attgaagcca cgaaggaagc ggaggaacag tggattcaaa cctgcgccga tattgcggag    1440
```

```
atgaccctgt tgccagaggc ccagagccag gttaaagggg cgaacattcc aggcaagaag    1500
gataccgcga tcaaatattt gggtgggctg aaaaactacc gctcagcttt ggcgaattgt    1560
aaaaatcatg cgtatgaagg ctttgatatt cagccgcaac gttctgacat caaacaacca    1620
gcgaatgcg                                                            1629
```

<210> SEQ ID NO 138
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 138

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln His Pro Asp Val Arg Asn Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Val Asp Ala Leu Trp Glu Val Thr Thr Glu Tyr
        115                 120                 125

Gly Asp Lys Tyr Thr Ala Arg Phe Leu Ile Thr Ala Leu Gly Ser Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ile Asn Asp Val Leu Ser Glu Glu Asp
    210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Tyr Ala Val Phe Glu Lys Ala Trp Gln
            260                 265                 270

Ser Gly Ala Gly Ile Ala Phe Tyr Ile Glu Thr Phe Gly Asp Ile Ala
        275                 280                 285

Thr Asn Arg Glu Ala Asn Ile Glu Ala Gln Asn Phe Ile Lys Gly Lys
    290                 295                 300

Ile Ala Glu Ile Val His Asp Pro Ala Ile Ala Gln Lys Leu Thr Pro
305                 310                 315                 320
```

```
Gln Asp Leu Lys Tyr Arg Arg Pro Leu Cys Asp Ser Gly Tyr Tyr Asn
            325                 330                 335

Thr Phe Asn Arg Asp Asn Val Arg Leu Glu Asp Val Lys Ala Asn Pro
        340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
            405                 410                 415

Asn Asn Tyr Pro Asn Met Phe Met Val Ser Gly Pro Asn Gly Pro Ser
        420                 425                 430

Gly Asn Ala Pro Pro Met Ile Glu Ser Gln Val Glu Trp Ile Ser Asp
        435                 440                 445

Thr Ile Gln Tyr Thr Val Glu Asn Asn Val Ser Ile Glu Ala Thr
    450                 455                 460

Lys Glu Ala Glu Glu Gln Trp Ile Gln Thr Cys Ala Asp Ile Ala Glu
465                 470                 475                 480

Met Thr Leu Leu Pro Glu Ala Gln Ser Gln Val Lys Gly Ala Asn Ile
            485                 490                 495

Pro Gly Lys Lys Asp Thr Ala Ile Lys Tyr Leu Gly Gly Leu Lys Asn
        500                 505                 510

Tyr Arg Ser Ala Leu Ala Asn Cys Lys Asn His Ala Tyr Glu Gly Phe
    515                 520                 525

Asp Ile Gln Pro Gln Arg Ser Asp Ile Lys Gln Pro Ala Asn Ala
530                 535                 540

<210> SEQ ID NO 139
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 139
atgtctacca agatggattt cgatgccatc gtgatcggtg ggggcttttgg cggtctgtat      60 gccgttaaaa aactgcgcga tgaactggag ctgaaggttc aagccttcga aaggcaact      120 gacgtaggcg gtacatggta ctggaaccgc tacccgggtg ccctgaccga taccgaaacc      180
catttgtatt gttattcctg ggacaaggaa ctgttgcaga gtatggaaat caaaaccaaa      240
tacgcgcaag gtccagacgt gcgcaactat ctgcagcagg ttgccgaaaa acacgtatta      300 aaaaaagtt accagttcaa caccgcaatg caatctgccc actacaacga agtcgacgct      360
ctgtgggaag taactacgga atacggggat aagtacaccg cacgtttcct gattactgcc      420
ttaggttctc tgtctgcacc taacctgcca aatatcaagg gcatcaatca gtttaaaggc      480
gacctgcacc atactgcccg ctggccggat gacgccagta tcgaaggcaa acgtgtgggt      540
gtgatcggca caggctctac cggcgtgcaa gttattacgg cagtggcgcc actggccaag      600
cacctgacgg tgttcagcg tacggcccag tactcggtcc gatcatcaa cgatgtactg      660 agcgaagaag acgtcaagaa gatcaaagat aactatgatg acatctggga tggtgttgg      720 aacagtaaac tgggttcgg cctgaatgaa tctactgtgc cggccatgtc cgtaagtgcg      780
gaagagcgtt acgcggttt tgagaaggcg tggcaatctg gcgcgggtat cgcgttttac      840
```

```
atcgaaacct tggtgatat tgcgacgaac cgtgaagcta acattgaggc acaaaatttt    900
atcaaaggta aaatcgcgga gatcgtccat gatccggcga tcgcccaaaa actgactccg    960
caggacctga agtttcgtcg ccctctgtgt gactccgggt actataatac gttcaatcgc   1020
gacaacgtac gtctggagga tgtcaaagca aatccgatcg tcgagatcac cgaaaacggc   1080
gtgaaactgg aaaacggcga tttcgtggag ctggacatgc tgatctgcgc gacgggtttt   1140
gatgcggtag acggcaacta tgttcgcatg gatatccaag gcgtaacgg tctggccatg    1200 aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattgaca cctgcgccga tattgcggag   1440
atgaccctgt tgccagaggc ccagagccag gttaaagggg cgaacattcc aaataagaag   1500
gataccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 140
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 140

```
Met Ser Thr Lys Met Asp Phe Asp Ala Ile Val Ile Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Thr Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln Gly Pro Asp Val Arg Asn Tyr Leu Gln Gln Val Ala Glu
                85                  90                  95

Lys His Val Leu Lys Lys Ser Tyr Gln Phe Asn Thr Ala Met Gln Ser
            100                 105                 110

Ala His Tyr Asn Glu Val Asp Ala Leu Trp Glu Val Thr Thr Glu Tyr
        115                 120                 125

Gly Asp Lys Tyr Thr Ala Arg Phe Leu Ile Thr Ala Leu Gly Ser Leu
    130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ile Asn Asp Val Leu Ser Glu Glu Asp
```

```
                    210                 215                 220
Val Lys Lys Ile Lys Asp Asn Tyr Asp Asp Ile Trp Asp Gly Val Trp
225                 230                 235                 240
Asn Ser Lys Leu Gly Phe Gly Leu Asn Glu Ser Thr Val Pro Ala Met
                245                 250                 255
Ser Val Ser Ala Glu Glu Arg Tyr Ala Val Phe Glu Lys Ala Trp Gln
                260                 265                 270
Ser Gly Ala Gly Ile Ala Phe Tyr Ile Glu Thr Phe Gly Asp Ile Ala
            275                 280                 285
Thr Asn Arg Glu Ala Asn Ile Glu Ala Gln Asn Phe Ile Lys Gly Lys
        290                 295                 300
Ile Ala Glu Ile Val His Asp Pro Ala Ile Ala Gln Lys Leu Thr Pro
305                 310                 315                 320
Gln Asp Leu Lys Phe Arg Arg Pro Leu Cys Asp Ser Gly Tyr Tyr Asn
                325                 330                 335
Thr Phe Asn Arg Asp Asn Val Arg Leu Glu Asp Val Lys Ala Asn Pro
                340                 345                 350
Ile Val Glu Ile Thr Glu Asn Gly Val Lys Leu Glu Asn Gly Asp Phe
            355                 360                 365
Val Glu Leu Asp Met Leu Ile Cys Ala Thr Gly Phe Asp Ala Val Asp
        370                 375                 380
Gly Asn Tyr Val Arg Met Asp Ile Gln Gly Arg Asn Gly Leu Ala Met
385                 390                 395                 400
Lys Asp Tyr Trp Lys Glu Gly Pro Ser Ser Tyr Leu Gly Val Thr Val
                405                 410                 415
Asn Asn Tyr Pro Asn Met Phe Met Val Ser Gly Pro Asn Gly Pro Ser
                420                 425                 430
Gly Asn Ala Pro Pro Met Ile Glu Ser Gln Val Glu Trp Ile Ser Asp
            435                 440                 445
Thr Ile Gln Tyr Thr Val Glu Asn Asn Val Glu Ser Ile Glu Ala Thr
        450                 455                 460
Lys Glu Ala Glu Glu Gln Trp Ile Asp Thr Cys Ala Asp Ile Ala Glu
465                 470                 475                 480
Met Thr Leu Leu Pro Glu Ala Gln Ser Gln Val Lys Gly Ala Asn Ile
                485                 490                 495
Pro Asn Lys Lys Asp Thr Ala Ile Lys Tyr Leu Gly Gly Leu Lys Asn
                500                 505                 510
Tyr Arg Ser Ala Leu Ala Asn Cys Lys Asn His Ala Tyr Glu Gly Phe
            515                 520                 525
Asp Ile Gln Pro Gln Arg Ser Asp Ile Lys Gln Pro Ala Asn Ala
        530                 535                 540

<210> SEQ ID NO 141
<211> LENGTH: 1629
<212> TYPE: DNA
<213> ORGANISM: Artificial Sequence
<220> FEATURE:
<223> OTHER INFORMATION: Variant of CHMO from Acinetobacter sp NCIMB9871

<400> SEQUENCE: 141
atgtctacca agatggattt cgatgccatc gtgatcggtg ggggctttgg cggtctgtat      60
gccgttaaaa aactgcgcga tgaactggag ctgaaggttc aagccttcga agaggcaggc     120
gacgtaggcg gtacatggta ctggaaccgc tacccgggtg ccctgaccga taccgaaacc     180
catttgtatt gttattcctg ggacaaggaa ctgttgcaga gtatggaaat caaaaccaaa     240
```

```
tacgcgcaac atccagacgt gcgcaactat ctgcagcagg ttgccgaaaa acacgtatta    300
aaaaaaagtt accagttcaa caccgcaatg caatctgccc actacaacga agtcgacgct    360
ctgtgggaag taactacgga atacggggat aagtacaccg cacgtttcct gattactgcc    420
ttaggttctc tgtctgcacc taacctgcca aatatcaagg gcatcaatca gtttaaaggc    480
gacctgcacc atactgcccg ctggccggat gacgccagta tcgaaggcaa acgtgtgggt    540
gtgatcggca caggctctac cggcgtgcaa gttattacgg cagtggcgcc actggccaag    600
cacctgacgg tgtttcagcg tacggcccag tactcggtcc cgatcatcaa cgatgtactg    660
agcgaagaag acgtcaagaa gatcaaagat aactatgatg acatctggga tggtgtttgg    720
aacagtaaac tggggttcgg cctgaatgaa tctactgtgc cggccatgtc cgtaagtgcg    780
gaagagcgtt acgcggtttt tgagaaggcg tggcaatctg cgcgggtat cggttttac    840 atcgaaacct ttggtgatat tgcgacgaac cgtgaagcta acattgaggc acaaaatttt    900
atcaaaggta aatcgcgga gatcgtcaaa gatccggcga tcgcccaaaa actgactccg    960
caggacctga agtttcgtcg ccctctgtgt gactccgggt actataatac gttcaatcgc   1020
gacaacgtac gtctggagga tgtcaaagca aatccgatcg tcgagatcac cgaaaacggc   1080
gtgaaactgg aaacggcga tttcgtggag ctggacatgc tgatctgcgc gacgggtttt   1140
gatgcggtag acggcaacta tgttcgcatg gatatccaag gcgtaacgg tctggccatg   1200 aaggattact ggaaagaggg cccgtctagc tacctgggcg taaccgtgaa taattaccca   1260
aacatgttta tggttagcgg tccaaacggt ccatctggta acgctccgcc tatgattgaa   1320
agtcaagttg aatggattag cgatactatc cagtataccg tcgaaaataa cgtggaatct   1380
attgaagcca cgaaggaagc ggaggaacag tggattgaca cctgcgccga tattgcggag   1440
atgaccctgt tgccagaggc ccagagccag gttaaagggg cgaacattcc aaataagaag   1500
gataccgcga tcaaatattt gggtgggctg aaaaactacc gctcagcttt ggcgaattgt   1560
aaaaatcatg cgtatgaagg ctttgatatt cagccgcaac gttctgacat caaacaacca   1620
gcgaatgcg                                                          1629
```

<210> SEQ ID NO 142
<211> LENGTH: 543
<212> TYPE: PRT
<213> ORGANISM: Artificial Sequence
<220> FEATURE:
<223> OTHER INFORMATION: Variant of CHMO from Acinetobacter sp NCIMB9871

<400> SEQUENCE: 142

```
Met Ser Thr Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Glu Lys Ala Gly Asp Val Gly Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Met Glu Ile Lys Thr Lys
65                  70                  75                  80

Tyr Ala Gln His Pro Asp Val Arg Asn Tyr Leu Gln Gln Val Ala Glu
                85                  90                  95

Lys His Val Leu Lys Lys Ser Tyr Gln Phe Asn Thr Ala Met Gln Ser
            100                 105                 110
```

```
Ala His Tyr Asn Glu Val Asp Ala Leu Trp Glu Val Thr Glu Tyr
    115                 120                 125

Gly Asp Lys Tyr Thr Ala Arg Phe Leu Ile Thr Ala Leu Gly Ser Leu
130                 135                 140

Ser Ala Pro Asn Leu Pro Asn Ile Lys Gly Ile Asn Gln Phe Lys Gly
145                 150                 155                 160

Asp Leu His His Thr Ala Arg Trp Pro Asp Asp Ala Ser Ile Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Thr
        195                 200                 205

Ala Gln Tyr Ser Val Pro Ile Ile Asn Asp Val Leu Ser Glu Glu Asp
    210                 215                 220

Val Lys Lys Ile Lys Asp Asn Tyr Asp Asp Ile Trp Asp Gly Val Trp
225                 230                 235                 240

Asn Ser Lys Leu Gly Phe Gly Leu Asn Glu Ser Thr Val Pro Ala Met
                245                 250                 255

Ser Val Ser Ala Glu Glu Arg Tyr Ala Val Phe Glu Lys Ala Trp Gln
            260                 265                 270

Ser Gly Ala Gly Ile Gly Phe Tyr Ile Glu Thr Phe Gly Asp Ile Ala
        275                 280                 285

Thr Asn Arg Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Thr Pro
305                 310                 315                 320

Gln Asp Leu Lys Phe Arg Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380

Gly Asn Tyr Val Arg Met Asp Ile Gln Gly Arg Asn Gly Leu Ala Met
385                 390                 395                 400

Lys Asp Tyr Trp Lys Glu Gly Pro Ser Ser Tyr Leu Gly Val Thr Val
                405                 410                 415

Asn Asn Tyr Pro Asn Met Phe Met Val Ser Gly Pro Asn Gly Pro Ser
            420                 425                 430

Gly Asn Ala Pro Pro Met Ile Glu Ser Gln Val Glu Trp Ile Ser Asp
        435                 440                 445

Thr Ile Gln Tyr Thr Val Glu Asn Asn Val Glu Ser Ile Glu Ala Thr
    450                 455                 460

Lys Glu Ala Glu Glu Gln Trp Ile Asp Thr Cys Ala Asp Ile Ala Glu
465                 470                 475                 480

Met Thr Leu Leu Pro Glu Ala Gln Ser Gln Val Lys Gly Ala Asn Ile
                485                 490                 495

Pro Asn Lys Lys Asp Thr Ala Ile Lys Tyr Leu Gly Gly Leu Lys Asn
            500                 505                 510

Tyr Arg Ser Ala Leu Ala Asn Cys Lys Asn His Ala Tyr Glu Gly Phe
        515                 520                 525
```

Asp Ile Gln Pro Gln Arg Ser Asp Ile Lys Gln Pro Ala Asn Ala
         530                 535                 540

<210> SEQ ID NO 143
<211> LENGTH: 759
<212> TYPE: DNA
<213> ORGANISM: Artificial Sequence
<220> FEATURE:
<223> OTHER INFORMATION: Variant of KRED from Lactobacillus kefiri

<400> SEQUENCE: 143

```
atgaccgatc gtctgaaggg caaagtagcc atcgtaaccg gcgggactct gggtatcggt    60
ttggcgatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattt tcgtttataa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttgagggct ggtaggcgat ccgacgggtg ggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                         759
```

<210> SEQ ID NO 144
<211> LENGTH: 252
<212> TYPE: PRT
<213> ORGANISM: Artificial Sequence
<220> FEATURE:
<223> OTHER INFORMATION: Variant of KRED from Lactobacillus kefiri

<400> SEQUENCE: 144

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Phe Val Tyr
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Gly Gly Ala Tyr Asn Ala Ser Lys
145                 150                 155                 160

```
Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Tyr Ile Lys
        180                 185                 190

Thr Pro Leu Val Asp Asp Leu Glu Gly Ala Glu Glu Met Met Ser Gln
    195                 200                 205

Arg Thr Lys Thr Pro Met Gly His Ile Gly Glu Pro Asn Asp Ile Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 145
<211> LENGTH: 759
<212> TYPE: DNA
<213> ORGANISM: Artificial Sequence
<220> FEATURE:
<223> OTHER INFORMATION: Variant of KRED from Lactobacillus kefiri

<400> SEQUENCE: 145
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat cgctttgtc     180 cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgtttttttc     360
ggcacccgtc tgggcattca gcgcatgaaa aataaaggct gggcgctag catcatcaat     420 atgagcagta ttgaggggct cgtaggcgat ccgacgctgg ggcatacaa cgcttccaag     480 ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtctggagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                            759

<210> SEQ ID NO 146
<211> LENGTH: 252
<212> TYPE: PRT
<213> ORGANISM: Artificial Sequence
<220> FEATURE:
<223> OTHER INFORMATION: Variant of KRED from Lactobacillus kefiri

<400> SEQUENCE: 146

Met Thr Asp Arg Leu Lys Gly Lys Val Ala Ile Val Thr Gly Gly Thr
1               5                  10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80
```

```
Phe Gly Pro Val Thr Thr Val Val Asn Asn Ala Gly Ile Ala Val Ser
                85              90              95

Lys Ser Val Glu Asp Thr Thr Thr Glu Glu Trp Arg Lys Leu Leu Ser
            100             105             110

Val Asn Leu Asp Gly Val Phe Phe Gly Thr Arg Leu Gly Ile Gln Arg
            115             120             125

Met Lys Asn Lys Gly Leu Gly Ala Ser Ile Ile Asn Met Ser Ser Ile
        130             135             140

Glu Gly Leu Val Gly Asp Pro Thr Leu Gly Ala Tyr Asn Ala Ser Lys
145             150             155             160

Gly Ala Val Arg Ile Met Ser Lys Ser Ala Ala Leu Asp Cys Ala Leu
                165             170             175

Lys Asp Tyr Asp Val Arg Val Asn Thr Val His Pro Gly Tyr Ile Lys
            180             185             190

Thr Pro Leu Val Asp Asp Leu Glu Gly Leu Glu Glu Met Met Ser Gln
        195             200             205

Arg Thr Lys Thr Pro Met Gly His Ile Gly Glu Pro Asn Asp Ile Ala
    210             215             220

Trp Ile Cys Val Tyr Leu Ala Ser Asp Glu Ser Lys Phe Ala Thr Gly
225             230             235             240

Ala Glu Phe Val Val Asp Gly Gly Tyr Thr Ala Gln
                245             250
```

BIOCATALYSTS AND METHODS FOR THE SYNTHESIS OF ARMODAFINIL

The present application is a Continuation of co-pending U.S. patent application Ser. No. 15/903,264, filed Feb. 23, 2018, now U.S. Pat. No. 10,087,426, which is a Continuation of U.S. patent application Ser. No. 15/698,319, filed Sep. 7, 2017, now U.S. Pat. No. 9,938,509, which is a Continuation of U.S. patent application Ser. No. 15/352,970, filed Nov. 16, 2016, now U.S. Pat. No. 9,765,306, which is a Continuation of U.S. patent application Ser. No. 15/159,578, filed May 19, 2016, now U.S. Pat. No. 9,528,095, which is a Continuation of U.S. patent application Ser. No. 14/997,277, filed Jan. 15, 2016, now U.S. Pat. No. 9,365,835, which is a Divisional of Ser. No. 13/992,138, filed Jun. 6, 2013, now U.S. Pat. No. 9,267,159, which claims priority to PCT/US2011/063809, filed Dec. 7, 2011, which claims priority to U.S. Prov. Pat. Appln. Ser. No. 61/421,123, filed Dec. 8, 2010, all of which are incorporated herein by reference, in their entireties and for all purposes.

TECHNICAL FIELD

This disclosure relates to biocatalysts and processes using the biocatalysts for the preparation of armodafinil.

REFERENCE TO SEQUENCE LISTING, TABLE OR COMPUTER PROGRAM

The Sequence Listing is concurrently submitted herewith with the specification as an ASCII formatted text file via EFS-Web with a file name of CX2-050USP1_ST25.txt with a creation date of Dec. 8, 2010, and a size of 510551 bytes. The Sequence Listing filed via EFS-Web is part of the specification and is hereby incorporated in its entirety by reference herein.

BACKGROUND

Armodafinil (Nuvigil) is the active (−)-(R)-enantiomer of the racemic drug modafinil (Provigil). Armodafinil, whose structure is shown herein as compound (2a), also has the chemical name (−)-2-[(R)-(diphenylmethyl)sulfinyl]acetamide.

(2a)

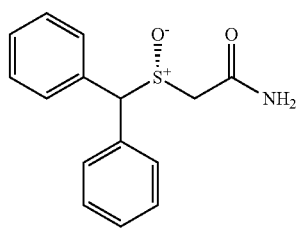

Armodafinil is a stimulant-like drug approved by the FDA for the treatment of narcolepsy and shift work sleep disorder, and as an adjunctive treatment for obstructive sleep apnea. It is also being evaluated as a treatment for other medical conditions such as bipolar depression, cognition abnormalities associated with schizophrenia, and fatigue in conditions such as Parkinson's disease and cancer.

The chemical process for preparing armodafinil involves either Kagan Sharpless-type oxidation (Ti(isopropoxide)$_4$/tartrate) of 2-(benzhydrysulfinyl)acetamide (see e.g., PCT Publ. No. WO2005/028428) or classic resolution of racemic modafinil acid by (R)-naphthylethylamine (see e.g., PCT Publ. No. WO2007/103221).

A biocatalytic route for the synthesis of armodafinil could provide significant advantages over above chemical processes if capable of high efficiency (e.g., high substrate loadings) and high enantioselectivity. An enzymatic oxidation has been described using a phenylacetone monooxygenase in a step for converting 2-benzhydrylthioacetic acid to 2-(benzhydrylsulfinyl)acetic acid (see e.g., US Publ. No. US2007/087422A1). Also, microbial oxidations of benzhydrylsulfanyl acetic acid or benzhydrylsulfanyl acetamide have been described that provide mixtures of (S)-modafinil and (R)-modafinil (see e.g., Olivo et al., "Microbial oxidation/amidation of benzhydrylsulfanyl acetic acid. Synthesis of (+)-modafinil," Tetrahedron Asymmetry (2005), 16(21), 3507-3511; PCT publ. no. WO2007/027328A2). Both processes, however, provide poor enantioselectivity and poor yield of product.

Cyclohexanone monooxygenases (CHMO) were originally identified for their ability to carry out the conversion of cyclohexanone to ε-caprolactone, a seven membered cyclic product. The CHMO biocatalytic reaction uses $O_2$ and a co-factor NAPDH to generate the caprolactone, oxidized cofactor NADP+, and $H_2O$. CHMOs are flavin dependent enzymes and contain a flavin prosthetic group, generally flavin adenine dinucleotide (FAD). This FAD prosthetic group is bound to the enzyme and is believed to participate in the catalytic reaction by forming a peroxyflavin intermediate (see, e.g., Sheng et al., 2001, Biochemistry 40(37): 11156-67; Malito et al., 2004, *Proc Natl Acad Sci USA* 101(36):13157-13162). CHMOs have also been used as biocatalysts for the enantioselective air-oxidation of prochiral thioethers to form chiral sulfoxides (see, e.g., Light et al., 1982, "Studies on the chirality of sulfoxidation catalyzed by bacterial flavoenzyme cyclohexanone monooxygenase and hog liver flavin adenine dinucleotide containing monooxygenase," *Biochemistry*, 21(10):2490-8; and Reetz et al., 2004, *Angew. Chem. Int. Ed.* 43:4078-4081). CHMOs also recognize a variety of aryl-alkyl sulfide substrates (see e.g., Pasta et al., 1995, *Tetrahedron: Asymmetry* 6(4):933-936; Yeung and Rettie, 2005, "Prochiral Sulfoxidation as a probe for Flavin-Containing Monooxygenases," in *Methods in Molecular Biology: Cytochrome P450 Protocols* 320:163-172; Colonna et al., 2000, Chirality 13(1):40-42; and Alphand et al., 2003, *Trends Biotechnology* 21(7):318-323). The wild-type CHMO from *Acinetobacter* sp. NCIMB9871 has been shown to catalyze the sulfoxidation of 4-tolyl-sulfide but the resulting product is predominantly the (S)-sulfoxide (S:R~86:13) (see e.g., Light, et al. 1982 supra).

There is a need for improved enzymes capable of being used in a biocatalytic process for preparing armodafinil. Particularly desirable would be CHMOs capable of increased activity in large scale processes having high substrate loadings, high percent conversion, and capable of yielding armodafinil as product in high purity and enantiomeric excess.

SUMMARY

The present disclosure is directed to non-naturally occurring polypeptides having cyclohexanone monooxygenase (CHMO) activity, polynucleotides encoding the polypeptides, methods of the making the polypeptides, and methods of using the polypeptides in biocatalytic processes for the preparation of armodafinil. Specifically, the disclosure processes for the preparation of armodafinil including either of the following two biocatalytic reactions: (i) conversion of the amide substrate 2-(benzhydrylsulfinyl)acetamide (compound (1a)) to the product armodafinil, (−)-2-[(R)-(diphenylmethyl)sulfinyl]acetamide (compound (2a)); or (ii) conversion of the acid substrate, benzhydryl-thioacetic acid (compound (1b)) (also referred to as BHTA) to (R)-2-(benzhydrylsulfinyl)acetic acid (compound (2b)) (also referred to as (R)-BHSO or (R)-modafinic acid), which is an acid intermediate easily converted to the amide product, armodafinil in enantiomeric excess.

While naturally occurring polypeptides having CHMO activity do not efficiently convert compound (1a) to compound (2a), or compound (1b) to compound (2b), in some embodiments, the non-naturally occurring (or engineered) polypeptides having CHMO activity of the present disclosure are capable of carrying out these conversions with improved properties including, high enantiomeric excess (e.g., at least about 90% e.e.), increased activity (e.g., at least about 10-fold increased activity relative to the reference wild-type polypeptide SEQ ID NO: 2), high percent conversion (e.g., at least about 90% conversion in 24 h), in the presence of high substrate loadings (e.g., at least about 5 g/L of substrate). In some embodiments, the present disclosure provides a non-naturally occurring polypeptide having CHMO activity capable of converting compound (1a) to compound (2a), and/or compound (1b) to compound (2b), with at least 2-fold, at least 10-fold, at least 25-fold, at least 40-fold, or at least 60-fold increased specific enzyme activity relative to the specific enzyme activity of the polypeptide of SEQ ID NO: 2.

In some embodiments the present disclosure provides a non-naturally occurring polypeptide having CHMO activity wherein the amino acid sequence of the polypeptide has at least 80%, 85%, 86%, 87%, 88%, 89%, 90%, 91%, 92%, 93%, 94%, 95%, 96%, 97%, 98%, or 99% sequence identity to SEQ ID NO: 2 and includes one or more amino acid differences relative to SEQ ID NO: 2 selected from the following: X143C, E, F, G, H, K, M, P, Q, S, T, or W; X246A, E, G, I, L, N, P, S, T, or V; X277C, D, E, G, H, L, M, P, S, T, V, or W; X278A, C, G, H, K, N, Q, S, T, or V; X280L, T, or W; X281A, C, H, K, L, M, N, R, T, V, W, or Y; X326A, D, E, F, G, H, L, M, N, P, R, V, or W; X426G, Q, or T; X432E, I, K, N, Q, T, V, or W; X433S; X435G, K, V, or Y; X490A, C, D, E, G, I, L, M, N, S, or Y; and X532M. In some embodiments, the polypeptide is capable of converting the acid substrate compound (1b) to compound (2b), and/or the polypeptide is capable of converting the acid substrate of compound (1b) to the R-enantiomer compound (2b) in at least 50% ee.

In some embodiments of the non-naturally occurring polypeptide having CHMO activity, the polypeptide amino acid sequence can comprise one or more amino acid differences relative to SEQ ID NO: 2 selected from: X143G; X278G; X326R; and X490L. Further, in some embodiments, the amino acid sequence can comprise at least the following amino acid differences relative to SEQ ID NO: 2: X277I; X278A, or G; X280T or Y; X281I; X326R; and X490L or X490Q. In additional embodiments, the polypeptide amino acid sequence may further comprise at least one combination of amino acid differences relative to SEQ ID NO: 2 selected from the exemplary CHMO polypeptides disclosed herein.

The present disclosure also provides non-naturally occurring polypeptides having CHMO activity comprising an amino acid sequence which have at least 80%, 85%, 86%, 87%, 88%, 89%, 90%, 91%, 92%, 93%, 94%, 95%, 96%, 97%, 98%, or 99% sequence identity to any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, or 142. In some embodiments, said non-naturally occurring polypeptide having CHMO activity further have at least 10-fold increase in specific enzyme activity in comparison with SEQ ID NO: 2 and at least 75% enantiomeric excess in converting compound (1a) to compound (2a), and/or compound (1b) to compound (2b).

In another aspect, provided herein are polynucleotides encoding the monooxygenase polypeptides, expression vectors comprising the polynucleotides, and host cells capable of expressing the polypeptides. Accordingly, in some embodiments, the present disclosure also provides methods of manufacturing the non-naturally occurring CHMO polypeptides capable of converting compound (1a) to compound (2a) and/or compound (1b) to compound (2b), wherein the methods comprise culturing a host cell capable of expressing a polynucleotide encoding the engineered transaminase polypeptide and isolating the polypeptide from the host cell. Exemplary polynucleotide sequences are provided in the sequence listing incorporated by reference herein and include SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, or 141.

The present disclosure is also directed to a method for preparing compound (2a) from compound (1a) in enantiomeric excess, the method comprising contacting compound (1a) with a non-naturally occurring polypeptide having CHMO activity of the present disclosure in the presence of cofactor NADPH or NADH under suitable reaction conditions. Similarly, the present disclosure also provides a method for preparing compound (2b) from compound (1b) in enantiomeric excess, the method comprising contacting compound (1b) with a non-naturally occurring CHMO polypeptide of the present disclosure in the presence of cofactor NADPH or NADH under suitable reaction conditions. Suitable reaction conditions can include a source of molecular oxygen 02, a cofactor recycling system (e.g., a KRED enzyme and a secondary alcohol), and a co-solvent (e.g., 2-7.5% NMP, or 5-15% PEG200).

Further, the present disclosure is also directed to a method for preparing compound (2a) from compound (1b) in enantiomeric excess. The method comprises the steps of: (a) preparing compound (2b) from compound (1b) with a non-naturally occurring polypeptide having CHMO activity of the present disclosure in the presence of cofactor NADPH or NADH under suitable reaction conditions, and (b) preparing compound (2a) from compound (2b) by esterification and amidation.

DETAILED DESCRIPTION 1.1 Definitions

The technical and scientific terms used in the descriptions herein will have the meanings commonly understood by one of ordinary skill in the art, unless specifically defined otherwise. Accordingly, the following terms are intended to have the following meanings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Non-naturally occurring" or "engineered" or "recombinant" when used in the present disclosure with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, a "reference sequence based on SEQ ID NO:2 having at the residue corresponding to X9 a threonine" refers to a reference sequence in which the corresponding residue at X9 in SEQ ID NO:2, which is a alanine, has been changed to threonine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered cyclohexanone monooxygenase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X3 as compared to SEQ ID NO: 2" refers to a change of the amino acid residue at the polypeptide position corresponding to position 3 of SEQ ID NO:2. Thus, if the reference polypeptide of SEQ ID NO: 2 has a glutamine at position 3, then a "residue difference at position X3 as compared to SEQ ID NO:2" an amino acid substitution of any residue other than glutamine at the position of the polypeptide corresponding to position 3 of SEQ ID NO: 2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in Tables 2A, 2B, and 2C), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where changes are made relative to the reference sequence. The present disclosure includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1 below:

TABLE 1

| Residue | Possible Conservative Substitutions |
| --- | --- |
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered CHMO enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered CHMO enzymes comprise insertions of one or more amino acids to the naturally occurring CHMO polypeptide as well as insertions of one or more amino acids to other improved CHMO polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of a full-length polypeptide.

"Improved enzyme property" refers to a functional property of a polypeptide that can be measured under suitable conditions and which exhibits improvement as compared to the same property of a reference polypeptide. For the engineered CHMO polypeptides described herein, the comparison is generally made to the wild-type CHMO enzyme, although in some embodiments, the reference polypeptide can be another improved engineered CHMO polypeptide. Enzyme properties for which improvement is desirable include, but are not limited to, enzymatic activity (which can be expressed in terms of percent conversion of the substrate), thermo stability, solvent stability, pH activity profile, cofactor requirements, refractoriness to inhibitors (e.g., substrate or product inhibition), stereospecificity, and stereoselectivity (including enantioselectivity).

"Suitable reaction conditions" refers to those conditions in the biocatalytic reaction solution (e.g., ranges of enzyme loading, substrate loading, cofactor loading, T, pH, buffers, co-solvents, etc.) under which a non-naturally occurring CHMO polypeptide of the present disclosure is capable of converting compound (1a) to compound (2a), or compound (1b) to compound (2b). Exemplary "suitable reaction conditions" are provided in the present disclosure and illustrated by the Examples.

"Increased enzymatic activity" or "increased activity" refers to an improved property of an engineered enzyme, which can be represented by an increase in enzyme activity (e.g., product produced/time/weight protein) or an increase in percent conversion of the substrate to the product (e.g., percent conversion of starting amount of substrate to product in a specified time period using a specified amount of cyclohexanone monooxygenase) as compared to a reference enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. The Cyclohexanone monooxygenase activity can be measured by any one of standard assays used for measuring cyclohexanone monooxygenases, such as change in substrate or product concentration, or change in concentration of the cofactor (in absence of a cofactor regenerating system). Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a CHMO polypeptide can be expressed as "percent conversion" of the substrate to the product.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess. "Highly stereoselective" refers to a chemical or enzymatic reaction that is capable of converting (i) a substrate 2-(benzhydrylsulfinyl)acetamide (compound (1a)) to (−)-2-[(R)-(diphenylmethyl)sulfinyl]acetamide (compound (2a), armodafinil), or (ii) a substrate benzhydrylthioacetic acid (compound (1b)) to (R)-2-(benzhydrylsulfinyl)acetic acid (compound (2b), (R)-modafinic acid); with at least about 85% stereoisomeric excess.

"Thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved CHMO enzymes may be present within a cell, present in the cellular medium, or prepared in various forms, such as lysates or isolated preparations. As such, in some embodiments, the engineered CHMO polypeptides of the present disclosure can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered CHMO polypeptide composition will comprise about 60% or more, about 70% or more, about 80% or more, about 90% or more, about 95% or more, and about 98% or more of all macromolecular species by mole or % weight present in the composition. Solvent species, small molecules (<500 Daltons), and elemental ion species are not considered macromolecular species. In some embodiments, the isolated improved CHMO polypeptide is a substantially pure polypeptide composition.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. In some embodiments, the polynucleotides encoding the CHMO enzymes may be codon optimized for optimal production from the host organism selected for expression.

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Cofactor regeneration system" refers to a set of reactants that participate in a reaction that reduces the oxidized form of the cofactor (e.g., NADP+ to NADPH). Cofactors oxidized by the cyclohexanone monooxygenase-catalyzed reduction of the substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

The term "glucose dehydrogenase" refers to an $NAD^+$ or $NADP^+$-dependent enzyme that catalyzes the conversion of D-glucose and $NAD^+$ or $NADP^+$ to gluconic acid and NADH or NADPH, respectively.

The term "an alcohol dehydrogenase" is used herein to refer to an $NAD^+$ or $NADP^+$-dependent enzyme that catalyzes the conversion of an alcohol (e.g., isopropanol) and $NAD^+$ or $NADP^+$ to a ketone and NADH or NADPH, respectively.

1.2 Non-Naturally Occurring or Engineered Cyclohexanone Monooxygenase Polypeptides The present disclosure provides highly stereoselective and efficient non-naturally occurring polypeptides having cyclohexanone monooxygenase (CHMO) activity. In some embodiments the non-naturally occurring polypeptides having CHMO activity are capable of mediating the biocatalytic conversion of: (i) 2-(benzhydrylsulfinyl)acetamide (compound (1a)) to (−)-2-[(R)-(diphenylmethyl)sulfinyl]acetamide (compound (2a)); or (ii) benzhydryl-thioacetic acid (compound (1b), or "BHTA") to (R)-2-(benzhydrylsulfinyl) acetic acid (compound (2b), or "(R)-BHSO," or "(R)-modafinic acid").

A general biocatalytic scheme for using an engineered CHMO polypeptide (i.e., "CHMO variant") of the present disclosure to convert the amide substrate of compound (1a) to the product of compound (2a) is shown in Scheme 1:

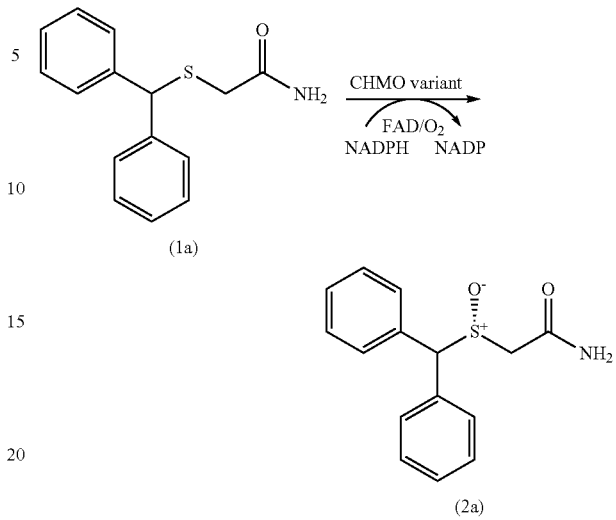

Alternatively, the engineered CHMO polypeptides of the present disclosure can be used in a biocatalytic scheme to convert the acid substrate of compound (1b) to the product of compound (2b) as shown in Scheme 2:

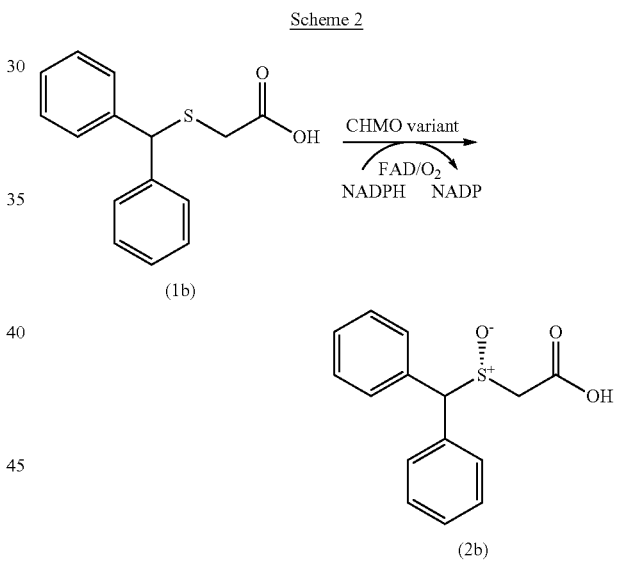

The acid substrate product of compound (2b) is an intermediate useful for the preparation of armodafinil (compound (2a)), in enantiomeric excess. The engineered polypeptides having CHMO activity described herein have been designed by changing the amino acid sequence of a naturally occurring CHMO to form polypeptides with the desired enzymatic properties, e.g., enzyme activity, stereoselectivity, by-product formation, thermostability, and expression. The following detailed description describes the CHMO polypeptides and processes for carrying out the conversion of either: (i) compound (1a) to compound (2a); or (ii) compound (1b) to compound (2b).

Naturally occurring polypeptides having CHMO activity do not efficiently convert compound (1a) to compound (2a), or compound (1b) to compound (2b). The engineered polypeptides having CHMO activity of the present disclosure have been designed starting from the cyclohexanone monooxygenase of *Acinetobacter* sp. NCIMB9871. In contrast to the wild-type enzyme, these engineered CHMO polypeptides are capable of carrying out this conversion with improved properties including, high enantiomeric excess (e.g., at least about 75% e.e.), increased enzyme activity (e.g., at least about 2-fold increased activity relative to the reference polypeptide SEQ ID NO: 2), high percent conversion (e.g., at least about 80% conversion in 24 h), in the presence of high substrate loadings (e.g., at least about 10 g/L of substrate compound (1a) or compound (2a)).

The non-naturally occurring polypeptides having CHMO activity of the present disclosure comprise amino acid sequences that have one or more residue differences as compared to the reference sequence of the wild-type *Acinetobacter* sp. NCIMB9871 CHMO polypeptide (SEQ ID NO: 2). The residue differences occur at residue positions that affect enzyme activity, stereoselectivity, thermostability, expression, or various combinations thereof. In some embodiments, the residue differences relative to the wild-type sequence allow the engineered polypeptides having CHMO activity to convert the amide substrate compound (1a) to compound (2a) and/or the acid substrate compound (1b) to compound (2b) with at least 2-fold, at least 10-fold, at least 25-fold, at least 40-fold, or at least 60-fold increased activity relative to the activity of a reference polypeptide of SEQ ID NO: 2, 4, or 38. Further, these engineered polypeptides are capable of highly stereoselective conversion of the amide substrate compound (1a) to compound (2a), and/or the acid substrate compound (1b) to compound (2b) in an enantiomeric excess (e.e.) of at least 75%, at least 80%, at least 85%, at least 90%, at least 95%, at least 97%, at least 98%, at least 99%, at least 99.8%, or more. Additionally, in some embodiments, the engineered polypeptides having CHMO activity of the present disclosure are capable of at least about 80%, or 85%, or 90% conversion of compound (1a) to compound (2a), or compound (1b) to compound (2b), in 24 hours with a substrate loading of at least about 10 g/L, or 20 g/L, or 30 g/L, or 50 g/L, or 75 g/L, or 100 g/L.

The biocatalytic conversions of Scheme 1 and Scheme 2 can be carried out using whole cells expressing the engineered polypeptides having CHMO activity, or purified or partially purified preparations of the polypeptides (e.g., shake-flask powders, downstream processed powders, or other fermentation powders). For in vitro applications, a cofactor (NADH or NADPH) and a cofactor regenerating system such as ketoreductase (KRED) along with a secondary substrate such as isopropyl alcohol (IPA) at e.g., 5% (v/v) concentration can be used in conjunction with the engineered CHMO polypeptides.

Structure and function information correlating the amino acid differences of the exemplary non-naturally occurring (or engineered) polypeptides having CHMO activity of the present disclosure with their improved functional capabilities in the biocatalytic reactions of Scheme 1 and Scheme 2 are shown below in Tables 2A, 2B, and 2C. The odd numbered sequence identifiers (i.e., SEQ ID NO) refer to the nucleotide sequence encoding the amino acid sequence provided by the even numbered sequence identifiers, and the sequences are provided in the electronic sequence listing file accompanying this disclosure, which is hereby incorporated by reference herein. The amino acid residue differences are based on comparison to the reference sequence of SEQ ID NO: 2, which is a wild-type CHMO of *Acinetobacter* NCIMB9871.

Initial high-throughput (HTP) assays of activity and enantioselectivity in the biocatalytic conversion of Scheme 1 showed that the wild-type CHMO polypeptide of SEQ ID NO: 2 does not produce the desired product enantiomer of compound (2a) in enantiomeric excess (−52.3% e.e.). However, directed evolution of the gene encoding the wild-type polypeptide of SEQ ID NO: 2 resulted in several engineered genes encoding polypeptides having CHMO activity capable of producing the desired product enantiomer of compound (2a) in enantiomer excess. For example, the engineered polypeptide of SEQ ID NO: 4 produced by directed evolution was capable the desired product enantiomer of compound (2a) in enantiomeric excess (88% e.e.) and with over 25-fold increased activity relative to the wild-type.

The engineered CHMO polypeptide sequence of SEQ ID NO: 4 has 10 amino acid residue differences (98.2% amino acid sequence identity) relative to the wild-type polypeptide of SEQ ID NO: 2 including the following: D37E, F277I, R278G, M280T, F281I, K326R, F432S, T433G, L435A, and W490L. Further rounds of directed evolution using the gene encoding SEQ ID NO: 4 as a starting "backbone" led to the development of the 60 other exemplary engineered CHMO polypeptides of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, or 142. Additionally, a subset of single residue difference engineered CHMO polypeptides were generated based on the following 14 positions that were identified during directed evolution: X37, X143, X246, X277, X278, X280, X281, X326, X426, X432, X433, X435, X490, and X532. The subset generated included an engineered CHMO polypeptide for each of the 19 amino acid differences (relative to the wild-type of SEQ ID NO: 2) at each of the 14 positions. Each of the single-change engineered CHMO polypeptides was screened for activity and enantioselectivity in the conversion of the acid substrate of compound (1b) to compound (2b), thereby providing further structural-functional correlation for a subset of single-amino acid residue changes. As shown in Tables 2A, 2B, 2C, and the Examples, these engineered polypeptides having CHMO activity are capable of producing compound (2a) and/or compound (2b) with increased activity and in increased enantiomeric excess relative to the wild-type CHMO. These exemplary engineered CHMO polypeptides also illustrate a wide range of amino acid differences that can be introduced across the length of the wild-type polypeptide sequence which correlate with this functional improvement in the enzyme properties. They also show that many of the 10 amino acid differences found in the polypeptide sequence of the backbone engineered CHMO polypeptide of SEQ ID NO: 4 can be varied and/or reverted to wild-type while maintaining increased activity over the wild-type and/or the ability to produce the desired enantiomer of compound (2a) in enantiomeric excess. For example, many engineered CHMO polypeptides having W490Q rather W490L, and/or F280Y rather than F280T, retain the desired improved properties of increased activity and ability to produce compound (2a) in enantiomeric excess. Additionally, the polypeptide of SEQ ID NO: 20 does not include the amino acid difference F432S yet produces compound (2a) in 99.1% e.e.

Table 2A summarizes the correlation between the structure of the engineered polypeptides having CHMO activity of the present disclosure and the activity and enantioselectivity of these enzymes in carrying out the biocatalytic conversion of the amide substrate of compound (1a) to the product of compound (2a) as in Scheme 1. The general SFP assay conditions used to determine amide substrate "Activity" and "% e.e." as summarized in Table 2A were as follows: 5-10 g/L substrate mixture of compound (1a), 3-10 g/L of SFP of the engineered CHMO polypeptide, 1 g/L KRED of SEQ ID NO: 144, 0.3-0.5 g/L NADP, in a solution of 25 mM-100 mM phosphate buffer, 5-10% (v/v) IPA, pH 8.0-8.5, 25° C. reaction temperature and 24 h reaction time (with 400 rpm stirring). Specific alterations to these general SFP assay conditions were made over the rounds of evolution and are noted in Table 2A. Further details of the SFP assays used are described in the Examples.

TABLE 2A

Engineered CHMO structure-function correlation in amide substrate reaction

| SEQ ID NO: (nt/aa) | Amino acid differences (relative to SEQ ID NO: 2) | Amide Substrate Activity relative to SEQ ID NO: 4 | % e.e. |
|---|---|---|---|
| 3/4 | D37E; F277I; R278G; M280T; F281I; K326R; F432S; T433G; L435A; W490L | 1.0[1] | 75 |
| 5/6 | D37E; A54V; L143G; V172M; F277I; R278G; M280Y; F281I; K326R; F432S; T433G; L435A; W490L; L532P | 2.8[1] | 98 |
| 7/8 | Q3T; D37E; A54V; L143G; V172M; F277I; R278G; M280Y; F281I; K326R; F432S; T433G; L435A; W490L; L532P | 4.2[1] | 98 |
| 9/10 | Q3T; D37E; A54V; L75M; L143G; V172M; F277I; R278G; M280Y; F281I; K326R; F432S; T433G; L435A; W490L; L532P | 9.7[2] | 98.8 |
| 11/12 | Q3T; D37E; L75M; L143G; F277I; R278G; M280Y; F281I; K326R; L426S; F432S; T433G; L435A; W490L; V503A; L532P | 17.4[2] | 99.1 |
| 13/14 | Q3T; D37E; L75M; F277I; R278G; M280Y; F281I; K326R; F432S; T433G; L435A; W490L | 15.5[2] | |
| 15/16 | Q3T; D37E; A43G; L75M; L143G; S166G; F277I; R278G; M280Y; F281I; K326R; L426S; F432S; T433G; L435A; W490L; V503A; E512N; L532P | 26.1[2] | 98.9 |
| 17/18 | Q3T; D37E; A43G; L75M; L143G; S166G; F277I; R278G; M280Y; F281I; A313E; K326R; L426S; F432S; T433G; L435A; W490L; V503A; L532P | 22.6[2] | |
| 19/20 | Q3T; D37E; A43G; L75M; L143G; S166G; F277I; R278G; M280Y; F281I; K326R; M412L; L426N; T433G; L435A; S489G; W490L; V503A; E512N; L532P | 29.5[2] | 99.1 |
| 21/22 | Q3T; D37E; V42I; A43G; L75M; L143G; S166G; F277I; R278G; M280Y; F281I; D322G; K326R; L426S; F432S; T433G; L435A; W490L; F492S; V503A; E512N; L532P | 34.7[2] | 98.2 |
| 23/24 | Q3T; D37E; V42I; A43G; L75M; L143G; S166G; F277I; R278G; M280Y; F281I; D322G; K326R; L426S; F432S; T433G; L435A; N477D; W490L; F492S; V503A; E512N; L532P | 34.7[2] | 98.5 |
| 25/26 | Q3T; D37E; A43G; L75M; L143G; S166G; F277I; R278G; M280Y; F281I; A288V; K326R; L426S; F432S; T433G; L435A; W490L; I491V; V503A; Y504I; E512N; L532P | 29.5[3] | 99.2 |
| 27/28 | Q3T; D37E; A43G; L75M; L143G; H163L; S166G; F277I; R278G; M280Y; F281I; A288V; D322G; K326R; A382R; L426S; F432S; T433G; L435A; N477D; W490L; I491V; V503A; Y504I; E512N; L532P | 56.0[3] | 99.8 |
| 29/30 | Q3T; D37E; A43G; L75M; L143G; S166G; F277I; R278G; M280Y; F281I; A288V; D322G; K326R; V348A; L426S; F432S; T433G; L435A; N477D; S489G; W490L; I491V; V503A; Y504I; E512N; L532P; K538E; | 58.9[3] | 99.7 |
| 31/32 | Q3T; D37E; V42I; A43G; L75M; L143G; S166G; F277I; R278G; M280Y; F281I; A288V; K326R; L426S; F432S; T433G; L435A; N477D; W490L; I491V; V503A; Y504I; E512N; L532P | 32.4[3] | 99.9 |
| 33/34 | Q3T; D37E; V42I; A43G; L75M; L143G; H163L; S166G; G176S; F277I; R278G; M280Y; F281I; A288V; D322G; K326R; A382R; L426S; F432S; T433G; L435A; N477D; S489G; W490L; I491V; V503A; Y504I; E512N; L532P | 56.0[3] | 99.8 |
| 35/36 | Q3T; D37E; A43G; L75M; L143G; H163L; S166G; G176S; F277I; R278G; M280Y; F281I; A288V; D322G; K326R; L426S; F432S; T433G; L435A; N477D; W490L; I491V; V503A; Y504I; E512N; L532P | 50.1[3] | 99.6 |
| 37/38 | Q3T; D37E; A43G; L75M; L143G; S166A; F277I; R278G; M280Y; F281I; A288V; K326R; E364K; K395R; M412L; L426S; F432S; T433G; L435A; W490L; I491V; V503A; Y504I; E512N; L532P | 58.9[3] | 99.8 |
| 39/40 | Q3T; D37E; A43G; L75M; L143G; S166A; F277I; R278G; M280Y; F281I; A288V; K326R; K395R; L426S; F432S; T433G; L435A; W490L; I491V; V503A; Y504I; E512N; L532P | 44.2[3] | 99.6 |

[1]Substrate: 5 g/L; CHMO: 3 g/L; NADP: 0.5 g/L; IPA: 10%; 25 mM phosphate, pH 8.5.
[2]Substrate: 10 g/L; CHMO: 10 g/L; NADP: 0.3 g/L; IPA: 5%; 100 mM phosphate, pH 8.0.
[3]Substrate: 10 g/L; CHMO: 5 g/L; NADP: 0.3 g/L; IPA: 5%; 100 mM phosphate, pH 8.0.

Table 2B summarizes the correlation between the structure of the engineered polypeptides having CHMO activity of the present disclosure and the activity and enantioselectivity of these enzymes in carrying out the biocatalytic conversion of the acid substrate of compound (1b) to the product of compound (2b) as in Scheme 2. The general SFP assay conditions used to determine acid substrate "Activity" and "% e.e." as summarized in Table 2B were as follows: 10-100 g/L substrate mixture of compound (1b), 5-10 g/L of SFP of the engineered CHMO polypeptide, 1 g/L KRED of SEQ ID NO: 144 or 146, 0.2-0.3 g/L NADP, in a solution of 100 mM phosphate buffer or TEA buffer, 5% (v/v) IPA, pH 8.3 or pH 9.0, 25° C. reaction temperature and 24 h reaction time (with 400 rpm stirring). Specific alterations to these general SFP assay conditions were made over the rounds of evolution and are noted in Table 2B. Further details of the SFP assays used are described in the Examples.

TABLE 2B

Engineered CHMO structure-function correlation in acid substrate reaction

| SEQ ID NO: (nt/aa) | Amino acid differences (relative to SEQ ID NO: 2) | Activity relative to SEQ ID NO: 38 | % e.e. |
|---|---|---|---|
| 37/38 | Q3T; D37E; A43G; L75M; L143G; S166A; F277I; R278G; M280Y; F281I; A288V; K326R; E364K; K395R; M412L; L426S; F432S; T433G; L435A; W490L; I491V; V503A; Y504I; E512N; L532P | 1.0[1] | 94 |
| 41/42 | Q3T; D37E; A43G; L75M; D99V; L143G; E161D; S166A; F174I; T273A; F277I; R278G; M280Y; F281I; A288V; D322M; Y324K; K326R; E364K; K395R; M412L; L426S; F432S; T433G; L435A; W490L; I491V; V503A; Y504I; E512N; L532P | 8.2[1] | 98.7 |
| 43/44 | Q3T; D37E; A43G; L75M; D99V; L143G; S166A; F174I; T273S; F277I; R278G; M280Y; F281I; A288V; D322M; K326R; E364K; K395R; M412L; L426S; F432S; T433G; L435A; W490L; I491V; V503A; Y504I; E512N; L532P | 8.9[1] | 95 |
| 45/46 | Q3T; D37E; A43G; L75M; E123A; L143G; S166A; F174I; T273S; F277I; R278G; M280Y; F281I; A288V; D322M; K326R; E364K; K395R; M412L; L426S; F432S; T433G; L435A; W490L; I491V; V503A; Y504I; E512N; L532P | 9.9[1] | 94.2 |
| 47/48 | Q3T; D37E; A43G; L75M; D99V; L143G; E161D; S166A; F174I; T273S; F277I; R278G; M280Y; F281I; A288V; Y324K; K326R; E364K; K395R; M412L; L426S; F432S; T433G; L435A; W490L; I491V; V503A; Y504I; E512N; L532P | 8.7[1] | 99 |
| 49/50 | Q3T; D37E; A43G; L75M; D99V; L143G; E161D; S166G; F174I; T273S; F277I; R278G; M280Y; F281I; A288V; Y324K; K326R; E364K; K395R; M412L; L426S; F432S; T433G; L435A; K486E; W490L; I491V; V503A; Y504I; E512N; L532P | 23.5[1] | 98.5 |
| 51/52 | Q3T; D37E; A43G; L75M; D99V; L143G; E161D; S166A; F174I; K227E; T273S; F277I; R278G; M280Y; F281I; A288V; Y324K; K326R; E364K; K395R; M412L; L426S; F432S; T433G; L435A; W490L; I491V; V503A; Y504I; E512N; L532P | 19.1[1] | 98.5 |
| 53/54 | Q3T; D37E; A43G; L75M; V82A; D99V; V110M; L143G; E161D; S166A; F174I; T273S; F277I; R278G; M280Y; F281I; A288V; Y324K; K326R; E364K; K395R; M412L; L426S; F432S; T433G; L435A; W490L; I491V; V503A; Y504I; E512N; L532P | 20.0[1] | 98.7 |
| 55/56 | Q3T; D37E; A43G; L75M; D99V; L143G; E161D; S166A; F174I; T273S; F277I; R278G; M280Y; F281I; A288V; Y324K; K326R; E364K; K395R; M412L; L426S; G430R; F432S; T433G; L435A; W490L; I491V; V503A; Y504I; E512N; L532P | 14.8[1] | 99.7 |
| 57/58 | Q3T; D37E; A43G; L75M; V82A; D99V; L143G; E161D; S166A; F174I; T273S; F277I; R278G; M280Y; F281I; A288V; Y324K; K326R; E364K; K395R; M412L; L426S; F432S; T433G; L435A; W490L; I491V; V503A; Y504I; E512N; L532P | 18.3[1] | 98.5 |
| 59/60 | Q3T; D37E; A43G; L75M; K79T; V82A; D99V; L143G; E161D; S166A; F174I; T273S; F277I; R278G; M280Y; F281I; A288V; Y324K; K326R; E364K; K395R; M412L; L426S; F432S; T433G; L435A; W490L; I491V; V503A; Y504I; E512N; L532P | 84.4[1] | 98.7 |
| 61/62 | Q3T; D37E; A43G; L75M; K79T; D99V; R135K; L143G; E161D; S166A; D171G; F174I; I182V; T273S; F277I; R278G; M280Y; F281I; A288V; I314T; Y324K; K326R; E364K; M373V; K395R; M412L; L426S; F432S; T433G; L435A; W490L; I491V; V503A; Y504I; E512N; L532P | 20.9[1] | 97.8 |
| 63/64 | Q3T; D37E; A43G; L75M; D99V; L143G; E161D; S166A; F174I; T273S; F277I; R278G; M280Y; F281I; A288V; Y324K; K326R; E364K; K395R; M412L; L426S; G430R; F432S; T433G; L435A; T472I; I478L; W490L; I491V; V503A; Y504I; E512N; L532P | 59.2[1] | 99.7 |
| 65/66 | Q3T; D37E; A43G; L75M; K79T; V82I; D99V; L143G; E161D; H163Y; S166A; F174I; T273S; F277I; R278G; M280Y; F281I; A288V; N290D; M319T; Y324K; K326R; E364K; K395R; M412L; L426S; G430R; F432S; T433G; L435A; W490L; I491V; V503A; Y504I; E512N; L532P | 74.8[1] | 99.7 |
| 67/68 | Q3T; D37E; A43G; L75M; K79T; V82A; D99V; L143G; E161D; H163Y; S166A; F174I; T273S; F277I; R278G; M280Y; F281I; A288V; Y324K; K326R; E364K; K395R; M412L; L426S; F432S; T433G; L435A; T472I; W490L; I491V; V503A; Y504I; E512N; L532P | 270.6[1] | 98.3 |
| 69/70 | Q3T; D37E; A43G; L75M; K79T; D99V; L143G; E161D; S166A; F174I; T273S; F277I; R278G; M280Y; F281I; A288V; Y324K; K326R; E364K; K395R; M412L; L426S; F432S; T433G; L435A; T472I; W490L; I491V; V503A; Y504I; E512N; L532P | 123.5[1] | 98.2 |
| 71/72 | Q3T; D37E; A43G; L75M; D99V; L143G; E161D; S166A; F174I; T273S; F277I; R278G; M280Y; F281I; Y324K; K326R; K395R; M412L; L426S; F432S; T433G; L435A; W490L; I491V; V503A; Y504I; E512N; L532P | 13.9[1] | 97 |

TABLE 2B-continued

Engineered CHMO structure-function correlation in acid substrate reaction

| SEQ ID NO: (nt/aa) | Amino acid differences (relative to SEQ ID NO: 2) | Activity relative to SEQ ID NO: 38 | % e.e. |
|---|---|---|---|
| 73/74 | Q3T; D37E; A43G; L75M; D99V; L143G; E161D; S166G; F174I; T273S; F277I; R278G; M280Y; F281I; A288V; Y324K; K326R; K395R; M412L; L426S; F432S; T433G; L435A; W490L; I491V; V503A; Y504I; E512N; L532P | 19.1[1] | 98 |
| 75/76 | Q3T; D37E; A43G; L75M; D99V; L143G; E161D; S166A; F174I; T273S; F277I; R278G; M280Y; F281I; A288V; Y324K; K326R; E364K; K395R; M412L; L426S; F432S; T433G; L435A; F484C; W490L; I491V; V503A; Y504I; E512N; L532P | 14.8[1] | 99.2 |
| 77/78 | Q3T; D37E; A43G; L75M; K79T; V82A; D99V; V110M; L143G; E161D; S166A; F174I; S208T; G216S; T273S; F277I; R278G; M280Y; F281I; A288L; Y324K; K326R; E364K; K395R; M412L; L426S; G430R; F432S; T433G; L435A; W490L; I491V; F492K; V503A; Y504I; F505K; E512N; L532P | 522[1] | 99.7 |
| 79/80 | Q3T; D37E; A43G; L75M; K79T; D99V; L143G; E161D; S166A; F174I; G216S; T273S; F277I; R278G; M280Y; F281I; A288V; Y324K; K326R; E364K; K395R; M412L; L426S; F432S; T433G; L435A; S438R; W490L; I491V; F492K; V503A; Y504I; F505K; E512N; L532P | 566[1] | 99.1 |
| 81/82 | Q3T; D37E; A43G; L75M; K79T; V82A; D99V; V110M; L143G; E161D; S166A; F174I; I192V; S208T; G216S; T273S; F277I; R278G; M280Y; F281I; A288V; Y324K; K326R; E364K; K395R; M412L; L426S; F432S; T433G; L435A; W490L; I491V; F492K; V503A; Y504I; F505K; E512N; L532P | 870[2] | 99.8 |
| 83/84 | Q3T; D37E; A43G; L75M; V82A; D99V; V110M; L143G; E161D; S166A; F174I; G216S; T273S; F277I; R278G; M280Y; F281I; A288V; Y324K; K326R; E364K; K395R; M412L; L426S; F432S; T433G; L435A; W490L; I491V; V503A; Y504I; F505K; E512N; L532P | 696[2] | 99.9 |
| 85/86 | Q3T; D37E; A43G; L75M; K79T; V82A; D99V; L143G; E161D; S166A; F174I; S208T; G216S; T273S; F277I; R278G; M280Y; F281I; A288V; Y324K; K326R; E364K; K395R; M412L; L426S; G430R; F432S; T433G; L435A; W490L; I491V; V503A; Y504I; F505K; E512N; L532P | 539[2] | 99.8 |
| 87/88 | Q3T; D37E; A43G; L75M; K79T; V82A; D99V; V110M; L143G; E161D; S166G; F174I; S208T; G216S; K227E; T273S; F277I; R278G; M280Y; F281I; A288L; Y324K; K326R; N336S; K395R; M412L; L426S; F432S; T433G; L435A; T472I; F484C; K486E; W490L; I491V; F492K; V503A; Y504I; F505K; E512N; L532P | 261[2] | 99.7 |
| 89/90 | Q3T; D37E; A43G; L75M; K79T; V82A; D99V; V110M; L143G; E161D; S166A; F174I; S208T; G216S; T273C; F277I; R278G; M280Y; F281I; Y324K; K326R; E364K; K395R; M412L; L426S; F432S; T433G; L435A; T472I; K486E; W490L; I491V; F492K; V503A; Y504I; F505K; E512N; L532P | 7830[3] | 99.7 |
| 91/92 | Q3T; D37E; A43G; L75M; K79T; V82A; D99V; V110M; L143G; E161D; S166A; F174I; S208T; G216S; T273C; F277I; R278G; M280Y; F281I; A288L; Y324K; K326R; E364K; K395R; M412L; L426S; F432S; T433G; L435A; T472I; K486E; W490L; I491V; F492K; V503A; Y504I; F505K; E512N; L532P; Q539E | 19140[3] | 99.8 |
| 93/94 | Q3T; D37E; A43G; L75M; K79E; V82A; D99V; V110M; L143G; E161D; S166A; F174I; I192V; S208T; G216S; T273C; F277I; R278G; M280Y; F281I; A288L; Y324K; K326R; K395R; M412L; L426S; F432S; T433G; L435A; T472I; F484C; K486E; W490L; I491V; F492K; V503A; Y504I; F505K; E512N; L532P | 21750[3] | 99.8 |
| 95/96 | Q3T; D37E; A43G; L75M; K79T; V82A; D99V; V110M; L143G; E161D; S166A; F174I; S208T; G216S; T273S; F277I; R278G; M280Y; F281I; A288L; I314L; Y324K; K326R; K395R; M412L; L426S; F432S; T433G; L435A; T472I; F484C; K486E; W490L; I491V; F492K; V503A; Y504I; F505K; E512N; L532P | 29580[3] | 99.8 |
| 97/98 | Q3T; D37E; A43G; L75M; K79T; V82A; D99V; V110M; L143G; E161D; S166A; F174I; I192V; S208T; G216S; T273S; F277I; R278G; M280Y; F281I; Y324K; K326R; K395R; M412L; L426S; F432S; T433G; L435A; T472I; K486E; W490L; I491V; F492K; V503A; Y504I; F505K; E512N; L532P | 13050[3] |  |
| 99/100 | Q3T; D37E; A43G; L75M; K79E; V82A; D99V; V110M; L143G; E161D; S166G; F174I; S208T; G216S; T273C; F277I; R278G; M280Y; F281I; A288L; I314L; Y324K; K326R; K395R; M412L; L426S; F432S; T433G; L435A; T472I; F484C; K486E; W490L; I491V; F492K; V503A; Y504I; F505K; E512N; L532P | 21750[3] | 99.7 |
| 101/102 | Q3T; D37E; A43G; L75M; K79T; V82A; D99V; V110M; L143G; E161D; S166A; F174I; S208T; G216S; T273S; F277I; R278G; M280Y; F281I; A288V; Y324K; K326R; K395R; M412L; L426S; F432S; T433G; L435A; T472I; F484C; K486E; W490L; I491V; F492K; V503A; Y504I; F505K; E512N; L532P | 10440[3] | 99.8 |

TABLE 2B-continued

Engineered CHMO structure-function correlation in acid substrate reaction

| SEQ ID NO: (nt/aa) | Amino acid differences (relative to SEQ ID NO: 2) | Activity relative to SEQ ID NO: 38 | % e.e. |
|---|---|---|---|
| 103/104 | Q3T; D37E; A43G; L75M; K79T; V82A; D99V; V110M; L143G; E161D; S166A; F174I; I192V; S208T; G216S; T273S; F277I; R278G; M280Y; F281I; A288V; Y324K; K326R; K395R; M412L; L426S; F432S; T433G; L435A; T472I; K486E; W490L; I491V; F492K; V503A; Y504I; F505K; E512N; L532P | 5220[3] | 99.8 |
| 105/106 | Q3T; D37E; A43G; L75M; K79T; V82A; D99V; V110M; L143G; E161D; S166A; F174I; S208T; G216S; T273C; F277I; R278A; M280Y; F281I; Y324K; K326R; E364K; K395R; M412L; L426S; F432S; T433G; L435A; T472I; K486E; W490L; I491V; F492K; V503A; Y504I; F505K; E512N; L532P | 26100[3] | 99.7 |
| 107/108 | Q3T; D37E; A43G; L75M; K79T; V82A; D99V; V110M; L143G; E161D; S166A; F174I; S208T; G216S; K234D; T273C; F277I; R278G; M280Y; F281I; Y324K; K326R; E364K; K395R; M412L; L426S; F432S; T433G; L435A; S438M; T472I; K486E; W490Q; I491V; V503A; Y504I; F505K; E512N; L532P | 50895[4] | 99.8 |
| 109/110 | Q3T; D37E; A43G; L75M; K79T; V82A; D99V; V110M; L143G; E161D; S166A; F174I; S208T; G216S; K227E; T273S; F277I; R278G; M280Y; F281I; Y324K; K326R; E364K; K395R; M412L; L426S; F432S; T433G; L435A; S438M; T472I; F484C; K486E; W490Q; I491V; V503A; Y504I; F505K; E512N; L532P | 23490[4] | 99.8 |
| 111/112 | Q3T; D37E; A43G; L75M; K79T; V82A; D99V; V110M; L143G; E161D; S166A; F174I; S208T; G216S; T273C; F277I; R278G; M280Y; F281I; K310E; Y324K; K326R; E364K; K395R; M412L; L426S; F432S; T433G; L435A; S438M; T472I; K486E; W490Q; I491V; F492K; V503A; Y504I; F505K; E512N; L532P | 23490[4] | 99.9 |
| 113/114 | Q3T; D37E; A43G; L75M; K79T; V82A; D99V; V110M; L143G; E161D; S166A; F174I; S208T; G216S; K227D; T273C; F277I; R278G; M280Y; F281I; K310E; Y324K; K326R; E364K; K395R; M412L; L426S; F432S; T433G; L435A; S438M; T472I; K486E; W490L; I491V; F492K; V503A; Y504I; F505K; E512N; L532P | 34452[4] | 99.9 |
| 115/116 | Q3T; D37E; A43G; L75M; K79T; V82A; D99V; V110M; L143G; E161D; S166A; F174I; S208T; G216S; K234D; T273S; F277I; R278G; M280Y; F281I; Y324K; K326R; E364K; K395R; M412L; L426S; F432S; T433G; L435A; S438M; T472I; F484C; K486E; W490Q; I491V; V503A; Y504I; F505K; E512N; L532P | 117059[5] | 99.9 |
| 117/118 | Q3T; D37E; A43G; L75M; K79T; V82A; D99V; V110M; L143G; E161D; S166A; F174I; S208T; G216S; K234D; T273S; F277I; R278G; M280Y; F281I; Y324K; K326R; E364K K395R; M412L; L426S; F432S; T433G; L435A; S438M; T472I; K486E; W490Q; I491V; F492K; V503A; Y504I; F505K; E512N; L532P | 61074[5] | 99.9 |
| 119/120 | Q3T; D37E; A43G; L75M; K79T; V82A; D99V; V110M; L143G; E161D; S166A; V172A; F174I; S208T; G216S; K234D; A243K; A245G; T273S; F277I; R278G; M280Y; F281I; M319T; Y324K; A325Y; K326R; K395R; M412L; L426S; F432S; T433G; L435A; S438M; T472I; K486E; W490Q; I491V; F492K; N501D; V503A; Y504I; F505K; E512N; L532P | 421411[5] | |
| 121/122 | Q3T; D37E; A43G; L75M; K79T; V82A; D99V; V110M; L143G; E161D; S166A; V172A; F174I; S208T; G216S; K234D; A243K; A245G; T273S; F277I; R278G; M280Y; F281I; M319T; Y324K; K326R; K395R; M412L; L426S; F432S; T433G; L435A; S438M; T472I; K486E; W490Q; I491V; F492K; V503A; Y504I; F505K; E512N; L532P | 374587[5] | |
| 123/124 | Q3T; D37E; A43G; L75M; K79T; V82A; D99V; V110M; L143G; E161D; S166A; V172A; F174I; S208T; G216S; K234D; A243K; A245G; T273S; F277I; R278G; M280Y F281I; M319L; Y324K; A325Y; K326R; E364K; K395R; M412L; L426S; F432S; T433G; L435A; S438M; T472I; K486E; W490Q I491V; V503A; Y504I; F505K; E512N; L532P | 280940[5] | |
| 125/126 | Q3T; D37E; A43G; L62V; L75M; K79T V82A; D99V; V110M; L143G; E161D; S166A; F174I; S208T; G216S; K234D; A243K; A245G; T273S; G275S; F277I; R278G; M280Y; F281I; Y324K; K326R; L329V; E364K; K395R; M412L; L426S; F432S; T433G; L435A; S438M; T472I; F484C; K486E; W490Q; I491V; V503A; Y504I; F505K; E512N; L532P | 374587[5] | 99.9 |
| 127/128 | Q3T; D37E; A43G; L62V; L75M; K79T V82A; D99V; V110M; L143G; E161D; S166A; F174I; S208T; G216S; K234D; A243K; A245G; T273S; G275N; F277I; R278G; M280Y; F281I; Y324K; K326R; L329V; E364K; K395R; M412L; L426S; F432S; T433G; L435A; S438M; T472I; F484C; K486E; W490Q; I491V; V503A; Y504I; F505K; E512N; L532P | 374587[5] | |

TABLE 2B-continued

Engineered CHMO structure-function correlation in acid substrate reaction

| SEQ ID NO: (nt/aa) | Amino acid differences (relative to SEQ ID NO: 2) | Activity relative to SEQ ID NO: 38 | % e.e. |
|---|---|---|---|
| 129/130 | Q3T; D37E; A43G; L75M; K79T; V82A; K89M; D99V; V110M; A118V; L143G; E161D; S166A; V172A; F174I; S208T; G216I; K234D; A243K; A245G; K264Y; T273S; F277I; R278G; M280Y; F281I; M291R; K310H; M319T; Y324K; A325Y; K326R; K395R; M412L; L426S; F432S; T433G; L435A; S438M; T472I; K486E; W490Q; I491V; F492K; N501D; V503A; Y504I; F505K; E512N; L532P | 547834[6] | 99.8 |
| 131/132 | Q3T; D37E; T40G; A43G; S74E; L75M K79T; V82A; K89M; D99V; V110M; A118V; L143G; E161D; S166A; V172A; F174I; S208T; G216I; K234D; A243K; A245G; K264Y; T273S; F277I; R278G; M280Y; F281I; M291R; M319T; Y324K; A325F; K326R; K395R; M412L; L426S; F432S; T433G; L435A; S438M; T472I; K486E; W490Q; I491V; F492K; G498N; N501D; V503A; Y504I; F505K; E512N; L532P | 602617[6] | |
| 133/134 | Q3T; K32E; D37E; A43G; L75M; K79T; V82A; K89M; D99V; V110M; A118V; L143S; E161D; S166A; V172A; F174I; S208T; G216I; P219V; K234D; A243K; A245G; K264Y; T273S; G275A; F277I; R278G; M280Y; F281I; M291R; K310H; M319T; Y324K; A325Y; K326R; K362S; K395R; M412L; L426S; F432S; T433G; L435A; S438M; T472I; K486E; W490Q; I491V; F492K; N501D; V503A; Y504I; F505K; E512N; L532P | 657401[7] | 99.8 |
| 135/136 | Q3T; D37E; A43G; L75M; K79T; V82A; G84H; K89N; D99V; V110M; A118V; L143S; E161D; S166A; V172A; F174I; S208T; G216I; P219V; K234D; A243K; A245G; K264Y; T273S; G275A; F277I; R278A; M280Y; F281I; M291R; K310H; M319T; Y324K; A325Y; K326R; K362S; K395R; M412L; L426S; F432S; T433G; L435A; S438M; T472I; Q473D; N477D; F484L; K486E; W490Q; I491V; F492K; G498N; N501D; V503A; Y504I; F505K; E512N; L532P | 1018971[8] | 99.8 |
| 137/138 | Q3T; D37E; A43G; L75M; K79T; V82A; G84H; K89N; D99V; V110M; A118V; L143S; E161D; S166A; V172A; F174I; S208T; G216I; P219V; K234D; A243K; A245G; K264Y; T273S; G275A; F277I; R278A; M280Y; F281I; M291R; K310H; M319T; Y324K; A325Y; K326R; K395R; M412L; L426S; F432S; T433G; L435A; S438M; T472I; N477D; F484L; K486E; W490Q; I491V; F492K; N501D; V503A; Y504I; F505K; E512N; L532P | 815177[8] | |
| 139/140 | Q3T; D37E; A43G; L75M; K79T; V82A; K89M; D99V; V110M; A118V; L143S; E161D; S166A; V172A; F174I; S208T; G216I; P219V; K234D; A243K; A245G; K264Y; T273S; G275A; F277I; R278A; M280Y; F281I; M291R; K310H; M319T; Y324K; A325F; K326R; K395R; M412L; L426S; F432S; T433G; L435A; S438M; T472I; Q473D; N477D; F484L; K486E; W490Q; I491V; F492K; G498N; N501D; V503A; Y504I; F505K; E512N; L532P | 992675[8] | |
| 141/142 | Q3T; D37E; T40G; A43G; L75M; K79T; V82A; G84H; K89M; D99V; V110M; A118V; L143S; E161D; S166A; V172A; F174I; S208T; G216I; P219V; K234D; A243K; A245G; K264Y; T273S; G275A; F277I; R278G; M280Y; F281I; M291R; M319T; Y324K; A325F; K326R; K395R; M412L; L426S; F432S; T433G; L435A; S438M; T472I; Q473D; N477D; F484L; K486E; W490Q; I491V; F492K; G498N; N501D; V503A; Y504I; F505K; E512N; L532P | 940083[8] | |

[1]Substrate: 10 g/L; CHMO: 10 g/L; NADP: 0.3 g/L; 100 mM phosphate, pH 9.0.
[2]Substrate: 25 g/L; CHMO: 10 g/L; NADP: 0.2 g/L; 100 mM TEA, pH 8.3.
[3]Substrate: 35 g/L; CHMO: 5 g/L; NADP: 0.2 g/L; 100 mM TEA, pH 8.3.
[4]Substrate: 50 g/L; CHMO: 5 g/L; NADP: 0.2 g/L; 100 mM TEA, pH 8.3.
[5]Substrate: 60 g/L; CHMO: 5 g/L; NADP: 0.2 g/L; 100 mM TEA, pH 8.3.
[6]Substrate: 30 g/L; CHMO: 0.5 g/L; NADP: 0.2 g/L; 100 mM TEA, pH 9.0; PEG200: 10% (v/v); Temperature: 35° C.
[7]Substrate: 30 g/L; CHMO: 0.5 g/L; NADP: 0.2 g/L; 100 mM TEA, pH 8.5; PEG200: 10% (v/v); Temperature: 35° C.
[8]Substrate: 100 g/L; CHMO: 2 g/L; NADP: 0.2 g/L; 100 mM TEA, pH 8.5; PEG200: 10% (v/v); Temperature: 35° C.

In some embodiments, the non-naturally occurring (or engineered) polypeptides having CHMO activity of the present disclosure comprise an amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, or 142; or an amino acid sequence having at least 80%, 85%, 86%, 87%, 88%, 89%, 90%, 91%, 92%, 93%, 94%, 95%, 96%, 97%, 98%, or 99% identity to any one of the above-listed exemplary sequences. In some embodiments, the non-naturally occurring polypeptide having CHMO activity is capable of converting compound (1a) to compound (2a) in enantiomeric excess and/or compound (1b) to compound (2b) in enantiomeric excess under suitable reaction conditions. For example, in some embodiments, the present disclosure provides an engineered polypeptide having CHMO activity capable of converting compound (1a) to compound (2a) and/or compound (1b) to compound (2b) in enantiomeric excess under suitable conditions, in which the amino acid sequence of the polypeptide has at least 96%, 97%, 98%, or 99% identity to SEQ ID NO: 38. In some embodiments, the present disclosure provides an engineered polypeptide having CHMO activity capable of converting compound (1a) to compound (2a) and/or compound (1b) to compound (2b) in enantiomeric excess under suitable conditions, in which the amino acid sequence of the polypeptide has at least 91%, 92%, 93%, 94%, 95%, 96%, 97%, 98%, or 99% identity to SEQ ID NO: 136.

Table 2C further summarizes the correlation between the structure of the engineered polypeptides having CHMO activity of the present disclosure and the activity and enantioselectivity of these enzymes in carrying out the biocatalytic conversion of the acid substrate of compound (1b) to the product of compound (2b). The single residue difference engineered CHMO polypeptides summarized in Table 2C were generating all 19 amino acid residue differences at 14 positions identified during directed evolution (X37, X143, X246, X277, X278, X280, X281, X326, X426, X432, X433, X435, X490, and X532) and screening each of the single-change engineered CHMO polypeptides in a HTP assay for improved activity and enantioselectivity in the conversion of the acid substrate of compound (1b) to compound (2b). Only single-change engineered CHMO polypeptides exhibiting at 2-fold improved activity relative to wild-type of SEQ ID NO: 2 in the conversion of compound (1b) to compound (2b) (or the opposite enantiomer of compound (2b)) are listed in Table 2C. Consequently, certain amino acid residue differences that appear in the engineered CHMO polypeptides of Tables 2A and 2B do not appear in Table 2C (e.g., D37E).

The HTP assay conditions and HPLC analysis used to determine acid substrate "Activity FIOP" and "% e.e." as summarized in Table 2C were generally as described in Example 1—assay in a 96-well deep well plate as a 24 h assay in 0.1 M TEA, pH 9 at room temperature. The assay was initiated by adding to each deep-well the following solutions: (1) 20 μL of a KRED-cofactor solution containing 1 g/L KRED polypeptide of SEQ ID NO: 144 and 0.2 g/L NADP$^+$ in 0.1 M TEA, pH 9; (2) 130 μL of E. coli cell-lysate containing the engineered CHMO polypeptide in 0.1 M TEA, pH 9 (prepared as in Example 1); (3) 40 μL of substrate stock containing 1 g/L of compound (1b) in 0.1 M TEA, pH 9; and (4) 10 μL of IPA. The plate was heat sealed for 3 s at 180° C., and then shaken at 200 rpm and 25° C. for ~20-24 h. Further details of HTP assay HPLC analysis methods used are described in the Examples.

TABLE 2C

| Amino acid difference (relative to SEQ ID NO: 2) | Activity Fold-Improvement (relative to SEQ ID NO: 2) | % ee of R-isomer |
|---|---|---|
| None (Wild-type) | 1.0 | 25.3 |
| L143C | 2.8 | 33.6 |
| L143E | 3.7 | 40.1 |
| L143F | 8.0 | 40.3 |
| L143G | 2.5 | 68.0 |
| L143H | 14.9 | 38.6 |
| L143K | 1.8 | 80.7 |
| L143M | 3.1 | 67.6 |
| L143P | 4.5 | 51.7 |
| L143Q | 4.7 | 50.1 |
| L143S | 3.6 | 62.0 |
| L143T | 1.8 | 35.0 |
| L143W | 17.0 | 89.5 |
| F246A | 6.8 | 77.0 |
| F246E | 3.7 | 76.6 |
| F246G | 1.8 | 75.2 |

TABLE 2C-continued

| Amino acid difference (relative to SEQ ID NO: 2) | Activity Fold-Improvement (relative to SEQ ID NO: 2) | % ee of R-isomer |
|---|---|---|
| F246I | 10.6 | 86.4 |
| F246L | 17.0 | 97.9 |
| F246N | 2.1 | 23.5 |
| F246P | 4.9 | 84.8 |
| F246S | 5.5 | 76.0 |
| F246T | 4.7 | 55.8 |
| F246V | 14.1 | 85.0 |
| F277C | 14.4 | -51.7 |
| F277D | 1.3 | -32.4 |
| F277E | 1.3 | 9.4 |
| F277G | 2.9 | 3.5 |
| F277H | 11.3 | -14.3 |
| F277L | 19.8 | 9.9 |
| F277M | 10.6 | -62.9 |
| F277P | 19.8 | -94.8 |
| F277S | 13.2 | -79.1 |
| F277T | 17.3 | -53.0 |
| F277V | 19.9 | -65.9 |
| F277W | 6.5 | 9.8 |
| R278A | 2.3 | 36.5 |
| R278C | 1.4 | 15.0 |
| R278G | 3.3 | 57.9 |
| R278H | 6.1 | 22.8 |
| R278K | 4.1 | 2.6 |
| R278N | 2.1 | 89.9 |
| R278Q | 3.1 | 49.9 |
| R278S | 2.7 | 41.5 |
| R278T | 3.1 | 12.2 |
| R278V | 1.3 | 16.7 |
| M280L | 3.8 | -30.8 |
| M280T | 1.1 | -48.4 |
| M280W | 14.1 | -24.1 |
| F281A | 1.5 | -43.6 |
| F281C | 1.6 | -33.0 |
| F281H | 6.6 | -86.5 |
| F281K | 2.0 | -47.7 |
| F281L | 1.6 | -38.7 |
| F281M | 2.0 | -57.1 |
| F281N | 1.4 | -61.0 |
| F281R | 1.6 | -56.3 |
| F281T | 2.3 | -59.8 |
| F281V | 1.7 | -53.4 |
| F281W | 3.5 | 2.5 |
| F281Y | 3.0 | -26.1 |
| K326A | 13.3 | -13.8 |
| K326C | 19.9 | 3.9 |
| K326D | 12.9 | -25.4 |
| K326E | 16.0 | -38.8 |
| K326F | 15.3 | -30.0 |
| K326G | 17.3 | 22.6 |
| K326H | 2.3 | 29.8 |
| K326L | 20.5 | 21.5 |
| K326M | 20.7 | -28.1 |
| K326N | 8.2 | -3.9 |
| K326P | 11.1 | 9.5 |
| K326R | 6.0 | 13.8 |
| K326S | 14.2 | 0.8 |
| K326T | 14.6 | -2.5 |
| K326V | 20.5 | -10.5 |
| K326W | 20.4 | -26.2 |
| L426G | 2.5 | 41.8 |
| L426Q | 2.3 | 57.2 |
| L426T | 5.0 | 82.0 |
| F432A | 3.4 | 15.0 |
| F432E | 1.4 | 52.6 |
| F432I | 11.4 | 59.4 |
| F432K | 3.0 | 21.5 |
| F432L | 13.2 | 77.5 |
| F432N | 5.4 | 27.3 |
| F432Q | 18.0 | 87.3 |
| F432S | 4.1 | 64.4 |
| F432T | 1.9 | 68.8 |
| F432V | 17.9 | 55.5 |
| F432W | 14.4 | 89.5 |
| T433A | 5.1 | 90.7 |
| T433S | 6.5 | 92.6 |

TABLE 2C-continued

| Amino acid difference (relative to SEQ ID NO: 2) | Activity Fold-Improvement (relative to SEQ ID NO: 2) | % ee of R-isomer |
|---|---|---|
| L435G | 12.8 | 57.4 |
| L435K | 2.0 | 91.5 |
| L435V | 2.5 | 46.5 |
| L435Y | 8.7 | 99.2 |
| W490A | 16.7 | 30.9 |
| W490C | 17.3 | 6.2 |
| W490D | 17.2 | 23.5 |
| W490E | 17.0 | 26.2 |
| W490G | 16.4 | 44.6 |
| W490I | 17.2 | 8.7 |
| W490K | 17.8 | 32.6 |
| W490L | 17.3 | 14.1 |
| W490M | 16.6 | 32.0 |
| W490N | 16.6 | 41.8 |
| W490R | 17.2 | 27.4 |
| W490S | 15.9 | 41.3 |
| W490Y | 16.2 | 21.7 |
| L532M | 2.8 | 65.1 |

It is contemplated that any of the single residue difference engineered CHMO polypeptides could be used as a starting backbone for further directed evolution to generate engineered CHMO polypeptides that comprise the single residue difference, the correlated improved functional property, and one or more additional amino acid differences, such as any residue difference or combination of residue differences listed in Tables 2A or 2B.

As shown in Table 2C, engineered CHMO polypeptides having at least one of the following amino acid differences relative to SEQ ID NO: 2 are capable of converting the acid substrate compound (1b) to compound (2b) (R-enantiomer) or its opposite enantiomer compound (S-enantiomer) with at least 2-fold improved activity relative to the wild-type polypeptide of SEQ ID NO: 2: X143C, E, F, G, H, K, M, P, Q, S, T, or W; X246A, E, G, I, L, N, P, S, T, or V; X277C, D, E, G, H, L, M, P, S, T, V, or W; X278A, C, G, H, K, N, Q, S, T, or V; X280L, T, or W; X281A, C, H, K, L, M, N, R, T, V, W, or Y; X326A, C, D, E, F, G, H, L, M, N, P, R, S, T, V, or W; X426G, Q, or T; X432A, E, I, K, L, N, Q, S, T, V, or W; X433A, or S; X435G, K, V, or Y; X490A, C, D, E, G, I, K, L, M, N, R, S, or Y; X532M.

Also as shown in Table 2C, engineered CHMO polypeptides having at least one of the following amino acid differences relative to SEQ ID NO: 2 are capable of converting the acid substrate of compound (1b) to the R-enantiomer compound (2b) in at least 50% ee: X143G, K, M, P, Q, S, or W; X246A, E, G, I, L, P, S, T, or V; X278G, or N; X426Q, or T; X432E, I, L, Q, S, T, V, or W; X433A, or S; X435G, K, or Y; X532M.

Further, as shown in Table 2C, engineered CHMO polypeptides having at least one of the following amino acid differences relative to SEQ ID NO: 2 are capable of converting the acid substrate of compound (1b) to the opposite enantiomer of compound (2b) (S-enantiomer) in at least 50% ee: X277C, M, P, S, T, or V; X281H, M, N, R, T, or V.

Accordingly, in some embodiments the present disclosure provides a non-naturally occurring (or engineered) polypeptide having cyclohexanone monooxygenase (CHMO) activity wherein the amino acid sequence of the polypeptide has at least 80%, 85%, 86%, 87%, 88%, 89%, 90%, 91%, 92%, 93%, 94%, 95%, 96%, 97%, 98%, or 99% sequence identity to SEQ ID NO: 2 and one or more amino acid differences relative to SEQ ID NO: 2 selected from the following: X143C, E, F, G, H, K, M, P, Q, S, T, or W; X246A, E, G, I, L, N, P, S, T, or V; X277C, D, E, G, H, L, M, P, S, T, V, or W; X278A, C, G, H, K, N, Q, S, T, or V; X280L, T, or W; X281A, C, H, K, L, M, N, R, T, V, W, or Y; X326A, D, E, F, G, H, L, M, N, P, R, V, or W; X426G, Q, or T; X432E, I, K, N, Q, T, V, or W; X433S; X435G, K, V, or Y; X490A, C, D, E, G, I, L, M, N, S, or Y; and X532M. In some embodiments, the polypeptide is capable of converting the acid substrate compound (1b) to compound (2b) (R-enantiomer) or its opposite enantiomer compound (S-enantiomer) with at least 2-fold improved activity relative to the wild-type polypeptide of SEQ ID NO: 2. In some embodiments, the amino acid sequence comprises one or more amino acid differences relative to SEQ ID NO: 2 selected from: X143G, K, M, P, Q, S, or W; X246A, E, G, I, L, P, S, T, or V; X278G, or N; X426Q, or T; X432E, I, L, Q, S, T, V, or W; X433A, or S; X435G, K, or Y; and X532M, and in such embodiments, the polypeptide is capable of converting the acid substrate of compound (1b) to the R-enantiomer compound (2b) in at least 50% ee.

In some embodiments of the non-naturally occurring (or engineered) polypeptide having CHMO activity, the polypeptide amino acid sequence comprises one or more amino acid differences relative to SEQ ID NO: 2 selected from: X143G; X278G; X326R; and X490L. Further, in some embodiments, the amino acid sequence comprises at least the following amino acid differences relative to SEQ ID NO: 2: X277I; X278A, or G; X280T or Y; X281I; X326R; and X490L or X490Q. In additional embodiments, the polypeptide amino acid sequence may further comprise at least one combination of amino acid differences relative to SEQ ID NO: 2 selected from the exemplary polypeptides listed in Tables 2A and 2B (as described below).

As shown in Tables 2A and 2B, the following amino acid differences relative to SEQ ID NO: 2 are associated with the increased activity and enantioselectivity properties found in all of the exemplary CHMO polypeptides: X37E; X277I; X278A or X278G; X280T or X280Y; X281I; X326R; and X490L or X490Q. Accordingly, in some embodiments, the present disclosure provides a non-naturally occurring polypeptide having CHMO activity wherein the amino acid sequence of the polypeptide has: (a) sequence identity of at least 90%, 91%, 92%, 93%, 94%, 95%, 96%, 97%, 98%, or 99% to any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, or 142; and (b) one or more amino acid differences relative to SEQ ID NO: 2 selected from: X37E; X277I; X278A or X278G; X280T or X280Y; X281I; X326R; and X490L or X490Q. In some embodiments, an engineered CHMO of the present disclosure can include the following amino acid differences relative SEQ ID NO: 2: X37E; X277I; X278A or X278G; X280T or X280Y; X281I; X326R; X433G; X435A; and X490L or X490Q.

In some embodiments, the present disclosure provides an engineered polypeptide having CHMO activity in which the amino acid sequence of the polypeptide has (a) at least 96%, 97%, 98%, or 99% identity to SEQ ID NO: 38; and (b) one or more amino acid differences relative to SEQ ID NO: 2 selected from: X37E; X277I; X278A or X278G; X280T or X280Y; X281I; X326R; and X490L or X490Q.

In some embodiments, the present disclosure provides an engineered polypeptide having CHMO activity in which the amino acid sequence of the polypeptide has (a) at least 91%, 92%, 93%, 94%, 95%, 96%, 97%, 98%, or 99% identity to SEQ ID NO: 136; and (b) one or more amino acid differences relative to SEQ ID NO: 2 selected from: X37E;

X277I; X278A or X278G; X280T or X280Y; X281I; X326R; and X490L or X490Q.

As shown in Tables 2A and 2B, combinations of amino acid differences present in the exemplary polypeptides are associated with improved properties in converting compound (1a) to compound (2a) relative to the wild-type polypeptide of SEQ ID NO: 2 or another reference polypeptide, such as the engineered polypeptide of SEQ ID NO: 4 or 38. Accordingly, in some embodiments the amino acid sequence of any of the engineered polypeptides having CHMO activity of the present disclosure can comprise or further comprise at least one combination of amino acid differences relative to SEQ ID NO: 2 selected from the following:

(a) X37E, X277I, X278G, X280T, X281I, X326R, X432S, X433G, X435A, and X490L;
(b) X3T, X143G, X280Y, X432S, X433G, X435A, and X532P;
(c) X3T, X75M, X143G, X280Y, X432S, X433G, X435A, and X532P;
(d) X3T, X75M, X143G, X280Y, X426S, X432S, X433G, X435A, X503A, and X532P;
(e) X3T, X43G, X75M, X143G, X280Y, X426S, X432S, X433G, X435A, X503A, X512N, and X532P;
(f) X3T, X43G, X75M, X143G, X280Y, X426S, X432S, X433G, X435A, X491V, X503A, X504I, X512N, and X532P; or
(g) X3T, X43G, X75M, X143G, X166A, X280Y, X395R, X412L, X426S, X432S, X433G, X435A, X491V, X503A, X504I, X512N, and X532P.

As shown in Tables 2A and 2B, combinations of amino acid differences present in the exemplary polypeptides are associated with improved properties in converting compound (1b) to compound (2b) relative to the wild-type polypeptide of SEQ ID NO: 2 or another reference peptide, such as the engineered polypeptide of SEQ ID NO: 4 or 38. Accordingly, in some embodiments the amino acid sequence of any of the engineered polypeptides having CHMO activity of the present disclosure can comprise or further comprise at least one combination of amino acid differences relative to SEQ ID NO: 2 selected from the following:

(a) X3T, X43G, X75M, X143G, X166A, X280Y, X395R, X412L, X426S, X432S, X433G, X435A, X491V, X503A, X504I, X512N, and X532P;
(b) X3T, X43G, X75M, X99V, X143G, X161D, X166A, X174I, X273S, X280Y, X324K, X395R, X412L, X426S, X432S, X433G, X435A, X491V, X503A, X504I, X512N, and X532P;
(c) X3T, X43G, X75M, X79T, X82A, X99V, X110M, X143G, X161D, X166A, X174I, X208T, X273S, X280Y, X324K, X395R, X412L, X426S, X432S, X433G, X435A, X491V, X503A, X504I, X505K, X512N, and X532P;
(d) X3T, X43G, X75M, X79T, X82A, X99V, X110M, X143G, X161D, X166A, X174I, X208T, X273S, X280Y, X324K, X395R, X412L, X426S, X432S, X433G, X435A, X472I, X486E, X491V, X503A, X504I, X505K, X512N, and X532P;
(e) X3T, X43G, X75M, X79T, X82A, X99V, X110M, X143G, X161D, X166A, X174I, X208T, X234D, X273S, X280Y, X324K, X395R, X412L, X426S, X432S, X433G, X435A, X438M, X472I, X486E, X490Q, X491V, X503A, X504I, X505K, X512N, and X532P;
(f) X3T, X43G, X75M, X79T, X82A, X99V, X110M, X143G, X161D, X166A, X174I, X208T, X273S, X280Y, X324K, X395R, X412L, X426S, X432S, X433G, X435A, X438M, X472I, X484C, X486E, X490Q, X491V, X503A, X504I, X505K, X512N, and X532P;
(g) X3T, X43G, X75M, X79T, X82A, X99V, X110M, X143G, X161D, X166A, X172A, X174I, X208T, X243K, A245G, X273S, X280Y, X319T, X324K, X325Y, X395R, X412L, X426S, X432S, X433G, X435A, X438M, X472I, X484C, X486E, X490Q, X491V, X492K, X501D, X503A, X504I, X505K, X512N, and X532P;
(h) X3T, X43G, X62V, X75M, X79T, X82A, X99V, X110M, X143G, X161D, X166A, X174I, X208T, X273S, X275S, X280Y, X324K, X329V, X395R, X412L, X426S, X432S, X433G, X435A, X438M, X472I, X484C, X486E, X490Q, X491V, X503A, X504I, X505K, X512N, and X532P;
(i) X3T, X43G, X75M, X79T, X82A, X99V, X110M, X118V, X143G, X161D, X166A, X172A, X174I, X208T, X216I, X264Y, X273S, X280Y, X291R, X310H, X319T, X324K, X325Y, X395R, X412L, X426S, X432S, X433G, X435A, X438M, X472I, X484C, X486E, X490Q, X491V, X492K, X501D, X503A, X504I, X505K, X512N, and X532P;
(j) X3T, X43G, X75M, X79T, X82A, X89N, X99V, X110M, X118V, X143S, X161D, X166A, X172A, X174I, X208T, X216I, X219V, X264Y, X273S, X275A, X280Y, X291R, X310H, X319T, X324K, X325Y, X362S, X395R, X412L, X426S, X432S, X433G, X435A, X438M, X472I, X484C, X486E, X490Q, X491V, X492K, X501D, X503A, X504I, X505K, X512N, and X532P; or
(k) X3T, X43G, X75M, X79T, X82A, X84H, X89N, X99V, X110M, X118V, X143S, X161D, X166A, X172A, X174I, X208T, X216I, X219V, X264Y, X273S, X275A, X280Y, X291R, X310H, X319T, X324K, X325Y, X362S, X395R, X412L, X426S, X432S, X433G, X435A, X438M, X472I, X473D, X477D, X484L, X486E, X490Q, X491V, X492K, X498N, X501D, X503A, X504I, X505K, X512N, and X532P.

In some embodiments, the present disclosure provides a non-naturally occurring polypeptide having CHMO activity capable of converting compound (1a) to compound (2a), and/or compound (1b) to compound (2b), with at least 2-fold, at least 10-fold, at least 25-fold, at least 40-fold, or at least 60-fold increased enzyme activity relative to the enzyme activity of the polypeptide of SEQ ID NO: 2. The non-naturally occurring polypeptide comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence SEQ ID NO: 2 and the following amino acid differences relative to SEQ ID NO: 2: X37E, X277I, X278G, X281I, X326R, X433G, and X435A. The amino acid sequence may further comprise X3T, X143G, X280Y, or a combination thereof. The amino acid sequence may further comprise X75M. The amino acid sequence may further comprise X426S, X503A, or a combination thereof. The amino acid sequence may further comprise X43G, X512N, or a combination thereof. The amino acid sequence may further comprise X491V, X504I, or a combination thereof. The amino acid sequence may further comprise X166A, X395R, X412L, or a combination thereof. The amino acid sequence may further comprise X99V, X161D, X174I, X273S, X324K, or a combination thereof. The amino acid sequence may further comprise X79T, X82A, X110M, X208T, X216S, X505K, or a combination thereof. The amino acid sequence may further comprise X472I, X486E, or a combination thereof. The amino acid sequence can further comprise X438M, X490Q, or a combination thereof. The amino acid sequence may further comprise X484C. The amino acid sequence can further comprise X62V, X275N, X329V, or a combination thereof; wherein X refers to a position relative to SEQ ID NO: 2.

As shown by the exemplary polypeptides disclosed in Tables 2A, 2B, and 2C, the engineered polypeptides having CHMO activity also have improved properties that correlate with the amino acid differences relative to SEQ ID NO: 2. Accordingly, in some embodiments, the non-naturally occurring polypeptides having CHMO activity described herein are capable of converting compound (1a) to compound (2a) and/or compound (1b) to compound (2b) in at least 75%, at least 85%, at least 90%, at least 95%, at least 98%, or at least 99% enantiomeric excess under suitable reaction conditions. In some embodiments, the non-naturally occurring CHMO polypeptides described herein are capable of converting compound (1a) to compound (2a) with an activity increased at least 2-fold, at least 4-fold, at least 10-fold, at least 25-fold, at least 40-fold, or at least 60-fold relative to the activity of the polypeptide of SEQ ID NO: 2 under suitable reaction conditions. In some embodiments, the non-naturally occurring CHMO polypeptides described herein are capable of converting compound (1b) to compound (2b) with an activity increased at least 2-fold, at least 4-fold, at least 10-fold, at least 25-fold, at least 40-fold, or at least 60-fold relative to the activity of the polypeptide of SEQ ID NO: 38 under suitable reaction conditions. In some embodiments, the non-naturally occurring CHMO polypeptides described above are capable of at least about 90% or greater conversion of compound (1b) to compound (2b) in 24 h with a substrate loading of about 50 g/L. As described elsewhere herein, the improved properties of the non-naturally occurring or engineered CHMO polypeptides provide for methods of use of these polypeptides in processes for preparing Armodafinil (compound (2a)) and analogs thereof.

Analysis of the relationship between the structural changes (i.e., amino acid differences) and improved properties of the exemplary polypeptides of Tables 2A, 2B, and 2C, further allows for the identification of specific amino acid differences that are associated with one or more improved properties including increased enantiomeric excess, increased activity, increased thermostability, and/or increased tolerance of high substrate and/or product concentration.

In some embodiments, the present disclosure provides a non-naturally occurring polypeptide having CHMO activity capable of converting the amide substrate of compound (1a) to compound (2a) with at least 2-fold, at least 10-fold, at least 25-fold, at least 40-fold, or at least 60-fold increased enzyme activity relative to the enzyme activity of the polypeptide of SEQ ID NO: 2 and in which the polypeptide amino acid sequence comprises one or more amino acid differences relative to SEQ ID NO: 2 associated with increased activity in converting compound (1a) to compound (2a). Accordingly, in some embodiments the present disclosure provides a non-naturally occurring polypeptide comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) at least one of the following amino acid differences relative to SEQ ID NO: 2 which are associated with increased activity in converting compound (1a) to compound (2a): Q3T; V42I; A43G; L75M; L143G; H163L or Y; S166A or G; D171G; G176S; R278G; M280Y; F281I; A288L or V; A313E; D322G or M; K326R; V348A; E364K; A382R; K395R; M412L; L426N or S; G430R; L435A; N477D; S489G; F492K or S; V503A; Y504I; E512N; L532P; and K538E.

In some embodiments, the present disclosure provides a non-naturally occurring polypeptide having CHMO activity which is capable of converting the acid substrate of compound (1b) to compound (2b) with at least 2-fold, at least 10-fold, at least 25-fold, at least 40-fold, or at least 60-fold increased enzyme activity relative to the enzyme activity of the polypeptide of SEQ ID NO: 2 and in which the polypeptide amino acid sequence comprises one or more amino acid differences relative to SEQ ID NO: 2 associated with increased activity in converting compound (1b) to compound (2b). Accordingly, in some embodiments the present disclosure provides a non-naturally occurring polypeptide comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) at least one of the following amino acid differences relative to SEQ ID NO: 2 which are associated with increased activity in converting compound (1b) to compound (2b): V42I; A43G; K79T; V82A or I; K89M or N; V110M; E123A; L143G or S; H163L or Y; S166A or G; V172A; G176S; I182V; I192V; S208T; G216I; K227D or E; A243K; A245G; T273A, C, or S; G275A; R278G; A288L or V; N290D; M291R; I314L or T; M319L or T; D322G or M; Y324K; A325Y; K326R; L329V; V348A; E364K; M373V; A382R; K395R; M412L; L426N or S; G430R; F432S; L435A; S438M or R; T472I; N477D; I478L; F484C; K486E; S489G; W490Q; I491V; F492K or S; N501D; V503A; F505K; E512N; K538E and Q539E.

In some embodiments, the present disclosure provides a non-naturally occurring polypeptide having CHMO activity which is capable of converting the acid substrate of compound (1a) to compound (2a) with at least 75%, or at least 80%, or at least 85%, or at least 90%, or at least 95%, or at least 97%, or at least 98%, of the enantiomeric excess (e.e.) and in which the polypeptide amino acid sequence comprises one or more amino acid differences relative to SEQ ID NO: 2 associated with increased enantioselectivity in converting compound (1a) to compound (2a). Accordingly, in some embodiments the present disclosure provides a non-naturally occurring polypeptide comprises non-naturally occurring polypeptide comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) at least one of the following amino acid differences relative to SEQ ID NO: 2 associated with increased enantioselectivity in converting compound (1a) to compound (2a): M280Y, L426N, L426S, G430R, L435A, and L532P.

In some embodiments, the present disclosure provides a non-naturally occurring polypeptide having CHMO activity which is capable of converting compound (1b) (acid substrate) to compound (2b) with at least 75%, or at least 80%, or at least 85%, or at least 90%, or at least 95%, or at least 97%, or at least 98%, of the enantiomeric excess (e.e.) and in which the polypeptide amino acid sequence comprises one or more amino acid differences relative to SEQ ID NO: 2 associated with increased enantioselectivity in converting compound (1b) to compound (2b). Accordingly, in some embodiments the present disclosure provides a non-naturally occurring polypeptide comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) at least one of the following amino acid differences relative to SEQ ID NO: 2 associated with increased enantioselectivity in converting compound (1b) to compound (2b): V110M; D322G, D322M, A325Y, G430R, F432S, and F505K.

In some embodiments, the non-naturally occurring polypeptides having CHMO activity also have increased thermostability as compared to the polypeptide of SEQ ID NO: 2 associated with certain amino acid differences relative to SEQ ID NO: 2. Increased thermostability can be determined by preincubating the polypeptide at a defined temperature and time, e.g., 4° C.-46° C. for 18-24 hours, followed by measuring the % residual activity using a defined assay. Exemplary preincubation conditions include preincubation at 30° C. for 18 h, or 40° C. for 24 h. Accordingly, in some embodiments, specific amino acid differences resulting in increased thermostability by having at least 1.5-fold, 2.5-fold, 5-fold, 7.5-fold, or more, relative to the reference polypeptide of SEQ ID NO: 2; those amino acid differences can be selected from the following substitutions: A43G; S166A or G; G216I; K264Y; M291R; Y324K; E364K; K395R; M412L; N477D; and E512N. Accordingly, in some embodiments the present disclosure provides a non-naturally occurring polypeptide having CHMO activity which also has at least 1.5-fold, 2.5-fold, 5-fold, 7.5-fold, or more increased thermostability relative to the reference polypeptide of SEQ ID NO: 2 and which comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) at least one of the following amino acid differences relative to SEQ ID NO: 2 associated with increased thermostability: A43G; S166A or G; G216I; K264Y; M291R; Y324K; E364K; K395R; M412L; N477D; and E512N.

In some embodiments, the non-naturally occurring polypeptides having CHMO activity which are capable of converting compound (1b) to compound (2b) have an increased tolerance of the presence of substrate of compound (1b) and/or the presence of the product of compound (2b) as compared to the polypeptide of SEQ ID NO: 2 associated with the following amino acid differences relative to SEQ ID NO: 2: K89N, L143S, G216I, A243K, A245G, G275A, and A325Y. Accordingly, in some embodiments the present disclosure provides a non-naturally occurring polypeptide having CHMO activity which is capable of converting at least 90% of compound (1b) at a concentration of at least 30 g/L, at least 50 g/L, at least 60 g/L, at least 70 g/L, at least 80 g/L, at least 90 g/L, or at least 100 g/L of to compound (2b) in 24 h under suitable reaction conditions, and which comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) at least one of the following amino acid differences relative to SEQ ID NO: 2 associated with increased substrate and/or product tolerance: K89N, L143S, G216I, A243K, A245G, G275A, and A325Y.

In some embodiments of the non-naturally occurring polypeptides having CHMO activity described herein, the amino acid sequence further comprises an amino acid difference relative to SEQ ID NO: 2 at one or more positions selected from the following: X3, X32, X40, X42, X43, X54, X62, X74, X75, X79, X82, X84, X89, X99, X110, X118, X123, X135, X143, X161, X163, X166, X171, X172, X174, X176, X182, X192, X208, X216, X219, X227, X234, X243, X245, X264, X273, X275, X288, X290, X291, X310, X313, X314, X319, X322, X324, X325, X329, X336, X348, X362, X364, X373, X382, X395, X412, X426, X430, X438, X472, X473, X477, X478, X484, X486, X489, X491, X492, X498, X501, X503, X504, X505, X512, X532, X538, and X539.

In some embodiments of the non-naturally occurring polypeptides having CHMO activity described above, the amino acid sequence further comprises an amino acid difference relative to SEQ ID NO: 2 selected from the following: X3T, X32E, X40G, X42I, X43G, X54V, X62V, X74E, X75M, X79T, X82A, X82I, X84H, X89M, X89N, X99V, X110M, X118V, X123A, X135K, X143G, X143S, X161D, X163L, X163Y, X166A, X166G, X171G, X172A, X172M, X174I, X176S, X182V, X192V, X208T, X216I, X216S, X219V, X227D, X227E, X234D, X243K, X245G, X264Y, X273A, X273C, X273S, X275A, X275N, X275S, X288L, X288V, X290D, X291R, X310E, X310H, X313E, X314L, X314T, X319L, X319T, X322G, X322M, X324K, X325F, X325Y, X329V, X336S, X348A, X362S, X364K, X373V, X382R, X395R, X412L, X426N, X426S, X430R, X438M, X438R, X472I, X473D, X477D, X478L, X484C, X484L, X486E, X489G, X491V, X492K, X492S, X498N, X501D, X503A, X504I, X505K, X512N, X532P, X538E, and X539E.

Based on modeling studies of the wild-type CHMO of *Acinetobacter* sp NCIMB9871 of SEQ ID NO:2, at least the following residue positions are within 8Å of the FAD prosthetic group on the enzyme: X14, X34, X43; X111, X141, X386, X388, X426, X432, X433, X435, and X438; at least the following residue positions are within 8Å of enzyme-bound NADPH cofactor X149, X209, X277, X326, X426, X432, X435, X438, X488, X489, and X490; and at least the following residue positions are within 8Å of enzyme-bound substrate X277, X326, X426, X432, X433, X435, X438, X489, X490, and X505. While these residue positions are in close proximity to bound substrate, FAD prosthetic group, and co-factor, it has been found that the amino acid residues at these residue positions as well as others disclosed herein can be varied to alter specific enzyme properties, including, among others, substrate binding, enzyme activity, and enantioselectivity. In some embodiments, the present disclosure also contemplates a non-naturally occurring polypeptide having CHMO activity which are capable of converting compound (1a) to compound (2a), or compound (1b) to compound (2b), with improved properties relative to the activity of the polypeptide of SEQ ID NO: 2, wherein the non-naturally occurring polypeptide comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, and further comprises a set of amino acid residue differences as compared to SEQ ID NO:2, wherein the amino acid differences are based on locations or regions in the structure of reference polypeptide (e.g., SEQ ID NO: 2) and/or the associated functional properties. Accordingly, referring to Table 3, a non-naturally occurring or engineered polypeptide having CHMO activity of the present disclosure can include an amino acid substitution at a particular residue at a location in the structure of the reference polypeptide as identified in Table 3. Exemplary substitutions at each of the relevant locations include those identified in Tables 2A, 2B, and 2C.

TABLE 3

Structural Locations Useful for Engineered CHMO Polypeptides

| Corresponding Position in SEQ ID NO: 2 | Structural Location |
|---|---|
| X3 | Surface |
| X14 | Buried-close to FAD |
| X15 | Buried-FAD-binding |
| X22 | Buried (non active site) |
| X32 | Surface |
| X34 | Surface |
| X37 | Partially Buried-FAD-Binding |
| X39 | Partially Buried (FAD-Binding site) |
| X40 | Surface |
| X42 | Partially Buried (non-active site) |
| X43 | Partially Buried-Near FAD |
| X44 | Buried-FAD-Binding |
| X54 | Partially Buried |
| X59 | Surface (near active site) |
| X62 | Surface |
| X71 | Partially Buried (non-active site) |
| X74 | Surface |
| X75 | Buried |
| X79 | Surface |
| X82 | Partially Buried (non-active site) |
| X83 | Surface |
| X84 | Surface |
| X89 | Surface |
| X92 | Surface |
| X99 | Surface |
| X103 | Surface |
| X107 | Surface |
| X110 | Buried (close to FAD) |
| X111 | Surface |
| X113 | Buried (non active site) |
| X114 | Surface |
| X118 | Surface |
| X123 | Surface |
| X135 | Surface |
| X141 | Buried-FAD-Binding |
| X143 | Active Site |
| X144 | Active Site |
| X145 | FAD-Binding |
| X146 | Partially Buried |

TABLE 3-continued

Structural Locations Useful for Engineered CHMO Polypeptides

| Corresponding Position in SEQ ID NO: 2 | Structural Location |
|---|---|
| X149 | Surface |
| X154 | Surface |
| X155 | Surface |
| X161 | Surface |
| X163 | Surface |
| X166 | Partially Buried (close to FAD) |
| X171 | Surface |
| X172 | Surface |
| X174 | Buried (non active site) |
| X176 | Surface |
| X182 | Interacts with NADP |
| X192 | Buried |
| X194 | Surface |
| X195 | Buried (non active site) |
| X199 | Buried (non active site) |
| X201 | Surface |
| X208 | Surface-close to NADP |
| X209 | Surface-close to NADP |
| X216 | Surface |
| X219 | Surface |
| X227 | Surface |
| X234 | Surface |
| X240 | Surface |
| X243 | Surface |
| X244 | Active Site |
| X245 | Active Site |
| X246 | Active Site |
| X248 | Surface |
| X264 | Surface |
| X273 | Surface |
| X275 | Partially Buried (active site) |
| X277 | Active Site |
| X278 | Surface |
| X280 | Partially Buried (active site) |
| X281 | Surface |
| X288 | Surface |
| X290 | Surface |
| X291 | Surface |
| X301 | Buried |
| X307 | Surface |
| X310 | Surface |
| X313 | Surface |
| X314 | Buried |
| X319 | Surface |
| X322 | Surface |
| X324 | Buried |
| X325 | Partially Buried (non-active site) |
| X326 | Partially Buried (Active Site) |
| X329 | Buried (active site main chain) |
| X330 | Buried (active site main chain) |
| X336 | Surface |
| X341 | Surface |
| X348 | Partially Buried (non-active site) |
| X354 | Surface |
| X362 | Surface |
| X364 | Partially Buried (non-active site) |
| X367 | Surface |
| X368 | Surface |
| X373 | Partially Buried (non-active site) |
| X382 | Buried (Active Site) |
| X383 | Active Site |
| X386 | Surface (FAD-Binding site) |
| X388 | Surface |
| X390 | Buried-FAD-Binding |
| X395 | Surface |
| X400 | Buried (non-active site) |
| X408 | Partially Buried (non active site) |
| X412 | Partially Buried (non-active site) |
| X415 | Buried (non active site) |
| X426 | Active Site |
| X428 | Buried (active site main chain) |
| X430 | Active Site |
| X432 | Active Site |
| X433 | Active Site |

TABLE 3-continued

Structural Locations Useful for
Engineered CHMO Polypeptides

| Corresponding Position in SEQ ID NO: 2 | Structural Location |
|---|---|
| X435 | Active Site |
| X438 | Active Site |
| X448 | Surface |
| X449 | Surface |
| X451 | Buried (non active site) |
| X454 | Surface |
| X459 | Surface |
| X472 | Surface |
| X473 | Surface |
| X475 | Buried (non active site) |
| X477 | Surface |
| X478 | Surface |
| X481 | Surface |
| X484 | Active Site |
| X486 | Surface |
| X487 | Active Site |
| X488 | Surface |
| X489 | Partially Buried-Active Site |
| X490 | Active Site |
| X491 | Active Site |
| X492 | Surface (Active Site) |
| X498 | Surface |
| X499 | Surface |
| X501 | Surface |
| X503 | Surface |
| X504 | Active Site |
| X505 | Active Site |
| X507 | Partially Buried (near active site) |
| X512 | Surface |
| X516 | Surface |
| X526 | Surface |
| X532 | Surface |
| X537 | Surface |
| X538 | Surface |
| X539 | Surface |
| X540 | Surface |

As will be apparent to the skilled artisan, various combinations of residue differences as compared to SEQ ID NO: 2 at residue positions affecting enzymatic activity, thermostability, can be made to form the engineered polypeptides having CHMO activity of the present disclosure.

In addition to the residue positions specified above, any of the non-naturally occurring polypeptides having CHMO activity disclosed herein can further comprise other residue differences relative to SEQ ID NO: 2 at other residue positions. Residue differences at these other residue positions provide for additional variations in the amino acid sequence without adversely affecting the CHMO activity of the polypeptide, including the ability to carry out the conversion of compound (1a) to compound (2a), or compound (1b) to compound (2b). In some embodiments, the polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, and 40 residue differences at other residue positions. The residue difference at these other positions can include conservative changes or non-conservative changes. In some embodiments, the residue differences can comprise conservative substitutions and non-conservative substitutions as compared to the wild-type CHMO of SEQ ID NO: 2. In some embodiments, these engineered polypeptides having CHMO activity are capable of converting compound (1a) to compound (2a) and/or compound (1b) to compound (2b) under suitable reaction conditions with improved properties relative to the naturally occurring CHMO polypeptide of SEQ ID NO: 2.

Amino acid residue differences at other positions relative to the wild-type CHMO amino acid sequence of SEQ ID NO: 2 and the affect of these differences on enzyme function are provide by the engineered CHMO polypeptides disclosed U.S. provisional patent application 61/267,812, filed Dec. 8, 2009, which is hereby incorporated by reference herein. Accordingly, in some embodiments, it is contemplated that one or more of the amino acid differences relative to SEQ ID NO: 2 disclosed in the engineered CHMO polypeptides of this US provisional patent application could also be introduced into a non-naturally occurring CHMO polypeptide of the present disclosure, including any one or more of the following: X14A; X34K; X71M; X111T; X141I; X141V; X149W; X149V; X174L; X209P; X240K; X246Y; X246W; X248C; X248N; X248V; X248S; X288I; X307R; X326T; X326C; X329N; X383I; X388K; X390R; X390I; X400I; X415A; X426F; X432A; X432L; X433A; X435S; X438I; X448V; X448W; X449M; X449F; X449L; X451R; X481K; X488K; X489C; X490R X499L; X505W; X505L; X516V; X526V; X537T; X540Q; and X540A. In some embodiments, the present disclosure provides engineered polypeptides having CHMO activity which have an amino acid sequence that comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) one or more of the following amino acid differences as compared to SEQ ID NO:2: X14A; X34K; X71M; X111T; X141I; X141V; X149W; X149V; X174L; X209P; X240K; X246Y; X246W; X248C; X248N; X248V; X248S; X288I; X307R; X326T; X326C; X329N; X383I; X388K; X390R; X390I; X400I; X415A; X426F; X432A; X432L; X433A; X435S; X438I; X448V; X448W; X449M; X449F; X449L; X451R; X481K; X488K; X489C; X490R X499L; X505W; X505L; X516V; X526V; X537T; X540Q; and X540A. In some embodiments, these engineered polypeptides having CHMO activity are capable of converting compound (1a) to compound (2a) and/or compound (1b) to compound (2b) under suitable reaction conditions with improved properties relative to the naturally occurring CHMO polypeptide of SEQ ID NO: 2.

Alternatively, in some embodiments the present disclosure provides an engineered polypeptide having CHMO activity wherein the amino acid sequence excludes one or more of the amino acid differences relative to SEQ ID NO: 2 disclosed in U.S. provisional patent application 61/267, 812, filed Dec. 8, 2009. Accordingly, in some embodiments, the present disclosure provides engineered polypeptides having CHMO activity which have an amino acid sequence that (a) comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) does not include one or more of the following amino acid differences as compared to SEQ ID NO:2: X14A; X34K; X71M; X111T; X141I; X141V; X149W; X149V; X174L; X209P; X240K; X246Y; X246W; X248C; X248N; X248V; X248S; X288I; X307R; X326T; X326C; X329N; X383I; X388K; X390R; X390I; X400I; X415A; X426F; X432A; X432L; X433A; X435S; X438I; X448V; X448W; X449M; X449F; X449L; X451R; X481K; X488K; X489C; X490R X499L; X505W; X505L; X516V; X526V; X537T; X540Q; and X540A. In some embodiments, these engineered polypeptides having CHMO activity are capable of converting compound (1a) to compound (2a) and/or compound (1b) to compound (2b) under suitable reaction conditions with improved properties relative to the naturally occurring CHMO polypeptide of SEQ ID NO: 2.

In some embodiments, the present disclosure provides engineered polypeptides having CHMO activity which have an amino acid sequence that comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) specifically excludes one or more of the following amino acid differences or sets of amino acid differences as compared to SEQ ID NO:2: D41N and F505Y; K78E and F432S; L143F; L220Q, P428S and T433A; F432S; F432I; L426P and A541V; F432Y and K500R; and L143F, E292G, L435Q, and T464A; D384H; K229I and L248P; Y132C, F246I, V361A, and T415A; and F16L and F277S. These excluded amino acid differences are disclosed in Mihovilovic et al., 2006, Organic Lett. 8(6): 1221-1224; Reetz et al., 2004, Angew. Chem. Int. Ed. 43:4075-4078; Reetz et al., 2004, Angew Chem. Int. Ed. 43:4078-4081; the disclosures of which are incorporated herein by reference. In some embodiments, these engineered polypeptides having CHMO activity are capable of converting compound (1a) to compound (2a) and/or compound (1b) to compound (2b) under suitable reaction conditions with improved properties relative to the naturally occurring CHMO polypeptide of SEQ ID NO: 2.

In some embodiments, the present disclosure provides engineered polypeptides having CHMO activity which have an amino acid sequence that comprises (a) an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (b) specifically excludes the following wild-type amino acid sequences (identified by UniProt databank accession numbers): (i) gi|81324523|sp|Q9F7E4|Q9F7E4_9 GAMM Cyclohexanone monooxygenase; (ii) gi|118066|sp|P12015.2|CYMO_ACISP RecName: Full=Cyclohexanone 1,2-monooxygenase; (iii) gi|123163966|sp|Q11Z78|Q11Z78_POLSJ Flavin-containing monooxygenase FMO; (iv) tr|A3U3H1|A3U3H1_9RHOB Flavin-containing monooxygenase FMO:FAD dependent oxidoreductase OS=*Oceanicola batsensis* HTCC2597 GN=OB2597_18631 PE=4 SV=1; (v) tr|A3T2M3|A3T2M3_9RHOB Flavin-containing monooxygenase FMO:FAD dependent oxidoreductase OS=*Sulfitobacter* sp. NAS-14.1 GN=NAS141_04678 PE=4 SV=1; and (vi) tr|A1W7Q2|A1W7Q2_ACISJ Cyclohexanone monooxygenase OS=*Acidovorax* sp. (strain JS42) GN=Ajs_2102 PE=4 SV=1. In some embodiments, these engineered polypeptides having CHMO activity are capable of converting compound (1a) to compound (2a) and/or compound (1b) to compound (2b) under suitable reaction conditions with improved properties relative to the naturally occurring CHMO polypeptide of SEQ ID NO: 2.

In some embodiments, the polypeptides can comprise deletions of the engineered CHMO polypeptides described herein. Thus, for each and every embodiment of the polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids of the polypeptides, as long as the functional activity of the polypeptide with respect to the conversion of compound (1a) to compound (2a), or compound (1b) to compound (2b) is present. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, or 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35, or 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

In some embodiments, the polypeptides can comprise fragments of the engineered polypeptides described herein. In some embodiments, the fragments can have about 80%, 90%, 95%, 98%, and 99% of the full-length polypeptide, as long as the functional activity of the polypeptide with respect to the conversion of compound from compound (1a) to compound (2a), or compound (1b) to compound (2b) is present.

In some embodiments, the polypeptides of the disclosure can be in the form of fusion polypeptides in which the engineered polypeptides are fused to other polypeptides, such as, by way of example and not limitation, antibody tags (e.g., myc epitope), purifications sequences (e.g., His tags for binding to metals), and cell localization signals (e.g., secretion signals). Thus, the engineered polypeptides described herein can be used with or without fusions to other polypeptides.

As will be understood by the skilled artisan, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-enantiomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Oct); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Oct); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those skilled in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered polypeptides having CHMO activity described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the engineered polypeptides having CHMO activity of the present disclosure can be provided on a substrate or otherwise immobilized on a solid support. "Substrate," "support," "solid support," "solid carrier," or "resin" in the context of refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having CHMO activity of the present disclosure can be immobilized on a solid support such that they retain their CHMO activity, improved activity relative to the polypeptide of SEQ ID NO: 2, enantioselectivity, and/or other improved properties relative to the wild-type. In such embodiments, the immobilized polypeptides can facilitate the biocatalytic conversion reactions of Scheme 1 or Scheme 2 (e.g., in processes for preparing armodafinil as described herein), and after the reaction is complete are easily retained (e.g., by retaining beads on which polypeptide is immobilized) and then reused or recycled in subsequent reactions. Such immobilized enzyme processes allow for further efficiency and cost reduction. Methods of enzyme immobilization are well-known in the art.

In some embodiments, the polypeptides can be provided in the form of an array in which engineered polypeptides having different sequences are immobilized in positionally distinct locations. Such arrays can be used to test a variety of aryl alkyl sulfides for conversion by the polypeptides. A plurality of supports can be configured on an array at various locations, addressable for robotic delivery of reagents, or by detection methods and/or instruments.

In certain embodiments, the kits of the present disclosure include arrays comprising a plurality of different engineered polypeptides having CHMO activity at different addressable position, wherein the different polypeptides are different variants of a reference sequence each having at least one different improved enzyme property. Such arrays comprising a plurality of engineered polypeptides and methods of their use are described in, e.g., WO2009/008908A2.

1.3 CHMO Polynucleotides, Expression Vectors, and Host Cells

In another aspect, the present disclosure provides polynucleotides encoding the non-naturally occurring or engineered polypeptides described herein. These polynucleotides may be operatively linked to one or more heterologous regulatory sequences that control gene expression to create a recombinant polynucleotide capable of expressing the polypeptide having CHMO activity. Expression constructs containing a heterologous polynucleotide encoding the engineered polypeptide having CHMO activity can be introduced into appropriate host cells to express the corresponding polypeptide.

Because of the knowledge of the codons corresponding to the various amino acids, availability of a protein sequence provides a description of all the polynucleotides capable of encoding the subject. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Tables 2A, 2B, and 2C.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the CHMO gene (e.g., because the natural sequence can have preferred codons and because use of preferred codons may not be required for all amino acid residues), codon optimized polynucleotides encoding the CHMO polypeptides may contain preferred codons at about 40%, 50%, 60%, 70%, 80%, or greater than 90% of codon positions of the full length coding region.

In some embodiments, the polynucleotide encodes a non-naturally occurring polypeptide having CHMO activity and comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142.

In some embodiments, the polynucleotide encodes a non-naturally occurring polypeptide having CHMO activity which is capable of converting compound (1a) to compound (2a), or compound (1b) to compound (2b) with at least 2-fold, at least 10-fold, at least 25-fold, at least 40-fold, or at least 60-fold increased enzyme activity relative to the enzyme activity of the polypeptide of SEQ ID NO: 2, and comprises an amino acid sequence having at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142, with the proviso that the amino acid sequence comprises any one of the set of residue differences as compared to SEQ ID NO: 2 contained in any one of the polypeptide sequences of SEQ ID NO:4 to SEQ ID NO: 142 listed in Tables 2A and 2B.

In some embodiments, the polynucleotides encoding the polypeptides having CHMO activity are selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, and 141.

In some embodiments, the polynucleotides are capable of hybridizing under highly stringent conditions to a polynucleotide comprising SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, or a complement thereof, where the highly stringently hybridizing polynucleotides encode a non-naturally occurring polypeptide having CHMO activity. In some embodiments, the encoded polypeptide is capable of converting compound (1a) to compound (2a), or compound (1b) to compound (2b), with at least 2-fold, at least 10-fold, at least 25-fold, at least 40-fold, or at least 60-fold increased activity relative to the activity of the polypeptide of SEQ ID NO: 2.

In some embodiments, the polynucleotides encode the polypeptides having CHMO activity described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered CHMO polypeptides described herein. In some embodiments, the polynucleotide is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, and 141.

An isolated polynucleotide encoding a non-naturally occurring polypeptide having CHMO activity of the disclosure may be manipulated in a variety of ways to provide for expression of the polypeptide. In some embodiments, the polynucleotides encoding the polypeptides can be provided as expression vectors where one or more control sequences is present to regulate the expression of the polynucleotides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

In some embodiments, the control sequences include among others, promoters, leader sequence, polyadenylation sequence, propeptide sequence, signal peptide sequence, and transcription terminator. Suitable promoters can be selected based on the host cells used. Exemplary bacterial promoters include *E. coli* lac operon, *E. coli* trp operon, bacteriophage□ 1, *Streptomyces coelicolor* agarase gene (dagA), *Bacillus subtilis* levansucrase gene (sacB), *Bacillus licheniformis* alpha-amylase gene (amyL), beta-lactamase gene, and tac promoter; exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus*

*nidulans* acetamidase, and *Fusarium oxysporum* trypsin-like protease, and mutant, truncated, and hybrid promoters thereof, and exemplary yeast cell promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase.

In some embodiments, the control sequence may also be a signal peptide coding region that codes for an amino acid sequence linked to the amino terminus of a polypeptide and directs the encoded polypeptide into the cell's secretory pathway. The signal sequence typically depends on the type of host cells being used to express the polypeptide. Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Exemplary signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase.

Other control sequences, such as leader sequence, polyadenylation sequence, and transcription terminator sequences can use those available in the art (see Sambrook, supra, and Current Protocols in Molecular Biology, supra).

In another aspect, the present disclosure is also directed to a recombinant expression vector comprising a polynucleotide encoding an engineered polypeptide having CHMO activity or a variant thereof, and one or more expression regulating regions such as a promoter and a terminator, a replication origin, etc., depending on the type of hosts into which they are to be introduced. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The expression vector preferably contains one or more selectable markers, which permit easy selection of transformed cells. A selectable marker is a gene the product of which provides for biocide or viral resistance, resistance to heavy metals, prototrophy to auxotrophs, resistance to chemical agents (e.g., antibiotics) and the like.

In another aspect, the present disclosure provides a host cell comprising a polynucleotide encoding an engineered polypeptide having CHMO activity of the present disclosure, the polynucleotide being operatively linked to one or more control sequences for expression of the CHMO polypeptide in the host cell. Host cells for use in expressing the CHMO polypeptides encoded by the expression vectors of the present disclosure are well known in the art and include but are not limited to, bacterial cells, such as *E. coli, Lactobacillus, Streptomyces* and *Salmonella typhimurium* cells; fungal cells, such as yeast cells; insect cells such as *Drosophila* S2 and *Spodoptera* Sf9 cells; animal cells such as CHO, COS, BHK, 293, and Bowes melanoma cells; and plant cells. Exemplary host cells are *Escherichia coli* BL21 and W3110.

Appropriate culture mediums and growth conditions for the above-described host cells are well known in the art. Polynucleotides for expression of the CHMO may be introduced into host cells by various methods known in the art (e.g., electroporation, biolistic particle bombardment, liposome mediated transfection, calcium chloride transfection, and protoplast fusion).

In the embodiments herein, the non-naturally occurring or engineered CHMO polypeptides and nucleotides encoding such polypeptides can be prepared using methods commonly used by those skilled in the art. In some embodiments, the parent polynucleotide sequence is codon optimized to enhance expression of the CHMO in a specified host cell.

The engineered CHMO polypeptides can be obtained by subjecting the polynucleotide encoding the naturally occurring CHMO to mutagenesis and/or directed evolution methods (see e.g., Stemmer, 1994, Proc Natl Acad Sci USA 91:10747-10751; PCT Publ. Nos. WO 95/22625, WO 97/0078, WO 97/35966, WO 98/27230, WO 00/42651, and WO 01/75767; U.S. Pat. Nos. 6,537,746, 6,117,679, 6,376,246, and 6,586,182; and U.S. Pat. Publ. Nos. 20080220990A1 and 20090312196A1; each of which is hereby incorporated by reference herein).

Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, Methods Mol. Biol. 57:369-74; Smith, 1985, Ann. Rev. Genet. 19:423-462; Botstein et al., 1985, Science 229:1193-1201; Carter, 1986, "Site-directed mutagenesis," Biochem. J. 237:1-7; Kramer et al., 1984, Cell 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; and Stemmer, 1994, Nature 370:389-391. All publications are incorporated herein by reference.

In some embodiments, the clones obtained following mutagenesis treatment are screened for non-naturally occurring CHMO having a desired enzyme property. Measuring CHMO enzyme activity from the expression libraries can be performed using the standard techniques, such as separation of the product (e.g., by HPLC) and detection of the product by measuring UV absorbance of the separated substrate and products and/or by detection using tandem mass spectroscopy (e.g., MS/MS). Clones containing a polynucleotide encoding the desired engineered polypeptides are then isolated, sequenced to identify the nucleotide sequence changes (if any), and used to express the enzyme in a host cell. Exemplary assays are provided below in the Examples.

Where the sequence of the polypeptide is known, the polynucleotides encoding the enzyme can be prepared by standard solid-phase methods, according to known synthetic methods, e.g., the classical phosphoramidite method described by Beaucage et al., 1981, Tet Lett 22:1859-69, or the method described by Matthes et al., 1984, EMBO J. 3:801-05. In some embodiments, fragments of up to about 100 bases can be individually synthesized, then joined (e.g., by enzymatic or chemical litigation methods, or polymerase mediated methods) to form any desired continuous sequence.

In some embodiments, the present disclosure also provides methods for preparing or manufacturing the non-naturally occurring polypeptides capable of converting compound (1a) to compound (2a), or compound (1b) to compound (2b), wherein the methods comprise: (a) culturing a host cell capable of expressing a polynucleotide encoding the non-naturally occurring polypeptide and (b) isolating the polypeptide from the host cell. The non-naturally occurring polypeptides can be expressed in appropriate cells (as described above), and isolated (or recovered) from the host cells and/or the culture medium using any one or more of the well known techniques used for protein purification, including, among others, lysozyme treatment, sonication, filtration, salting-out, ultra-centrifugation, and chromatography. Chromatographic techniques for isolation of the CHMO polypeptide include, among others, reverse phase chromatography high performance liquid chromatography, ion exchange chromatography, gel electrophoresis, and affinity chromatography.

In some embodiments, the non-naturally occurring polypeptide of the disclosure can be prepared and used in various isolated forms including but not limited to crude extracts (e.g., cell-free lysates), powders (e.g., shake-flask powders), lyophilizates, and substantially pure preparations (e.g., DSP powders), as further illustrated in the Examples below.

In some embodiments, the non-naturally occurring polypeptide of the disclosure can be prepared and used in purified form. Generally, conditions for purifying a particular enzyme will depend, in part, on factors such as net charge, hydrophobicity, hydrophilicity, molecular weight, molecular shape, etc., and will be apparent to those having skill in the art. To facilitate purification, it is contemplated that in some embodiments the engineered polypeptides having CHMO activity of the present disclosure can be expressed as fusion proteins with purification tags, such as His-tags having affinity for metals, or antibody tags for binding to antibodies, e.g., myc epitope tag.

1.4 Methods of Using the Engineered CHMO Polypeptides and Compounds Prepared Therewith In some embodiments, the engineered polypeptides having CHMO activity described herein can be used in a method for preparing compound (2a) by converting compound (1a) to compound (2a) as shown in Scheme 1. Compound (2a) is the active pharmaceutical ingredient, armodafinil, or analogs thereof. The engineered CHMO polypeptides described herein also can be used in a method for preparing compound (2b) by converting compound (1b) to compound (2b), as shown in Scheme 2. Compound (2b) is an intermediate that can be used in further methods for preparing the active pharmaceutical ingredient of compound (2a), or analogs thereof. Accordingly, in some embodiments the present disclosure also provides a process for preparing armodafinil, or an analog thereof, in which the process comprises a step of using an engineered polypeptide having CHMO activity described herein in a method for converting compound (1a) to compound (2a) or converting compound (1b) to compound (2b).

The methods and processes using the biocatalytic conversions compound (1a) to compound (2a) (as in Scheme 1) or compound (1b) to compound (2b) (as in Scheme 2) can be facilitated by the addition of a NAD$^+$ or NADP$^+$ cofactor recycling system that includes a ketoreductase (KRED) enzyme and secondary substrate for the KRED—e.g., isopropyl alcohol (IPA). In such embodiments, the engineered CHMO polypeptide catalyzes the enantioselective addition of a single oxygen atom from molecular oxygen into the substrate of compound (1a) or compound (1b), followed by the reduction of a second oxygen atom to water. The KRED enzyme recycles the cofactor NAD$^+$ to NADH or the cofactor NADP$^+$ to NADPH using the secondary substrate, IPA (which is converted to acetone), as a reducing agent.

In some embodiments, the disclosure provides a method for preparing compound (2a) in enantiomeric excess comprising: contacting compound (1a) with an engineered polypeptide of the present disclosure (e.g., as described in Tables 2A, 2B, 2C and elsewhere herein) in the presence of NADPH or NADH cofactor under suitable reaction conditions. Scheme 1 described above illustrates the method of biocatalytic conversion of 2-(benzhydrylsulfinyl)acetamide (compound (1a)) to (−)-2-[(R)-(diphenylmethyl)sulfinyl]acetamide (compound (2a)). Suitable reactions conditions for the conversion of compound (1a) to compound (2a) using the engineered CHMO polypeptides of the present disclosure are described in greater detail below and some exemplary suitable reaction conditions also are provided in the Examples.

In brief, the non-naturally occurring CHMO polypeptide of the present disclosure, KRED, and NADP are added to a vial. TEA buffer at basic pH is used to dissolve the enzyme powder. The mixture is stirred gently until a homogenous solution is obtained. 2-(benzhydrylsulfinyl)acetamide (compound (1a)) is added as a solid powder into the enzyme solution followed by the secondary substrate for the KRED, IPA. The pH of the slurry mixture was re-measured to ensure the reaction pH is 9. The progress of the reaction for conversion compound (1a) to compound (2a) (armodafinil) can be monitored by achiral or chiral chromatography, e.g., HPLC methods as described in Examples.

In some embodiments, the disclosure provides methods for preparing compound (2b) in enantiomeric excess comprising: contacting compound (1b) with an engineered polypeptide of the present disclosure (e.g., as described in Tables 2A, 2B, 2C and elsewhere herein) in the presence of NADPH or NADH cofactor under suitable reaction conditions. Scheme 2 described above illustrates the biocatalytic conversion of benzhydryl-thioacetic acid (compound (1b), BHTA) to (R)-2-(benzhydrylsulfinyl)acetic acid (compound (2b), (R)-BHSO, (R)-modafinic acid), which is an intermediate that can be further used to prepare the amide of compound (2a) (armodafinil). Suitable reactions conditions for the conversion of compound (1b) to compound (2b) using the engineered polypeptides of the present disclosure are described in greater detail below and some exemplary suitable reaction conditions also are provided in the Examples.

The active pharmaceutical ingredient, armodafinil, which is the amide of compound (2a), can be prepared from the R-modafinic acid of compound (2b) by esterification and amidation. In brief, the R-modafinic acid is mixed with methanol, and HCl to form a suspension. The methyl ester of R-modafinic acid then is isolated using standard methods and mixed with methanol. Subsequently, ammonia is added into the mixture and stirred to form the amide of compound (2a). Crystals of the amide of compound (2a) are precipitated and collected.

Alternatively, R-modafinic acid, is mixed with methanol, and thionyl chloride and reacted at room temperature. The methyl ester of R-modafinic acid is precipitated, filtered and dried. The methyl ester of R-modafinic acid then is mixed with methanol and ammonia hydroxide is added to the mixture. The mixture is allowed to react thereby forming the amide of compound (2a). Crystals of the amide of compound (2a) are precipitated and collected.

In some embodiments, the biocatalytic methods for the conversion of the substrate of compound (1a) to compound (2a) or the substrate of compound (1b) to compound (2b) can be carried out wherein a deuterated version of the substrate of compound (1a) (i.e., a molecule have the same structure as compound (1a) but with one or more the hydrogen atoms of compound (1a) substituted with a deuterium atom) or the substrate of compound (1b) is used (e.g., US Pat. Publ. No. 20090082461A1). The resulting deuterated products of compound (2a) or compound (2b) would be produced and could be isolated and further used as described above for the corresponding non-deuterated product compounds.

As described further below, and illustrated in the Examples, the present disclosure contemplates ranges of suitable reaction conditions that can be used in the methods, including but not limited to ranges of pH, temperature, buffer, solvent system, substrate loading, mixture of substrate compound enantiomers, polypeptide loading, cofactor loading, atmosphere, and reaction time. Further suitable reaction conditions for carrying out the method for biocatalytic conversion of compound (1a) to compound (2a) or compound (1b) to compound (2b) using an engineered CHMO polypeptide described herein can be readily optimized by routine experimentation that includes, but is not limited to, contacting the engineered CHMO polypeptide and the substrate of compound (1a) or compound (1b) under experimental reaction conditions of concentration, pH, temperature, solvent conditions, and detecting the production of the corresponding amide product of compound (2a) or acid product of compound (2b), for example, using the methods described in the Examples provided herein.

As described above, the present disclosure provides a non-naturally occurring CHMO polypeptide capable of converting compound (1a) to compound (2a) in enantiomeric excess and/or compound (1b) to compound (2b) in enantiomeric excess under suitable reaction conditions, wherein the amino acid sequence of the polypeptide has: (a) sequence identity of at least 85%, 90%, 91%, 92%, 93%, 94%, 95%, 96%, 97%, 98%, or 99% to any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, or 142; and (b) one or more amino acid differences relative to SEQ ID NO: 2 selected from: X37E; X277I; X278A or X278G; X280T or X280Y; X281I; X326R; and X490L or X490Q. In some embodiments, the engineered CHMO can include at least the following amino acid differences relative SEQ ID NO: 2: X37E; X277I; X278A or X278G; X280T or X280Y; X281I; X326R; X433G; X435A; and X490L or X490Q. In some embodiments, the amino acid sequence of the engineered CHMO can include one or more further amino acid differences relative to SEQ ID NO: 2 selected from the following: X3T, X32E, X40G, X42I, X43G, X54V, X62V, X74E, X75M, X79T, X82A, X82I, X84H, X89M, X89N, X99V, X110M, X118V, X123A, X135K, X143G, X143S, X161D, X163L, X163Y, X166A, X166G, X171G, X172A, X172M, X174I, X176S, X182V, X192V, X208T, X216I, X216S, X219V, X227D, X227E, X234D, X243K, X245G, X264Y, X273A, X273C, X273S, X275A, X275N, X275S, X288L, X288V, X290D, X291R, X310E, X310H, X313E, X314L, X314T, X319L, X319T, X322G, X322M, X324K, X325F, X325Y, X329V, X336S, X348A, X362S, X364K, X373V, X382R, X395R, X412L, X426N, X426S, X430R, X438M, X438R, X472I, X473D, X477D, X478L, X484C, X484L, X486E, X489G, X491V, X492K, X492S, X498N, X501D, X503A, X504I, X505K, X512N, X532P, X538E, and X539E.

The improved enzymatic activity of the engineered CHMO polypeptides of the present disclosure in the conversion of compound (1a) to compound (2a) in enantiomeric excess and/or compound (1b) to compound (2b) in enantiomeric excess provides for methods wherein higher percentage conversion can be achieved with lower concentrations of the engineered polypeptide. The use of lower concentration of the engineered polypeptide in a method comprising a conversion of compound (1a) to compound (2a) or compound (1b) to compound (2b) also reduces the amount of residual protein that may need to be removed in subsequent steps for purification of the products of compound (2a) or compound (2b). In some embodiments, the methods for preparing compound (2a) or compound (2b) of the present disclosure can be carried out wherein the suitable reaction conditions comprise an engineered CHMO polypeptide concentration of about 0.1-3.0 g/L, about 0.5-2.75 g/L, about 1.0-2.5 g/L, about 1.5-2.5 g/L, about 3 g/L, about 2 g/L, about 1.5 g/L, about 1.0 g/L, about 0.75 g/L, or even lower concentration.

The engineered CHMO polypeptides of the present disclosure have increased thermal stability relative to the naturally occurring CHMO polypeptide of SEQ ID NO: 2. This allows the engineered polypeptides to be used in methods for converting compound (1a) to compound (2a) or compound (1b) to compound (2b) at higher temperatures which can result in increased conversion rates and improved substrate solubility characteristics for the reaction. The temperature can be chosen to maximize the reaction rate at higher temperatures while maintaining the activity of the enzyme for sufficient duration for efficient conversion of the substrate to the product. Where higher temperatures are used, polypeptides with increased thermostability can be selected to carry out the process. In certain embodiments, the method can be carried out wherein the suitable reaction conditions comprise a temperature of about 10° C. to 50° C., about 20° C. to about 40° C., about 25° C. to about 40° C., about 23° C. to about 37° C., about 25° C. to about 35° C., about 26° C. to about 32° C., about 28° C. to about 30° C. In certain embodiments, the temperature during the enzymatic reaction can be maintained at ambient (e.g., 25° C.), 27° C., 30° C., 32° C., 35° C., 37° C., 40° C.; or in some embodiments adjusted over a temperature profile during the course of the reaction.

In some embodiments of the methods for converting compound (1a) to compound (2a) or compound (1b) to compound (2b) using the engineering polypeptides having CHMO activity of the present disclosure can be carried out wherein the suitable reaction conditions comprise a pH of about 7.5 to a pH of about 10.5, a pH of about 8.0 to a pH of about 10.0, a pH of about 8.5 to a pH of about 9.5, or a pH of about 8.3 to a pH of about 8.7. In some embodiments, the suitable reaction conditions comprise a pH of about 8.5.

During the course of the reaction, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer.

In some embodiments, the methods for preparing compound (2a) or compound (2b) of the present disclosure can be carried out wherein the suitable reaction conditions comprise a solution comprising an aqueous buffer solution. In some embodiments, the suitable reaction conditions comprise a solution comprising an aqueous buffer solution and an organic solvent, or a co-solvent system. In some embodiments, the aqueous buffer solution is selected from TEA (e.g., about 0.025 M to about 0.25 M TEA) and potassium phosphate (e.g., about 0.025 M to about 0.25 M phosphate). Suitable buffers to maintain desired pH ranges are known in the art and include, for example, phosphate buffer, triethanolamine buffer, and the like. Combinations of buffering and acid or base addition may also be used. In some embodiments, the suitable reaction condition comprise TEA at a buffer concentration of from about 50 mM to about 125 mM, or in some embodiments a TEA buffer concentration of about 100 mM. In some embodiments, the suitable reaction condition comprises a phosphate buffer concentration of about 5 to 50 mM. In certain embodiments, the solution is a co-solvent system comprising about 70% (v/v) to about 99% (v/v) of an aqueous buffer solution (e.g., about 0.1 M TEA) and about 30% to about 1% of an organic solvent solution (e.g., IPA). In some embodiments, the suitable reaction conditions comprise a 0.1 M TEA buffer, 5% (v/v) IPA, and a pH of about 8.5. In some embodiments, the reaction conditions comprise water as a suitable solvent with no buffer present.

In some embodiments, the suitable reaction conditions comprise a co-solvent. Co-solvents can reduce the formation of aggregates which can affect the rate and scalability of the process. At substrate loading of 75 g/L or higher, the use of a co-solvent is desirable. Suitable co-solvents include: MeOH, EtOH, isopropanol (IPA), acetone, toluene, MeCN, methyl tert-butyl ether (MTBE), N-methyl-2-pyrrolidone (NMP), dimethylacetamide (DMAc), dimethylformamide (DMF), propylene glycol, polyethylene glycol (PEG) (e.g., PEG200), tetramethylurea, N-ethylpyrollidinone, tetraglyme, 1,3-Dimethyl-3,4,5,6-tetrahydro-2(1H)-pyrimidinone (DMPU), DMIU, hexamethylphosphoramide (HMPA) and dimethylsulfoxide (DMSO).

Choice of co-solvent can be based on evaluating a combination of factors including: compound solubility, compound stability, reaction/process safety, toxicity, allowable level of solvent in the product (e.g., an API product); the effectiveness of the co-solvent in preventing agglomeration of the product, and stability of the monooxygenase to the co-solvent. NMP and PEG200 are particularly suitable co-solvents for reactions with high substrate loading. Accordingly, in some embodiments with higher substrate loadings (e.g., 100 g/L of compound (1b)), the suitable reaction conditions comprise about 2%-7.5% (v/v) NMP as a co-solvent. In some embodiments (particularly with higher substrate loadings—e.g., 100 g/L of compound (1b)), the suitable reaction conditions can comprise PEG200 as a co-solvent at a concentration of at least about 5-15% (v/v), or about 10% (v/v).

The biocatalytic conversion processes described herein (i.e., Scheme 1 and Scheme 2) also consumes molecular oxygen as reagent and an oxygen atom is transferred to a sulfide intermediate to yield the sulfoxide found in the product of compound (2a) and compound (2b). In some embodiments of the methods for converting compound (1a) to compound (2a) or compound (1b) to compound (2b) using the engineered polypeptides having CHMO activity of the present disclosure can be carried out wherein the suitable reaction conditions comprise adding dissolved $O_2$ to the reaction solution. Dissolved $O_2$ can be increased by direct sparging of $O_2$ gas into the reaction solution (e.g., U.S. Pat. No. 6,478,964). In some embodiments, oxygenation of the reaction solution is done by bubble free processes. For example, oxygen mass transfer across PTFE membrane for bubble free aeration is described in Schneider et al., 1995, Enzyme and Microbial Technology 17(9):839-847 and European Patent publication no. EP 0 172 478, which is incorporated herein by reference. Dissolved $O_2$ also can be increased by increasing the partial pressure of 02 above the reaction solution to higher than atmospheric pressure. Accordingly, in some embodiments of the methods the suitable reaction conditions comprise an 02 partial pressure of at least about 1.25 atm, at least about 1.5 atm, at least about 1.75 atm, at least about 2.0 atm, or greater.

As shown in Scheme 1 and Scheme 2, a cofactor is used in the biocatalytic reaction converting compound (1a) to compound (2a) or compound (1b) to compound (2b). The cofactor operates in combination with the polypeptides of the disclosure in the process. Suitable cofactors include, but are not limited to, $NADP^+$ (nicotinamide adenine dinucleotide phosphate), NADPH (the reduced form of $NADP^+$), $NAD^+$ (nicotinamide adenine dinucleotide) and NADH (the reduced form of $NAD^+$). Generally, the reduced form of the cofactor is added to the reaction mixture prior to the start of the reaction. The amount of cofactor used is the amount needed to drive the biocatalytic reaction of Scheme 1 or Scheme 2 to completion (e.g., 95% conversion or greater) and depends on the substrate loading. In certain embodiments, the method can be carried out wherein the suitable reaction conditions comprise an NADH or NADPH cofactor concentration of about 0.03-0.5 g/L, about 0.05-0.3 g/L, about 0.1-0.2 g/L, about 0.5 g/L, about 0.1 g/L, or about 0.2 g/L.

In some embodiments of the methods for converting compound (1a) to compound (2a) or compound (1b) to compound (2b) using the engineered polypeptides having CHMO activity of the present disclosure can be carried out wherein the suitable reaction conditions comprise using a cofactor recycling system to regenerate cofactor NADPH/NADH form $NADP^+/NAD^+$ produced in the reaction. The use of a cofactor recycling system allows the various embodiments of the methods to be carried out without adding further cofactor during the reaction. Optionally, the cofactor can replenished by dosing throughout the course of the reaction if no recycling system is used.

In some embodiments of the process, an optional cofactor recycling system can be used to regenerate cofactor NADPH/NADH form NADP+/NAD+ produced in the reaction. A cofactor recycling system refers to a set of reactants that participate in a reaction that reduces the oxidized form of the cofactor (e.g., $NADP^+$ to NADPH). Cofactors oxidized by the polypeptide reduction of the keto substrate are regenerated in reduced form by the cofactor recycling system. Cofactor recycling systems comprise a stoichiometric reductant that is a source of reducing hydrogen equivalents and is capable of reducing the oxidized form of the cofactor. The cofactor recycling system may further comprise a catalyst, for example an enzyme catalyst that catalyzes the reduction of the oxidized form of the cofactor by the reductant. Various cofactor recycling systems to regenerate NADH or NADPH from $NAD^+$ or $NADP^+$, respectively, are known in the art and may be used in the methods described herein.

Suitable exemplary cofactor recycling systems that may be employed include, but are not limited to: an alcohol (e.g., isopropanol) and an alcohol dehydrogenase or ketoreductase; glucose and glucose dehydrogenase; formate and formate dehydrogenase; glucose-6-phosphate and glucose-6-phosphate dehydrogenase; phosphite and phosphite dehydrogenase, molecular hydrogen and hydrogenase; and the like. These systems may be used in combination with either $NADP^+$/NADPH or $NAD^+$/NADH as the cofactor. Electrochemical regeneration using hydrogenase may also be used as a cofactor recycling system. See, e.g., U.S. Pat. Nos. 5,538,867 and 6,495,023, both of which are incorporated herein by reference. Chemical cofactor recycling systems comprising a metal catalyst and a reducing agent (for example, molecular hydrogen or formate) are also suitable. See, e.g., PCT publication WO 2000/053731, which is incorporated herein by reference.

In some embodiments, the co-factor recycling system can comprise an alcohol dehydrogenase or ketoreductase (KRED), which is an $NAD^+$ or $NADP^+$-dependent enzyme that catalyzes the conversion of an alcohol and $NAD^+$ or $NADP^+$ to an aldehyde or ketone and NADH or NADPH, respectively. Alcohol dehydrogenases and ketoreductases that are suitable for use as cofactor regenerating systems in the processes described herein include naturally occurring and non-naturally occurring alcohol dehydrogenases and ketoreductases. Naturally occurring alcohol dehydrogenases include known alcohol dehydrogenase/ketoreductase from, *Thermoanerobium brockii, Rhodococcus etythropolis, Lactobacillus kefiri, and Lactobacillus brevis*, and non-naturally occurring alcohol dehydrogenase/ketoreductase include engineered alcohol dehydrogenase/ketoreductase derived therefrom. In some embodiments, non-naturally occurring alcohol dehydrogenase/ketoreductases engineered for thermo- and solvent stability can be used. Such engineered alcohol dehydrogenases/ketoreductases are described in the following patent publications each of which are incorporated by reference herein: US 20080318295A1; US 20090093031A1; US 20090155863A1; US 20090162909A1; US 20090191605A1; US 20100055751A1; WO/2010/025238A2; WO/2010/025287A2; US 20100062499A1; and WO 2008/151324A1. Suitable alcohols to be used with a KRED in the co-factor recycling system include lower secondary alkanols and aryl-alkyl carbinols. Examples of lower secondary alcohols include isopropanol (IPA), 2-butanol, 3-methyl-2-butanol, 2-pentanol, 3-pentanol, 3,3-dimethyl-2-butanol, and the like. In one embodiment, the secondary alcohol is isopropanol. Suitable aryl-alkyl carbinols include unsubstituted and substituted 1-arylethanols.

In some embodiments, the cofactor recycling system can comprise glucose dehydrogenase (GDH), which is a $NAD^+$ or $NADP^+$-dependent enzyme that catalyzes the conversion of D-glucose and $NAD^+$ or $NADP^+$ to gluconic acid and NADH or NADPH, respectively. Glucose dehydrogenases suitable for use in the practice of the processes described herein include both naturally occurring glucose dehydrogenases, as well as non-naturally occurring glucose dehydrogenases. Naturally occurring glucose dehydrogenase encoding genes have been reported in the literature, e.g., the *Bacillus subtilis* 61297 GDH gene, *B. cereus* ATCC 14579 and *B. megaterium*. Non-naturally occurring glucose dehydrogenases generated using, for example, mutagenesis, directed evolution, and the like and are provided in PCT publ. no. WO 2005/018579, and US publication Nos. 2005/0095619 and 2005/0153417. All of these sequences are incorporated herein by reference.

In some embodiments, the cofactor recycling system can comprise a formate dehydrogenase, which is a $NAD^+$ or $NADP^+$-dependent enzyme that catalyzes the conversion of formate and $NAD^+$ or $NADP^+$ to carbon dioxide and NADH or NADPH, respectively. Formate dehydrogenases that are suitable for use as cofactor regenerating systems in the CHMO reactions described herein include naturally occurring and non-naturally occurring formate dehydrogenases. Suitable formate dehydrogenases are described in PCT publication WO 2005/018579. Formate may be provided in the form of a salt, typically an alkali or ammonium salt (for example, $HCO_2Na$, $KHCO_2NH_4$, and the like), in the form of formic acid, typically aqueous formic acid, or mixtures thereof. A base or buffer may be used to provide the desired pH.

In some embodiments, the co-factor recycling system can comprise a phosphite dehydrogenase, which catalyzes the conversion of phosphite and $NAD^+$ or $NADP^+$ to a phosphate and NADH or NADPH, respectively. Phosphite dehydrogenases that are suitable for use as cofactor regenerating systems in the processes described herein include naturally occurring and non-naturally occurring phosphite dehydrogenases. Naturally occurring phosphite dehydrogenases include those from, *Pseudomonas stutzeri* and *Alcaligenes faecalis*, and non-naturally occurring phosphite dehydrogenases include engineered phosphite dehydrogenases derived therefrom. Phosphite dehydrogenases are described in Johannes et al., 2005, Applied and Environmental Microbiology 71(10):5728-5734; Woodyer et al., 2003, Biochemistry 42 (40):11604-11614; Vrtis et al., 2002, Angewandte Chemie 41(17):3257-3259; Johannes et al., 2006, Biotechnology and Bioengineering Volume 96(1):18-26; and McLachlan et al., 2008, Biotechnology and Bioengineering 99(2):268-274.

In some embodiments where the cofactor recycling system produces a volatile product from the secondary substrate, such as acetone from IPA. The volatile product can be removed by sparging the reaction solution with a non-reactive gas or by applying a vacuum to lower the reaction pressure and removing the volatile present in the gas phase. A non-reactive gas is any gas that does not react with the reaction components. Various non-reactive gases include nitrogen and noble gases (e.g., inert gases). In some embodiments, the non-reactive gas is nitrogen gas. For example, acetone formed by oxidation of isopropanol can be removed by sparging with nitrogen gas or applying a vacuum to the reaction solution and removing the acetone from the gas phase by an acetone trap, such as a condenser or other cold trap.

In the embodiments herein, the non-naturally occurring polypeptides for carrying out the conversion of and any enzymes comprising the optional cofactor recycling system, may be added to the reaction mixture in the form of the purified enzymes, whole cells transformed with gene(s) encoding the enzymes, and/or cell extracts and/or lysates of such cells. The gene(s) encoding the polypeptides disclosed herein and the optional cofactor recycling enzymes can be transformed into host cells separately or together into the same host cell. Whole cells transformed with gene(s) encoding the engineered CHMO enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

In some embodiments of the methods for converting compound (1a) to compound (2a) or compound (1b) to compound (2b) using the engineering CHMO polypeptides of the present disclosure can be carried out wherein the suitable reaction conditions comprise a substrate loading of compound (1a) or compound (1b) of at least about 20 g/L, about 40 g/L, about 50 g/L, about 75 g/L, about 100 g/L, about 200 g/L, about 250 g/L, about 300 g/L, about 400 g/L, or even greater. In certain embodiments, methods for preparing compound (2a) or compound (2b) of the present disclosure can be carried out the suitable reaction conditions comprise a substrate loading of compound (1a) or compound (1b) of about 50-100 g/L, about 50-200 g/L, about 50-300 g/L, about 50-400 g/L, about 100 g/L, about 200 g/L, about 300 g/L or about 400 g/L.

The values for substrate loadings provided herein are based on the molecular weights of the substrates of compound (1a) or compound (1b), however it also contemplated that the equivalent molar amounts of various hydrates and salts of compound (1a) or compound (1b) also can be used in the methods (e.g., a sodium or calcium salt of the acid substrate of compound (1b)). Accordingly, in some embodiments of the methods for converting compound (1b) to compound (2b) using an engineered CHMO polypeptide the suitable reaction conditions comprise using a sodium salt of compound (1b).

The order of addition of reactants is not critical. The reactants may be added together at the same time to a solvent (e.g., monophasic solvent, biphasic aqueous co-solvent system, and the like), or alternatively, some of the reactants may be added separately, and some together at different time points.

In some embodiments, the methods for preparing compound (2a) or compound (2b) of the present disclosure can be carried out using a combination of any suitable reaction conditions disclosed above or elsewhere herein, e.g., in the Examples. Accordingly, in some embodiments, the methods of the present disclosure can be carried out wherein the suitable reaction conditions comprise: (1) substrate loading of about 25-200 g/L compound (1a) or compound (1b); (2) an engineered CHMO polypeptide concentration of about 1.5-5.0 g/L; (3) NADPH cofactor concentration of about 0.1-0.2 g/L; (4) a KRED concentration of about 0.25-0.75 g/L; (5) a co-solvent solution of an aqueous buffer and about 2.5-7% (v/v) IPA; (6) about pH 7.5 to about pH 10.0; and (7) temperature of about 25-45° C. In some embodiments, the suitable reaction conditions can optionally further comprise a co-solvent of PEG200 at a concentration of about 5-15% (v/v). In some embodiments, the suitable reaction conditions can optionally further comprise 0.04 vol % of catalase.

In some embodiments, the methods for preparing compound (2a) or compound (2b) of the present disclosure can be carried out wherein the suitable reaction conditions comprise: (1) substrate loading of about 100 g/L compound (1a) or compound (1b); (2) engineered CHMO polypeptide concentration of about 2.5 g/L; (3) NADPH cofactor concentration of about 0.1 g/L; (4) a KRED concentration of about 0.5 g/L; (5) a co-solvent solution of an aqueous buffer of 0.1M TEA and about 5% (v/v) IPA; (6) about pH 8.5; and (7) temperature of about 35° C. In some embodiments, the suitable reaction conditions can optionally further comprise a co-solvent of PEG200 at a concentration of about 10% (v/v). In some embodiments, the suitable reaction conditions can optionally further comprise 0.04 vol % of catalase.

Generally, in the methods disclosed herein, the biocatalytic reaction with an engineered CHMO polypeptide under suitable reaction conditions is allowed to proceed until essentially complete, or near complete, conversion of amide substrate compound (1a) to product compound (2a) or the conversion of acid substrate compound (1b) to product compound (2b) is obtained. This conversion of substrate to product can be monitored using known methods by detecting substrate and/or product. Suitable methods include gas chromatography, HPLC, and the like, and are described in the Examples.

In some embodiments, the methods for preparing compound (2b) of the present disclosure result in at least about 90% conversion of compound (1b) at 100 g/L loading to compound (2b) in 36 h, when carried out under reaction conditions of: engineered CHMO polypeptide concentration of about 1.0-3.0 g/L; NADPH cofactor concentration of about 0.1 g/L; a KRED concentration of 0.5 g/L; a co-solvent system of 0.1 M TEA at pH 8.5, at least 5% (v/v) IPA, and 10% (v/v) PEG200; and a temperature of 35° C. In some embodiments, the methods of the present disclosure when carried out under these suitable reaction conditions (e.g., 100 g/L compound (1b) loading) result in at least about 91%, 92%, 93%, 94%, 95%, 96%, 97%, 98%, 99% or greater conversion of the acid substrate compound (1b) to product compound (2b) in 24 h.

In some embodiments, the methods for preparing compound (2b) of the present disclosure when carried out with 100 g/L compound (1b) loading result in an enantiomeric excess of compound (2b) of at least 97%, 98, 99%, 99.1%, 99.2%, 99.3%, 99.4%, 99.5%, 99.6%, 99.7%, 99.8%, or 99.9% in 24 h.

In some embodiments, the engineered polypeptides of the present disclosure can be used in methods for preparing structurally similar analogs of compounds (2a) or (2b). Such structurally similar analog compounds can include pharmaceutically active compounds useful for the treatment of sleep disorders which are described in e.g., U.S. Pat. Nos. 4,489, 095, 6,6492,396 B2, and 6,670,358 B2, US patent publication US2002/0183334 A1, or PCT publication WO 2001/087830 A2, each of which is hereby incorporated by reference here. Accordingly, structurally similar analogs of compound (2b) that can be prepared using the engineered polypeptides, methods, and reaction conditions disclosed herein for use in making of compounds (2a) or (2b), include compounds of structural formula (II), which can be prepare from compound of structural formula (I) as shown in Scheme 3 below:

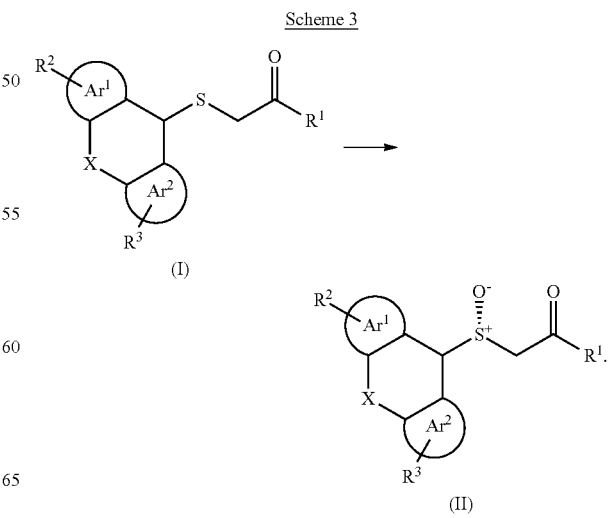

The structurally similar analog compounds of structural formula (II) that can be prepared from compounds of formula (I) using the engineered polypeptides, methods and conditions described herein can include the following range of structural features:

$R^1$ is —OH, —OCH$_3$, —OCH$_2$CH$_3$, —NH$_2$, —NHCH$_3$, —N(CH$_3$)$_2$, —NHOH;

$Ar^1$ and $Ar^2$ are each independently monocyclic or bicyclic aryl or heteroaryl group having 5-6 ring atoms, are each independently, optionally substituted 1 to 3 times with groups $R^2$ and/or $R^3$, and are optionally connected either
(i) via a group X, wherein X is O, NR, S, CH$_2$, CH$_2$CH$_2$. CH=CH; or
(ii) where X is absent and rings $Ar^1$ and $Ar^2$ are connected directly via a bond; and
$R^2$ and $R^3$ are independently —H, —F, —Cl, —Br, —CF$_3$, —CH$_3$, —CH$_2$CH$_3$, —NH$_2$, —NHCH$_3$, or —N(CH$_3$)$_2$.

Thus, in some embodiments, the disclosure provides a method for preparing a compound of structural formula (II) (wherein $Ar^1$, $Ar^2$, $R^1$, $R^2$ and $R^3$ are as defined above) in enantiomeric excess comprising: contacting a compound of structural formula (I) (wherein $Ar^1$, $Ar^2$, $R^1$, $R^2$ and $R^3$ are as defined for formula (II)) with an engineered polypeptide of the present disclosure (e.g., as described in Tables 2A, 2B, 2C and elsewhere herein) in the presence of NADPH or NADH cofactor under suitable reaction conditions. Suitable reaction conditions for use in the method of Scheme 3 include those described above for the methods of preparing compounds (2a) or (2b) (e.g., useful in the methods of Scheme 1 or 2). Specific compounds having structural formula (II) that can be made according to this method include the pharmaceutically active compounds described in U.S. Pat. Nos. 4,489,095, 6,6492,396 B2, and 6,670,358 B2, US patent publication US2002/0183334 A1, or PCT publication WO 2001/087830 A2, each of which is hereby incorporated by reference here.

In the processes herein, the reaction is generally allowed to proceed until essentially complete, or near complete. Conversion of substrate to product can be monitored using known methods by detecting substrate and/or product. Suitable methods include gas chromatography, HPLC, and the like.

EXAMPLES

Various features and embodiments of the disclosure are illustrated in the following representative examples, which are intended to be illustrative, and not limiting.

Example 1: Synthesis, Optimization, and Screening of Engineered Cyclohexanone Monooxygenase (CHMO) Polypeptides Gene Synthesis and Optimization:

The gene encoding the wild type cyclohexanone monooxygenase (CHMO) from *Acinetobacter* sp NCIMB9871 (SEQ ID NO: 2) was designed for expression in *E. coli* using standard codon optimization to yield the nucleotide sequence of SEQ ID NO: 1 (standard codon-optimization methods and software are reviewed in e.g., "OPTIMIZER: a web server for optimizing the codon usage of DNA sequences," Puigbò et al., Nucleic Acids Res. 2007 July; 35(Web Server issue): W126-31. Epub 2007 Apr. 16). The optimized gene was synthesized using oligonucleotides composed of 42 nucleotides and cloned into expression vector pCK110900 (which is depicted as FIG. 3 in US Patent Application Publication 20060195947, which is hereby incorporated by reference herein) under the control of a lac promoter. The pCK110900 expression vector also contained the P15a origin of replication and the chloramphenicol resistance gene. The resulting plasmid was transformed into *E. coli* W3110 using standard methods. Directed evolution of the codon-optimized wild-type CHMO gene of SEQ ID NO: 1 was carried out via iterative rounds of variant library generation (e.g., by gene synthesis) followed by screening for expressed engineered polypeptides with improved properties (including primary HTP assays and secondary SFP assays). The variant polynucleotides encoding engineered CHMO polypeptides having improved enzyme properties were sequenced and used to generate new variant libraries. Variant polynucleotides were cloned into vector pCK110900 for expression in *E. coli* W3110 according to the same procedures described above for the wild type gene. Engineered CHMO nucleotide and amino acid sequences resulting from this directed evolution are listed in the Sequence Listing incorporated by reference herein. The amino acid residue differences and altered enzyme properties of these engineered CHMO polypeptides are summarized in Tables 2A, 2B, 2C, above and described further in the Examples below.

Production of Shake Flask Powders (SFP):

A shake-flask procedure was used to generate engineered transaminase polypeptide powders used in secondary screening assays or in the biocatalytic methods of converting compound (1a) to compound (2a) or compound (1b) to compound (2b) disclosed herein. Shake flask powder (SFP) include approximately 30% total protein and accordingly provide a more purified preparation of an engineered enzyme as compared to the cell lysate used in HTP assays. A single microbial colony of *E. coli* containing a plasmid encoding an engineered CHMO gene of interest was inoculated into 50 mL Luria Bertani broth containing 30 μg/ml chloramphenicol and 1% glucose. Cells were grown overnight (at least 16 hours) in an incubator at 30° C. with shaking at 250 rpm. The culture was diluted into 250 mL Terrific Broth (12 g/L bacto-tryptone, 24 g/L yeast extract, 4 mL/L glycerol, 65 mM potassium phosphate, pH 7.0, 1 mM MgSO$_4$) containing 30 μg/mL chloramphenicol, in a 1 L flask to an optical density of 0.2 at 600 nm (OD$_{600}$) and allowed to grow at 30° C. Expression of the CHMO gene was induced by addition of isopropyl-β-D-thiogalactoside (IPTG) to a final concentration of 1 mM when the OD$_{600}$ of the culture is 0.6 to 0.8, and incubation was then continued overnight (at least 16 hours). Cells were harvested by centrifugation (5000 rpm, 15 mM, 4° C.) and the supernatant discarded. The cell pellet was resuspended with an equal volume of cold (4° C.). 25 mM phosphate buffer, pH 9.0, and harvested by centrifugation as above. The washed cells were resuspended in two volumes of the cold phosphate buffer and passed through a French Press twice at 12,000 psi while maintained at 4° C. Cell debris was removed by centrifugation (9000 rpm, 45 minutes, 4° C.). The clear lysate supernatant was collected and stored at −20° C. Lyophilization of frozen clear lysate provided a dry shake-flask powder of CHMO polypeptide. Alternatively, the cell pellet (before or after washing) was stored at 4° C. or −80° C.

HTP Assay of CHMO Polypeptides:

Primary screening used to guide optimization was carried out in a ~200 μL volume in 96-well plate high-throughput (HTP) assay protocol using cell lysates. The general HTP assay conditions were: 1-100 g/L substrate (i.e., compound (1a) or (1b)), 10-200 μL of clear cell lysate containing the engineered CHMO polypeptide, 0.05-1.0 g/L NADP cofactor, 1 g/L ketoreductase (KRED) polypeptide for cofactor recycling, 0.025-0.100 M phosphate or TEA buffer solution containing 3.5%-10% (v/v) IPA (and optionally, 1.5% acetone or 10% PEG200) co-solvent, pH 8-9, 25° C. reaction temperature and 20 h reaction time (with 200 rpm shaking). The HTP assay conditions were changed slightly over the different rounds of the directed evolution of the CHMO variant polypeptide disclosed in order to detect those variants most improved in enzyme properties. Table 4 shows the HTP assay conditions used to perform primary screening of those variant polypeptides whose improved properties were confirmed by SFP assay as summarized in Tables 2A and 2B. Rounds 1-6 assays used the amide substrate of compound (1a) and Rounds 7-16 assays used the acid substrate of compound (1b).

tration and was carried out at a higher substrate concentration at which the parent round polypeptide showed low or minimal activity (e.g., less than or equal to 5% conversion after 24 hrs).

The general protocol for HTP assays was carried out as follows with adjustments of various reagent concentrations in accordance with assays conditions at different rounds as described in Table 4. Clear cell lysate containing the engineered CHMO polypeptide variant to be screened was prepared by shaking cells for 1.5 h to 2 h at room temperature in a 96-well deep well plate containing 500 μL/well of 1.0 g/L Lysozyme, 0.5 g/L PMBS, 0.1 M TEA, pH 9. Shaking was followed by centrifugation at 4000 rpm and 4° C. for 20 min. A stock KRED-cofactor solution containing 1 g/L KRED polypeptide of SEQ ID NO: 144 or 146, and the

TABLE 4

HTP assay conditions

| Round | SEQ ID NOs assayed | Substrate (g/L) | CHMO lysate (μL) | NADP load (g/L) | Buffer | % IPA (v/v) | pH | T (° C.) |
|---|---|---|---|---|---|---|---|---|
| 1 | 2-6 | 1 | 200 | 1 | 25 mM phosphate | 10 | 8.5 | 25 |
| 2 | 8 | 1 | 25 | 0.3 | 100 mM phosphate | 5 | 8 | 25 |
| 3 | 10 | 1 | 20 | 0.3 | 100 mM phosphate | 5 | 8 | 25 |
| 4 | 12-14 | 1 | 15 | 0.3 | 100 mM phosphate | 5 | 8 | 25 |
| 5 | 16-24 | 2 | 10 | 0.3 | 100 mM phosphate | 3.5% IPA + 1.5% acetone | 8 | 25 |
| 6 | 26-36 | 2 | 10 | 0.3 | 100 mM phosphate | 3.5% IPA + 1.5% acetone | 8 | 25 |
| 7 | 38-46 | 8 | 150 | 0.1 | 100 mM phosphate | 5 | 9 | 25 |
| 8 | 48-80 | 20 | 175 | 0.3 | 100 mM TEA | 5 | 9 | 25 |
| 9a | 82-88 | 17.5 | 20 | 0.1 | 100 mM TEA | 5 | 9 | 25 |
| 9b | 82-88 | 31 | 175 | 0.1 | 100 mM TEA | 5 | 9 | 25 |
| 10a | 90-106 | 20 | 15 | 0.05 | 100 mM TEA | 5 | 9 | 25 |
| 10b | 90-106 | 30 | 120 | 0.1 | 100 mM TEA | 5 | 9 | 25 |
| 11a | 108-114 | 20 | 15 | 0.05 | 100 mM TEA | 5 | 9 | 25 |
| 11b | 108-114 | 35 | 120 | 0.05 | 100 mM TEA | 5 | 9 | 25 |
| 12a | 116-118 | 35 | 80 | 0.05 | 100 mM TEA | 5 | 9 | 25 |
| 12b | 116-118 | 65 | 120 | 0.05 | 100 mM TEA | 5 | 9 | 25 |
| 13 | 126-128 | 70 | 30 | 0.2 | 100 mM TEA | 5 | 9 | 25 |
| 14 | 120-124 | 70 | 45 | 0.2 | 100 mM TEA | 5 | 9 | 35 |
| 15a | 130-132 | 30 | 10 | 0.2 | 100 mM TEA | 5% IPA + 10% PEG200 | 9 | 35 |
| 15b | 130-132 | 100 | 30 | 0.2 | 100 mM TEA | 5% IPA + 10% PEG200 | 9 | 35 |
| 16a | 134-142 | 100 | 30 | 0.2 | 100 mM TEA | 5% IPA + 10% PEG200 | 9 | 35 |
| 16b | 134-142 | 100 | 55 | 0.2 | 100 mM TEA | 5% IPA + 10% PEG200 | 9 | 45 |

At rounds 9-12, additional HTP assays denoted "b" were carried out using higher substrate concentrations. The purpose of the "a" assay was to identify CHMO polypeptides with improved activity (i.e., "rate of conversion") and was carried out at a substrate concentration at which the enzymatic rate of the parent round polypeptide is highest. The purpose of the "b" assay was to identify variants with improved tolerance towards to increased substrate concendesired concentration of NADP cofactor (0.05-1.0 g/L) was prepared in phosphate or TEA buffer, and adjusted to the desired pH (8-9). A stock substrate solution at the desired concentration also was prepared in the same buffer and adjusted to the same desired pH. Generally, the assay was run in a total volume of 200-250 μL in a 96-well deep-well plate. To each well was added the appropriate volume of the stock KRED-cofactor solution, the clear cell lysate, and the stock substrate solution, to reach the desired conditions for the particular assay. For example, 75 μL of the stock KRED-cofactor solution, 120 μL volume of the clear cell lysate, and 90 μL of the stock substrate solution. The reaction was initiated by adding 15 μL of isopropyl alcohol. The reaction initiated by the addition of 15 μL of isopropyl alcohol and then the plate heat sealed and shaken at 200 rpm and 25° C. for ~20 h. The HTP assay reaction was quenched by addition of 500 μL/well of a solution of acetonitrile/0.8% trifluoroacetic acid, followed by heat sealing and a further 200 rpm shaking for 15-20 min at room temperature. The plate was then centrifuged at 4000 rpm for 20 min at 25° C. Then 5 μL of the quenched solution was transferred to a shallow well round bottom plate containing 195 μL acetonitrile which was sealed and shaken for 10 min then stored at 4° C. until activity and/or enantioselectivity analysis is carried out using HPLC.

SFP Assay of CHMO Polypeptides:

Lysates containing CHMO polypeptides identified as hits in the HTP assay (e.g., 1.2-fold improved activity over parent or increased enantioselectivity) were screened in a secondary assay carried out on a 2.00 mL scale using shake-flask powder (SFP) preparations of the engineered CHMO polypeptides. The general SFP assay conditions used to determine activity and enantioselectivity (% e.e.) with the amide substrate of compound (1a) were as follows: 5-10 g/L substrate mixture of compound (1a), 3-10 g/L of SFP of the engineered CHMO polypeptide, 0.3-0.5 g/L NADP cofactor, 1 g/L KRED (for cofactor recycling), in a solution of 25 mM-100 mM phosphate buffer, 5-10% (v/v) IPA, pH 8.0-8.5, 25° C. reaction temperature and 24 h reaction time (with 400 rpm stirring). The general SFP assay conditions used to determine activity and enantioselectivity (% e.e.) with the acid substrate of compound (1b) were as follows: 10-100 g/L substrate mixture of compound (1b), 5-10 g/L of SFP of the engineered CHMO polypeptide, 1 g/L KRED polypeptide of SEQ ID NO: 144 or 146, 0.2-0.3 g/L NADP, in a solution of 100 mM phosphate buffer or TEA buffer, 5% (v/v) IPA, pH 8.3 or pH 9.0, 25° C. reaction temperature and 24 h reaction time (with 400 rpm stirring). The specific SFP assay conditions used for the amide and acid substrate SFP assays at the different rounds of the evolution are noted above in Tables 2A and 2B.

The general SFP assay protocol was as follows. An enzyme solution was prepared by charging a glass vial equipped with a cross shape stir bar with 8 mg of engineered CHMO polypeptide shake-flask powder (SFP), 4 mg KRED polypeptide of SEQ ID NO: 144 or 146, 0.8 mg NADP cofactor, and 1.8 mL 100 mM TEA buffer at 25° C. A substrate solution was prepared by charging another glass vial with the desired amount amide substrate of compound (1a) or acid substrate of compound (1b) (e.g., 120 mg for 30 g/L activity assays, or 240 mg for 60 g/L substrate tolerance assays) and 2 mL of 100 mM TEA buffer at 25° C. The pH of the substrate solution was adjusted to pH 9 with 10 M NaOH solution. The substrate solution then was added to the vial containing the enzyme solution and 0.2 mL IPA (which acts as a substrate for the KRED) was added to start the biocatalytic reaction. The reaction was stirred at 25° C. and conversion of substrate to product was monitored over time using HPLC (as described below). Enantioselectivity (% e.e.) was determined by chiral HPLC analysis (as described below) of samples taken at the end of the biocatalytic reactions.

HPLC Sample Preparation and Activity Analysis:

An aliquot of 10 μL reaction mixture was diluted into 990 μL of 0.1% TFA in acetonitrile. The sample was centrifuged to remove precipitated enzyme. The sample was injected into HPLC for analysis using the instrumental parameters and conditions of Table 5.

TABLE 5

| HPLC instrumentation and chromatographic conditions | | | |
|---|---|---|---|
| Instrument | Agilent 1200 HPLC system | | |
| Column | Eclipse XDB C18 4.6 × 150 mm, 5 μm | | |
| Mobile Phase | A: H$_2$O + 0.1% TFA | | |
|  | B: ACN + 0.1% TFA | | |
|  | Time (min) | % A | % B |
|  | 0 | 70 | 30 |
|  | 10 | 0 | 100 |
| Column temperature | 30° C. | | |
| Flow rate | 1.5 mL/min | | |
| Injection volume | 5 μL | | |
| UV Wavelength | 210 nm | | |
| Runtime (Postime) | 10 min (2 min) | | |
| (R)-BHSO | 3.56 min | | |
| BHTA | 5.88 min | | |
| Linearity | 1.999 (R$^2$ at 10-70 g/L product) | | |

The % Conversion was calculated from the HPLC trace as follows:

$$\% \text{ Conversion} = \frac{[\text{Peak Area of } (R)\text{-}BHSO]}{[\text{Peak Area of } (R)\text{-}BHSO] + [\text{Peak Area of } BHTA]} \times 100\%$$

The response factor for (R)-BHSO to BHTA at 210 nm was determined to be 1.15:1, based on the relative intensity of signals using a 1:1 molar ratio standard solution of (R)-BHSO and BHTA.

Chiral HPLC Sample Preparation and Analysis of Product Enantioselectivity (% e.e.):

9.8 mg of isolated (R)-BHSO sample was weighed into a 50 mL volumetric flask and dissolved in 20 mL of EtOH. The mixture was sonicated for 5 min and volume up with EtOH. The sample was injected into HPLC for analysis using the instrumental parameters and conditions of Table 6.

TABLE 6

| HPLC instrumentation and chromatographic conditions | |
|---|---|
| Instrument | Agilent HPLC 1200 series |
| Column | Chiralpak AD-H 4.6 × 250 mm |
| Mobile Phase (premixed) | 90/10 Hexane/IPA + 0.05% TFA |
| Flow Rate | 1.50 mL/min |
| Detection Wavelength | 225 nm |
| Column Temperature | Ambient |
| Injection Volume | 5 μL |
| Run time | 15 min |
| Diluent | Ethanol |
| LOD | 0.45 mg/L (S/N ~3-5) |
| LOQ | 1.75 g/L (S/N ~8-10) |

HTP Assay Results:

Representative results in the primary screening using the HTP assay for both the amide substrate (compound (1a)) and the acid substrate (compound (2a)) are shown below in Tables 7 and 8.

TABLE 7

| SEQ ID NO: | HTP Activity amide substrate (relative to SEQ ID NO: 2) | % ee |
|---|---|---|
| 1/2 | 1.0 | −52.3 |
| 3/4 | 27.8 | 87.8 |
| 5/6 | 462 | 97.9 |
| 7/8 | 692 | |
| 9/10 | 1177 | |
| 11/12 | 2095 | |
| 13/14 | 2236 | |
| 15/16 | 9426 | |
| 17/18 | 9845 | |
| 19/20 | 14800 | |
| 21/22 | 15930 | |
| 23/24 | 18290 | |
| 25/26 | 15460 | |
| 27/28 | 39110 | |
| 29/30 | 41430 | |
| 31/32 | 33700 | |
| 33/34 | 34160 | |
| 35/36 | 40190 | |
| 37/38 | 27670 | |
| 39/40 | 26120 | |

TABLE 8

| SEQ ID NO: | HTP Activity Acid Substrate (sodium salt) in substrate tolerance (relative to SEQ NO: 82) |
|---|---|
| 81/82 | 1 |
| 83/84 | |
| 85/86 | |
| 87/88 | 9.6 |
| 89/90 | 2.0 |
| 91/92 | 9.1 |
| 93/94 | 8.1 |
| 95/96 | 10.8 |
| 97/98 | 7.4 |
| 99/100 | 4.0 |
| 101/102 | 4.0 |
| 103/104 | 3.8 |
| 105/106 | 2.4 |
| 107/108 | 7.8 |
| 109/110 | 5.8 |
| 111/112 | 7.6 |
| 113/114 | 7.2 |
| 115/116 | 30.8 |
| 117/118 | 36.2 |
| 119/120 | 139 |
| 121/122 | 142 |
| 123/124 | 142 |
| 125/126 | 120 |
| 127/128 | 155 |

Example 2: Preparation of (R)-2-(Benzhydrylsulfinyl)acetic Acid (Compound (2b)) at 5 g Scale A 250 mL 3-neck round bottle flask (RBF) was charged sequentially with 20 mL of 100 mM TEA buffer solution (pH 10.34), 0.02 g of NADP, 0.1 g of KRED polypeptide of SEQ ID NO: 144, and 0.5 g of CHMO polypeptide of SEQ ID NO: 136. The enzyme mixture was stirred gently at 150 rpm until the solid was dissolved. A 50 mL beaker was charged sequentially with 1.5 g benzhydrylthioacetic acid (BHTA) (>98%; for preparation see e.g., US patent publication 2004/0106829A1 and references therein). 20 mL 100 mM TEA buffer solution (pH 10.34) and 560 μL 10 M NaOH (QTёc™). The BHTA mixture was stirred at 25° C. for 15 min to dissolve the solid (pH about 9) and this liquid mixture was charged into the RBF containing the enzyme solution. An additional 5.5 mL of 100 mM TEA buffer solution (pH 10.34) was used to rinse the beaker and the rinse solution was added to the RBF. 10 μL of 10 M NaOH was charged into the RBF to adjust the pH of the resultant mixture from 8.87 to 9. The mixture was stirred for 1 minute at 350 rpm at 25° C. to obtain homogeneity. 2.5 mL of isopropyl alcohol (IPA) was added to start the enzymatic reaction.

Another 50 mL beaker was charged sequentially with 3.5 g of BHTA, 36 mL of 100 mM TEA buffer solution containing 5% IPA (pH 10.08), and 1300 μL of 10 M NaOH. The BHTA mixture was stirred at 25° C. for 15 min to dissolve the solid and resulting in a substrate solution pH of about 9. The BHTA mixture was transferred to a 50 mL syringe. An additional 9 mL of 100 mM TEA buffer solution containing 5% IPA (pH 10.08) was used to rinse the beaker and the rinse solution was added into the syringe. The volume of substrate solution in the syringe is 48 mL and the concentration is 73 g/L.

The mixture in the RBF was stirred at 350 rpm at 25° C. (internal temperature) for 1 h. BHTA solution (in the syringe) was added to the RBF at a rate of 3 mL/h for 16 hours via a syringe pump. The concentration of the substrate and product in the reaction mixture was periodically monitored and analyzed by HPLC. After the full conversion to (R)-BHSO (Na salt) at 32 h, the RBF was cooled down to 15° C. (internal temperature) and the pH of the reaction mixture was adjusted from pH 8.9 to 3.0 with 4.9 mL of 6M HCl solution. The mixture was stirred at 250 rpm to precipitate out the (R)-BHSO product as a free solid.

The white slurry mixture was filtered though a standard G4 sintered glass funnel under vacuum, dried under air at 25° C. for 1 h and re-dissolved in 50 mL of tetrahydrofuran (Sigma; >99.9% HPLC Grade) at 40° C. The mixture was stirred for 20 min until most of the solid dissolved and was filtered through a pad of Celite (3 g) in a standard G4 sintered glass funnel under reduced pressure.

The combined product filtrate was concentrated to 10 mL under vacuum. 20 mL of heptane (Sigma; >99.9% HPLC Grade) was added to further enhance the precipitation of (R)-BHSO. The product was filtered though a standard G4 sintered glass funnel and dried under vacuum, providing 4.9 g (92.4% isolated yield) of (R)-BHSO as an off white solid with a chemical purity of ~99.9%, as measured by HPLC.

Example 3: Preparation of (R)-2-(Benzhydrylsulfinyl)acetic Acid (Compound (2b)) at a 15 g Scale Using a CHMO Variant This example illustrates a process for preparing the armodafinil intermediate compound, (R)-2-(Benzhydrylsulfinyl)acetic acid (compound (2b)) in enantiomeric excess at a 15 g scale via a biocatalytic conversion using an engineered CHMO polypeptide of the disclosure (e.g., a polypeptide of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, or 142.) The procedure described below resulted in 15.9 g (100% yield) of compound (2b) in a single crop as a white solid, and a chemical purity of 99.9% as determined by HPLC.

A. Biocatalytic Reaction Protocol:

A 100 mL beaker equipped with a cross shape stir bar was charged sequentially with: 15 g of benzhydrylthioacetic acid (BHTA) substrate (>98%; US patent publication 2004/0106829A1 and references therein), 77 mL of 100 mM TEA buffer solution (pH 10.3), 5.56 mL, of 10 M NaOH, and 15 mL of PEG 200 (Sigma Reagent Grade). This substrate mixture was stirred at 35° C. for 20 min until all of the solid dissolved, resulting in a pH of about 8.3. A 300 mL Parr reactor vessel was fitted with a turbine impeller, an oxygen gas inlet/outlet and a dosing needle inlet. The reaction vessel at 35° C. was charged sequentially with: 30 mL of 100 mM TEA buffer solution (pH 10.3), 0.03 g of NADP, 0.15 g of KRED polypeptide of SEQ ID NO: 144, and 0.3 g of engineered CHMO polypeptide of SEQ ID NO: 136. This enzyme mixture was stirred gently at 150 rpm until all the solid powder dissolved, affording a homogenous yellow solution. The substrate solution mixture was charged into the Parr reactor vessel containing the enzyme solution. The pH of the resultant mixture was 8.54. The mixture was stirred for 1 minute at 350 rpm at 35° C. to obtain homogeneity. 7.5 mL of IPA (Sigma; >99.9% HPLC Grade) was added to initiate the KRED cofactor recycling reaction and thereby start the CHMO enzymatic reaction. The final pH was found to be 8.50. The reaction course was followed periodically by taking samples from the reaction mixture, quenching, and analyzing as described in Method 1. For the purposes of tracking the process, t=0 was set at the time at which IPA was added. The in-process reaction profile was determined using achiral HPLC analysis as described above in Example 1. The in-process sample analyses are summarized in Table 9 below.

TABLE 9

Reaction Profile

| Time (h) | % Conversion |
|---|---|
| 0 | 0 |
| 3 | 20.5 |
| 6 | 36.5 |
| 26 | 94.5 |
| 30 | 97.6 |
| 33 | 98.8 |
| 36 | 99.4 |
| 48 | 99.9 |

A % conversion of >99% within 36 hours can be estimated from the kinetic profile of the reaction. The reaction mixture 48 hours after start was taken for product work-up and isolation as described below.

B. Reaction Work-Up Protocol:

The reaction vessel was cooled to 15° C. (internal temperature) and the pH of the reaction mixture was adjusted from pH 8.25 to 3.0 by adding 11.1 mL of 6 M HCl solution with continuous stirring at 250 rpm to precipitate out the (R)-2-(benzhydrylsulfinyl)acetic acid product as a free solid. The white slurry mixture was filtered though a standard G4 sintered glass funnel under vacuum and the reaction vessel was twice rinsed with 15 mL of cold deionized water at 5° C. (acidified with HCl to pH 3) and the filter cake was then washed with the deionized water rinse. HPLC analysis of the mother liquor indicated that 0.5% of (R)-2-(benzhydrylsulfinyl)acetic acid product was still present. The product was dried under vacuum to afford 15.9 g (100% isolated yield, 99.85% e.e.) of (R)-2-(benzhydrylsulfinyl)acetic acid as a white solid.

Example 4: Process I for the Preparation of Armodafinil from (R)-2-(Benzhydrylsulfinyl)acetic Acid (Compound (2b)) (Use of 32% HCl Treatment)

In the first step, a 50 mL flask was charged with R-modafinic acid (5 g), methanol (5 mL) and HCl 32% (0.1 mL) to form a suspension. The suspension was stirred at ambient temperature for 24 hours to obtain a crystalline precipitate, which were collected by filtration and analyzed to be the corresponding methyl ester. In the second step, the wet isolated methyl ester was mixed with methanol. Subsequently, ammonia (gas) was bubbled into the mixture for 30 min and the mixture was stirred for 12 hours. Precipitated crystals were collected and identified as armodafinil.

Example 5: Process II for the Preparation of Armodafinil from (R)-2-(Benzhydrylsulfinyl)acetic Acid (R-Modafinic Acid) (Treatment with Thienyl Chloride)

A 100 mL flask was charged with modafinic acid (3.0 g) and methanol (50 mL) and cooled to 0° C. Thionyl chloride (0.8 g, 0.5 eq.) was added drop wise. The reaction mixture was maintained at room temperature for at least 3 hours, and then cooled to 0° C. The methyl ester of modafinic acid was precipitated, filtered and dried. The methyl ester of modafinic acid was mixed with methanol (5 mL/g) and ammonia hydroxide (15 mL/g) was added to the mixture. The mixture was stirred overnight and the precipitated crystals were collected and determined to be armodafinil.

Example 6: Biocatalytic Preparation of Armodafinil (Compound (2a)) from 2-(benzhydrylsulfinyl)acetamide (Compound (1a))

40 mg of the engineered CHMO polypeptide SFP of SEQ ID NO: 38, 4 mg of KRED enzyme of SEQ ID NO: 146, and 0.8 mg of NADP were added to a 20 mL vial equipped with a cross shaped stirring bar. 3.8 mL of 100 mM TEA buffer at pH 9 was used to dissolve the enzyme powder. The mixture was stirred gently until a homogenous yellow solution was obtained. 80 mg of 2-(benzhydrylsulfinyl)acetamide (compound (1a)) was added as a solid powder into the enzyme solution followed by 0.2 mL of IPA. The pH of the slurry mixture was re-measured to ensure the reaction pH is 9. The progress of the reaction was monitored by HPLC.

The invention, and the manner and process of making and using it, are now described in such full, clear, concise and exact terms as to enable any person skilled in the art to which it pertains, to make and use the same. It is to be understood that the foregoing describes preferred embodiments of the present disclosure and that modifications can be made therein without departing from the scope of the present invention as set forth in the claims. To particularly point out and distinctly claim the subject matter regarded as the invention, the following claims conclude this specification.

What is claimed is:

1. A non-naturally occurring polypeptide having cyclohexanone monooxygenase (CHMO) activity wherein the amino acid sequence of the polypeptide has at least 90% sequence identity to SEQ ID NO: 2, and one or more amino acid substitutions at one or more positions corresponding to positions in SEQ ID NO: 2 selected from the group consisting of 75, 79, 82, 99, 110, 166, 172, 208, 216, 273, 324, 364, 395, 412, 491, 503, and 504.

2. The non-naturally occurring polypeptide of claim 1, wherein said non-naturally occurring polypeptide is further capable of converting the acid substrate compound (1b) to compound (2b) (R-enantiomer) or its opposite enantiomer compound (S-enantiomer)

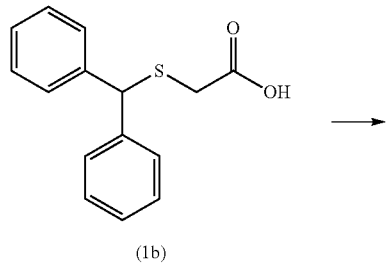

(1b)

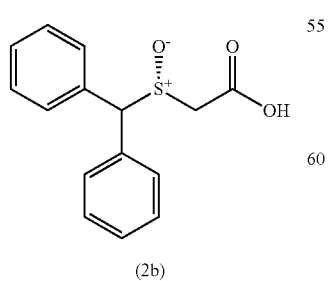

(2b)

with at least 2-fold improved activity relative to the wild-type polypeptide of SEQ ID NO: 2.

3. The non-naturally occurring polypeptide of claim 1, wherein said non-naturally occurring polypeptide further comprises one or more amino acid substitutions relative to SEQ ID NO: 2, wherein the polypeptide comprises an alanine, glutamic acid, glycine, isoleucine, lysine, proline, serine, threonine, or valine at a position corresponding to position 246 of SEQ ID NO:2.

4. The non-naturally occurring polypeptide of claim 1, wherein said non-naturally occurring polypeptide is further capable of converting the acid substrate of compound (1b) to the R-enantiomer compound (2b)

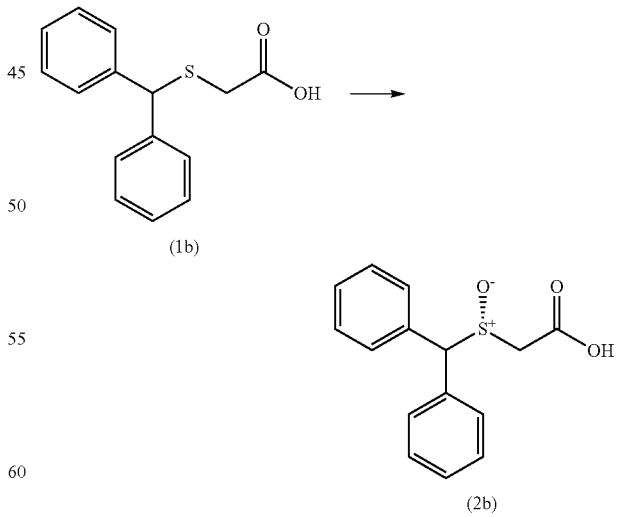

in at least 50% enantiomeric excess.

5. The non-naturally occurring polypeptide of claim 1, wherein said non-naturally occurring polypeptide further comprises one or more amino acid differences relative to SEQ ID NO: 2, wherein said polypeptide further comprises one or more substitutions corresponding to substitutions in SEQ ID NO: 2 selected from the group consisting of a glycine at position 143, a glycine at position 278, an arginine at position 326, and a lysine at position 490.

6. The non-naturally occurring polypeptide of claim 1, wherein said non-naturally occurring polypeptide further comprises an isoleucine at a position corresponding to position 277 of SEQ ID NO: 2, an alanine or glycine at a position corresponding to position 278 of SEQ ID NO: 2, a threonine or tyrosine at a position corresponding to position 280 of SEQ ID NO: 2, an isoleucine at a position corresponding to position 281 of SEQ ID NO: 2, an arginine at a position corresponding to position 326 of SEQ ID NO: 2, and a lysine or glutamine at a position corresponding to position 490 of SEQ ID NO: 2.

7. The non-naturally occurring polypeptide of claim 1, wherein said non-naturally occurring polypeptide is further capable of converting compound (1a) to compound (2a)

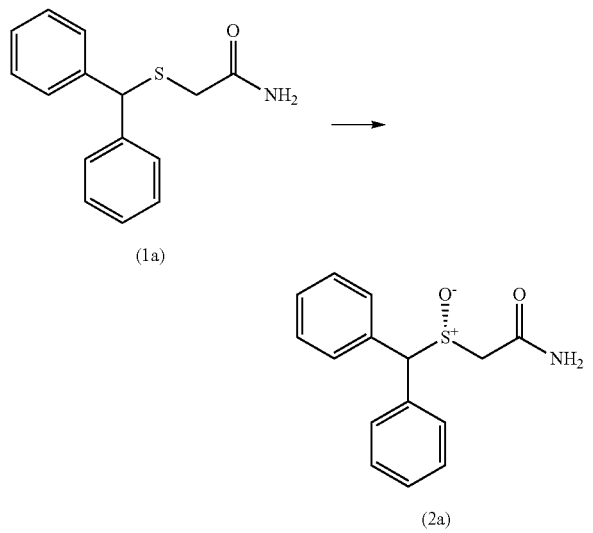

(1a)

(2a)

in at least 75% enantiomeric excess under suitable reaction conditions.

8. The non-naturally occurring polypeptide of claim 1, wherein said non-naturally occurring polypeptide is further capable of converting compound (1a) to compound (2a)

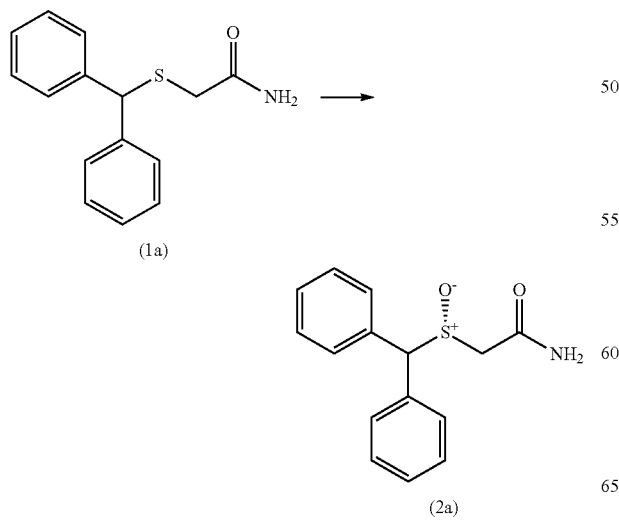

(1a)

(2a)

with an activity increased at least 2-fold relative to the activity of the polypeptide of SEQ ID NO: 2, under suitable reaction conditions.

9. The non-naturally occurring polypeptide of claim 6, wherein said non-naturally occurring polypeptide sequence further comprises a combination of amino acid substitutions relative to SEQ ID NO: 2, selected from the following group consisting of:

(a) the amino acid at position 3 is threonine, the amino acid at position 43 is glycine, the amino acid at position 75 is methionine, the amino acid at position 143 is glycine, the amino acid at position 166 is alanine, the amino acid at position 280 is tyrosine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 491 is valine, the amino acid at position 503 is alanine, the amino acid at position 504 is isoleucine, the amino acid at position 512 is asparagine, and the amino acid at position 532 is proline;

(b) the amino acid at position 3 is threonine, the amino acid at position 43 is glycine, the amino acid at position 75 is methionine, the amino acid at position 99 is valine, the amino acid at position 143 is glycine, the amino acid at position 161 is aspartic acid, the amino acid at position 166 is alanine, the amino acid at position 174 is isoleucine, the amino acid at position 273 is serine, the amino acid at position 280 is tyrosine, the amino acid at position 324 is lysine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 491 is valine, the amino acid at position 503 is alanine, the amino acid at position 504 is isoleucine, the amino acid at position 512 is asparagine, and the amino acid at position 532 is proline;

(c) the amino acid at position 3 is threonine, the amino acid at position 43 is glycine, the amino acid at position 75 is methionine, the amino acid at position 79 is threonine, the amino acid at position 82 is alanine, the amino acid at position 99 is valine, the amino acid at position 110 is methionine, the amino acid at position 143 is glycine, the amino acid at position 161 is aspartic acid, the amino acid at position 166 is alanine, the amino acid at position 174 is isoleucine, the amino acid at position 208 is threonine, the amino acid at position 273 is serine, the amino acid at position 280 is tyrosine, the amino acid at position 324 is lysine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 491 is valine, the amino acid at position 503 is alanine, the amino acid at position 504 is isoleucine, the amino acid at position 505 is lysine, the amino acid at position 512 is asparagine, and the amino acid at position 532 is proline;

(d) the amino acid at position 3 is threonine, the amino acid at position 43 is glycine, the amino acid at position 75 is methionine, the amino acid at position 79 is threonine, the amino acid at position 82 is alanine, the amino acid at position 99 is valine, the amino acid at position 110 is methionine, the amino acid at position 143 is glycine, the amino acid at position 161 is aspartic acid, the amino acid at position 166 is alanine, the amino acid at position 174 is isoleucine, the amino acid at position 208 is threonine, the amino acid at position 273 is serine, the amino acid at position 280 is tyrosine, the amino acid at position 324 is lysine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 472 is isoleucine, the amino acid at position 486 is glutamic acid, the amino acid at position 491 is valine, the amino acid at position 503 is alanine, the amino acid at position 504 is isoleucine, the amino acid at position 505 is lysine, the amino acid at position 512 is asparagine, and the amino acid at position 532 is proline;

(e) the amino acid at position 3 is threonine, the amino acid at position 43 is glycine, the amino acid at position 75 is methionine, the amino acid at position 79 is threonine, the amino acid at position 82 is alanine, the amino acid at position 99 is valine, the amino acid at position 110 is methionine, the amino acid at position 143 is glycine, the amino acid at position 161 is aspartic acid, the amino acid at position 166 is alanine, the amino acid at position 174 is isoleucine, the amino acid at position 208 is threonine, the amino acid at position 234 is aspartic acid, the amino acid at position 273 is serine, the amino acid at position 280 is tyrosine, the amino acid at position 324 is lysine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 438 is methionine, the amino acid at position 472 is isoleucine, the amino acid at position 486 is glutamic acid, the amino acid at position 490 is glutamine, the amino acid at position 491 is valine, the amino acid at position 503 is alanine, the amino acid at position 504 is isoleucine, the amino acid at position 505 is lysine, the amino acid at position 512 is asparagine, and the amino acid at position 532 is proline;

(f) the amino acid at position 3 is threonine, the amino acid at position 43 is glycine, the amino acid at position 75 is methionine, the amino acid at position 79 is threonine, the amino acid at position 82 is alanine, the amino acid at position 99 is valine, the amino acid at position 110 is methionine, the amino acid at position 143 is glycine, the amino acid at position 161 is aspartic acid, the amino acid at position 166 is alanine, the amino acid at position 174 is isoleucine, the amino acid at position 208 is threonine, the amino acid at position 273 is serine, the amino acid at position 280 is tyrosine, the amino acid at position 324 is lysine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 438 is methionine, the amino acid at position 472 is isoleucine, the amino acid at position 484 is cysteine, the amino acid at position 486 is glutamic acid, the amino acid at position 490 is glutamine, the amino acid at position 491 is valine, the amino acid at position 503 is alanine, the amino acid at position 504 is isoleucine, the amino acid at position 505 is lysine, the amino acid at position 512 is asparagine, and the amino acid at position 532 is proline;

(g) the amino acid at position 3 is threonine, the amino acid at position 43 is glycine, the amino acid at position 75 is methionine, the amino acid at position 79 is threonine, the amino acid at position 82 is alanine, the amino acid at position 99 is valine, the amino acid at position 110 is methionine, the amino acid at position 143 is glycine, the amino acid at position 161 is aspartic acid, the amino acid at position 166 is alanine, the amino acid at position 172 is alanine, the amino acid at position 174 is isoleucine, the amino acid at position 208 is threonine, the amino acid at position 243 is lysine, the amino acid at position 245 is glycine, the amino acid at position 273 is serine, the amino acid at position 280 is tyrosine, the amino acid at position 319 is threonine, the amino acid at position 324 is lysine, the amino acid at position 325 is tyrosine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 438 is methionine, the amino acid at position 472 is isoleucine, the amino acid at position 484 is cysteine, the amino acid at position 486 is glutamic acid, the amino acid at position 490 is glutamine, the amino acid at position 491 is valine, the amino acid at position 492 is lysine, the amino acid at position 501 is aspartic acid, the amino acid at position 503 is alanine, the amino acid at position 504 is isoleucine, the amino acid at position 505 is lysine, the amino acid at position 512 is asparagine, and the amino acid at position 532 is proline;

(h) the amino acid at position 3 is threonine, the amino acid at position 43 is glycine, the amino acid at position 62 is valine, the amino acid at position 75 is methionine, the amino acid at position 79 is threonine, the amino acid at position 82 is alanine, the amino acid at position 99 is valine, the amino acid at position 110 is methionine, the amino acid at position 143 is glycine, the amino acid at position 161 is aspartic acid, the amino acid at position 166 is alanine, the amino acid at position 174 is isoleucine, the amino acid at position 208 is threonine, the amino acid at position 273 is serine, the amino acid at position 275 is serine, the amino acid at position 280 is tyrosine, the amino acid at position 324 is lysine, the amino acid at position 329 is valine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 438 is methionine, the amino acid at position 472 is isoleucine, the amino acid at position 484 is cysteine, the amino acid at position 486 is glutamic acid, the amino acid at position 490 is glutamine, the amino acid at position 491 is valine, the amino acid at position 503 is alanine, the amino acid at position 504 is isoleucine, the amino acid at position 505 is lysine, the amino acid at position 512 is asparagine, and the amino acid at position 532 is proline;

(i) the amino acid at position 3 is threonine, the amino acid at position 43 is glycine, the amino acid at position 75 is methionine, the amino acid at position 79 is threonine, the amino acid at position 82 is alanine, the amino acid at position 99 is valine, the amino acid at position 110 is methionine, the amino acid at position 118 is valine, the amino acid at position 143 is glycine, the amino acid at position 161 is aspartic acid, the amino acid at position 166 is alanine, the amino acid at position 172 is alanine, the amino acid at position 174 is isoleucine, the amino acid at position 208 is threonine, the amino acid at position 216 is isoleucine, the amino acid at position 264 is tyrosine, the amino acid at position 273 is serine, the amino acid at position 280 is tyrosine, the amino acid at position 291 is arginine, the amino acid at position 310 is histidine, the amino acid at position 319 is threonine, the amino acid at position 324 is lysine, the amino acid at position 325 is tyrosine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 438 is methionine, the amino acid at position 472 is isoleucine, the amino acid at position 484 is cysteine, the amino acid at position 486 is glutamic acid, the amino acid at position 490 is glutamine, the amino acid at position 491 is valine, the amino acid at position 492 is lysine, the amino acid at position 501 is aspartic acid, the amino acid at position 503 is alanine, the amino acid at position 504 is isoleucine, the amino acid at position 505 is lysine, the amino acid at position 512 is asparagine, and the amino acid at position 532 is proline;

(j) the amino acid at position 3 is threonine, the amino acid at position 43 is glycine, the amino acid at position 75 is methionine, the amino acid at position 79 is threonine, the amino acid at position 82 is alanine, the amino acid at position 89 is asparagine, the amino acid at position 99 is valine, the amino acid at position 110 is methionine, the amino acid at position 118 is valine, the amino acid at position 143 is serine, the amino acid at position 161 is aspartic acid, the amino acid at position 166 is alanine, the amino acid at position 172 is alanine, the amino acid at position 174 is isoleucine, the amino acid at position 208 is threonine, the amino acid at position 216 is isoleucine, the amino acid at position 219 is valine, the amino acid at position 264 is tyrosine, the amino acid at position 273 is serine, the amino acid at position 275 is alanine, the amino acid at position 280 is tyrosine, the amino acid at position 291 is arginine, the amino acid at position 310 is histidine, the amino acid at position 319 is threonine, the amino acid at position 324 is lysine, the amino acid at position 325 is tyrosine, the amino acid at position 362 is serine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 438 is methionine, the amino acid at position 472 is isoleucine, the amino acid at position 477 is aspartic acid, the amino acid at position 484 is cysteine, the amino acid at position 486 is glutamic acid, the amino acid at position 490 is glutamine, the amino acid at position 491 is valine, the amino acid at position 492 is lysine, the amino acid at position 501 is aspartic acid, the amino acid at position 503 is alanine, the amino acid at position 504 is isoleucine, the amino acid at position 505 is lysine, the amino acid at position 512 is asparagine, and the amino acid at position 532 is proline; and (k) the amino acid at position 3 is threonine, the amino acid at position 43 is glycine, the amino acid at position 75 is methionine, the amino acid at position 79 is threonine, the amino acid at position 82 is alanine, the amino acid at position 84 is histidine, the amino acid at position 89 is asparagine, the amino acid at position 99 is valine, the amino acid at position 110 is methionine, the amino acid at position 118 is valine, the amino acid at position 143 is serine, the amino acid at position 161 is aspartic acid, the amino acid at position 166 is alanine, the amino acid at position 172 is alanine, the amino acid at position 174 is isoleucine, the amino acid at position 208 is threonine, the amino acid at position 216 is isoleucine, the amino acid at position 219 is valine, the amino acid at position 264 is tyrosine, the amino acid at position 273 is serine, the amino acid at position 275 is alanine, the amino acid at position 278 is alanine, the amino acid at position 280 is tyrosine, the amino acid at position 291 is arginine, the amino acid at position 310 is histidine, the amino acid at position 319 is threonine, the amino acid at position 324 is lysine, the amino acid at position 325 is tyrosine, the amino acid at position 362 is serine, the amino acid at position 395 is arginine, the amino acid at position 412 is leucine, the amino acid at position 426 is serine, the amino acid at position 432 is serine, the amino acid at position 433 is glycine, the amino acid at position 435 is alanine, the amino acid at position 438 is methionine, the amino acid at position 472 is isoleucine, the amino acid at position 473 is aspartic acid, the amino acid at position 484 is leucine, the amino acid at position 486 is glutamic acid, the amino acid at position 490 is glutamine, the amino acid at position 491 is valine, the amino acid at position 492 is lysine, the amino acid at position 498 is asparagine, the amino acid at position 501 is aspartic acid, the amino acid at position 503 is alanine, the amino acid at position 504 is isoleucine, the amino acid at position 505 is lysine, the amino acid at position 512 is asparagine, and the amino acid at position 532 is proline.

10. The non-naturally occurring polypeptide of claim 1, wherein said non-naturally occurring polypeptide is further capable of converting compound (1b) to compound (2b)

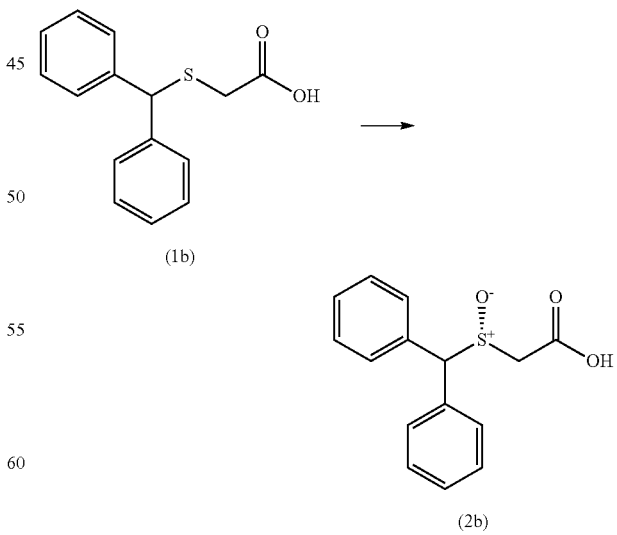

in enantiomeric excess under suitable reaction conditions.

11. The non-naturally occurring polypeptide of claim 6, wherein said non-naturally occurring polypeptide is further capable of converting compound (1b) to compound (2b)

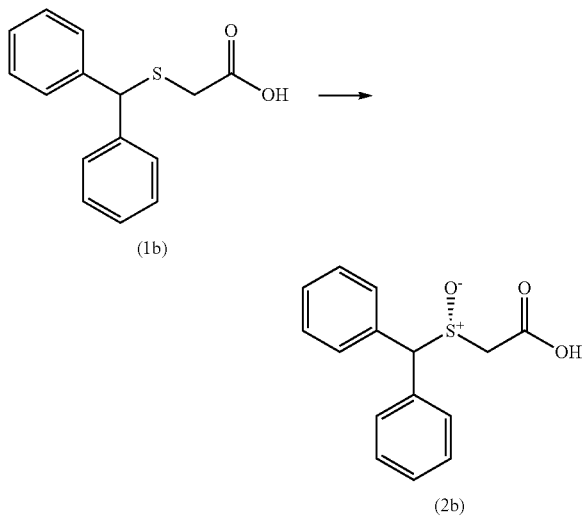

(1b)

(2b)

in at least 75% enantiomeric excess under suitable reaction conditions.

12. The non-naturally occurring polypeptide of claim 6, wherein said non-naturally occurring polypeptide is further capable of converting compound (1b) to compound (2b)

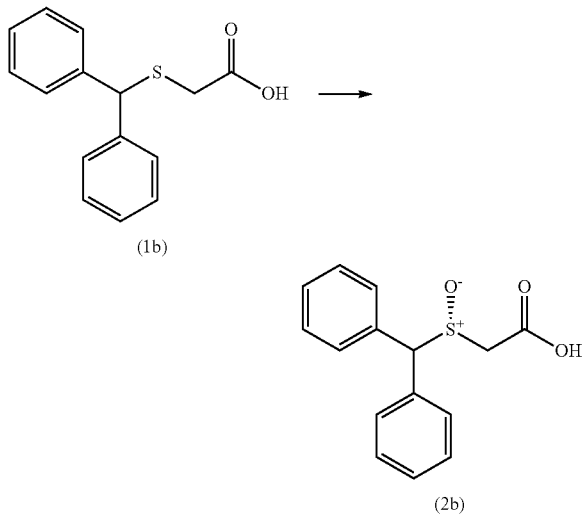

(1b)

(2b)

with an activity increased at least 2-fold relative to the activity of the polypeptide of SEQ ID NO: 2, under suitable reaction conditions.

13. The non-naturally occurring polypeptide of claim 10, wherein said non-naturally occurring polypeptide is capable of at least 90% or greater conversion of compound (1b) to compound (2b) in 24 h with a substrate loading of about 50 g/L.

14. The non-naturally occurring polypeptide of claim 1, wherein said non-naturally occurring polypeptide further comprises at least one amino acid substitution at positions corresponding to positions in SEQ ID NO: 2, selected from 32, 40, 42, 54, 62, 74, 123, 135, 163, 171, 176, 182, 192, 227, 264, 288, 290, 313, 314, 322, 329, 336, 348, 373, 382, 430, 472, 478, 489, 538, and 539.

15. The non-naturally occurring polypeptide of claim 14, wherein said non-naturally occurring polypeptide comprises one or more substitutions corresponding to substitutions in SEQ ID NO:2, selected from the group consisting of: the amino acid at position 32 is glutamic acid, the amino acid at position 40 is glycine, the amino acid at position 42 is isoleucine, the amino acid at position 54 is valine, the amino acid at position 62 is valine, the amino acid at position 74 is glutamic acid, the amino acid at position 123 is alanine, the amino acid at position 135 is lysine, the amino acid at position 163 is leucine or tyrosine, the amino acid at position 171 is glycine, the amino acid at position 176 is serine, the amino acid at position 182 is valine, the amino acid at position 192 is valine, the amino acid at position 227 is aspartic acid or glutamic acid, the amino acid at position 264 is tyrosine, the amino acid at position 288 is leucine or valine, the amino acid at position 290 is aspartic acid, the amino acid at position 313 is glutamic acid, the amino acid at position 314 is leucine or threonine, the amino acid at position 322 is glycine or methionine, the amino acid at position 329 is valine, the amino acid at position 336 is serine, the amino acid at position 348 is alanine, the amino acid at position 373 is valine, the amino acid at position 382 is arginine, the amino acid at position 430 is arginine, the amino acid at position 489 is glycine, the amino acid at position 538 is glutamic acid, and the amino acid at position 539 is glutamic acid.

* * * * *